United States Patent
Howard et al.

(10) Patent No.: US 10,799,595 B2
(45) Date of Patent: Oct. 13, 2020

(54) PYRROLOBENZODIAZEPINE CONJUGATES

(71) Applicant: MedImmune Limited, Cambridge, Cambridgeshire (GB)

(72) Inventors: Philip Wilson Howard, Cambridge (GB); Stephen John Gregson, Cambridge (GB)

(73) Assignee: MedImmune Limited, Cambridge, Cambridgesh (GB)

( * ) Notice: Subject to any disclaimer, the term of this patent is extended or adjusted under 35 U.S.C. 154(b) by 0 days.

(21) Appl. No.: 16/340,973

(22) PCT Filed: Oct. 13, 2017

(86) PCT No.: PCT/EP2017/076162
§ 371 (c)(1),
(2) Date: Apr. 10, 2019

(87) PCT Pub. No.: WO2018/069490
PCT Pub. Date: Apr. 19, 2018

(65) Prior Publication Data
US 2019/0282705 A1    Sep. 19, 2019

(30) Foreign Application Priority Data
Oct. 14, 2016    (GB) .................................. 1617466.6

(51) Int. Cl.
| | |
|---|---|
| *C07D 487/04* | (2006.01) |
| *C07H 7/06* | (2006.01) |
| *A61K 47/68* | (2017.01) |
| *A61K 47/55* | (2017.01) |
| *A61P 35/00* | (2006.01) |
| *C07H 15/203* | (2006.01) |

(52) U.S. Cl.
CPC .......... *A61K 47/6803* (2017.08); *A61K 47/55* (2017.08); *A61K 47/6855* (2017.08); *A61K 47/6863* (2017.08); *A61K 47/6889* (2017.08); *A61P 35/00* (2018.01); *C07H 15/203* (2013.01)

(58) Field of Classification Search
CPC ............................... C07D 487/04; C07H 7/06
See application file for complete search history.

(56) References Cited

U.S. PATENT DOCUMENTS

| | | | |
|---|---|---|---|
| 3,361,742 A | 1/1968 | Julius et al. | |
| 3,523,941 A | 8/1970 | Leimgruber et al. | |
| 3,524,849 A | 8/1970 | Batcho et al. | |
| 3,794,644 A | 2/1974 | Karlyone et al. | |
| 4,185,016 A | 1/1980 | Takanabe et al. | |
| 4,239,683 A | 12/1980 | Takanabe et al. | |
| 4,309,437 A | 1/1982 | Ueda et al. | |
| 4,353,827 A | 10/1982 | Hunkeler et al. | |
| 4,382,032 A | 5/1983 | Hunkeler et al. | |
| 4,386,028 A | 5/1983 | Hunkeler et al. | |
| 4,405,516 A | 9/1983 | Hunkeler et al. | |
| 4,405,517 A | 9/1983 | Hunkeler et al. | |
| 4,407,752 A | 10/1983 | Hunkeler et al. | |
| 4,427,587 A | 1/1984 | Kaneko et al. | |
| 4,427,588 A | 1/1984 | Kaneko et al. | |
| 4,701,325 A | 10/1987 | Ueda et al. | |
| 4,816,567 A | 3/1989 | Cabilly et al. | |
| 4,923,984 A | 5/1990 | Matsumura et al. | |
| 5,362,852 A | 11/1994 | Geoghegan | |
| 5,418,241 A | 5/1995 | Jegham et al. | |
| 5,440,021 A | 8/1995 | Chuntharapai et al. | |
| 5,561,119 A | 10/1996 | Jacquesy et al. | |
| 5,583,024 A | 12/1996 | McElroy et al. | |
| 5,621,002 A | 4/1997 | Bosslet et al. | |
| 5,644,033 A | 7/1997 | Seon | |
| 5,674,713 A | 10/1997 | McElroy et al. | |
| 5,700,670 A | 12/1997 | Yamagishi et al. | |
| 5,773,223 A | 6/1998 | Shyamala et al. | |
| 5,792,616 A | 8/1998 | Persico et al. | |
| 5,854,399 A | 12/1998 | Salomon et al. | |
| 5,869,445 A | 2/1999 | Cheever et al. | |
| 5,976,551 A | 11/1999 | Mottez et al. | |
| 6,011,146 A | 1/2000 | Mottez et al. | |

(Continued)

FOREIGN PATENT DOCUMENTS

| | | |
|---|---|---|
| CN | 101171257 | 4/2008 |
| EP | 0522868 | 1/1993 |

(Continued)

OTHER PUBLICATIONS

Adair; et al., "Antibody-drug conjugates—a perfect synergy," Exp. Opin. Biol. Ther. (2012), pp. 1-16.

(Continued)

*Primary Examiner* — Bruck Kifle
(74) *Attorney, Agent, or Firm* — Casimir Jones, S.C.; Melissa E. Kolom

(57) ABSTRACT

A compound of formula (I): (I) and its conjugates.

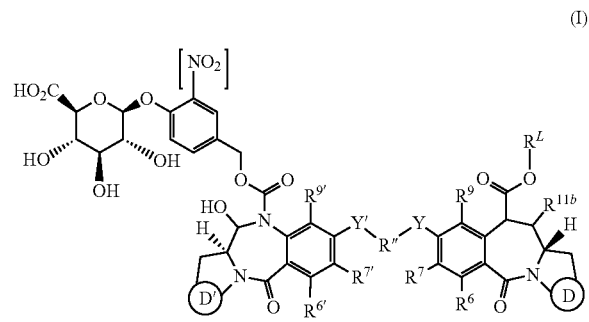

26 Claims, 2 Drawing Sheets

(56) References Cited

U.S. PATENT DOCUMENTS

| | | | |
|---|---|---|---|
| 6,153,408 A | 11/2000 | Abastado et al. | |
| 6,214,345 B1 | 4/2001 | Firestone et al. | |
| 6,218,519 B1 | 4/2001 | Kenten et al. | |
| 6,268,488 B1 | 7/2001 | Barbas, III et al. | |
| 6,362,331 B1 | 3/2002 | Kamal et al. | |
| 6,518,404 B1 | 2/2003 | Li et al. | |
| 6,534,482 B1 | 3/2003 | Fikes et al. | |
| 6,555,339 B1 | 4/2003 | Liaw et al. | |
| 6,562,806 B1 | 5/2003 | Thurston et al. | |
| 6,602,677 B1 | 8/2003 | Wood et al. | |
| 6,608,192 B1 | 8/2003 | Thurston et al. | |
| 6,660,742 B2 | 12/2003 | Lee | |
| 6,660,856 B2 | 12/2003 | Wang | |
| 6,677,435 B2 | 1/2004 | Barbas, III et al. | |
| 6,747,144 B1 | 6/2004 | Thurston et al. | |
| 6,759,509 B1 | 7/2004 | King et al. | |
| 6,835,807 B1 | 12/2004 | Sasaki et al. | |
| 6,884,799 B2 | 4/2005 | Kamal et al. | |
| 6,909,006 B1 | 6/2005 | Thurston et al. | |
| 7,049,311 B1 | 5/2006 | Thurston et al. | |
| 7,067,511 B2 | 6/2006 | Thurston et al. | |
| 7,223,837 B2 | 5/2007 | De Groot et al. | |
| 7,244,724 B2 | 7/2007 | Liu et al. | |
| 7,265,105 B2 | 9/2007 | Thurston et al. | |
| 7,375,078 B2 | 5/2008 | Feng | |
| 7,407,951 B2 | 8/2008 | Thurston et al. | |
| 7,429,658 B2 | 9/2008 | Howard et al. | |
| 7,511,032 B2 | 3/2009 | Liu et al. | |
| 7,521,541 B2 | 4/2009 | Eigenbrot et al. | |
| 7,528,126 B2 | 5/2009 | Howard et al. | |
| 7,557,099 B2 | 7/2009 | Howard et al. | |
| 7,612,062 B2 | 11/2009 | Gregson et al. | |
| 7,704,924 B2 | 4/2010 | Thurston et al. | |
| 7,723,485 B2 | 5/2010 | Junutula et al. | |
| 7,741,319 B2 | 6/2010 | Howard et al. | |
| 8,034,808 B2 | 10/2011 | Delavault et al. | |
| 8,163,736 B2 | 4/2012 | Gauzy et al. | |
| 8,321,774 B2 | 11/2012 | Barthel et al. | |
| 8,487,092 B2 | 7/2013 | Howard et al. | |
| 8,501,934 B2 | 8/2013 | Howard et al. | |
| 8,592,576 B2 | 11/2013 | Howard et al. | |
| 8,633,185 B2 | 1/2014 | Howard et al. | |
| 8,637,664 B2 | 1/2014 | Howard et al. | |
| 8,697,688 B2 | 4/2014 | Howard et al. | |
| 8,829,184 B2 | 9/2014 | Howard et al. | |
| 8,940,733 B2 | 1/2015 | Howard et al. | |
| 9,102,704 B2 | 8/2015 | Howard | |
| 9,242,013 B2 | 1/2016 | Howard et al. | |
| 9,321,774 B2 | 4/2016 | Howard et al. | |
| 9,376,440 B2 | 6/2016 | Howard et al. | |
| 9,387,259 B2 | 7/2016 | Jeffrey et al. | |
| 9,388,187 B2 | 7/2016 | Howard et al. | |
| 9,399,073 B2 | 7/2016 | Howard et al. | |
| 9,399,641 B2 | 7/2016 | Howard et al. | |
| 9,415,117 B2 | 8/2016 | Howard | |
| 9,464,141 B2 | 10/2016 | Asundi et al. | |
| 9,526,798 B2 | 12/2016 | Jeffrey et al. | |
| 9,562,049 B2 | 2/2017 | Howard | |
| 9,592,240 B2 | 3/2017 | Howard et al. | |
| 9,624,227 B2 | 4/2017 | Howard et al. | |
| 9,649,390 B2 | 5/2017 | Howard et al. | |
| 9,707,301 B2 | 7/2017 | Jeffrey et al. | |
| 9,713,647 B2 | 7/2017 | Jeffrey et al. | |
| 9,732,084 B2 | 8/2017 | Howard et al. | |
| 9,745,303 B2 | 8/2017 | Howard et al. | |
| 9,889,207 B2 | 2/2018 | Howard | |
| 9,956,298 B2 | 5/2018 | Howard et al. | |
| 2001/0055751 A1 | 12/2001 | Reiter et al. | |
| 2002/0034749 A1 | 3/2002 | Billing-Medel et al. | |
| 2002/0042366 A1 | 4/2002 | Thompson et al. | |
| 2002/0150573 A1 | 10/2002 | Nussenzweig | |
| 2002/0193567 A1 | 12/2002 | Jacobs et al. | |
| 2003/0060612 A1 | 3/2003 | Goddard et al. | |
| 2003/0062401 A1 | 4/2003 | Hasz et al. | |
| 2003/0064397 A1 | 4/2003 | Spancake et al. | |
| 2003/0065143 A1 | 4/2003 | Eaton et al. | |
| 2003/0091580 A1 | 5/2003 | Mitcham et al. | |
| 2003/0096743 A1 | 5/2003 | Senter et al. | |
| 2003/0096961 A1 | 5/2003 | Baker et al. | |
| 2003/0105292 A1 | 6/2003 | Liaw et al. | |
| 2003/0109676 A1 | 6/2003 | Li et al. | |
| 2003/0118592 A1 | 6/2003 | Ledbetter et al. | |
| 2003/0119121 A1 | 6/2003 | Baker et al. | |
| 2003/0119122 A1 | 6/2003 | Baker et al. | |
| 2003/0119125 A1 | 6/2003 | Baker et al. | |
| 2003/0119126 A1 | 6/2003 | Baker et al. | |
| 2003/0119128 A1 | 6/2003 | Baker et al. | |
| 2003/0119129 A1 | 6/2003 | Baker et al. | |
| 2003/0119130 A1 | 6/2003 | Baker et al. | |
| 2003/0119131 A1 | 6/2003 | Baker et al. | |
| 2003/0124140 A1 | 7/2003 | Bangur et al. | |
| 2003/0124579 A1 | 7/2003 | Mack et al. | |
| 2003/0129192 A1 | 7/2003 | Chenault et al. | |
| 2003/0130189 A1 | 7/2003 | Senter et al. | |
| 2003/0134790 A1 | 7/2003 | Langenfeld | |
| 2003/0143557 A1 | 7/2003 | Penner | |
| 2003/0157089 A1 | 8/2003 | Xu et al. | |
| 2003/0165504 A1 | 9/2003 | Retter et al. | |
| 2003/0185830 A1 | 10/2003 | Xu et al. | |
| 2003/0186372 A1 | 10/2003 | Baker et al. | |
| 2003/0186373 A1 | 10/2003 | Baker et al. | |
| 2003/0194704 A1 | 10/2003 | Penn et al. | |
| 2003/0195196 A1 | 10/2003 | Thurston et al. | |
| 2003/0206918 A1 | 11/2003 | Fanger et al. | |
| 2003/0219806 A1 | 11/2003 | Glucksmann et al. | |
| 2003/0224411 A1 | 12/2003 | Stanton et al. | |
| 2003/0224454 A1 | 12/2003 | Ryseck et al. | |
| 2003/0228319 A1 | 12/2003 | Frantz et al. | |
| 2003/0232056 A1 | 12/2003 | Fanger et al. | |
| 2003/0232350 A1 | 12/2003 | Afar et al. | |
| 2004/0001827 A1 | 1/2004 | Dennis | |
| 2004/0005320 A1 | 1/2004 | Thompson et al. | |
| 2004/0005538 A1 | 1/2004 | Chen et al. | |
| 2004/0005563 A1 | 1/2004 | Mack et al. | |
| 2004/0005598 A1 | 1/2004 | DeVaux et al. | |
| 2004/0018194 A1 | 1/2004 | Francisco et al. | |
| 2004/0018553 A1 | 1/2004 | Billing-Medel et al. | |
| 2004/0022727 A1 | 2/2004 | Stanton et al. | |
| 2004/0044179 A1 | 3/2004 | Baker et al. | |
| 2004/0044180 A1 | 3/2004 | Baker et al. | |
| 2004/0052793 A1 | 3/2004 | Carter et al. | |
| 2004/0101874 A1 | 5/2004 | Ghosh et al. | |
| 2004/0101899 A1 | 5/2004 | Dillon et al. | |
| 2004/0121940 A1 | 6/2004 | De Groot et al. | |
| 2004/0138269 A1 | 7/2004 | Sun et al. | |
| 2004/0197325 A1 | 10/2004 | Law et al. | |
| 2004/0198722 A1 | 10/2004 | Thurston et al. | |
| 2004/0249130 A1 | 12/2004 | Stanton et al. | |
| 2005/0271615 A1 | 12/2005 | Shabat et al. | |
| 2006/0116422 A1 | 6/2006 | De Groot et al. | |
| 2007/0072846 A1 | 3/2007 | Vishnuvajjala et al. | |
| 2007/0154906 A1 | 7/2007 | Martin et al. | |
| 2007/0185336 A1 | 8/2007 | Rossen et al. | |
| 2007/0191349 A1 | 8/2007 | Howard et al. | |
| 2007/0232592 A1 | 10/2007 | Delavault et al. | |
| 2007/0249591 A1 | 10/2007 | Howard et al. | |
| 2008/0090812 A1 | 4/2008 | Pepper et al. | |
| 2008/0092940 A1 | 4/2008 | Nakajima | |
| 2008/0112961 A1 | 5/2008 | Stavenhagen et al. | |
| 2008/0206239 A1 | 8/2008 | Jones et al. | |
| 2008/0213289 A1 | 9/2008 | Francisco et al. | |
| 2008/0214525 A1 | 9/2008 | Howard et al. | |
| 2009/0036431 A1 | 2/2009 | Gauzy et al. | |
| 2009/0148942 A1 | 6/2009 | McDonagh et al. | |
| 2009/0149449 A1 | 6/2009 | Liu et al. | |
| 2009/0274713 A1 | 11/2009 | Chari et al. | |
| 2009/0304710 A1 | 12/2009 | Park et al. | |
| 2010/0028346 A1 | 2/2010 | Lutz et al. | |
| 2010/0047257 A1 | 2/2010 | Blanc et al. | |
| 2010/0113425 A1 | 5/2010 | Howard et al. | |
| 2010/0203007 A1 | 8/2010 | Li et al. | |
| 2010/0316656 A1 | 12/2010 | Bouchard et al. | |
| 2011/0039969 A1 | 2/2011 | Muratoglu et al. | |
| 2011/0070227 A1 | 3/2011 | Novotney-Barry et al. | |

(56) References Cited

U.S. PATENT DOCUMENTS

| | | | |
|---|---|---|---|
| 2011/0091372 A1 | 4/2011 | Ghayur et al. |
| 2011/0160192 A1 | 6/2011 | Howard et al. |
| 2011/0195021 A1 | 8/2011 | Deckert et al. |
| 2011/0195022 A1 | 8/2011 | Deckert et al. |
| 2011/0196148 A1 | 8/2011 | Howard et al. |
| 2011/0201803 A1 | 8/2011 | Howard et al. |
| 2011/0256157 A1 | 10/2011 | Howard et al. |
| 2012/0233172 A1 | 9/2012 | Skillcorn et al. |
| 2012/0238731 A1 | 9/2012 | Fishkin et al. |
| 2013/0028917 A1 | 1/2013 | Howard et al. |
| 2013/0028919 A1 | 1/2013 | Howard et al. |
| 2013/0137659 A1 | 5/2013 | Commercon et al. |
| 2013/0244171 A1 | 9/2013 | Yamasaki et al. |
| 2013/0266595 A1 | 10/2013 | Flygare et al. |
| 2013/0266596 A1 | 10/2013 | Li et al. |
| 2013/0302359 A1 | 11/2013 | Li et al. |
| 2013/0304357 A1 | 11/2013 | Koci et al. |
| 2014/0030279 A1 | 1/2014 | Polakis et al. |
| 2014/0030280 A1 | 1/2014 | Polakis |
| 2014/0066435 A1 | 3/2014 | Howard et al. |
| 2014/0088089 A1 | 3/2014 | Chari |
| 2014/0120118 A1 | 5/2014 | Howard |
| 2014/0127239 A1 | 5/2014 | Howard |
| 2014/0155590 A1 | 6/2014 | Commercon et al. |
| 2014/0234346 A1 | 8/2014 | Howard |
| 2014/0274907 A1 | 9/2014 | Howard et al. |
| 2014/0275522 A1 | 9/2014 | Howard et al. |
| 2014/0286970 A1 | 9/2014 | Jeffrey et al. |
| 2014/0294868 A1 | 10/2014 | Howard et al. |
| 2014/0302066 A1 | 10/2014 | Jeffrey et al. |
| 2015/0111880 A1 | 4/2015 | Howard et al. |
| 2015/0126495 A1 | 5/2015 | Howard et al. |
| 2015/0133435 A1 | 5/2015 | Howard et al. |
| 2015/0158869 A1 | 6/2015 | Howard |
| 2015/0183883 A1 | 7/2015 | Asundi |
| 2015/0265722 A1 | 9/2015 | Van Berkel |
| 2015/0273077 A1 | 10/2015 | Van Berkel |
| 2015/0273078 A1 | 10/2015 | Van Berkel |
| 2015/0274737 A1 | 10/2015 | Howard et al. |
| 2015/0283258 A1 | 10/2015 | Van Berkel |
| 2015/0283262 A1 | 10/2015 | Van Berkel |
| 2015/0283263 A1 | 10/2015 | Van Berkel |
| 2015/0297746 A1 | 10/2015 | Van Berkel |
| 2015/0315196 A1 | 11/2015 | Howard et al. |
| 2015/0344482 A1 | 12/2015 | Howard et al. |
| 2016/0015828 A1 | 1/2016 | Torgor |
| 2016/0031887 A1 | 2/2016 | Howard et al. |
| 2016/0075787 A1 | 3/2016 | Zheng et al. |
| 2016/0144052 A1 | 5/2016 | Howard et al. |
| 2016/0074527 A1 | 7/2016 | Flygare et al. |
| 2016/0250344 A1 | 9/2016 | Howard et al. |
| 2016/0250345 A1 | 9/2016 | Howard et al. |
| 2016/0250346 A1 | 9/2016 | Howard et al. |
| 2016/0256561 A1 | 9/2016 | Howard et al. |
| 2016/0263242 A1 | 9/2016 | Howard et al. |
| 2016/0310611 A1 | 10/2016 | Flygare et al. |
| 2017/0239365 A1 | 8/2017 | Howard et al. |
| 2017/0290924 A1 | 10/2017 | Jeffrey et al. |
| 2017/0298137 A1 | 10/2017 | Jeffrey et al. |
| 2017/0340752 A1 | 11/2017 | Howard |
| 2018/0125997 A1 | 5/2018 | Howard et al. |
| 2018/0134717 A1 | 5/2018 | Howard et al. |

FOREIGN PATENT DOCUMENTS

| | | |
|---|---|---|
| EP | 0875569 | 11/1998 |
| EP | 1295944 | 3/2003 |
| EP | 1347046 | 9/2003 |
| EP | 1394274 | 3/2004 |
| EP | 1439393 | 7/2004 |
| EP | 1813614 | 8/2007 |
| EP | 2019104 | 1/2009 |
| EP | 2298817 | 3/2011 |
| EP | 2528625 | 7/2013 |
| FR | 2027356 | 12/1969 |
| FR | 2586683 | 3/1987 |
| GB | 1299198 | 12/1972 |
| GB | 2053894 | 2/1981 |
| JP | 5382792 | 7/1978 |
| JP | 57131791 | 8/1982 |
| JP | 58180487 | 10/1983 |
| JP | 05003790 | 1/1993 |
| JP | 2004113151 | 4/2004 |
| WO | WO 199102536 | 3/1991 |
| WO | WO 199207574 | 5/1992 |
| WO | WO 199217497 | 10/1992 |
| WO | WO 199219620 | 11/1992 |
| WO | WO 199318045 | 9/1993 |
| WO | WO 199410312 | 5/1994 |
| WO | WO 199428931 | 12/1994 |
| WO | WO 199504718 | 2/1995 |
| WO | WO 199630514 | 10/1996 |
| WO | WO 199707198 | 2/1997 |
| WO | WO 199744452 | 11/1997 |
| WO | WO 199813059 | 4/1998 |
| WO | WO 199837193 | 8/1998 |
| WO | WO 199840403 | 9/1998 |
| WO | WO 199851805 | 11/1998 |
| WO | WO 199851824 | 11/1998 |
| WO | WO 199928468 | 6/1999 |
| WO | WO 199946284 | 9/1999 |
| WO | WO 199958658 | 11/1999 |
| WO | WO 200003291 | 1/2000 |
| WO | WO 200012506 | 3/2000 |
| WO | WO 200012507 | 3/2000 |
| WO | WO 200012508 | 3/2000 |
| WO | WO 200012509 | 3/2000 |
| WO | WO 200014228 | 3/2000 |
| WO | WO 200020579 | 4/2000 |
| WO | WO 200022129 | 4/2000 |
| WO | WO 200032752 | 6/2000 |
| WO | WO 200036107 | 6/2000 |
| WO | WO 200040614 | 7/2000 |
| WO | WO 200044899 | 8/2000 |
| WO | WO 200012130 | 9/2000 |
| WO | WO 200053216 | 9/2000 |
| WO | WO 200055351 | 9/2000 |
| WO | WO 200075655 | 12/2000 |
| WO | WO 200100244 | 1/2001 |
| WO | WO 200116104 | 3/2001 |
| WO | WO 200116318 | 3/2001 |
| WO | WO 200138490 | 5/2001 |
| WO | WO 200140269 | 6/2001 |
| WO | WO 200140309 | 6/2001 |
| WO | WO 200141787 | 6/2001 |
| WO | WO 200145746 | 6/2001 |
| WO | WO 200146232 | 6/2001 |
| WO | WO 200146261 | 6/2001 |
| WO | WO 200148204 | 7/2001 |
| WO | WO 200153463 | 7/2001 |
| WO | WO 200157188 | 8/2001 |
| WO | WO 200162794 | 8/2001 |
| WO | WO 200166689 | 9/2001 |
| WO | WO 200172830 | 10/2001 |
| WO | WO 200172962 | 10/2001 |
| WO | WO 200175177 | 10/2001 |
| WO | WO 200177172 | 10/2001 |
| WO | WO 200188133 | 11/2001 |
| WO | WO 200190304 | 11/2001 |
| WO | WO 200194641 | 12/2001 |
| WO | WO 200198351 | 12/2001 |
| WO | WO 200202587 | 1/2002 |
| WO | WO 200202624 | 1/2002 |
| WO | WO 200202634 | 1/2002 |
| WO | WO 200206317 | 1/2002 |
| WO | WO 200206339 | 1/2002 |
| WO | WO 200210187 | 2/2002 |
| WO | WO 200210382 | 2/2002 |
| WO | WO 200212341 | 2/2002 |
| WO | WO 200213847 | 2/2002 |
| WO | WO 200214503 | 2/2002 |
| WO | WO 200216413 | 2/2002 |
| WO | WO 200222153 | 3/2002 |
| WO | WO 200222636 | 3/2002 |

(56) References Cited

FOREIGN PATENT DOCUMENTS

| | | |
|---|---|---|
| WO | WO 200222660 | 3/2002 |
| WO | WO 200222808 | 3/2002 |
| WO | WO 200224909 | 3/2002 |
| WO | WO 200226822 | 4/2002 |
| WO | WO 200230268 | 4/2002 |
| WO | WO 200238766 | 5/2002 |
| WO | WO 200254940 | 7/2002 |
| WO | WO 200259377 | 8/2002 |
| WO | WO 200260317 | 8/2002 |
| WO | WO 200261087 | 8/2002 |
| WO | WO 200264798 | 8/2002 |
| WO | WO 200271928 | 9/2002 |
| WO | WO 200272596 | 9/2002 |
| WO | WO 200278524 | 10/2002 |
| WO | WO 200281646 | 10/2002 |
| WO | WO 200283866 | 10/2002 |
| WO | WO 200286443 | 10/2002 |
| WO | WO 200288170 | 11/2002 |
| WO | WO 200288172 | 11/2002 |
| WO | WO 200289747 | 11/2002 |
| WO | WO 200292836 | 11/2002 |
| WO | WO 200294852 | 11/2002 |
| WO | WO 200298358 | 12/2002 |
| WO | WO 200299074 | 12/2002 |
| WO | WO 200299122 | 12/2002 |
| WO | WO 2002101075 | 12/2002 |
| WO | WO 2002102235 | 12/2002 |
| WO | WO 200216429 | 1/2003 |
| WO | WO 2003000842 | 1/2003 |
| WO | WO 2003002717 | 1/2003 |
| WO | WO 2003003906 | 1/2003 |
| WO | WO 2003003984 | 1/2003 |
| WO | WO 2003004529 | 1/2003 |
| WO | WO 2003004989 | 1/2003 |
| WO | WO 2003008537 | 1/2003 |
| WO | WO 2003009814 | 2/2003 |
| WO | WO 2003014294 | 2/2003 |
| WO | WO 2003016475 | 2/2003 |
| WO | WO 2003016494 | 2/2003 |
| WO | WO 2003018621 | 3/2003 |
| WO | WO 2003022995 | 3/2003 |
| WO | WO 2003023013 | 3/2003 |
| WO | WO 2003024392 | 3/2003 |
| WO | WO 2003025138 | 3/2003 |
| WO | WO 2003025148 | 3/2003 |
| WO | WO 2003025228 | 3/2003 |
| WO | WO 2003026493 | 4/2003 |
| WO | WO 2003026577 | 4/2003 |
| WO | WO 2003029262 | 4/2003 |
| WO | WO 2003029277 | 4/2003 |
| WO | WO 2003029421 | 4/2003 |
| WO | WO 2003034984 | 5/2003 |
| WO | WO 2003035846 | 5/2003 |
| WO | WO 2003042661 | 5/2003 |
| WO | WO 2003043583 | 5/2003 |
| WO | WO 2003045422 | 6/2003 |
| WO | WO 2003048202 | 6/2003 |
| WO | WO 2003054152 | 7/2003 |
| WO | WO 2003055439 | 7/2003 |
| WO | WO 2003055443 | 7/2003 |
| WO | WO 2003060612 | 7/2003 |
| WO | WO 2003062401 | 7/2003 |
| WO | WO 2003072035 | 9/2003 |
| WO | WO 2003072036 | 9/2003 |
| WO | WO 2003077836 | 9/2003 |
| WO | WO 2003081210 | 10/2003 |
| WO | WO 2003083041 | 10/2003 |
| WO | WO 2003083047 | 10/2003 |
| WO | WO 2003083074 | 10/2003 |
| WO | WO 2003087306 | 10/2003 |
| WO | WO 2003087768 | 10/2003 |
| WO | WO 2003088808 | 10/2003 |
| WO | WO 2003089624 | 10/2003 |
| WO | WO 2003089904 | 10/2003 |
| WO | WO 2003093444 | 11/2003 |
| WO | WO 2003097803 | 11/2003 |
| WO | WO 2003101283 | 12/2003 |
| WO | WO 2003101400 | 12/2003 |
| WO | WO 2003104270 | 12/2003 |
| WO | WO 2003104275 | 12/2003 |
| WO | WO 2003104399 | 12/2003 |
| WO | WO 2003105758 | 12/2003 |
| WO | WO 2004000221 | 12/2003 |
| WO | WO 2004000997 | 12/2003 |
| WO | WO 2004001004 | 12/2003 |
| WO | WO 2004005598 | 1/2004 |
| WO | WO 2004009622 | 1/2004 |
| WO | WO 2004011611 | 2/2004 |
| WO | WO 2004015426 | 2/2004 |
| WO | WO 2004016225 | 2/2004 |
| WO | WO 2004020583 | 3/2004 |
| WO | WO 2004020595 | 3/2004 |
| WO | WO 2004022709 | 3/2004 |
| WO | WO 2004022778 | 3/2004 |
| WO | WO 2004027049 | 4/2004 |
| WO | WO 2004031238 | 4/2004 |
| WO | WO 2004032828 | 4/2004 |
| WO | WO 2004032842 | 4/2004 |
| WO | WO 2004040000 | 5/2004 |
| WO | WO 2004042346 | 5/2004 |
| WO | WO 2004043361 | 5/2004 |
| WO | WO 2004043963 | 5/2004 |
| WO | WO 2004044178 | 5/2004 |
| WO | WO 2004045516 | 6/2004 |
| WO | WO 2004045520 | 6/2004 |
| WO | WO 2004045553 | 6/2004 |
| WO | WO 2004046342 | 6/2004 |
| WO | WO 2004047749 | 6/2004 |
| WO | WO 2004048938 | 6/2004 |
| WO | WO 2004053079 | 6/2004 |
| WO | WO 2004058309 | 7/2004 |
| WO | WO 2004063355 | 7/2004 |
| WO | WO 2004063362 | 7/2004 |
| WO | WO 2004063709 | 7/2004 |
| WO | WO 2004065576 | 8/2004 |
| WO | WO 2004065577 | 8/2004 |
| WO | WO 2004074320 | 9/2004 |
| WO | WO 2005023814 | 3/2005 |
| WO | WO 2005040170 | 5/2005 |
| WO | WO 2005042535 | 5/2005 |
| WO | WO 2005079479 | 9/2005 |
| WO | WO 2005082023 | 9/2005 |
| WO | WO 2005085177 | 9/2005 |
| WO | WO 2005085250 | 9/2005 |
| WO | WO 2005085251 | 9/2005 |
| WO | WO 2005085259 | 9/2005 |
| WO | WO 2005085260 | 9/2005 |
| WO | WO 2005105113 | 11/2005 |
| WO | WO 2005110423 | 11/2005 |
| WO | WO 2006111759 | 10/2006 |
| WO | WO 2007039752 | 4/2007 |
| WO | WO 2007044515 | 4/2007 |
| WO | WO 2007085930 | 8/2007 |
| WO | WO 2008010101 | 1/2008 |
| WO | WO 2008022152 | 2/2008 |
| WO | WO 2008047242 | 4/2008 |
| WO | WO 2008050140 | 5/2008 |
| WO | WO 2008070593 | 6/2008 |
| WO | WO 2009016516 | 2/2009 |
| WO | WO 2009052249 | 4/2009 |
| WO | WO 2009060208 | 5/2009 |
| WO | WO 2009060215 | 5/2009 |
| WO | WO 2009117531 | 9/2009 |
| WO | WO 2010010347 | 1/2010 |
| WO | WO 2010043877 | 4/2010 |
| WO | WO 2010043880 | 4/2010 |
| WO | WO 2010091150 | 8/2010 |
| WO | WO 2010095031 | 8/2010 |
| WO | WO 2011023883 | 3/2011 |
| WO | WO 2011038159 | 3/2011 |
| WO | WO 2011100227 | 8/2011 |
| WO | WO 2011128650 | 10/2011 |
| WO | WO 2011130598 | 10/2011 |
| WO | WO 2011130613 | 10/2011 |

(56) References Cited

FOREIGN PATENT DOCUMENTS

| WO | WO 2011130615 | 10/2011 |
|---|---|---|
| WO | WO 2011130616 | 10/2011 |
| WO | WO 2011133039 | 10/2011 |
| WO | WO 2012014147 | 2/2012 |
| WO | WO 2012064733 | 5/2012 |
| WO | WO 2012112687 | 8/2012 |
| WO | WO 2012112708 | 8/2012 |
| WO | WO 2012128868 | 9/2012 |
| WO | WO 2013041606 | 3/2013 |
| WO | WO 2013053871 | 4/2013 |
| WO | WO 2013053872 | 4/2013 |
| WO | WO 2013053873 | 4/2013 |
| WO | WO 2013055987 | 4/2013 |
| WO | WO 2013055990 | 4/2013 |
| WO | WO 2013055993 | 4/2013 |
| WO | WO 2013164592 | 11/2013 |
| WO | WO 2013164593 | 11/2013 |
| WO | WO 2013177481 | 11/2013 |
| WO | WO 2014011518 | 1/2014 |
| WO | WO 2014011519 | 1/2014 |
| WO | WO 2014022679 | 2/2014 |
| WO | WO 2014031566 | 2/2014 |
| WO | WO 2014057072 | 4/2014 |
| WO | WO 2014057073 | 4/2014 |
| WO | WO 2014057074 | 4/2014 |
| WO | WO 2014057113 | 4/2014 |
| WO | WO 2014057114 | 4/2014 |
| WO | WO 2014057115 | 4/2014 |
| WO | WO 2014057117 | 4/2014 |
| WO | WO 2014057118 | 4/2014 |
| WO | WO 2014057119 | 4/2014 |
| WO | WO 2014057120 | 4/2014 |
| WO | WO 2014057122 | 4/2014 |
| WO | WO 2014080251 | 5/2014 |
| WO | WO 2014096365 | 6/2014 |
| WO | WO 2014096368 | 6/2014 |
| WO | WO 2014130879 | 8/2014 |
| WO | WO 2014140174 | 9/2014 |
| WO | WO 2014140862 | 9/2014 |
| WO | WO 2014159981 | 10/2014 |
| WO | WO 2014174111 | 10/2014 |
| WO | WO 2015031693 | 3/2015 |
| WO | WO 2015052321 | 4/2015 |
| WO | WO 2015052322 | 4/2015 |
| WO | WO 2015052332 | 4/2015 |
| WO | WO 2015052333 | 4/2015 |
| WO | WO 2015052334 | 4/2015 |
| WO | WO 2015052335 | 4/2015 |
| WO | WO 2015052532 | 4/2015 |
| WO | WO 2015052533 | 4/2015 |
| WO | WO 2015052534 | 4/2015 |
| WO | WO 2015052535 | 4/2015 |
| WO | WO 2015095124 | 6/2015 |
| WO | WO 2015159076 | 10/2015 |
| WO | WO 2016037644 | 3/2016 |
| WO | WO 2016040868 | 3/2016 |
| WO | WO 2016044560 | 3/2016 |

OTHER PUBLICATIONS

Adams et al., "Molecular modelling of a sequence-specific DNA-binding agent based on the pyrrolo[2,1-c][1,4]benzodiazepines," Pharm. Pharmacol. Commun. (1999) 5:555-560.

Aird, R.E. et al., "ABCB1 genetic polymorphism influences the pharmacology of the new pyrrolobenzodiazepine derivative SJG-136," Pharmacogenomics Journal (2008) 8(4):289-296.

Alley, M.C. et al., ""SJG-136 (NSC 694501), a novel rationally designed DNA minor groove interstrand cross-linking agent with potent and broad spectrum antitumor activity. Part 2: Efficacy evaluations,"" Cancer Res. (2004) 64:6700-6706.

Alley, M.C., "Efficacy evaluations of SJG-136 (NSC 694501), a novel pyrrolobenzodiazepine dimer with broad spectrum antitumor activity," Proceedings of the American Association for Cancer Research Annual Meeting (Mar. 2002) 43:63.

Alley, S. C., "Contribution of Linker Stability to the Activities of Anticancer Immunoconjugates" Bioconjugate Chem 2008, 19, 759-765.

Althius, T. H. and Hess, H. J., "Synthesis and Identification of the Major Metabolites of Prazosin Formed in Dog and Rat," J. Medicinal Chem. (1977) 20(1):146-148.

Altuvia et al., "Ranking potential binding peptides to MHC molecules by a computational threading approach." J. Mol. Biol., 249, 244-250 (1995).

Amiel J., et al., "Heterozygous endothelin receptor B {EDNRB) mutations in isolated Hirschsprung disease," Hum. Mol. Genet. 5, 355-357, 1996.

Amir et al., "Self-Immolative Dendrimers," (2003) Angew. Chem. Int. Ed. 42:4494-4499.

Amsberry, et al, "The Lactonization of 2'-Hydroxyhydrocinnamic Acid Amides: A Potential Prodrug for Amines," (1990) J. Org. Chem. 55:5867-5877.

Antonow, D. et al., ""Synthesis of DNA-Interactive Pyrrolo [2,1-c][1,4] benzodiazepines (PBDs)"" Chemical Reviews, 2011, 111(4):2815-2864.

Antonow, D. et al., "Structure-activity relationships of monomeric C2-aryl pyrrolo[2,1-c][1,4]benzodiazepine (PBD) antitumor agents." J Med Chem. Apr. 8, 2010;53(7):2927-41.

Antonow, D. et al.,"Parallel synthesis of a novel C2-aryl pyrrolo[2,1-c][1,4]benzodiazepine (PBD) library," J. Comb. Chem. (2007) 9:437-445.

Arai H., et al., ""Molecular cloning of human endothelin receptors and their expressiOn in vascular endothelial cells and smooth muscle cells,"" Jpn. Circ. J. 56, 1303-1307, 1992.

Arai H., et al., "The Human Endotbelin-B Receptor Gene. Structural Organization and Chromosomal Assignment," J. Biol. Chem. 268, 3463-3470, 1993.

Arima et al., "Studies on Tomaymycin, a New Antibiotic. I. Isolation and Properties of Tomaymycin," J. Antibiotics (1972) 25:437-444.

Arnould, S., ""Impact on the cell cycle and involvement of ATM, ATR, chk1 and chk2 kinases in the cytotoxicity of SJG-136, a new pyrrolobenzodiazepine dimer,"" Proceedings of the American Association for Cancer Research Annual Meeting (Mar. 2004) 45:1298, Abstract No. 5618.

Arnould, S., "Time-dependent cytotoxicity induced by SJG-136 (NSC 694501): influence of the rate of interstrand cross-link formation on DNA damage signaling," Mol. Canc. Therap. 5(6):1602-1609 (2006).

Attie T., et al., "Mutation of the endothelin-receptor B gene in Waardenburg-Hirschsprung disease," Hum. Mol. Genet. 4, 2407-2409, 1995.

Auricchio A., et al., "Endothelin-B receptor mutations in patients with isolated Hirschsprung disease from a non-inbred population," Hum. Mol. Genet. 5:351-354, 1996.

Axup et al., "Synthesis of site-specific antibody-drug conjugates using unnatural amino acids." Proc Natl Acad Sci U S A. Oct. 2, 2012; 109(40)1 6101-6.

Bahrenberg et al., ""Reduced Expression of PSCA, a Member of the LY-6 Family of Cell Surface Antigens, in Bladder, Esophagus, and Stomach Tumors,"" Biochem. Biophys. Res. Commun. (2000) 275(3):783-788.

Banker, G.S. et al., "Modern Pharmaceutics", Third edition, Marcel Dekker, New York (1996) 451 and 596.

Barel M., et al., "Evidence for a new transcript of the Epstein-Barr virus/C3d receptor (CR2, CD21) which is due to alternative exon usage," Mol. Immunol. 35, 1025-1031, 1998.

Barella et al., "Sequence variation of a novel heptahelical leucocyte receptor through alternative transcript formation," (1995) Biochem. J. 309:773-779.

Barnett T., et al., "Carcinoembryonic Antigen Family: Characterization of cDNAs Coding for NCA and CEA and Suggestion of Nonrandom Sequence Variation in Their Conserved Loop-Domains," Genomics 3, 59-66, 1988.

Batisse, et al., "A new delivery system for Auristatin in STxB-drug conjugate therapy." European

(56) References Cited

OTHER PUBLICATIONS

Beck et al., "DNA Sequence Analysis of 66 kb of the Human MHC Class II Region Encoding a Cluster of Genes for Antigen Processing," (1992) J. Mol. Biol. 228:433-441.

Beck et al., "Evolutionary Dynamics of Non-coding Sequences Within the Class II Region of the Human MHC," (1996) J. Mol. Biol. 25 255:1-13.

Berge et al., "Pharmaceutical Salts," J. Pharm. Sci. (1977) 66:1-19.

Berry, J. M. et al., "Solid-phase synthesis of DNA-interactive pyrrolo[2,1-c][1,4]benzodiazepines," Tetrahedron Letters (2000) 41:6171-6174.

Berry, J.M. et al., "Synthesis and biological evaluation of an N10-Psec substituted pyrrolo[2,1-c][1,4]benzodiazepine prodrug," Bioorg. Med. Chem. Lett. (2002) 12:1413-1416.

Blanc et al., "SAR3419: an anti-CD19-Maytansinoid Immunoconjugate for the treatment of B-cell malignancies," Clin Cancer Res., 2011, 17(20):6448-58.

Blumberg H., et al., ""Interleukin 20: Discovery, Receptor Identification, and Role in Epidermal Function,"" Cell 104, 9-19, 2001.

Bose et al., "New Approaches to Pyrrolo[2,1-c][1,4]benzodiazepines: Synthesis, DNA-binding and cytotoxicity of DC-81," Tetrahedron, 48, 751-758 (1992).

Bose, D.S. et al., "Effect of linker length on DNA-binding affinity, cross-linking efficiency and cytotoxicity of C8 linked pyrrolobenzodiazepine dimers," J. Chem. Soc. Chem. Commun. (1992) 20:1518-1520.

Bose, D.S. et al., "Rational Design of a Highly Efficient Irreversible DNA Interstrand Cross-Linking Agent Based on the Pyrrolobenzodiazepine Ring System," J. Am. Chem. Soc., 114, 4939-4941 (1992).

Bourgeois C., et al., "Endothelin-1 and ETA Receptor Expression in Vascular Smooth Muscle Cells from Human Placenta: A New ETA Receptor Messenger Ribonucleic Acid Is Generated by Alternative Splicing of Exon 3," J. Clin. Endocrinol. Metab. 82, 3116-3123, 1997.

Brand et al., Prospect for anti-HER2 receptor therapy in breast cancer. Anticancer Res. Jan.-Feb. 2006;26(1B):463-70.

Brinster et al., "Introits increase transcriptional efficiency in transgenic mice,"(1988) Proc. Natl. Acad. Sci. USA 85:836-840.

Buchman et al., "Comparison of Intron-Dependent and Intron-Independent Gene Expression," (1988) Mol. Cell. Biol. 8:4395-4405.

Buhrow, S.A., "LC-MS/MS assay and dog pharmacokinetics of the dimeric pyrrolobenzodiazepine SJG-136 (NSC 694501)," J. Chromat. B: Anal. Tech. Biomed. Life Sci. (2006) 840(1):56-62.

Burke, P.J. et al., "Anti-CD70 antibody-drug conjugates containing pyrrolobenzodiazepine dimers demonstrate robust antitumor activity," AACR National Meeting, Apr. 2012, Chicago, Illinois, Abstract No. 4631.

Burke, P.J. et al., "Novel immunoconjugates comprised of streptonigrin and 17-amino-geldanamycin attached via a dipeptide-p-aminobenzylamine linker system," Bioorg. Med. Chem. Lett., Apr. 2009, 19(10):2650-2653.

Calcutt, M.W., "Determination of chemically reduced pyrrolobenzodiazepine SJG-136 in human plasma by HPLC-MS/MS: application to an anticancer phase I dose escalation study," J. Mass Spectrom. (2008) 43(1):42-52.

Carl et al., "A Novel Connector Linkage Applicable in Prodrug Design," (1981) J. Med. Chem. 24:479-480.

Carlsson et al., "Protein Thiolation and Reversible Protein-Protein Conjugation," (1978) Biochem. J. 173:723-737.

Carter, P., "Potent antibody therapeutics by design," (2006) Nature Reviews Immunology 6:343-357.

Casset et al., "A peptide mimetic of an anti-CD4 monoclonal antibody by rational design." Biochem Biophys Res Commun. Jul. 18, 2003; 307(1):198-205.

CellTiter-Glo Luminescent Cell Viability Assay, Promega Corp. Technical Bulletin TB288, dated Jan. 13, 2012 (14 pages).

Chakravarty et al., "Plasmin-Activated Prodrugs for Cancer Chemotherapy. 2. Synthesis and Biological Activity of Peptidyl Derivatives of Doxorubicin," (1983) J. Med. Chem. 26:638-644.

Chan, J. and Watt, V.M., "eek and erk, new members of the eph subclass of receptor protein-tyrosine kinases," Oncogene 6 (6), 1057-1061 (1991).

Chang et al., "Molecular cloning of mesothelin, a differentiation antigen present on mesothelium, mesotheliomas, and ovarian cancers," Proc. Natl. Acad. Sci. U.S.A. 93 (1):136-140 (1996).

Chen, Z. et al., ""A novel approach to the synthesis of cytotoxic C2-C3 unsaturated pyrrolo[2,1-c][1,4]benzodiazepines (PBDs) with conjugated acrylyl C2-substituents,"" Biorg. Med. Chem. Lett. (2004) 14:1547-1549.

Cheung, A., "Direct liquid chromatography determination of the reactive imine SJG-136 (NSC 694501)," J. Chromat. B: Anal. Techn. Biomed. Life Sci. (2005) 822(1-2):10-20.

Child et al., "Translational Control by an Upstream Open Reading Frame in the HER-2/neu Transcript," (1999) J. Bioi. Chem. 274: 24335-24341.

Cho et al., "Structure of the extracellular region of HER2 alone and in complex with the Herceptin Fab," Nature 421, 756-760, 2003.

Ciccodicola, et al., "Molecular characterization of a gene of the 'EGF family' expressed in undifferentiated human NTERA2 teratocarcinoma cells," EMBO J. 8 (7):1987-1991 (1989).

Cipolla, L., "Pyrrolo[2,1-c][1,4]benzodiazepine as a scaffold for the design and synthesis of anti-tumour drugs," Anti-Cancer Agents in Medicinal Chemistry (Jan. 2009) 9(1):1-31.

Clackson et al., "Making antibody fragments using phage display libraries," (1991) Nature, 352:624-628.

Clark H.F., et al., "The Secreted Protein Discovery Initiative (SPDI], a Large-Scale Effort to Identify Novel Human Secreted and Transmembrane Proteins: A Bioinformatics Assessment," Genome Res. 13, 2265-2270, 2003.

Clingen, P.H., "The role of nucleotide excision repair and homologous recomination in the sensitivity of mammalian cells to the minor groove crosslinking pyrrolo[2,1-c][1,4]benzodiazepine dimer SJG-136 (NSC694501)," Proceedings of the American Association for Cancer Research Annual Meeting (Jul. 2003) 44:524.

Clingen, P.H., "The XPF-ERCC1 endonuclease and homologous recombination contribute to the repair of minor groove DNA interstrand crosslinks in mammalian cells produced by the pyrrolo[2,1-c][1,4]benzodiazepine dimer SJG-136," Nucl. Acids Res. (2005) 33(10):3283-3291.

Clinical Trial, "Translational research: 4 ways to fix the clinical trial." 2011, http://www.nature.com/news/2011/110928/full/477526a.html.

Collins, "Generation and initial analysis of more than 15,000 full-length human and mouse eDNA sequences," Proc. Natl. Acad. Sci. U.S.A. 99 (26):16899-16903 (2002).

Cooper, N. et al., "Synthesis of novel PBDs as anti-tumour agents," Chem. Commun. (2002) 16:1764-1765.

Cooper, N., "Design, Synthesis and Evaluation of Novel C2-Aryl Pyrrolobenzodiazepines as Potential Anticancer Agents," Thesis submitted to School of Pharmacy, University of London, Dated Oct. 5, 2006.

Corey et al., "LuCap35: a new model of prostate cancer progression to androgen independence." The Prostate 2003; 55:239-46.

Courtney, S. M. et al., "A new convenient procedure for the synthesis of pyrrolo[2,1-c][1,4]benzodiazepines", Tetrahedron Letters, vol. 34, No. 33, 5327-28 (1993).

Coussens L., et al., "Tyrosine Kinase Receptor with Extensive Homology to EGF Receptor Shares Chromosomal Location With neu Oncogene," Science (1985) 230(4730):1132-1139.

Cragg et al., "The alternative transcript of CD79b is overexpressed in B-CLL and inhibits signaling for apoptosis," Blood (2002) 100 (9):3068-3076.

Cree et al., "Methotrexate chemosensitivity by ATP luminescence in human leukemia cell lines and in breast cancer primary cultures: comparison of the TCA-100 assay with a clonogenic assay," (1995) AntiCancer Drugs 6:398-404.

Crouch et al., "The use• of ATP bioluminescence as a measure of cell proliferation and cytotoxicity," (1993) J. Immunol. Meth. 160:81-88.

(56) References Cited

OTHER PUBLICATIONS

Dall'Acqua, W. F. et al., "Antibody humanization by framework shuffling" Methods, 36, 43-60 (2005).
Dattolo, G. et al., "Polycondensed nitrogen heterocycles. IX. 5,6-dihydro-7H-pyrrolo[1,2- d][1,4]benzodiazepin-6-one," J. Heterocyclic. Chem. (1980) 17:701-703.
Davis et al., "Identification of a family of Fc receptor homo logs with preferential B cell expression," (2001) Proc. Natl. Acad. Sci. USA 98(17):9772-9777.
De Groot et al., "Cascade-Release Dendrimers "Liberate All End Groups upon a Single Triggering Event in the Dendritic Core,""" (2003) Angew. Chem. Int. Ed. 42:4490-4494.
De Groot et al., "Elongated Multiple Electronic Cascade and Cyclization Spacer Systems in Activatible Anticancer Prodrug for Enhanced Drug Release," (2001) J. Org. Chem. 66:8815-8830.
De Pascalis et al., "Grafting of "abbreviated" complementarity-determining regions containing specificity-determining residues essential for ligand contact to engineer a less immunogenic humanized monoclonal antibody." J Immunol. Sep. 15, 2002;169(6):3076-84.
Dennis et al., (2002) "Albumin Binding As a General Strategy for Improving the Pharmacokinetics of Proteins" J Biol Chem. 277:35035-35043.
Dijke, P., et al., "Characterization of Type I Receptors for Transforming Growth Factor-beta and Activin," Science 264 (5155):101-104 (1994).
Dobner et al., "Differentiation-specific expression of a novel G protein-coupled receptor from Burkitt's lymphoma," (1992) Eur. J. Immunol. 22:2795-2799.
Dong, Q. et al., "Reductive cleavage of TROC groups under neutral conditions with cadmium-lead couple," Tetrahedron Lett. (1995) 36(32):5681-5682.
Dono et al., "Isolation and Characterization of the CRI PTO Autosomal Gene and Its X-linked Related Sequence," Am. J. Hum. Genet. 49:555-565, 1991.
Dornan et al., "Therapeutic potential of an anti-CD79b antibody-drug conjugate, anti-CD79b-vc-MMAE, for the treatment of non-Hodgkin lymphoma," (2009) Blood 114(13):2721-2729.
Doronina et al., "Enhanced Activity of Monomethylauristatin F through Monoclonal Antibody Delivery: Effects of Linker Technology on Efficacy and Toxicity," (2006) Bioconj. Chem. 17:114-124.
Doronina, S.O. et al., "Development of potent monoclonal antibody auristatin conjugates for cancer therapy," Nature Biotech. (2003) 21:778-784.
Dorwald, F.Z., Side Reactions in Organic Synthesis: a Guide to Successful Synthesis Design, Weinheim: Wiley-VCH Verlag GmbH & Co., KGaA (2005) Preface.
Doyle, M., "Response of *Staphylococcus aureus* to subinhibitory concentrations of a sequence-selective, DNA minor groove cross-linking pyrrolobenzodiazepine dimer," J. Antimicrob. Chemo., Aug. 2009, 64(5):949-959.
Dubowchik et al, "Cathepsin B-sensitive dipeptide prodrugs. 2. Models of anticancer drugs paclitaxel (Taxol), mitomycin C and doxorubicin." Bioorganic & Medicinal Chemistry Letters, 8:3347-3352, (1998).
Dubowchik et al, "Cathepsin B-sensitive dipeptide prodrugs. 1. A model study of structural requirements for efficient release of doxorubicin." Bioorg Med Chem Lett. Dec. 1, 1998; 8(23):3341-6.
Dubowchik et al., "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity," Bioconjugate Chem. (2002) 13, 855-869.
Dubowchik et al., "Monomethoxytrityl (MMT) as a Versatile Amino Protecting Group for Complex Prodrugs of Anticancer Compounds Sensitive to Strong Acids, Bases and Nucleophiles," (1997) Tetrahedron Letters. 38:5257-5260.
Dumoutier L., et al., "Cutting Edge: STAT Activation by IL-19, IL-20 and mda-7 Through IL-20 Receptor Complexes of Two Types," J. Immunol. 167, 3545-3549, 2001.
Dupont, C. et al., "Synthesis of rhazinilam analogue acting as an inhibitor of tubulin assembly," Tetrahedron Lett. (2000) 41:5853-5856.
Ehsani A., et al., "Characterization of a New Allele of the Human ERBB2 Gene by Allele-Specific Competition Hybridization," (1993) Genomics 15, 426-429.
Eliel et al., Stereochemistry of Organic Compounds, John Wiley & Sons, Inc., New York (1994).
Elshourbagy N.A., et al., "Molecular Characterization and Regulation of the Human Endothelin Receptors," J. Biol. Chem. 268, 3873-3879, 1993.
Erickson et al., "Antibody-Maytansinoid Conjugates Are Activated in Targeted Cancer Cells by Lysosomal Degradation and Linker-Dependent Intracellular Processing," (2006) Cancer Res. 66(8): 4426-4433.
Farmer, J.D. et al., "Synthesis and DNA crosslinking ability of a dimeric anthramycin analog," Tetrahedron Letters (1988) 29(40):5105-5108, Abstract only.
Farmer, J.D. et al., "DNA binding properties of a new class of linked anthramycin analogs,", Chemical Abstracts, Abstract No. 239940r, vol. 114, No. 25, 25 899-903 (1991).
Feild, J.A., et al., "Cloning and Functional Characterization of a Sodium-Dependent Phosphate Transporter Expressed in Human Lung and Small Intestine," (1999) Biochem. Biophys. Res. Commun. 258 (3):578-582.
Fey, T. et al., "Silica-supported TEMPO catalyst: synthesis and application in the anelli oxidation of alcohols," J. Org. Chem. (2001) 66:8154-8159.
Fields, G. and Noble, R. (1990) "Solid phase peptide synthesis utilizing 9-fluoroenylmethoxycarbonyl amino acids", Int. J. Peptide Protein Res. 35:161-214.
Firsching, A. et al., "Antiproliferative and angiostatic activity of suramin analogues," Cancer Res. (1995) 55:4957-4961.
Flanagan et al., "The ephrins and Eph receptors in neural development," Annu. Rev. Neurosci. 21:309-345 (1998).
Flygare, "Antibody-drug conjugates for the treatment of cancer," Chem. Biol. & Drug Design (2013) 81(1):113-121.
Foloppe, M.P. et al., "DNA-binding properties of pyrrolo[2,1-c][1,4]benzodiazephine N10-C11 amidines," Eur. J. Med. Chem., 31, 407-410 (1996).
Fox et al., "cDNA cloning and tissue distribution of five human EPH-like receptor protein-tyrosine kinases," Oncogene 10 (5):897-905 (1995).
Fuchs S., et al., "Functional Characterization of Three Mutations of the Endothelin B Receptor Gene in Patients With Hirschsprung's Disease: Evidence for Selective Loss of Gi Coupling," Mol. Med. 7, 115-124, 2001.
Fujisaku et al., "Genomic Organization and Polymorphisms of the Human C3d/Epstein-Barr Virus Receptor," (1989) J. Biol. Chem. 264 (4):2118-2125.
Fujisawa Pharmaceutical Co. Ltd., "Benzodiazepine derivatives," SciFinder Scholar, 2-3 (2002).
Fujisawa Pharmaceutical Co., Ltd., Abstract No. 139983k, "Benzodiazepine derivatives", Chemical Abstracts, vol. 99, No. 17, 603 (1983).
Fujisawa Pharmaceutical Co., Ltd., Abstract No. 72145x, "Benzodiazepine derivatives", Chemical Abstracts, vol. 98, No. 9, 638 (1983).
Fukuyama, T. et al., "Total Synthesis of (+)-Porothramycin B," Tetrahedron Letters, vol. 34, 16, 2577-2580 (1993).
Gallmeier, E., "Targeted disruption of FANCC and FANCG in human cancer provides a preclinical model for specific therapeutic options," Gastroenterology (2006) 130(7):2145-2154.
Gary S.C., et al., "cDNA cloning chromosomal localization, and expression analysis of human BEHAB/brevican, a brain specific proteoglycan regulated during cortical development and in glioma," Gene 256, 139-147, 2000.
Gaugitsch, H.W., et al., "A novel transiently expressed, integral membrane protein linked to cell activation. Molecular cloning via the rapid degradation signal AUUUA.," (1992) J. Biol. Chem. 267 (16):11267-11273.
Gavezzotti, A., "Are crystal structures predictable?" Acc. Chem. Res. (1994) 27:309-314.

(56) References Cited

OTHER PUBLICATIONS

Geiser et al "Automation of solid-phase peptide synthesis" in Macromolecular Sequencing and Synthesis, Alan R. Liss, Inc., 1988, pp. 199-218.
Genbank accession No. 11038674 (2013).
Genbank accession No. 20 NM_006424 (2013).
Genbank accession No. AB040878 (2001).
Genbank accession No. AF116456 (1999).
Genbank accession No. AF179274 (2001).
Genbank accession No. AF361486 (2003).
Genbank accession No. AF369794 (2001).
Genbank accession No. AF397453 (2001).
Genbank accession No. AF455138 (2003).
Genbank accession No. AJ297436 (2008).
Genbank accession No. AK026467 (2006).
Genbank accession No. AK089756 (2010).
Genbank accession No. AK090423 (2006).
Genbank accession No. AK090475 (2006).
Genbank accession No. AL834187 (2008).
Genbank accession No. AX092328 (2001).
Genbank accession No. AY158090 (2003).
Genbank accession No. AY260763 (2003).
Genbank accession No. AY275463 (2003).
Genbank accession No. AY358085 (2003).
Genbank accession no. AY358628 (2003).
Genbank accession No. AY358907 (2003).
Genbank accession No. AY506558 (2004).
Genbank accession No. BC017023 (2006).
Genbank accession No. CAA76847.1 (2001).
Genbank accession No. CAF85723 (2004).
Genbank accession No. CQ782436 (2004).
Genbank accession No. M11730 (1995).
Genbank accession No. M18728 (1995).
Genbank accession No. M26004 (1993).
Genbank accession No. NM_000626 (2013).
Genbank accession No. NM_001178098.1 (2012).
Genbank accession No. NM_001203 (2013).
Genbank accession No. NM_003212 (2013).
Genbank accession No. NM_003486 (2013).
Genbank accession No. NM_004442 (2013).
Genbank accession No. NM_005823 (2013).
Genbank accession No. NM_012449 (2013).
Genbank accession No. NM_017636 (2013).
Genbank accession No. NM_030764 (2013).
Genbank accession No. Np 002111.1 (2013).
Genbank accession No. NP_001171569.1 (1992).
Genbank accession No. NP_001194 (2013).
Genbank accession No. NP_001707.1 (2013).
Genbank accession No. NP_001773.1 (2013).
Genbank accession No. NP_001774.10 (2013).
Genbank accession No. NP_002552.2 (2013).
Genbank accession No. NP_003203 (2013).
Genbank accession No. NP_005573.1 (2007).
Genbank accession No. NP_112571.1 (2007).
Geoghegan & Stroh, "Site-Directed Conjugation of Nonpeptide Groups to Peptides and Proteins via Periodate Oxidation of a 2-Amino Alcohol. Application to Modification at N-Terminal Serine," (1992) Bioconjugate Chem. 3:138-146.
Getz Et al., "A Comparison between the Sulfhydryl Reductants Tris(2-carboxyethyl)phosphine and Dithiothreitol for Use in Protein Biochemistry," (1999) Anal. Biochem. vol. 273:73-80.
Glynne-Jones et al., "TENB2, a proteogl ycan identified in prostate cancer that is associated with disease progression and androgen independence," (2001) Int J Cancer. Oct. 15; 94(2): 178-184.
Gordon et al., "Somatic hypermutation of the B cell receptor genes B29 (Igβ, CD79b) and mb1 (Igα, CD79a)," PNAS, Apr. 11, 2003, vol. 100, No. 7, 4126-4131.
Greene, T.W. and Wuts, P.G.M., Protective Groups in Organic Synthesis, John Wiley & Sons, 2nd ed., Ch 7, 315-345 (1991).

Greene, T.W. et al., Protective Groups in Organic Synthesis, John Wiley & Sons (1999) 3rd Edition, 23-200.
Greene, T.W. et al., Protective Groups in Organic Synthesis, John Wiley & Sons (1999) 3rd Edition, 503-549.
Gregson, S. et al., "Synthesis of a novel C2/C2'-exo unsaturated pyrrolobenzodiazepine cross-linking agent with remarkable DNA binding affinity and cytotoxicity," Chemical Communications, 797-798 (1999).
Gregson, S.J. et al., "Effect of C2/C3-endo unsaturation on the cytotoxicity and DNA-binding reactivity of pyrrolo-[2,1-c][1,4]-benzodiazepines," Bioorg. Med. Chem. Lett. (2000) 10(16):1849-1851.
Gregson, S.J. et al., "Linker length modulates DNA cross-linking reactivity and cytotoxic potency of C8/C8' ether-linked C2-exo-unsaturated pyrrolo[2,1-c][1,4]benzodiazepine (PBD) dimers," J. Med. Chem. (2004) 1161-1174.
Gregson, S.J. et al., "Synthesis of the first example of a C2-C3/C2'-C3'-endo unsaturated pyrrolo[2,1- c][1,4]benzodiazepine dimer," Biorg. Med. Chem. Lett. (2001) 11:2859-2862.
Gregson, S.J. et al., "Synthesis of the first examples of A-C8/C-C2 amide-linked pyrrolo[2,1-c][1,4]benzodiazepine dimers," Biorg. Med. Chem. Lett. (2003) 13:2277-2280.
Gregson, S.J. et al., "Design, Synthesis and Evaluation of a Novel Pyrrolobenzodiazepine DNA-Interactive Agent with Highly Efficient Cross-Linking Ability and Potent Cytotoxicity", J. Med. Chem., 44: 737-748 (2001).
Gregson, S.J. et al., "Effect of C2-exo Unsaturation on the Cytotoxicity and DNA-Binding Reactivity of Pyrrolo[2,1-c]1,4]benzodiazepines", Bioorganic & Medicinal Chemistry Letters, 10: 1845-1847 (2000).
Gu Z., et al., "Prostate stem cell antigen (PSCA) expression increases with high gleason score, advanced stage and bone metastasis in prostate cancer," Oncogene 19, 1288-1296, 2000.
Guichard, S.M., "Influence of P-glycoprotein expression on in vitro cytotoxicity and in vivo antitumour activity of the novel pyrrolobenzodiazepine dimer SJG-136," Eur. J. Cancer (2005) 41(12):1811-1818.
Guiotto, A. et al., "Synthesis of novel C7-aryl substituted pyrrolo[2,1-c][1,4]benzodiazepines (PBDs) via Pro-N10-troc protection and suzuki coupling," Bioorganic & Medicinal Chemistry Letters, 8, No. 21, 3017-3018 (1998).
Guselnikov et al., "A family of highly diverse human and mouse genes structurally links leukocyte FcR, gp42 and PECAM-1," Immunogenetics 54 (2):87-95 (2002).
Ha et al., "molecular cloning and expression pattern of a human gene homologous to the murine mb-1 gene," (1992) J. Immunol. 148(5):1526-1531.
Hadjivassileva, T., "Antibacterial activity of pyrrolobenzodiazepine dimers, a novel group of DNA-binding compounds," Abstracts of the Interscience Conference on Antimicrobial Agents and Chemotherapy (Oct.-Nov. 2004) 44:202.
Hadjivassileva, T., "Interactions of pyrrolobenzodiazepine dimers and duplex DNA from methicillin-resistant *Staphylococcus aureus*," Int. J. Antimicrob. Agents (2007) 29(6):672-678.
Hadjivassileva, T., "Pyrrolobenzodiazepine dimers: novel sequence-selective, DNA-interactive, cross-linking agents with activity against Gram-positive bacteria," J. Antimicrob. Chemo. (2005) 56(3):513-518.
Haendler B., et al., "Molecular Cloning of Human Endothelin (ET) Receptors ETA and ETB," J. Cardiovasc. Pharmacal. 20, s1-S4, 1992.
Haisma et al., "Comparison of two antracycline-based prodrugs for activation by a monoclonal antibody-β-glucuronidase conjugate in the specific treatment of cancer." Cell biophysics, Humana Press Inc. 1994, 24/25: 185-192.
Hamaguchi, A., "DNA cross-linking and in vivo antitumour activity of the extended pyrrolo[2,1- c][1,4]benzodiazepine dimer SG2057 (DRG-16)," EJC Supplements (Nov. 2006) 4(12):96.
Hamann P. "Monoclonal antibody-drug conjugates," (2005) Expert Opin. Ther. Patents 15(9):1087-1103.
Hamblett et al., "Effects of Drug Loading on the Antitumor Activity of a Monoclonal Antibody Drug Conjugate," (2004) Clin. Cancer Res. 10:7063-7070.

(56) References Cited

OTHER PUBLICATIONS

Handbook of Food Additives, 2nd Ed. (eds. M. Ash and I. Ash), Synapse Information Resources, Inc., Endicott, New York, USA (2001).
Handbook of Pharmaceutical Excipients, 2nd edition, 1994, Edited by Ainley Wade and Paul J. Weller.
Hara et al., "DC 102, a new glycosidic pyrrolo(1,4)benzodiazepine antibiotic produced by streptomyces sp.", J. Antibiotics, 41, 702-704 (1988).
Hartley JA: "The development of pyrrolobenzodiazepines as antitumour agents", Expert Opinion on Investigational Drugs, Ashley Publications Ltd., vol. 28, No. 6, Jan. 1, 2011, pp. 733-744.
Hartley, J.A. et al., "Abstract 2856: pyrrolobenzodiazepine (PBD) dimers—potent next generation warheads in antibody drug conjugates (ADCs) targeted at both solid and haematological tumors," Cancer Res. (2013) 78(8)Supp 1:2856.
Hartley, J.A. et al., "SG2285, a novel C2-aryl-substituted pyrrolobenzodiazepine dimer prodrug that cross-links DNA and exerts highly potent antitumor activity," Cancer Res., Sep. 2010, 70(17):6849-6858.
Hartley, J.A. et al., "SJG-136 (NSC 694501), a novel rationally designed DNA minor groove interstrand cross-linking agent with potent and broad spectrum antitumor activity. Part 1: Cellular pharmacology, in vitro and initial in vivo antitumor activity," Cancer Res. (2004) 64:6693-6699.
Hartley, J.A., "In vitro antitumor activity and in vivo DNA interstrand crosslinking by the novel pyrrolobenzodiazepine dimer SJG-136 (NSC 694501)," Proceedings of the American Association for Cancer Research Annual Meeting (Mar. 2002) 43:489.
Hartley, J.A., "SJG-136 (NSC-D694501)—a novel DNA sequence specific minor groove crosslinking agent with significant antitumor activity," Proceedings of the American Association for Cancer Research Annual Meeting (Mar. 2000) 41:425.
Hashimoto et al., "Chromosomal localization, genomic structure, and allelic polymorphism of the human CD79a (Ig-alpha/mb-1) gene," (1994) Immunogenetics 40(4 ):287-295.
Hay et al., "A 2-nitroimidazole carbamate prodrug of 5-amin0-1-(chloromethyl)-3-[(5,6,7-trimethoxyindol-2-yl)carbonyl]-1,2-dihydr0-3h-benz[e]indole (amino-seco-cbi-tmi) for use with adept and gdept," (1999) Bioorg. Med. Chem. Lett. 9:2237-2242.
Herdwijn et al., "Synthesis of trans(+ )6-phenoxyacetamido-1-methylene- 3,3-dicarboxymethyl-1-carbapenam," Canadian Journal of Chemistry. 1982, 60, 2903-2907.
Hermanson, G.T., "Heterobifunctional Cross-linkers," (1996) Bioconjugate Techniques; Academic Press: New York, p. 228-286.
Hochhauser, D., "Phase I study of sequence-selective minor groove DNA binding agent SJG-136 in patients with advanced solid tumors," Clin. Cancer Res., Mar. 2009, 15(6):2140-2147.
Hochlowski, J. et al., "Abbeymycin, a new anthramycin-type antibiotic produced by a streptomycete," J. Antibiotics, 40, 145-148 (1987).
Hofstra R.M.W., et al., "A homozygous mUtation in the endothelin-3 gene associated with a combined Waardenburg type 2 and Hirschsprung phenotype (Shah-Waardenburg syndrome)" Nat. Genet. 12, 445-447, 1996.
Hofstra R.M.W., et al., "Mutations in Hirschsprung Disease: When Does a Mutation Contribute to the Phenotype," Eur. J. Hum. Genet. 5, 180-185, 1997.
Horie et al., "Identification and Characterization of TMEFF2, a Novel Surviv Factor for Hippocampal and Mesencephalic Neurons," (2000) Genomics 67: 146-152.
Howard, P.W. et al., "Design, synthesis and biological evaluation of ZC-423, a novel C2-aryl substituted pyrrolobenzodiazepine (PBD) dimer," Clinical Cancer Research (2005) 11(23):9015S-9016S (A205).
Howard, P.W. et al., "Synthesis of a novel C2/C2'-aryl-substituted pyrrolo[2,1-c][1,4]benzodiazepine dimer prodrug with improved water solubility and reduced DNA reaction rate," Bioorg. Med. Chem., Sep. 2009, In Press, 4 pages now: Sep. 2009, 19:6463-6466.
Howard, P.W. et al., "The design, synthesis and biological evaluation of a set of C2-aryl substituted pyrrolo[2,1- c][1,4]benzodiazepine dimers," EJC Supplements (2006) 4(12):95—Poster Abstract 301.
Howard, P.W., "Design, synthesis and biological evaluation of novel C2-aryl-substituted pyrrolo[2,1- c][1,4]benzodiazepine monomers," Proceedings of the American Association for Cancer Research Annual Meeting (Apr. 2006) 47:132.
Hubert, R.S., et al., "STEAP: A prostate-specific cell-surface antigen highly expressed in human prostate tumors," (1999) Proc. Natl. Acad. Sci. U.S.A. 96 (25):14523-14528.
Hurley, L. and Needham-Vandevanter, D., "Covalent Binding of Antitumor Antibiotics in the Minor Groove of DNA. Mechanism of Action of CC-1065 and the yrrolo(1,4)benzodiazepines," Acc. Chem. Res., 19, 230-237 (1986).
Ide et al., "Cloning of human bone morphogenetic protein type IB receptor (BMPRIB) and its expression in prostate cancer in comparison with other BMPRs," Oncogene (1997) 14, 1377-1382.
Iida, H. et al. "Design and synthesis of pyrrolo[2,1-c][1,4]benzodiazepine (PBD)-polyaminoalkyl conjugates by the use of SNA4 reaction 2-nitro-5-fluorobenzoate precursor as key reaction," Heterocycles (2004) 62:693-711.
International Search Report and Written Opinion for Application No. PCT/EP2012/070233 dated Jan. 28, 2013 (8 pages).
International Search Report and Written Opinion for Application No. PCT/EP2013/071346 dated Feb. 5, 2014 (11 pages).
International Search Report and Written Opinion for Application No. PCT/EP2014/054958 dated Jul. 2, 2014 (13 pages).
International Search Report and Written Opinion for Application No. PCT/US2011/032664 dated Aug. 19, 2011 (13 pages).
International Search Report and Written Opinion for Application No. PCT/GB2015/052629 dated Nov. 2, 2015 (12 pages).
International Search Report and Written Opinion for Application No. PCT/US2011/032668 dated May 26, 2011 (12 pages).
International Search Report and Written Opinion for Application No. PCT/US2015/050634 dated Jan. 29, 2016 (14 pages).
Itoh et al., "Sibanomicin, a new pyrrolo(1,4)benzodiazepine antitumor antibiotic produced by a micromonospora sp." J. Antibiotics, 41, 1281-1284 (1988).
Janjigian, Y.Y., "A phase I trial of SJG-136 (NSC#694501) in advanced solid tumors," Cancer Chemotherapy and Pharmacology , Aug. 2009, 65(5):833-838.
Jeffrey et al., "Development and properties of beta-glucuronide linkers for monoclonal antibody-drug conjugates." Bioconjugate Chemistry, 5, 2006, 17, 831-840. (Abstract).
Jeffrey, S.C. et al., "Development of Pyrrolobenzodiazepine-Based Antibody-Drug Conjugates for Cancer," AACR Annual Meeting 2013, Abstract No. 4321.
Jeffrey, S.C., "Design, synthesis, and in vitro evaluation of dipeptide-based antibody minor groove binder conjugates," J. Med. Chem. (2005) 48(5):1344-1358.
Jespers, L. S., "Guiding the Selection of Human Antibodies from Phage Display Repertoires to a Single Epitope of an Antigen" Nature Biotech., 12, 899-903 (1994).
Jia, L., "Interspecies differences in pharmacokinetics and time-dissociated toxicokinetics of SJG-136," Proceedings of the American Association for Cancer Research Annual Meeting (Mar. 2004) 45:487.
Jia, L., "Use of the comet assay as a surrogate biomarker for the in vivo measurement of DNA damage to lymphocytes," Proceedings of the American Association for Cancer Research Annual Meeting (Mar. 2004) 45:452-453.
Johnson & Goldin, "The clinical impact of screening and other experimental tumor studies." Cancer Treat Rev. Mar. 1975; 2(1):1-31.
Jordan, V.C., "Tamoxifen: a most unlikely pioneering medicine," Nature Reviews: Drug Discovery (2003) 2:205-213.
Junutula et al., "Rapid identification of reactive cysteine residues for site-specific labeling of antibody-Fabs," (2008) Jour of Immun. Methods 332:41-52.
Junutula, et al., "Site-specific conjugation of a cytotoxic drug to an antibody improves the therapeutic index," 2008b Nature Biotech., 26(8):925-932.

(56) References Cited

OTHER PUBLICATIONS

Kamal et al., "Synthesis and DNA-binding affinity of A-C8/C-C2 alkoxyamido-linked pyrrolo[2,1- c][1,4]benzodiazepine dimers" Biorg. Med. Chem. Lett. (2003) 13(22): 3955-3958.

Kamal, A. et al., "Design, synthesis and evaluation of new noncross-linking pyrrolobenzodiazepine dimers with efficient DNA binding ability and potent antitumor activity," J. Med. Chem. (2002) 45:4679-4688.

Kamal, A., "Development of pyrrolo[2,1-c][1,4]benzodiazepine beta-galactoside prodrugs for selective therapy of cancer by ADEPT and PMT," Chemmedchem (2008) 3:794-802.

Kamal, A., "Remarkable DNA binding affinity and potential anticancer activity of pyrrolo[2,1- c][1,4]benzodiazepine-naphthalamide conjugates linked through piperazine side-armed alkane spacers," Bioorg. Med. Chem. (2008) 16(15):7218-7224.

Kamal, A., "Remarkable enhancement in the DNA-binding ability of C2-fluoro substituted pyrrolo[2,1- c][1,4]benzodiazepines and their anticancer potential," Bioorg. Med. Chem., Jan. 2009, 17(4):1557-1572.

Kamal, A., "Synthesis of fluorinated analogues of SJG-136 and their DNA-binding potential," Bioorg. Med. Chem. Lett (2004) 14(22):5699-5702.

Kamal, A., et al., "An Efficient Synthesis of Pyrrolo[2,1-c][1,4] Benzodiazepine Antibiotics via Reductive Cyclization," Bioorg. Med. Chem. Ltrs, 7, No. 14, 1825-1828 (1997).

Kamal, A., et al., "Synthesis of Pyrrolo [2,1-c][1,4]-Benzodiazepene Antibiotics: Oxidation of Cyclic Secondary Amine with TPAP", Tetrahedron, v. 53, No. 9, 3223-3230 (1997).

Kamal, et al., "Synthesis of pyrrolo[2,1-c][1,4]benzodiazepines via reductive cyclization of w-azido carbonyl compounds by TMSI: an efficient preparation of antibiotic DC-81 and its dimers," Biorg. Med. Chem. Lett. (2000) 10:2311-2313.

Kamal et a., "Pyrrolo[2,1-c][1,4]benzodiazepine-β-glucuronide prodrugs with a potential for selective therapy of solid tumors by PMT and ADEPT strategies" Bioorganic & Medicinal Chemistry Letters 2008, 18:3769-3773.

Kaneko, T. et al., "Bicyclic and tricyclic analogues of anthramycin," J. Med. Chem. (1985) 28:388-392.

Kang, G.-D. et al., "Synthesis of a novel C2-aryl substituted 1,2-unsaturated pyrrolobenzodiazepine," Chem. Commun. (2003) 1680-1689.

Kasahara et al., "Nucleotide sequence of a chimpanzee DOB eDNA clone," (1989) Immunogenetics 30(1):66-68.

King et al., "Facile synthesis of maleimide bifunctional Jinkers," (2002) Tetrahedron Letters 43:1987-1990.

Kingsbury et al., ""Novel Peptide Delivery System Involving Peptidase Activated Prodrugs as Antimicrobial Agents. Synthesis and Biological Activity of Peptidyl Derivatives of 5 Fluorouracil,"" (1984) J. Med. Chern. 27:1447-1451.

Kohler et al., "Continuous cultures of fused cells secreting antibody of predefined specificity," (1975) Nature 256:495-497.

Kohn, K., "Anthramycin," Antibiotics III, Springer-Verlag, NY, 3-11 (1975).

Kojima et al., "Molecular Cloning and Expression of Megakaryocyte Potentiating Factor eDNA," The Journal of Biological Chemistry, vol. 270, No. 37, Issue of Sep. 15, pp. 21984-21990, 1995.

Konishi, M. et al., "Chicamycin, a new antitumor antibiotic II. Structure determination of chicamycins A and B," J. Antibiotics, 37, 200-206 (1984).

Kovtun et al., "Antibody-Drug Conjugates Designed to Eradicate Tumors with Homogeneous and Heterogeneous Expression of the Target Antigen," Cancer Res. 66(6):3214-3121.

Kuhns J.J., et al., "Poor Binding of a HER-2/neu Epitope (GP2) to HLA-A2.1 Is due to a Lack of Interactions with the Center of the Peptide," J. Biol. Chem. 274, 36422-36427, 1999.

Kunimoto et al., "Mazethramycin, a new member of anthramycin group antibiotics," J. Antibiotics, 33, 665-667 (1980).

Kurebayashi et al., "Isolation and characterization of a new human breast cancer cell line, KPL-4, expressing the Erb B family receptors and interleukin.6," (1999) Brit. Jour. Cancer 79(5-6):707-717.

Lambert, "Drug-conjugated monoclonal antibodies for the treatment of cancer," (2005) Current Opin. In Pharmacal. 5:543-549.

Langley, D.R. and Thurston, D.E., "A versatile and efficient synthesis of carbinolamine-containing pyrrolo[1,4]benzodiazepines via the cyclization of N-92-aminobenzoyl)pyrrolidine-2-carboxaldehyde diethyl thioacetals: total synthesis of prothracarcin," J. Org. Chem., 52, 91-97 (1987).

Langlois, N. et al., "Synthesis and cytotoxicity on sensitive and doxorubicin-resistant cell lines of new pyrrolo[2,1-c][1,4]benzodiazepines related to anthramycin," J. Med. Chem. (2001) 44:3754-3757.

Larhammar et al., "Sequence of Gene and eDNA Encoding Murine Major Histocompatibility Complex Class II Gene AP2*," (1985) J. Biol. Chem. 260(26):14111-14119.

Launay et al., "TRPM4 Is a Ca2+-Activated Nonselective Cation Channel Mediating Cell Membrane Depolarization," Cell 109 (3):397-407 (2002).

Law et al., "Lymphocyte Activation Antigen CD70 Expressed by Renal Cell Carcinoma Is a Potential Therapeutic Target for Anti-CD70 Antibody-Drug Conjugates," (2006) Cancer Res. 66(4):2328-2337.

Lazar et al., "A molecular immunology approach to antibody humanization and functional optimization" Molecular Immunology, 2007, 44(8), 1986-1998.

Le et al., "Primary structure and expression of a naturally truncated human P2X ATP receptor subunit from brain and immune system," (1997) FEBS Lett. 418(1-2):195-199.

Leabman; et al., "Effects of altered FcγR binding on antibody pharmacokinetics in cynomolgus monkeys." MAbs. Nov.-Dec. 2013; 5(6):896-903.

Leber, J.D. et al., "A revised structure for sibiromycin," J. Am. Chem. Soc., 110, 2992-2993 (1988).

Leimgruber, W. et al., "Isolation and characterization of anthramycin, a new antitumor antibiotic," J. Am. Chem. Soc., 87, 5791-5793 (1965).

Leimgruber, W. et al., "The structure of anthramycin," J. Am. Chem. Soc., 87, 5793-5795 (1965).

Leimgruber, W. et al., "Total synthesis of anthramycin," J. Am. Chem. Soc., 90, 5641-5643 (1968).

Leonard et al., "Phase I/II trial of epratuzumab (humanized anti-CD22 antibody) in indolent non-Hodgkin's lymphoma," J. Clin. Oncology (2003) 21(16):3051-3059.

Leonard et al., "Preclinical and clinical evaluation of epratuzumab (anti-CD22 IgG) in B-cell malignancies," Oncogene (2007) 26:3704-3713.

Leung et al., "Construction and characterization of a humanized, internalizing, B-cell (CD22)-specific, leukemia/lymphoma antibody, LL2," Mol. Immunol. (1995) 32(17-18):1413-1427.

Levenson et al., "MCF-7: The First Hormone-responsive Breast Cancer Cell Line," (1997) Cancer Res. 57(15):3071-3078.

Lewis Phillips et al., "Targeting HER2-Positive Breast Cancer with Trastuzumab-DM1, an Antibody—Cytotoxic Drug Conjugate," Cancer Res, 2008, 68: (22).

Liang et al., "The Gene for a Novel Transmembrane Protein Containing Epidermal Growth Factor and Follistatin Domains Is Frequently Hypermethylated in Human Tumor Cells," (2000) Cancer Res. 60:4907-4912.

Linden et al., "Dose-fractionated radioimmunotherapy in non-Hodgkin's lymphoma using DOTA-conjugated, 90Y-radiolabeled, humanized anti-CD22 monoclonal antibody, epratuzumab," J. Clin. Cancer Res. (2005) 11:5215-5222.

Lonberg, "Fully Human antibodies from transgenic mouse and phage display platforms" Curr. Opinion, 20(4), 450-459 (2008).

Lown et al., "Molecular Mechanism of Binding of Pyrrolo(1,4)benzodiazepine antitumour agents to deoxyribonucleic acid—anthramycin and tomaymycin," Biochem. Pharmacol. (1979), 28 (13), 2017-2026.

Manfre et al., "Syntheses of Proline Analogues as Potential Mechanism-Based Inhibitors of Proline Dehydrogenase: 4-Methylene-L-, (E)- and (Z)-4-(Fluoromethylene)-L-, cis- and trans-5-Ethynyl-(±)-, and cis- and trans-5-Vinyl-L-proline," J. Org. Chem. 1992, 57, 2060-2065.

(56) References Cited

OTHER PUBLICATIONS

Marin, D., "Voltammetric studies of the interaction of pyrrolo[2,1-c][1,4]benzodiazepine (PBD) monomers and dimers with DNA," J. Electroanal. Chem. (2006) 593(1-2):241-246.

Marks et al., "By-passing Immunization, Human Antibodies from V-gene Libraries Displayed on Phage," (1991) J. Mol. Biol., 222:581-597.

Martin, C. et al., "Sequence-selective interaction of the minor-groove interstrand cross-linking agent SJG-136 with naked and cellular DNA: footprinting and enzyme inhibition studies," Biochem. (2005) 44(11):4135-4147.

Mastroberardino et al., "Amino-acid transport by heterodimers of 4F2hc/CD98 and members of a permease family," Nature 395 (6699):288-291 (1998).

Matsumoto, K. et al., "Synthesis of polyaminoalkyl substituted conjugates of pyrrolo[2,1-c][1,4]benzodiazepine (PBD)-polyaminoalkyl involving SNA4 reaction of 2-nitro-5-fluorobenzoate precursors," Heterocycles (2000) 52(3):1015-1020.

McDonagh, "Engineered antibody-drug conjugates with defined sites and stoichiometries of drug attachment," (2006) Protein Eng. Design & Sel. 19(7): 299-307.

Mendoza et al., "Inhibition of Ligand-mediated HER2 Activation in Androgen-independent Prostate Cancer," (2002) Cancer Res. 62:5485-5488.

Miller et al., "Design, Construction, and in Vitro Analyses of Multivalent Antibodies," (2003) Jour. of Immunology 170:4854-4861.

Miller et al., "IRTAs: a new family of immunoglobulinlike receptors differentially expressed in B cells," Blood 99 (8):2662-2669 (2002).

Miura et al., "Molecular cloning of a human RP105 homologue and chromosomal localization of the mouse and human RP105 genes (Ly64 and LY64)." Genomics. Dec. 15, 1996; 38(3):299-304.

Miura et al., "RP105 Is Associated With MD-1 and Transmits an Activation Signal in Human B Cells," (1998) Blood 92:2815-2822.

Moore M., et al., "Molecular cloning of the cDNA encoding the Epstein-Barr virus/C3d receptor (complement receptor type 2) of human B lymphocytes," Proc. Natl. Acad. Sci. U.S.A. 84, 9194-9198, 1987.

Mori, M. et al., "Total syntheses of prothracarcin and tomaymycin by use of palladium catalyzed carbonylation," Tetrahedron (1986) 42(14):3793-3806.

Morrison et al., "Chimeric human antibody molecules: Mouse antigen-binding domains with human constant region domains," (1984) Proc. Natl. Acad. Sci. USA, 81:6851-6855.

Mountzouris, J.A. et al., "Comparison of a DSB-120 DNA interstrand cross-linked adduct with the corresponding bis-Tomamycin adduct," J. Med. Chem. (1994) 37:3132-3140.

Muller et al., "Cloning and sequencing of the cDNA encoding the human homologue of the murine immunoglobulin-associated protein B29," (1992) Eur. J. Immunol. 22 (6): 1621-1625.

Mungall A.J., et al., "The DNA sequence and analysis of human chromosome 6," Nature 425, 805-811, 2003.

Nadler et al., "B4, a human B lymphocyte-associated antigen expressed on normal, mitogen-activated, and malignant B lymphocytes," Journal of Immunology, 1983, 131(1):244-250.

Nagasaka, T. and Koseki, Y, "Stereoselective Synthesis of Tilivalline," Journal of Organic Chemistry, vol. 63, No. 20, 6797-6801 (1998).

Nagasaka, T. et al., "Stereoselective Synthesis of Tilivalline," Tetrahedron Letters, 30:14, 1871-1872 (1989).

Nagase T., et al., "Prediction of the Coding Sequences of Unidentified Human Genes. XVII. The Complete Sequences of 100 New cDNA Clones from Brain Which Code for Large Proteins in vitro," (2000) DNA Res. 7 (2):143-150.

Nakamuta M., et al., "Cloning and sequence analysis of a cDNA encoding human non-selective type of endothelin receptor," Biochem. Biophys. Res. Commun. 177, 34-39, 1991.

Nakayama et al., "Altered Gene Expression upon BCR Cross-Linking in Burkitt's Lymphoma B Cell Line," (2000) Biochem. Biophys. Res. Commun. 277(1):124-127.

Narayanaswamy, M., "A novel HPLC/MS assay to measure DNA interstrand cross-linking efficacy in oligonucleotides of varying sequence," EJC Supplements (Nov. 2006) 4(12):92-93.

Narayanaswamy, M., "An assay combining high-performance liquid chromatography and mass spectrometry to measure DNA interstrand cross-linking efficiency in oligonucleotides of varying sequences," Anal. Biochem. (2008) 374(1):173-181.

Narayanaswamy, M., "Use of HPLC-MS to characterize novel mono and intrastrand cross-linked DNA adducts formed by the sequence-selective DNA-interactive agent SJG-136," Proceedings of the American Association for Cancer Research Annual Meeting (Apr. 2007) 48:760-761.

Narukawa, Y., "General and efficient synthesis of 2-alkylcarbapenems synthesis of dethia carba analogs of clinically useful carbapenems via palladium-catalyzed cross-coupling reaction," Tetrahedron (1997) 53:539-556.

Naruse et al., "The HLA-DOB gene displays limited polymorphism with only one amino acid substitution," (2002) Tissue Antigens 59:512-519.

Neuberger and Williams, "The intron requirement for immunoglobulin gene expression is dependent upon the promoter," (1988) Nucleic Acids Res. 16:6713-6724.

Nicolaou et al., "Calicheamicin θ: A Rationally Designed Molecule with Extremely Potent and Selective DNA Cleaving Properties and Apoptosis Inducing Activity," Angew Chem. Intl. Ed. Engl. (1994) 33:183-186.

Nilius et al., "Voltage Dependence of the Ca2+ -activated Cation Channel TRPM4," The Journal of Biological Chemistry, vol. 278, No. 33, Issue of Aug. 15, pp. 30813-30820, 2003.

O'Neil, Chemical Abstract No. 171573p, "The synthesis of Functionalized Pyrrolo-[2,1-c][1,4]-Benzodiazepines", Chemical Abstracts, vol. 126, No. 13, 618 (1997).

O'Neil, I.A., et al., "The Synthesis of Functionalized Pyrrolo-[2,1-c][1,4]-Benzodiazepines," Synlett, 75-78 (1997).

O'Neil, I.A. et al., "DPPE: A Convenient Replacement for Triphenylphosphine in the Staudinger and Mitsunobu Reactions", Tetrahedron Letters, vol. 39, No. 42, 7787-7790 (1998).

Ogawa Y., et al., "Molecular Cloning of a Non-Isopeptide-Selective Human Endothelin Receptor," Biochem. Biophys. Res. Commun. 178, 248-255, 1991.

Okamoto Y., et al. "Palmitoylation of Human Endothelin B," Biol. Chem. 272, 21589-21596, 1997.

Parrish-Novak J., et al., "Interleukins 19, 20, and 24 Signal through Two Distinct Receptor Complexes," J. Biol. Chem. 277, 47517-47523, 2002.

Paul, Fundamental Immunology, 3rd Edition, pp. 292-295.

Payne, G. "Progress in immunoconjugate cancer therapeutics," (2003) Cancer Cell 3:207-212.

PCT/US2012/059864 International Search Report and Written Opinion dated Dec. 21, 2012 (7 pages).

Pepper, C., "Fludarabine-mediated suppression of the excision repair enzyme ERCC1 contributes to the cytotoxic synergy with the DNA minor groove crosslinking agent SJG-136 (NSC 694501) in chronic lymphocytic leukaemia cells," Br. J. Cancer (2007) 97(2):253-259.

Pepper, C.J. et al., "The novel sequence-specific DNA cross-linking agent SJG-136 (NSC 694501) has potent and selective in vitro cytotoxicity in human B-cell chronic lymphocytic leukemia cells with evidence of a p53-independent mechanism of cell kill," Cancer Res. (2004) 64:6750-6755.

Phillips et al., "Targeting HER2-Positive Breast Cancer with Trastuzumab-DM1, an Antibody-Cytotoxic Drug Conjugate," (2008) Cancer Res. 68(22):9280-9290.

Pingault V., et al., "SOX10 mutations in chronic intestinal pseudo-obstruction suggest a complex physiopathological mechanism," (2002) Hum. Genet. 111, 198-206.

Pletnev S., et al., "Characterization of the Recombinant Extracellular Domains of Human Interleukin-20 Receptors and Their Complexe with Interleukin-19 and Interleukin-20," (2003) Biochemistry 42:12617-12624.

Porkaa et al., "Cloning and Characterization of a Novel Six-Transmembrane Protein STEAP2, Expressed in Normal and Malignant Prostate," Lab. Invest. 82 (11):1573-1582 (2002).

(56) References Cited

OTHER PUBLICATIONS

Prasad et al.,"Human LAT1, a Subunit of System L Amino Acid Transporter: Molecular Cloning and Transport Function," Biochem. Biophys. Res. Commun. 255 (2), 283-288 (1999).
Preud'Homme et al., "Structure and expression of the mb-1 transcript in human lymphoid cells," (1992) Clin. Exp. Immunol. 90(1):141-146.
Puffenberger E.G., et al., "A Missense Mutation of the Endothelin-B Receptor Gene in Multigenic Hirschsprung's Disease," Cell 79, 1257-1266, 1994.
Purser, et al., "Fluorine in Medicinal Chemistry." Chem. Soc. Rev., 2008, 37, 320-330.
Puzanov, I., "Phase I and pharmacokinetic trial of SJG-136 administered on a daily x5 schedule," EJC Supplements (Nov. 2006) 4(12):93.
Quintas-Cardama, A., "Sequencing of subcloned PCR products facilitates earlier detetction of BCR-ABL1 and other mutants compared to direct sequencing of the ABL1 kinase domain," Leukemia (2008) 22(4):877-878.
Rahman et al. "Antistaphylococcal activity of DNA-interactive pyrrolobenzodiazepine (PBD) dimers and PBD-biaryl conjugates." J Antimicrob Chemother. Jul. 2012; 67(7):1683-96.
Rahman, K.M., "Effect of microwave irradiation on covalent ligand-DNA interactions," Chem. Commun. (Cambridge, UK), Apr. 2009, 20:2875-2877.
Rahman, K.M., "Rules of DNA adduct formation for pyrrolobenzodiazepine (PBD) dimers," Proceedings of the American Association for Cancer Research Annual Meeting (Apr. 2010) 51:851.
Rahman, K.M., "The pyrrolobenzodiazepine dimer SJG-136 forms sequence-dependent intrastrand DNA cross-lins and monoalkylated adducts in addition to interstrand cross-links," J. Am. Chem. Soc., Sep. 2009, 131(38):13756-13766.
Rao et al., "Influence of diet on mammary cancer in transgenic mice bearing an oncogene expressed in mammary tissue," (1997) Breast Cancer Res. and Treatment 45:149-158.
Reid, J.M., "LC-MS/MS assay and rat pharmacokinetics and metabolism of the dimeric pyrrolobenzodiazepine SJG-136," Proceedings of the American Association for Cancer Research Annual Meeting (Mar. 2004) 45:1248.
Reiter R.E., et al., "Prostate stem cell antigen: A cell surface marker overexpressed in prostate cancer," Proc. Natl. Acad. Sci. U.S.A. 95, 1735-1740, 1998.
Remmers et al., "Conformations of complexes between pyrrolo[1,4]benzodiazepines and DNA segments," J Med Chem. Dec. 1986;29(12):2492-2503.
Rich, I.N., "Validation and development of a predictive paradigm for hemotoxicology using a multifunctional bioluminescence colony-forming proliferation assay," Toxicological Sci. (2005) 87(2):427-441.
Rodrigues et al., "Synthesis and beta-lactamase-mediated activation of a cephalosporin-taxol prodrug," (1995) Chemistry Biology 2:223-227.
Roguska et al., "A comparison of two murine monoclonal antibodies humanized by CDR-grafting and variable domain resurfacing," Protein Eng, 1996, 9(10):895-904.
Roguska et al., "Humanization of murine monoclonal antibodies through variable domain resurfacing," PNAS, 1994, 91(3):969-973.
Ross et al., "Prostate Stem Cell Antigen as Therapy Target: Tissue Expression and in Vivo Efficacy of an Immunoconjugate," (2002) Cancer Res. 62:2546-2553.
Rudikoff et al., Single amino acid substitution altering antigen-binding specificity. Proc Natl Acad Sci U S A. Mar. 1982; 79(6):1979-83.
Sagnou, M.J. et al., "Design and Synthesis of Novel Pyrrolobenzodiazepine (PDB) Prodrugs for ADEPT and GDEPT," Bioorganic & Medicinal Chemistry Letters, 10, 2083-2086 (2000).
Sakaguchi et al., "8 lymphocyte lineage-restricted expression of mb-1, a gene with CD3-like structural properties," (1988) EMBO J. 7(11):3457-3464.

Sakamoto A, Yanagisawa M., et al., "Cloning and Functional Expression of Human cDNA for the ETB Endothelin Receptor," Biochem. Biophys. Res. Commun. 178, 656-663, 1991.
Sanderson et al., "In vivo Drug-Linker Stability of an Anti-CD30 Dipeptide-Linked Auristatin Immunoconjugate," (2005) Clin. Cancer Res. 11:843-852.
Scholler et al., "Soluble member(s) of the mesothelin/ megakaryocyte potentiating factor family are detectable in sera from patients with ovarian carcinoma," Proc. Natl. Acad. Sci. USA vol. 96, pp. 11531-11536, Sep. 1999.
Schroder and Lubke, The Peptides, vol. 1. pp. 76-136 (1965) Academic Press.
Schweikart, K., "In vitro myelosuppression of SJG-136, a pyrrolobenzodiazepine dimer: comparison to bizelesin," Proceedings of the American Association for Cancer Research Annual Meeting (Mar. 2004) 45:486.
Segawa et al., "Growth-related Renal Type II Na/Pi Cotransporter," The Journal of Biolocjcal Chemistry, vol. 277. No. 22, Issue of May 31, pp. 19665-19672, 2002.
Semba K., et al., "A v-erbB-related protooncogene, c-erbB-2, is distinct from the c-erbB-1 /epidermal growth factor-receptor gene and is amplified in a human salivary gland adenocarcinoma," 15 Proc. Natl. Acad. Sci. U.S.A 82, 6497-6501, 1985.
Servenius et al., "Class II Genes of the Human Major Histocompatibility Complex, the DOBeta Gene Is a Divergent Member of the Class II P Gene Family," (1987) J. Biol. Chem. 262:8759-8766.
Shamis et al., "Bioactivation of Self-Immolative Dendritic Prodrugs by Catalytic Antibody 38C2," (2004) J . Am. Chem. Soc. 126:1726-1731.
Sharkey et al., "Epratuzumab-SN-38: a new antibody-drug conjugate for the therapy of hematologic malignancies," Mol. Cancer Ther. (2012) 11(1):224-234.
Sheikh F., et al., "Cutting Edge: IL-26 Signals through a Novel Receptor Complex Composed of IL-20 Receptor 1 and IL-10 Receptor 21," (2004) J.Immunol, 172, 2006-2010.
Shen et al., "Conjugation site modulates the in vivo stability and therapeutic activity of antibody-drug conjugates," (2012) Nature Biotech., 30(2):184-191.
Shimizu, K et al., "Prothracarcin, a Novel Antitumor Antibiotic," J. Antibiotics, 35, 972-978 (1982).
Sinha S.K., et al., "Characterization of the EBV /C3d Receptor on the Human Jurkat T Cell Line: Evidence for a Novel Transcript," (1993) J. Immunol. 150, 5311-5320.
Smellie, M. et al., "Cellular pharmacology of novel C8-linked anthramycin-based sequence-selective DNA minor groove cross-linking agents," Br. J. Cancer (1994) 70:48-53.
Smellie, M. et al., "Sequence selective recognition of duplex DNA through covalent interstrand cross-linking," Biochem. (2003) 42:8232-8239.
Smith, P. K. et al., "Measurement of protein using bicinchoninic acid." Anal Biochem. Oct. 1985; 150(1):76-85.
Souillac, P. et al., "Characterization of delivery systems, differential scanning calorimetry," Encyclopedia of Controlled Drug Delivery (1999) 212-227 (pp. 217-218).
Storm et al., "Effect of Small Changes in Orientation on Reaction Rate," (1972) J. Amer. Chem. Soc. 94:5815-5825.
Strausberg et al., "Generation and initial analysis of more than 15,000 full-length human and mouse Edna sequences," (2002) Proc. Natl. Acad. Sci USA 99:16899-16903.
Suggitt, M., "The hollow fibre model—facilitating anti-cancer pre-clinical pharmacodynamics and improving animal welfare," Int. J. Oncol. (2006) 29(6):1493-1499.
Suggs, J.W. et al., "Synthesis and structure of anthramycin analogs via hydride reduction of dilactams," Tetrahedron Letters, 26, No. 40, 4871-4874 (1985).
Sun et al., "Enabling ScFvs as Multi-Drug Carriers: A Dendritic Approach," (2003) Bioorganic & Medicinal Chemistry 11:1761-1768.
Sun et al., "Syntheses of Dendritic Linkers Containing Chlorambucil Residues for the Preparation of Antibody—Multidrug Immunoconjugates," (2002) Bioorganic & Medicinal Chemistry Letters 12:2213-2215.

(56) References Cited

OTHER PUBLICATIONS

Sutherland, M.S.K. et al., "SGN-CD33A: a novel CD33-directed antibody-drug conjugate, utilizing pyrrolobenzodiazepine dimers, demonstrates preclinical anti-tumor activity against multi-drug resistant human AML," American Society of Hematology (Dec. 8-12, 2012) Atlanta, Georgia, Abstract No. 3589.
Svensson P.J., et al., "Phenotypic variation in a family with mutations in two Hirschsprung-related genes (RET and endothelin receptor B)," Hum. Genet. 103, 145-148, 1998.
Swiercz J.M., et al., "Plexin-81 /RhoGEF-mediated Rho A activation involves the receptor tyrosine kinase ErbB-2," J. Cell Biol. 165, 869-880, 2004.
Syrigos and Epenetos, "Antibody Directed Enzyme Prodrug Therapy (ADEPT): A Review of the Experimental and Clinical Considerations," (1999) Anticancer Research 19:605-614.
Takeuchi, T. et al., "Neothramycins A and B, New Antitumor Antibiotics," J. Antibiotics, 29, 93-96 (1976).
Tawaragi Y., et al., "Primary structure of nonspecific crossreacting antigen (NCA), a member of carcinoembryonic antigen (cea) gene family, deduced from cdna sequence," Biochem. Biophys. Res. Commun. 150, 89-96, 1988.
Tercel, M. et al., "Unsymmetrical DNA cross-linking agents: combination of the CBI and PBD pharmacophores," J. Med. Chem. (2003) 46:2132-2151.
Thompson J.S., et al., "Baff-R, a Newly Identified TNF Receptor That Specifically Interacts with BAFF," Science 293 (5537), 2108-2111 (2001).
Thurston, "Advances in the study of Pyrrolo[2,1-c][1,4] benzodiazepine (PBD) Antitumour Antibiotics", Molecular Aspects of Anticancer Drug-DNA Interaction, Neidle, S. and Waring, M.J., Eds.; Macmillan Press Ltd, 1:54-88 (1993).
Thurston, D.E. and Bose, D.S., "Synthesis of DNA-Interactive Pyrrolo[2,1-c][1,4]benzodiazepines," Chem. Rev., 94:433-465 (1994).
Thurston, D.E. and Thompson, A.S., "The molecular recognition of DNA," Chem. Brit., 26, 767-772 (1990).
Thurston, D.E. et al., "Effect of A-ring modifications on the DNA-binding behavior and cytotoxicity of pyrrolo[2,1-c][1,4]benzodiazepines", Journal of Medicinal Chemistry, 42:1951-1964 (1999).
Thurston, D.E. et al., "Synthesis of Sequence-selective C8-linked Pyrrolo [2,1-c][1,4] Benzodiazepine DNA Interstrand Cross-linking Agent," J. Org. Chem., 61:8141-8147 (1996).
Thurston, D.E. et al., "Synthesis of a novel GC-specific covalent-binding DNA affinity-cleavage agent based on pyrrolobenzodiazepines (PBDs)," Chemical Communications, 563-565 (1996).
Thurston, D.E., "Nucleic acid targeting: therapeutic strategies for the 21st century," Brit. J. Cancer (1999) 80(1):65-85.
Tiberghien, A.C. et al., "Application of the stille coupling reaction to the synthesis of C2-substituted endo-exo unsaturated pyrrolo[2,1-c][1,4]benzodiazepines (PBDs)," Biorg. Med. Chem. Lett. (2004) 14:5041-5044.
Tiberghien, A.C., "Application of the stille coupling reaction to the synthesis of C2-substituted endo-exo unsaturated pyrrolo[2,1-c][1,4]benzodiazepines (PBDs)," Bioorg. Med. Chem. Lett. (2008) 18(6):2073-2077.
Toki et al., "Protease-Mediated Fragmentation of p-Amidobenzyl Ethers: A New Strategy for the Activation of Anticancer Prodrugs," (2002) J. Org. Chem. 67:1866-1872.
Tonnelle et al., "DO Beta a new chain gene in HLA-D with a distinct regulation of expression," (1985) EMBO J. 4(11):2839-2847.
Touchman et al., "The Genomic Region Encompassing the Nephropathic Cystinosis Gene (CTNS): Complete Sequencing of a 200-kb Segment and Discovery of a Novel Gene within the Common Cystinosis-Causing Deletion," (2000) Genome Res. 10:165-173.
Tozuka et al., "Studies on tomaymycin. II. Total synthesis of the antitumor antibiotics, E-and Z-tomaymycins," J. Antibiotics (Tokyo) (1983) 36:276-282.
Trail et al., "Monoclonal antibody drug immunoconjugates for targeted treatment of cancer," (2003) Cancer Immunol. Immunother. 52:328-337.
Tsunakawa, M. et al., "Porothramycin, a new antibiotic of the anthramycin group: Production, isolation, structure and biological activity," J. Antibiotics, 41:1366-1373 (1988).
Tsutsumi M., et al., "Novel endothelin B receptor transcripts with the potential of generating a new receptor," Gene 228, 43-49, 1999.
Uchida et al., "A Novel Epidermal Growth Factor-like Molecule Containing Two Follistatin Modules Stimulates Tyrosine Phosphorylation of erbB-4 in MKN28 Gastric Cancer Cells," (1999) Biochem. Biophys. Res. Commun. 266:593-602.
Umezawa, H. et al. "Mazethramycins," SciFinder Scholar, 2-3 (2002).
Umezawa, H. et al., Chemical Abstract No. 4427a, "Mazethramycins" Chemical Abstracts, vol. 90, No. 1, 428 (1979).
Verheij J.B., et al., "ABCD Syndrome Is Caused by a Homozygous Mutation in the EDNRB Gene," Am. J. Med. 15 Genet. 108, 223-225, 2002.
Vippagunta, S.R. et al., "Crystalline solids," Adv. Drug Delivery Rev. (2001) 48:3-26.
Von Hoegen et al., "Identification of a human protein homologous to the mouse Lyb-2 B cell differentiation antigen and sequence of the corresponding cDNA," (1990) J. Immunol. 144(12):4870-4877.
Wang, J.H., "Determination of antitumor agent AJG-136 in human serum by HPLC with tandem mass spectrometric detection (HPLC-MS/MS)," Abstracts of Papers American Chemical Society (Mar. 13, 2005) 229(1):U119.
Webster et al., "Mammary tumorigenesis and metastasis in transgenic mice," (1994) Semin. Cancer Biol. 5:69-76.
Weidner-Wells, M.A. et al., "Photochemical approach to the synthesis of the pyrrolo[1,4]benzodiazepine antibiotics," J. Org. Chem. (1989) 54:5746-5758.
Weis J.J., et al., "Identification of a partial eDNA clone for the C3d/Epstein-Barr virus receptor of human B lymphocytes: Homology with the receptor for fragments C3b and C4b of the third and fourth components of complement," Proc. Natl. Acad. Sci. U.S.A. 83, 5639-5643, 1986.
Weis J.J., et al., "Structure of the human b lymphocyte receptor for c3d and the epstein-barr virus and relatedness to other members of the family of C3/C4 binding proteins," J. Exp. Med. 167, 1047-1066, 1988.
Wells, G. et al., "Design, synthesis and biophysical and biological evaluation of a series of pyrrolobenzodiazepine-poly(N-methylpyrrole) conjugates," J. Med. Chem. (2006) 49:5442-5461.
Wikipedia, "How many types of cancer are there?", 2012, 3 pages; http://wiki.answers.com/Q/How-many-different-types_of_cancer_are_there.
Wikipedia, "Management of Cancer," 2012, 1 page; http://en.wikipedia.org/wiki/Management of cancer.
Wilkinson "Eph Receptors and Ephrins: Regulators of Guidance and Assembly," Int. Rev. Cytol. 196:177-244 (2000).
Wilkinson, G.P., "Pharmacokinetics and intracellular pharmacological characteristics of the novel pyrrolobenzodiazepine (PBD) dimer SJG-136," Proceedings of the American Association for Cancer Research Annual Meeting (Jul. 2003) 44:320.
Wilkinson, G.P., "Pharmacokinetics, metabolism and glutathione reactivity of SJG-136," Br. J. Cancer (2003) 88(Supp. 1):S29.
Wilkinson, G.P., "Preliminary pharmacokinetic and bioanalytical studies of SJG-136 (NSC 694501), a sequence-selective pyrrolobenzodiazepine dimer DNA-cross-linking agent," Investigational New Drugs (2004) 22(3):231-240.
Wilson et al., "eDNA Cloning of the B Cell Membrane Protein CD22: A Mediator of B-B Cell Interactions," (1991) J. Exp. Med. 173:137-146.
Wilson, S.C. et al., "Design and Synthesis of a Novel Epoxide-Containing Pyrrolo[2,1-c][1,4]benzodiazepine (PBD) via a New Cyclization Procedure," Tetrahedron Letters, 36, No. 35, 6333-6336 (1995).
Wilson, S.C. et al., "Design, Synthesis, and Evaluation of a Novel Sequence-Selective Epoxide-Containing DNA Cross-Linking Agent Based on the Pyrrolo[2,1-c][1,4]benzodiazepine System", J. Med. Chem. 42: 4028-4041 (1999).
Wolff, M.E., Burger's Medicinal Chemistry, 4th Edition, Part I, Wiley: New York (1979) 336-337.

(56) References Cited

OTHER PUBLICATIONS

Wolff, M.E., Burger's Medicinal Chemistry, 5th Edition, Part I, John Wiley & Sons (1995) 975-977.

Workman, P. et al., "United Kingdom Co-ordinating Committee on Cancer Research (UKCCCR) guidelines for the welfare of animals in experimental neoplasia (second edition)," Br. J. Cancer (1998) 77(1):1-10.

Wu et al., "Arming antibodies: prospects and challenges for immunoconjugates," (2005) Nature Biotech. 23(9):1137-1145.

Xie et al., "In vivo behaviour of antibody-drug conjugates for the targeted treatment of cancer," (2006) Expert. Opin Biol. Ther. 6(3):281-291.

Xie, G. et al., "Bisindolylmaleimides linked to DNA minor groove binding lexitropsins: synthesis, inhibitory activity against topoisomerasel, and biological evaluation," J. Med. Chem. (1996) 39:1049-1055.

Xu et al., "Molecular Cloning, Functional Characterization, Tissue Distribution, and Chromosomal Localization of a Human, Small Intestinal Sodium-Phosphate (Na + -Pi) Transporter (SLC34A2)," Genomics 62 (2):281-284 (1999).

Xu, M.J., et al., "Molecular Cloning and Characterization of SPAP1, an Inhibitory Receptor," (2001) Biochem. Biophys. Res. Commun. 280 (3):768-775.

Xu, X.Z., et al., "Regulation of melastatin, a TRP-related protein, through interaction with a cytoplasmic isoform," Proc. Natl. Acad. Sci. U.S.A. 98 (19):10692-10697 (2001).

Yamaguchi, N., et al., "A Novel Cytokine Exhibiting Megakaryocyte Potentiating Activity From a Human Pancreatic Tumor Cell Line HPC-Y5," Biol. Chem. 269 (2), 805-808 (1994).

Yamamoto T., et al., "Similarity of protein encoded by the human c-erb-B-2 gene to epidermal growth factor receptor," Nature 319, 230-234, 1986.

Yang et al., "Murine Six-Transmembrane Epithelial Antigen of the Prostate, Prostate Stem Cell Antigen, and Prostate-specific Membrane Antigen: Prostate-specific Cell-Surface Antigens Highly Expressed in Prostate Cancer of Transgenic Adenocarcinoma Mouse Prostate Mice," Cancer Research, 61, 5857-5860. Aug. 1, 2001.

Yin & Lloyd, "Molecular Cloning of the CA125 Ovarian Cancer Antigen," J. Biol. Chem. 276 (29):27371-27375 (2001).

Younes et al., "Phase I multidose-escalation study of the anti-CD19 maytansinoid immunoconjugate SAR3419 administered by intravenous infusion every 3 weeks to patients with relapsed/refractory B-cell lymphoma," J Clin Oncol., 2012, 30(22):2776-82.

Yu et al., "Human mb-1 gene: complete edna sequence and its expression in b cells bearing membrane Ig of various isotypes," (1992) J. Immunol. 148(2) 633-637.

Zammarchi et al., "Pre-Clinical Development of Adct-402, a Novel Pyrrolobenzodiazepine (PBD)-Based Antibody Drug Conjugate (ADC) Targeting CD19-Expressing B-Cell Malignancies," Blood, 2015, 126:1564, Abstract.

PYRROLOBENZODIAZEPINE CONJUGATES

CROSS REFERENCE TO RELATED APPLICATIONS

The present application is a national phase application under 35 U.S.C. § 371 of PCT International Application No. PCT/EP2017/076162, filed Oct. 13, 2017, which claims priority to Great Britain Application No. 1617466.6, filed Oct. 14, 2016, each of which are hereby incorporated by reference in its entirety.

The present invention relates to conjugates comprising pyrrolobenzodiazepines and related dimers (PBDs), and the precursor drug linkers used to make such conjugates.

BACKGROUND TO THE INVENTION

Some pyrrolobenzodiazepines (PBDs) have the ability to recognise and bond to specific sequences of DNA; the preferred sequence is PuGPu. The first PBD antitumour antibiotic, anthramycin, was discovered in 1965 (Leimgruber, et al., *J. Am. Chem. Soc.*, 87, 5793-5795 (1965); Leimgruber, et al., *J. Am. Chem. Soc.*, 87, 5791-5793 (1965)). Since then, a number of naturally occurring PBDs have been reported, and over 10 synthetic routes have been developed to a variety of analogues (Thurston, et al., *Chem. Rev.* 1994, 433-465 (1994)). Family members include abbeymycin (Hochlowski, et al., *J. Antibiotics*, 40, 145-148 (1987)), chicamycin (Konishi, et al., *J. Antibiotics*, 37, 200-206 (1984)), DC-81 (Japanese Patent 58-180 487; Thurston, et al., *Chem. Brit.*, 26, 767-772 (1990); Bose, et al., *Tetrahedron*, 48, 751-758 (1992)), mazethramycin (Kumimoto, et al., *J. Antibiotics*, 33, 665-667 (1980)), neothramycins A and B (Takeuchi, et al., *J. Antibiotics*, 29, 93-96 (1976)), porothramycin (Tsunakawa, et al., *J. Antibiotics*, 41, 1366-1373 (1988)), prothracarcin (Shimizu, et al, *J. Antibiotics*, 29, 2492-2503 (1982); Langley and Thurston, *J. Org. Chem.*, 52, 91-97 (1987)), sibanomicin (DC-102)(Hara, et al., *J. Antibiotics*, 41, 702-704 (1988); Itoh, et al., *J. Antibiotics*, 41, 1281-1284 (1988)), sibiromycin (Leber, et al., *J. Am. Chem. Soc.*, 110, 2992-2993 (1988)) and tomamycin (Arima, et al., *J. Antibiotics*, 25, 437-444 (1972)). PBDs are of the general structure:

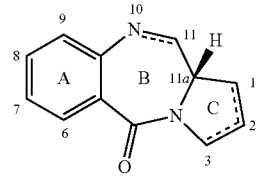

They differ in the number, type and position of substituents, in both their aromatic A rings and pyrrolo C rings, and in the degree of saturation of the C ring. In the B-ring there is either an imine (N=C), a carbinolamine (NH—CH(OH)), or a carbinolamine methyl ether (NH—CH(OMe)) at the N10-C11 position which is the electrophilic centre responsible for alkylating DNA. All of the known natural products have an (S)-configuration at the chiral C11a position which provides them with a right-handed twist when viewed from the C ring towards the A ring. This gives them the appropriate three-dimensional shape for isohelicity with the minor groove of B-form DNA, leading to a snug fit at the binding site (Kohn, In *Antibiotics III*. Springer-Verlag, New York, pp. 3-11 (1975); Hurley and Needham-VanDeventer, *Acc. Chem. Res.*, 19, 230-237 (1986)). Their ability to form an adduct in the minor groove, enables them to interfere with DNA processing, hence their use as antitumour agents.

It has been previously disclosed that the biological activity of this molecules can be potentiated by joining two PBD units together through their C8/C'-hydroxyl functionalities via a flexible alkylene linker (Bose, D. S., et al., *J. Am. Chem. Soc.*, 114, 4939-4941 (1992); Thurston, D. E., et al., *J. Org. Chem.*, 61, 8141-8147 (1996)). The PBD dimers are thought to form sequence-selective DNA lesions such as the palindromic 5'-Pu-GATC-Py-3' interstrand cross-link (Smellie, M., et al., *Biochemistry*, 42, 8232-8239 (2003); Martin, C., et al., *Biochemistry*, 44, 4135-4147) which is thought to be mainly responsible for their biological activity.

One example of a PBD dimer is SG2000 (SJG-136):

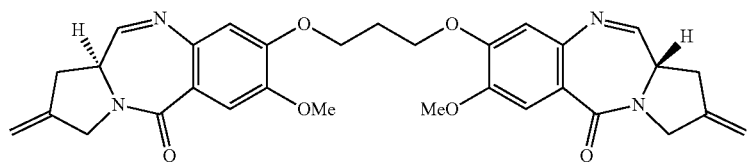

(Gregson, S., et al., *J. Med. Chem.*, 44, 737-748 (2001); Alley, M. C., et al., *Cancer Research*, 64, 6700-6706 (2004); Hartley, J. A., et al., *Cancer Research*, 64, 6693-6699 (2004)) which has been involved in clinical trials as a standalone agent, for example, NCT02034227 investigating its use in treating Acute Myeloid Leukemia and Chronic Lymphocytic Leukemia (see: https://www.clinicaltrials.gov/ct2/show/NCT02034227).

Dimeric PBD compounds bearing C2 aryl substituents, such as SG2202 (ZC-207), are disclosed in WO 2005/085251:

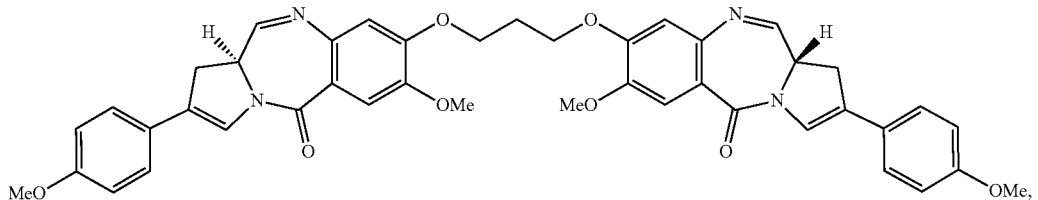

ZC-207 and in WO2006/111759, bisulphites of such PBD compounds, for example SG2285 (ZC-423):

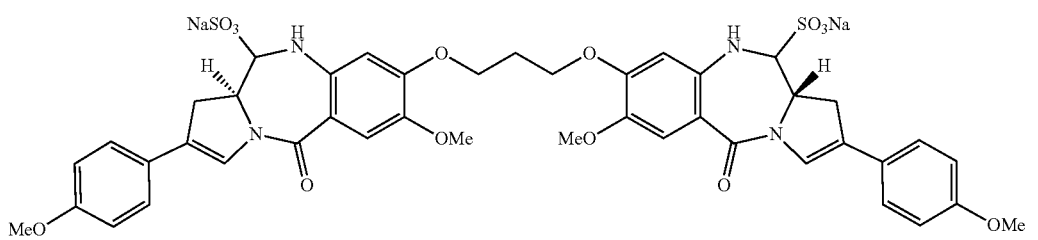

ZC-423

These compounds have been shown to be highly useful cytotoxic agents (Howard, P. W., et al., *Bioorg. Med. Chem.* (2009), doi: 10.1016/j.bmcl.2009.09.012).

WO 2007/085930 describes the preparation of dimer PBD compounds having linker groups for connection to a cell binding agent, such as an antibody. The linker is present in the bridge linking the monomer PBD units of the dimer.

Dimer PBD compounds having linker groups for connection to a cell binding agent, such as an antibody, are described in WO 2011/130598. The linker in these compounds is attached to one of the available N10 positions, and are generally cleaved by action of an enzyme on the linker group. If the non-bound N10 position is protected with a capping group, the capping groups exemplified have the same cleavage trigger as the linker to the antibody.

WO 2014/057074 describes two specific PBD dimer conjugates bound via the N10 position on one monomer, the other PBD monomer being in imine form.

WO 2015/052322 describes a specific PBD dimer conjugate bound via the N10 position on one monomer, the other PBD monomer being in imine form. It also describes a specific PBD dimer conjugate bound via the N10 position on one monomer, the other PBD monomer having a capping group with the same cleavage trigger as the linker to the antibody:

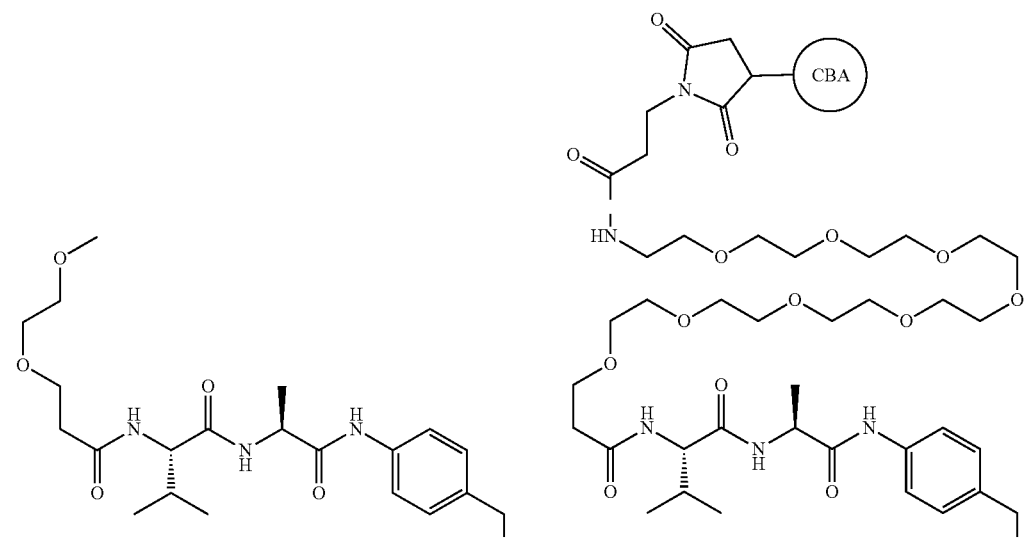

ConjC

-continued

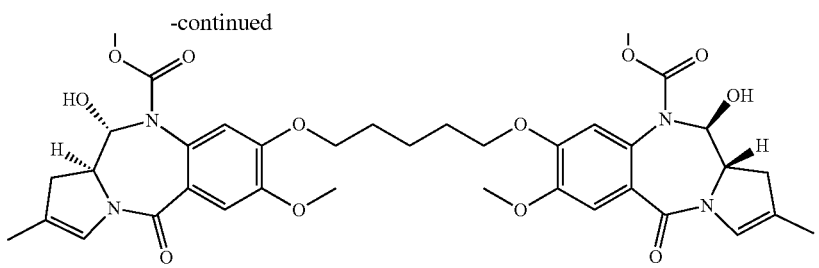

DISCLOSURE OF THE INVENTION

The present invention provides PBD and related dimer conjugates where the N10-C11 group that is not bound to the ligand unit is a β-glucuronide capping group. The cleavage trigger for the linking unit to the ligand unit is non-glucuronide cleavable.

Use of the glucuronide capping unit in these conjugates is believed to be advantageous, as if the conjugate is cleaved from the antibody outside the target cell, the released protected compound remains inactive as it is unable to permeate cell membranes due to its hydrophilicity.

The present invention also provided PBD and related dimer drug linkers, suitable for conjugating to a ligand unit, where the N10-C11 group that is not intended to be bound to the ligand unit is a glucuronide capping group. The cleavage trigger for the linking unit is a non-glucuronide capping unit.

Use of the glucuronide capping unit in these drug linkers is believed to be advantageous, as it increases the hydrophilicity of the generally hydrophobic drug linker, making the drug linkers easier to conjugate to a ligand unit.

A first aspect of the present invention comprises a compound with the formula I:

-continued

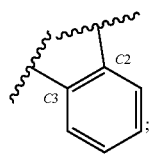
D2 the dotted line indicates the optional presence of a double bond between C2 and C3;

when there is a double bond present between C2 and C3, $R^2$ is selected from the group consisting of:

(ia) $C_{5-10}$ aryl group, optionally substituted by one or more substituents selected from the group comprising: halo, nitro, cyano, ether, carboxy, ester, $C_{1-7}$ alkyl, $C_{3-7}$ heterocyclyl and bis-oxy-$C_{1-3}$ alkylene;

(ib) $C_{1-5}$ saturated aliphatic alkyl;

(ic) $C_{3-6}$ saturated cycloalkyl;

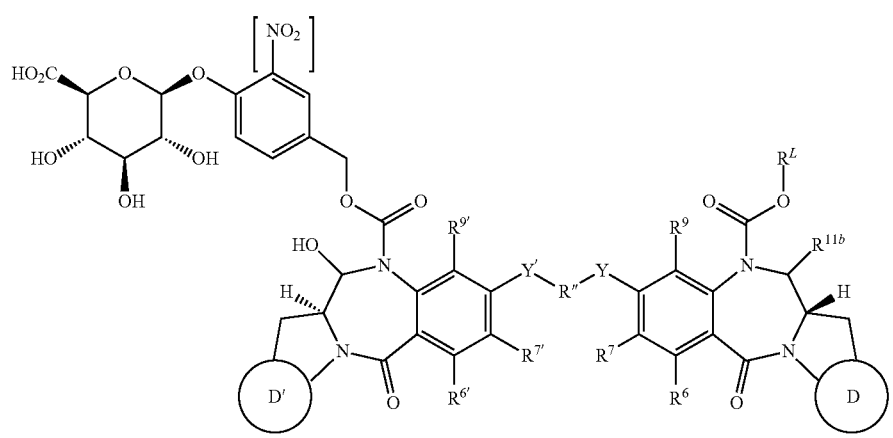

I and salts and solvates thereof, wherein:
the square brackets indicate the $NO_2$ group is optional;
D represents either group D1 or D2:

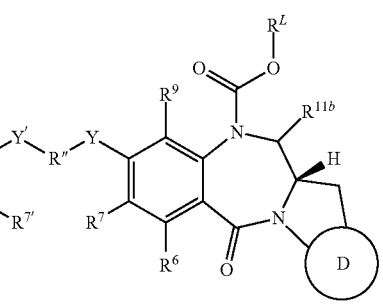
D1

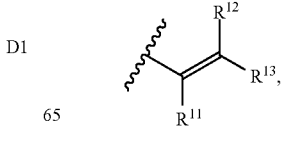
(id)

wherein each of $R^{11}$, $R^{12}$ and $R^{13}$ are independently selected from H, $C_{1-3}$ saturated alkyl, $C_{2-3}$ alkenyl, $C_{2-3}$ alkynyl and cyclopropyl, where the total number of carbon atoms in the $R^2$ group is no more than 5;

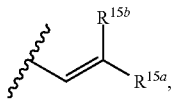
(ie)

wherein one of $R^{15a}$ and $R^{15b}$ is H and the other is selected from: phenyl, which phenyl is optionally substituted by a group selected from halo, methyl, methoxy; pyridyl; and thiophenyl; and

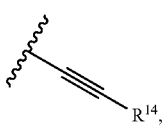
(if)

where $R^{14}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;
when there is a single bond present between C2 and C3, $R^2$ is selected from H, OH, F, diF and

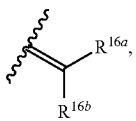

where $R^{16a}$ and $R^{16b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{16a}$ and $R^{16b}$ is H, the other is selected from nitrile and a $C_{1-4}$ alkyl ester;
D' represents either group D'1 or D'2:

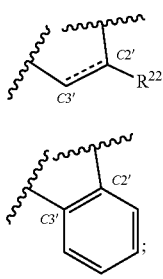

wherein the dotted line indicates the optional presence of a double bond between C2' and C3';
when there is a double bond present between C2' and C3', $R^{12}$ is selected from the group consisting of:
(iia) $C_{5-10}$ aryl group, optionally substituted by one or more substituents selected from the group comprising: halo, nitro, cyano, ether, carboxy, ester, $C_{1-7}$ alkyl, $C_{3-7}$ heterocyclyl and bis-oxy-$C_{1-3}$ alkylene;

(iib) $C_{1-5}$ saturated aliphatic alkyl;
(iic) $C_{3-6}$ saturated cycloalkyl;

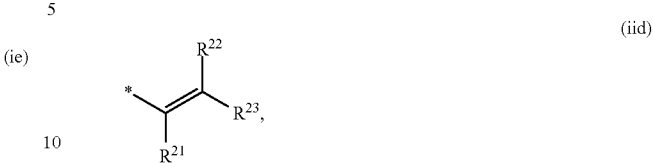
(iid)

wherein each of $R^{21}$, $R^{22}$ and $R^{23}$ are independently selected from H, $C_{1-3}$ saturated alkyl, $C_{2-3}$ alkenyl, $C_{2-3}$ alkynyl and cyclopropyl, where the total number of carbon atoms in the $R^{12}$ group is no more than 5;

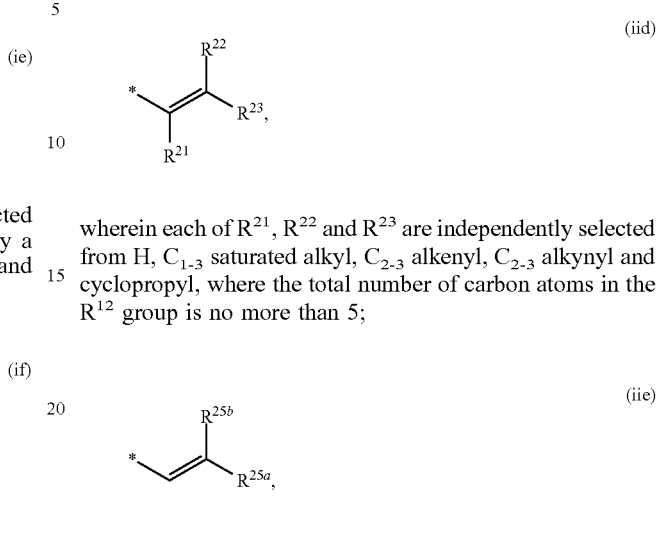
(iie)

wherein one of $R^{25a}$ and $R^{25b}$ is H and the other is selected from: phenyl, which phenyl is optionally substituted by a group selected from halo, methyl, methoxy; pyridyl; and thiophenyl; and

(iif)

where $R^{24}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;
when there is a single bond present between C2' and C3', $R^{12}$ is selected from H, OH, F, diF and

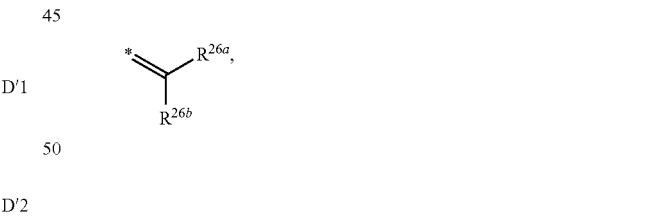

where $R^{26a}$ and $R^{26b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or,
when one of $R^{26a}$ and $R^{26b}$ is H, the other is selected from nitrile and a $C_{1-4}$ alkyl ester;
$R^6$ and $R^9$ are independently selected from H, R, OH, OR, SH, SR, $NH_2$, NHR, NRR', nitro, $Me_3Sn$ and halo;
where R and R' are independently selected from optionally substituted $C_{1-12}$ alkyl, $C_{3-20}$ heterocyclyl and $C_{5-20}$ aryl groups;
$R^7$ is selected from H, R, OH, OR, SH, SR, $NH_2$, NHR, NRR', nitro, $Me_3Sn$ and halo;

R" is a $C_{3-12}$ alkylene group, which chain may be interrupted by one or more heteroatoms, e.g. O, S, $NR^{N2}$ (where $R^{N2}$ is H or $C_{1-4}$ alkyl), and/or aromatic rings, e.g. benzene or pyridine;

Y and Y' are selected from O, S, or NH;

$R^{6'}$, $R^{7'}$, $R^{9'}$ are selected from the same groups as $R^6$, $R^7$ and $R^9$ respectively;

$R^{11b}$ is selected from OH, $OR^A$, where $R^A$ is $C_{1-4}$ alkyl; and $R^L$ is a linker for connection to a cell binding agent, which is selected from:

(iiia):

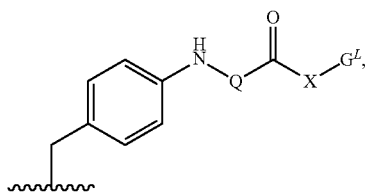

IIIa wherein

Q is:

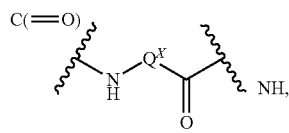

where $Q^X$ is such that Q is an amino-acid residue, a dipeptide residue or a tripeptide residue;

X is:

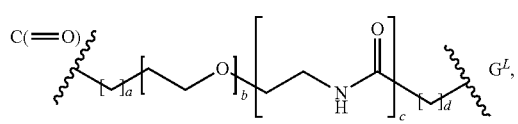

where a=0 to 5, b=0 to 16, c=0 or 1, d=0 to 5;

$G^L$ is a linker for connecting to a Ligand Unit; and (iiib):

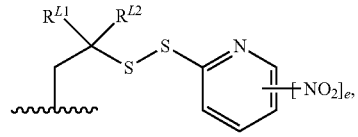

IIIb where $R^{L1}$ and $R^{L2}$ are independently selected from H and methyl, or together with the carbon atom to which they are bound form a cyclopropylene or cyclobutylene group;

and e is 0 or 1.

A second aspect of the present invention provides Conjugates of formula II:

$$L\text{-}(D^L)_p \qquad (II)$$

wherein L is a Ligand unit (i.e., a targeting agent), $D^L$ is a Drug Linker unit of formula I':

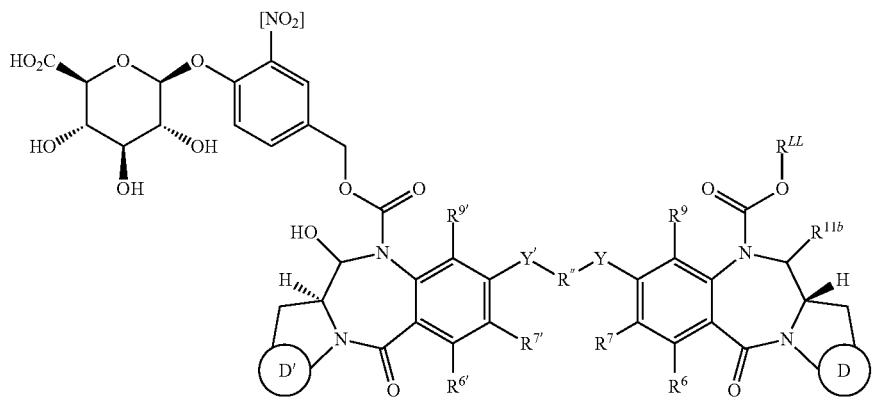

I' wherein D, $R^2$, $R^6$, $R^7$, $R^9$, $R^{11b}$, Y, R", Y', D', $R^{6'}$, $R^{7'}$, $R^{9'}$ and $R^{12}$ (including the presence or absence of double bonds between C2 and C3 and C2' and C3' respectively, and the $NO_2$ group) are as defined in the first aspect of the invention;

$R^{LL}$ is a linker for connection to a cell binding agent, which is selected from:

(iiia):

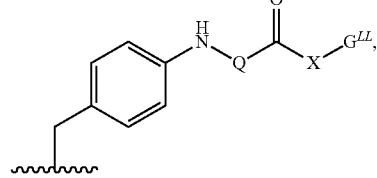

IIIa' where Q and X are as defined in the first aspect and $G^{LL}$ is a linker connected to a Ligand Unit; and (iiib):

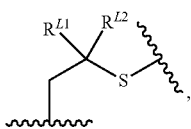

where $R^{L1}$ and $R^{L2}$ are as defined in the first aspect;
wherein p is an integer of from 1 to 20.

The Ligand unit, described more fully below, is a targeting agent that binds to a target moiety. The Ligand unit can, for example, specifically bind to a cell component (a Cell Binding Agent) or to other target molecules of interest. The Ligand unit can be, for example, a protein, polypeptide or peptide, such as an antibody, an antigen-binding fragment of an antibody, or other binding agent, such as an Fc fusion protein.

A third aspect of the present invention provides the use of a conjugate of the second aspect of the invention in the manufacture of a medicament for treating a proliferative disease. The third aspect also provides a conjugate of the second aspect of the invention for use in the treatment of a proliferative disease. The third aspect also provides a method of treating a proliferative disease comprising administering a therapeutically effective amount of a conjugate of the second aspect of the invention to a patient in need thereof.

One of ordinary skill in the art is readily able to determine whether or not a candidate conjugate treats a proliferative condition for any particular cell type. For example, assays which may conveniently be used to assess the activity offered by a particular compound are described in the examples below.

A fourth aspect of the present invention provides the synthesis of a conjugate of the second aspect of the invention comprising conjugating a compound (drug linker) of the first aspect of the invention with a Ligand Unit.

DEFINITIONS

Substituents

Figure 1:
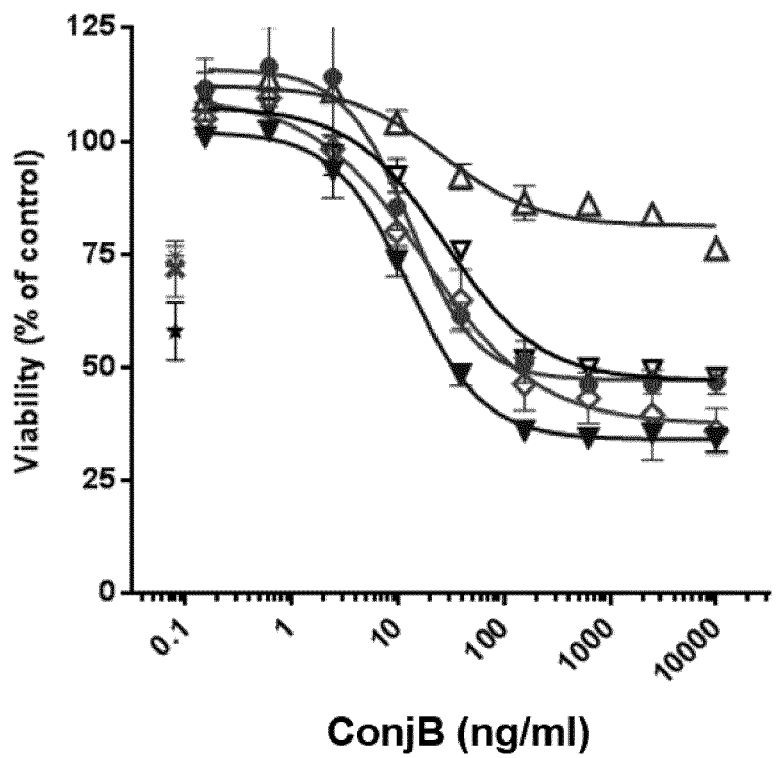
FIG. 1 shows the effect on viability of SKOV3 cells following incubation with a conjugate of the present invention.

The phrase "optionally substituted" as used herein, pertains to a parent group which may be unsubstituted or which may be substituted.

Unless otherwise specified, the term "substituted" as used herein, pertains to a parent group which bears one or more substituents. The term "substituent" is used herein in the conventional sense and refers to a chemical moiety which is covalently attached to, or if appropriate, fused to, a parent group. A wide variety of substituents are well known, and methods for their formation and introduction into a variety of parent groups are also well known.

Examples of substituents are described in more detail below.

$C_{1-12}$ alkyl: The term "$C_{1-12}$ alkyl" as used herein, pertains to a monovalent moiety obtained by removing a hydrogen atom from a carbon atom of a hydrocarbon compound having from 1 to 12 carbon atoms, which may be aliphatic or alicyclic, and which may be saturated or unsaturated (e.g. partially unsaturated, fully unsaturated). The term "$C_{1-4}$ alkyl" as used herein, pertains to a monovalent moiety obtained by removing a hydrogen atom from a carbon atom of a hydrocarbon compound having from 1 to 4 carbon atoms, which may be aliphatic or alicyclic, and which may be saturated or unsaturated (e.g. partially unsaturated, fully unsaturated). Thus, the term "alkyl" includes the sub-classes alkenyl, alkynyl, cycloalkyl, etc., discussed below.

Examples of saturated alkyl groups include, but are not limited to, methyl ($C_1$), ethyl ($C_2$), propyl ($C_3$), butyl ($C_4$), pentyl ($C_5$), hexyl ($C_6$) and heptyl ($C_7$).

Examples of saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$) and n-heptyl ($C_7$).

Examples of saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

$C_{2-12}$ Alkenyl: The term "$C_{2-12}$ alkenyl" as used herein, pertains to an alkyl group having one or more carbon-carbon double bonds.

Examples of unsaturated alkenyl groups include, but are not limited to, ethenyl (vinyl, —CH=$CH_2$), 1-propenyl (—CH=CH—$CH_3$), 2-propenyl (allyl, —CH—CH=$CH_2$), isopropenyl (1-methylvinyl, —C($CH_3$)=$CH_2$), butenyl ($C_4$), pentenyl ($C_5$), and hexenyl ($C_6$).

$C_{2-12}$ alkynyl: The term "$C_{2-12}$ alkynyl" as used herein, pertains to an alkyl group having one or more carbon-carbon triple bonds.

Examples of unsaturated alkynyl groups include, but are not limited to, ethynyl (—C≡CH) and 2-propynyl (propargyl, —$CH_2$—C≡CH).

$C_{3-12}$ cycloalkyl: The term "$C_{3-12}$ cycloalkyl" as used herein, pertains to an alkyl group which is also a cyclyl group; that is, a monovalent moiety obtained by removing a hydrogen atom from an alicyclic ring atom of a cyclic hydrocarbon (carbocyclic) compound, which moiety has from 3 to 7 carbon atoms, including from 3 to 7 ring atoms.

Examples of cycloalkyl groups include, but are not limited to, those derived from:

saturated monocyclic hydrocarbon compounds:
cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$) and methylcyclohexane ($C_7$);

unsaturated monocyclic hydrocarbon compounds:
cyclopropene ($C_3$), cyclobutene ($C_4$), cyclopentene ($C_5$), cyclohexene ($C_6$), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene ($C_7$) and methylcyclohexene ($C_7$); and saturated polycyclic hydrocarbon compounds:
norcarane ($C_7$), norpinane ($C_7$), norbornane ($C_7$).

$C_{3-20}$ heterocyclyl: The term "$C_{3-20}$ heterocyclyl" as used herein, pertains to a monovalent moiety obtained by removing a hydrogen atom from a ring atom of a heterocyclic compound, which moiety has from 3 to 20 ring atoms, of which from 1 to 10 are ring heteroatoms. Preferably, each ring has from 3 to 7 ring atoms, of which from 1 to 4 are ring heteroatoms.

In this context, the prefixes (e.g. $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl", as used herein, pertains to a heterocyclyl group having 5 or 6 ring atoms.

Examples of monocyclic heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_5$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Examples of substituted monocyclic heterocyclyl groups include those derived from saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

$C_{5-20}$ aryl: The term "$C_{5-20}$ aryl", as used herein, pertains to a monovalent moiety obtained by removing a hydrogen atom from an aromatic ring atom of an aromatic compound, which moiety has from 3 to 20 ring atoms. The term "$C_{5-7}$ aryl", as used herein, pertains to a monovalent moiety obtained by removing a hydrogen atom from an aromatic ring atom of an aromatic compound, which moiety has from 5 to 7 ring atoms and the term "$C_{5-10}$ aryl", as used herein, pertains to a monovalent moiety obtained by removing a hydrogen atom from an aromatic ring atom of an aromatic compound, which moiety has from 5 to 10 ring atoms. Preferably, each ring has from 5 to 7 ring atoms.

In this context, the prefixes (e.g. $C_{3-20}$, $C_{5-7}$, $C_{5-6}$, $C_{5-10}$, etc.) denote the number of ring atoms, or range of number of ring atoms, whether carbon atoms or heteroatoms. For example, the term "$C_{5-6}$ aryl" as used herein, pertains to an aryl group having 5 or 6 ring atoms.

The ring atoms may be all carbon atoms, as in "carboaryl groups".

Examples of carboaryl groups include, but are not limited to, those derived from benzene (i.e. phenyl) ($C_6$), naphthalene ($C_{10}$), azulene ($C_{10}$), anthracene ($C_{14}$), phenanthrene ($C_{14}$), naphthacene ($C_{18}$), and pyrene ($C_{16}$).

Examples of aryl groups which comprise fused rings, at least one of which is an aromatic ring, include, but are not limited to, groups derived from indane (e.g. 2,3-dihydro-1H-indene) ($C_9$), indene ($C_9$), isoindene ($C_9$), tetraline (1,2,3,4-tetrahydronaphthalene) ($C_{10}$), acenaphthene ($C_{12}$), fluorene ($C_{13}$), phenalene ($C_{13}$), acephenanthrene ($C_{15}$), and aceanthrene ($C_{16}$).

Alternatively, the ring atoms may include one or more heteroatoms, as in "heteroaryl groups". Examples of monocyclic heteroaryl groups include, but are not limited to, those derived from:

$N_1$: pyrrole (azole) ($C_5$), pyridine (azine) ($C_6$);

$O_1$: furan (oxole) ($C_5$);

$S_1$: thiophene (thiole) ($C_5$);

$N_1O_1$: oxazole ($C_5$), isoxazole ($C_5$), isoxazine ($C_6$);

$N_2O_1$: oxadiazole (furazan) ($C_5$);

$N_3O_1$: oxatriazole ($C_5$);

$N_1S_1$: thiazole ($C_5$), isothiazole ($C_5$);

N2: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$);

$N_3$: triazole ($C_5$), triazine ($C_6$); and, $N_4$: tetrazole ($C_5$).

Examples of heteroaryl which comprise fused rings, include, but are not limited to:

$C_9$ (with 2 fused rings) derived from benzofuran ($O_1$), isobenzofuran ($O_1$), indole ($N_1$), isoindole ($N_1$), indolizine ($N_1$), indoline ($N_1$), isoindoline ($N_1$), purine ($N_4$) (e.g., adenine, guanine), benzimidazole ($N_2$), indazole ($N_2$), benzoxazole ($N_1O_1$), benzisoxazole ($N_1O_1$), benzodioxole ($C_2$), benzofurazan ($N_2O_1$), benzotriazole ($N_3$), benzothiofuran ($S_1$), benzothiazole ($N_1S_1$), benzothiadiazole ($N_2S$);

$C_{10}$ (with 2 fused rings) derived from chromene ($O_1$), isochromene ($O_1$), chroman ($O_1$), isochroman ($O_1$), benzodioxan ($C_2$), quinoline ($N_1$), isoquinoline ($N_1$), quinolizine ($N_1$), benzoxazine ($N_1O_1$), benzodiazine ($N_2$), pyridopyridine ($N_2$), quinoxaline ($N_2$), quinazoline ($N_2$), cinnoline ($N_2$), phthalazine ($N_2$), naphthyridine ($N_2$), pteridine ($N_4$);

$C_{11}$ (with 2 fused rings) derived from benzodiazepine ($N_2$);

$C_{13}$ (with 3 fused rings) derived from carbazole ($N_1$), dibenzofuran ($O_1$), dibenzothiophene ($S_1$), carboline ($N_2$), perimidine ($N_2$), pyridoindole ($N_2$); and, $C_{14}$ (with 3 fused rings) derived from acridine ($N_1$), xanthene ($O_1$), thioxanthene ($S_1$), oxanthrene ($C_2$), phenoxathiin ($O_1S_1$), phenazine ($N_2$), phenoxazine ($N_1O_1$), phenothiazine ($N_1S_1$), thianthrene ($S_2$), phenanthridine ($N_1$), phenanthroline ($N_2$), phenazine ($N_2$).

The above groups, whether alone or part of another substituent, may themselves optionally be substituted with one or more groups selected from themselves and the additional substituents listed below.

Halo: —F, —Cl, —Br, and —I.

Hydroxy: —OH.

Ether: —OR, wherein R is an ether substituent, for example, a $C_{1-7}$ alkyl group (also referred to as a $C_{1-7}$ alkoxy group, discussed below), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$ alkyl group.

Alkoxy: —OR, wherein R is an alkyl group, for example, a $C_{1-7}$ alkyl group. Examples of $C_{1-7}$ alkoxy groups include, but are not limited to, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy).

Acetal: —CH(OR$^1$)(OR$^2$), wherein R$^1$ and R$^2$ are independently acetal substituents, for example, a C$_{1-7}$ alkyl group, a C$_{3-20}$ heterocyclyl group, or a C$_{5-20}$ aryl group, preferably a C$_{1-7}$ alkyl group, or, in the case of a "cyclic" acetal group, R$^1$ and R$^2$, taken together with the two oxygen atoms to which they are attached, and the carbon atoms to which they are attached, form a heterocyclic ring having from 4 to 8 ring atoms. Examples of acetal groups include, but are not limited to, —CH(OMe)$_2$, —CH(OEt)$_2$, and —CH(OMe)(OEt).

Hemiacetal: —CH(OH)(OR$^1$), wherein R$^1$ is a hemiacetal substituent, for example, a C$_{1-7}$ alkyl group, a C$_{3-20}$ heterocyclyl group, or a C$_{5-20}$ aryl group, preferably a C$_{1-7}$ alkyl group. Examples of hemiacetal groups include, but are not limited to, —CH(OH)(OMe) and —CH(OH)(OEt).

Ketal: —CR(OR$^1$)(OR$^2$), where R$^1$ and R$^2$ are as defined for acetals, and R is a ketal substituent other than hydrogen, for example, a C$_{1-7}$ alkyl group, a C$_{3-20}$ heterocyclyl group, or a C$_{5-20}$ aryl group, preferably a C$_{1-7}$ alkyl group. Examples ketal groups include, but are not limited to, —C(Me)(OMe)$_2$, —C(Me)(OEt)$_2$, —C(Me)(OMe)(OEt), —C(Et)(OMe)$_2$, —C(Et)(OEt)$_2$, and —C(Et)(OMe)(OEt).

Hemiketal: —CR(OH)(OR$^1$), where R$^1$ is as defined for hemiacetals, and R is a hemiketal substituent other than hydrogen, for example, a C$_{1-7}$ alkyl group, a C$_{3-20}$ heterocyclyl group, or a C$_{5-20}$ aryl group, preferably a C$_{1-7}$ alkyl group. Examples of hemiacetal groups include, but are not limited to, —C(Me)(OH)(OMe), —C(Et)(OH)(OMe), —C(Me)(OH)(OEt), and —C(Et)(OH)(OEt).

Oxo (keto, -one): =O.

Thione (thioketone): =S.

Imino (imine): =NR, wherein R is an imino substituent, for example, hydrogen, C$_{1-7}$ alkyl group, a C$_{3-20}$ heterocyclyl group, or a C$_{5-20}$ aryl group, preferably hydrogen or a C$_{1-7}$ alkyl group. Examples of ester groups include, but are not limited to, =NH, =NMe, =NEt, and =NPh.

Formyl (carbaldehyde, carboxaldehyde): —C(=O)H.

Acyl (keto): —C(=O)R, wherein R is an acyl substituent, for example, a C$_{1-7}$ alkyl group (also referred to as C$_{1-7}$ alkylacyl or C$_{1-7}$ alkanoyl), a C$_{3-20}$ heterocyclyl group (also referred to as C$_{3-20}$ heterocyclylacyl), or a C$_{5-20}$ aryl group (also referred to as C$_{5-20}$ arylacyl), preferably a C$_{1-7}$ alkyl group. Examples of acyl groups include, but are not limited to, —C(=O)CH$_3$ (acetyl), —C(=O)CH$_2$CH$_3$ (propionyl), —C(=O)O(CH$_3$)$_3$ (t-butyryl), and —C(=O)Ph (benzoyl, phenone).

Carboxy (carboxylic acid): —C(=O)OH.

Thiocarboxy (thiocarboxylic acid): —C(=S)SH.

Thiolocarboxy (thiolocarboxylic acid): —C(=O)SH.

Thionocarboxy (thionocarboxylic acid): —C(=S)OH.

Imidic acid: —C(=NH)OH.

Hydroxamic acid: —C(=NOH)OH.

Ester (carboxylate, carboxylic acid ester, oxycarbonyl): —C(=O)OR, wherein R is an ester substituent, for example, a C$_{1-7}$ alkyl group, a C$_{3-20}$ heterocyclyl group, or a C$_{5-20}$ aryl group, preferably a C$_{1-7}$ alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substituent, for example, a C$_{1-7}$ alkyl group, a C$_{3-20}$ heterocyclyl group, or a C$_{5-20}$ aryl group, preferably a C$_{1-7}$ alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Oxycarboyloxy: —OC(=O)OR, wherein R is an ester substituent, for example, a C$_{1-7}$ alkyl group, a C$_{3-20}$ heterocyclyl group, or a C$_{5-20}$ aryl group, preferably a C$_{1-7}$ alkyl group. Examples of ester groups include, but are not limited to, —OC(=O)OCH$_3$, —OC(=O)OCH$_2$CH$_3$, —OC(=O)OC(CH$_3$)$_3$, and —OC(=O)OPh.

Amino: —NR$^1$R$^2$, wherein R$^1$ and R$^2$ are independently amino substituents, for example, hydrogen, a C$_{1-7}$ alkyl group (also referred to as C$_{1-7}$ alkylamino or di-C$_{1-7}$ alkylamino), a C$_{3-20}$ heterocyclyl group, or a C$_{5-20}$ aryl group, preferably H or a C$_{1-7}$ alkyl group, or, in the case of a "cyclic" amino group, R$^1$ and R$^2$, taken together with the nitrogen atom to which they are attached, form a heterocyclic ring having from 4 to 8 ring atoms. Amino groups may be primary (—NH$_2$), secondary (—NHR$^1$), or tertiary (—NHR$^1$R$^2$), and in cationic form, may be quaternary (—$^+$NR$^1$R$^2$R$^3$). Examples of amino groups include, but are not limited to, —NH$_2$, —NHCH$_3$, —NHC(CH$_3$)$_2$, —N(CH$_3$)$_2$, —N(CH$_2$CH$_3$)$_2$, and —NHPh. Examples of cyclic amino groups include, but are not limited to, aziridino, azetidino, pyrrolidino, piperidino, piperazino, morpholino, and thiomorpholino.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinocarbonyl.

Thioamido (thiocarbamyl): —C(=S)NR$^1$R$^2$, wherein R$^1$ and R$^2$ are independently amino substituents, as defined for amino groups. Examples of amido groups include, but are not limited to, —C(=S)NH$_2$, —C(=S)NHCH$_3$, —C(=S)N(CH$_3$)$_2$, and —C(=S)NHCH$_2$CH$_3$.

Acylamido (acylamino): —NR$^1$C(=O)R$^2$, wherein R$^1$ is an amide substituent, for example, hydrogen, a C$_{1-7}$ alkyl group, a C$_{3-20}$ heterocyclyl group, or a C$_{5-20}$ aryl group, preferably hydrogen or a C$_{1-7}$ alkyl group, and R$^2$ is an acyl substituent, for example, a C$_{1-7}$ alkyl group, a C$_{3-20}$ heterocyclyl group, or a C$_{5-20}$ aryl group, preferably hydrogen or a C$_{1-7}$ alkyl group. Examples of acylamide groups include, but are not limited to, —NHC(=O)CH$_3$, —NHC(=O)CH$_2$CH$_3$, and —NHC(=O)Ph. R$^1$ and R$^2$ may together form a cyclic structure, as in, for example, succinimidyl, maleimidyl, and phthalimidyl:

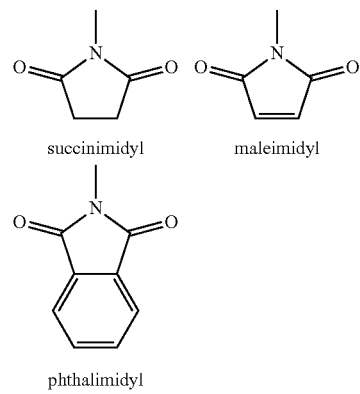

succinimidyl  maleimidyl phthalimidyl

Aminocarbonyloxy: —OC(=O)NR$^1$R$^2$, wherein R$^1$ and R$^2$ are independently amino substituents, as defined for amino groups. Examples of aminocarbonyloxy groups include, but are not limited to, —OC(=O)NH$_2$, —OC(=O)NHMe, —OC(=O)NMe$_2$, and —OC(=O)NEt$_2$.

Ureido: —N(R$^1$)CONR$^2$R$^3$ wherein R$^2$ and R$^3$ are independently amino substituents, as defined for amino groups, and R$^1$ is a ureido substituent, for example, hydrogen, a C$_{1-7}$ alkyl group, a C$_{3-20}$ heterocyclyl group, or a C$_{5-20}$ aryl group, preferably hydrogen or a C$_{1-7}$ alkyl group. Examples of ureido groups include, but are not limited to, —NHCONH$_2$, —NHCONHMe, —NHCONHEt, —NHCONMe$_2$, —NHCONEt$_2$, —NMeCONH$_2$, —NMeCONHMe, —NMeCONHEt, —NMeCONMe$_2$, and —NMeCONEt$_2$.

Guanidino: —NH—C(=NH)NH$_2$.

Tetrazolyl: a five membered aromatic ring having four nitrogen atoms and one carbon atom,

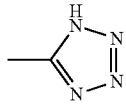

Imino: =NR, wherein R is an imino substituent, for example, for example, hydrogen, a C$_{1-7}$ alkyl group, a C$_{3-20}$ heterocyclyl group, or a C$_{5-20}$ aryl group, preferably H or a C$_{1-7}$ alkyl group. Examples of imino groups include, but are not limited to, =NH, =NMe, and =NEt.

Amidine (amidino): —C(=NR)NR$_2$, wherein each R is an amidine substituent, for example, hydrogen, a C$_{1-7}$ alkyl group, a C$_{3-20}$ heterocyclyl group, or a C$_{5-20}$ aryl group, preferably H or a C$_{1-7}$ alkyl group. Examples of amidine groups include, but are not limited to, —C(=NH)NH$_2$, —C(=NH)NMe$_2$, and —C(=NMe)NMe$_2$.

Nitro: —NO$_2$.

Nitroso: —NO.

Azido: —N$_3$.

Cyano (nitrile, carbonitrile): —CN.

Isocyano: —NC.

Cyanato: —OCN.

Isocyanato: —NCO.

Thiocyano (thiocyanato): —SCN.

Isothiocyano (isothiocyanato): —NCS.

Sulfhydryl (thiol, mercapto): —SH.

Thioether (sulfide): —SR, wherein R is a thioether substituent, for example, a C$_{1-7}$ alkyl group (also referred to as a C$_{1-7}$ alkylthio group), a C$_{3-20}$ heterocyclyl group, or a C$_{5-20}$ aryl group, preferably a C$_{1-7}$ alkyl group. Examples of C$_{1-7}$ alkylthio groups include, but are not limited to, —SCH$_3$ and —SCH$_2$CH$_3$.

Disulfide: —SS—R, wherein R is a disulfide substituent, for example, a C$_{1-7}$ alkyl group, a C$_{3-20}$ heterocyclyl group, or a C$_{5-20}$ aryl group, preferably a C$_{1-7}$ alkyl group (also referred to herein as C$_{1-7}$ alkyl disulfide). Examples of C$_{1-7}$ alkyl disulfide groups include, but are not limited to, —SSCH$_3$ and —SSCH$_2$CH$_3$.

Sulfine (sulfinyl, sulfoxide): —S(=O)R, wherein R is a sulfine substituent, for example, a C$_{1-7}$ alkyl group, a C$_{3-20}$ heterocyclyl group, or a C$_{5-20}$ aryl group, preferably a C$_{1-7}$ alkyl group. Examples of sulfine groups include, but are not limited to, —S(=O)CH$_3$ and —S(=O)CH$_2$CH$_3$.

Sulfone (sulfonyl): —S(=O)$_2$R, wherein R is a sulfone substituent, for example, a C$_{1-7}$ alkyl group, a C$_{3-20}$ heterocyclyl group, or a C$_{5-20}$ aryl group, preferably a C$_{1-7}$ alkyl group, including, for example, a fluorinated or perfluorinated C$_{1-7}$ alkyl group. Examples of sulfone groups include, but are not limited to, —S(=O)$_2$CH$_3$ (methanesulfonyl, mesyl), —S(=O)$_2$CF$_3$ (triflyl), —S(=O)$_2$CH$_2$CH$_3$ (esyl), —S(=O)$_2$C$_4$F$_9$ (nonaflyl), —S(=O)$_2$CH$_2$CF$_3$ (tresyl), —S(=O)$_2$CH$_2$CH$_2$NH$_2$ (tauryl), —S(=O)$_2$Ph (phenylsulfonyl, besyl), 4-methylphenylsulfonyl (tosyl), 4-chlorophenylsulfonyl (closyl), 4-bromophenylsulfonyl (brosyl), 4-nitrophenyl (nosyl), 2-naphthalenesulfonate (napsyl), and 5-dimethylamino-naphthalen-1-ylsulfonate (dansyl).

Sulfinic acid (sulfino): —S(=O)OH, —SO$_2$H.

Sulfonic acid (sulfo): —S(=O)$_2$OH, —SO$_3$H.

Sulfinate (sulfinic acid ester): —S(=O)OR; wherein R is a sulfinate substituent, for example, a C$_{1-7}$ alkyl group, a C$_{3-20}$ heterocyclyl group, or a C$_{5-20}$ aryl group, preferably a C$_{1-7}$ alkyl group. Examples of sulfinate groups include, but are not limited to, —S(=O)OCH$_3$ (methoxysulfinyl; methyl sulfinate) and —S(=O)OCH$_2$CH$_3$ (ethoxysulfinyl; ethyl sulfinate).

Sulfonate (sulfonic acid ester): —S(=O)$_2$OR, wherein R is a sulfonate substituent, for example, a C$_{1-7}$ alkyl group, a C$_{3-20}$ heterocyclyl group, or a C$_{5-20}$ aryl group, preferably a C$_{1-7}$ alkyl group. Examples of sulfonate groups include, but are not limited to, —S(=O)$_2$OCH$_3$ (methoxysulfonyl; methyl sulfonate) and —S(=O)$_2$OCH$_2$CH$_3$ (ethoxysulfonyl; ethyl sulfonate).

Sulfinyloxy: —OS(=O)R, wherein R is a sulfinyloxy substituent, for example, a C$_{1-7}$ alkyl group, a C$_{3-20}$ heterocyclyl group, or a C$_{5-20}$ aryl group, preferably a C$_{1-7}$ alkyl group.

Examples of sulfinyloxy groups include, but are not limited to, —OS(=O)CH$_3$ and —OS(=O)CH$_2$CH$_3$.

Sulfonyloxy: —OS(=O)$_2$R, wherein R is a sulfonyloxy substituent, for example, a C$_{1-7}$ alkyl group, a C$_{3-20}$ heterocyclyl group, or a C$_{5-20}$ aryl group, preferably a C$_{1-7}$ alkyl group. Examples of sulfonyloxy groups include, but are not limited to, —OS(=O)$_2$CH$_3$ (mesylate) and —OS(=O)$_2$CH$_2$CH$_3$ (esylate).

Sulfate: —OS(=O)$_2$OR; wherein R is a sulfate substituent, for example, a C$_{1-7}$ alkyl group, a C$_{3-20}$ heterocyclyl group, or a C$_{5-20}$ aryl group, preferably a C$_{1-7}$ alkyl group. Examples of sulfate groups include, but are not limited to, —OS(=O)$_2$OCH$_3$ and —SO(=O)$_2$OCH$_2$CH$_3$.

Sulfamyl (sulfamoyl; sulfinic acid amide; sulfinamide): —S(=O)NR$^1$R$^2$, wherein R$^1$ and R$^2$ are independently amino substituents, as defined for amino groups. Examples of sulfamyl groups include, but are not limited to, —S(=O)NH$_2$, —S(=O)NH(CH$_3$), —S(=O)N(CH$_3$)$_2$, —S(=O)NH(CH$_2$CH$_3$), —S(=O)N(CH$_2$CH$_3$)$_2$, and —S(=O)NHPh.

Sulfonamido (sulfinamoyl; sulfonic acid amide; sulfonamide): —S(=O)$_2$NR$^1$R$^2$, wherein R$^1$ and R$^2$ are independently amino substituents, as defined for amino groups. Examples of sulfonamido groups include, but are not limited to, —S(=O)$_2$NH$_2$, —S(=O)$_2$NH(CH$_3$), —S(=O)$_2$N(CH$_3$)$_2$, —S(=O)$_2$NH(CH$_2$CH$_3$), —S(=O)$_2$N(CH$_2$CH$_3$)$_2$, and —S(=O)$_2$NHPh.

Sulfamino: —NR$^1$S(=O)$_2$OH, wherein R$^1$ is an amino substituent, as defined for amino groups. Examples of sulfamino groups include, but are not limited to, —NHS(=O)$_2$OH and —N(CH$_3$)S(=O)$_2$OH.

Sulfonamino: —NR$^1$S(=O)$_2$R, wherein R$^1$ is an amino substituent, as defined for amino groups, and R is a sulfonamino substituent, for example, a C$_{1-7}$ alkyl group, a C$_{3-20}$ heterocyclyl group, or a C$_{5-20}$ aryl group, preferably a C$_{1-7}$ alkyl group. Examples of sulfonamino groups include, but are not limited to, —NHS(=O)$_2$CH$_3$ and —N(CH$_3$)S(=O)$_2$C$_6$H$_5$.

Sulfinamino: —NR$^1$S(=O)R, wherein R$^1$ is an amino substituent, as defined for amino groups, and R is a sulfinamino substituent, for example, a C$_{1-7}$ alkyl group, a C$_{3-20}$ heterocyclyl group, or a C$_{5-20}$ aryl group, preferably a C$_{1-7}$ alkyl group. Examples of sulfinamino groups include, but are not limited to, —NHS(=O)CH$_3$ and —N(CH$_3$)S(=O)C$_6$H$_5$.

Phosphino (phosphine): —PR$_2$, wherein R is a phosphino substituent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphino groups include, but are not limited to, —PH$_2$, —P(CH$_3$)$_2$, —P(CH$_2$CH$_3$)$_2$, —P(t-Bu)$_2$, and —P(Ph)$_2$.

Phospho: —P(=O)$_2$.

Phosphinyl (phosphine oxide): —P(=O)R$^2$, wherein R is a phosphinyl substituent, for example, a C$_{1-7}$ alkyl group, a C$_{3-20}$ heterocyclyl group, or a C$_{5-20}$ aryl group, preferably a C$_{1-7}$ alkyl group or a C$_{5-20}$ aryl group. Examples of phosphinyl groups include, but are not limited to, —P(=O)(CH$_3$)$_2$, —P(=O)(CH$_2$CH$_3$)$_2$, —P(=O)(t-Bu)$_2$, and —P(=O)(Ph)$_2$.

Phosphonic acid (phosphono): —P(=O)(OH)$_2$.

Phosphonate (phosphono ester): —P(=O)(OR)$_2$, where R is a phosphonate substituent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphonate groups include, but are not limited to, —P(=O)(OCH$_3$)$_2$, —P(=O)(OCH$_2$CH$_3$)$_2$, —P(=O)(O-t-Bu)$_2$, and —P(=O)(OPh)$_2$.

Phosphoric acid (phosphonooxy): —OP(=O)(OH)$_2$.

Phosphate (phosphonooxy ester): —OP(=O)(OR)$_2$, where R is a phosphate substituent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphate groups include, but are not limited to, —OP(=O)(OCH$_3$)$_2$, —OP(=O)(OCH$_2$CH$_3$)$_2$, —OP(=O)(O-t-Bu)$_2$, and —OP(=O)(OPh)$_2$.

Phosphorous acid: —OP(OH)$_2$.

Phosphite: —OP(OR)$_2$, where R is a phosphite substituent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphite groups include, but are not limited to, —OP(OCH$_3$)$_2$, —OP(OCH$_2$CH$_3$)$_2$, —OP(O-t-Bu)$_2$, and —OP(OPh)$_2$.

Phosphoramidite: —OP(OR$^1$)—NR$^2$$_2$, where R$^1$ and R$^2$ are phosphoramidite substituents, for example, —H, a (optionally substituted) C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphoramidite groups include, but are not limited to, —OP(OCH$_2$CH$_3$)—N(CH$_3$)$_2$, —OP(OCH$_2$CH$_3$)—N(i-Pr)$_2$, and —OP(OCH$_2$CH$_2$CN)—N(i-Pr)$_2$.

Phosphoramidate: —OP(=O)(OR$^1$)—NR$^2$$_2$, where R$^1$ and R$^2$ are phosphoramidate substituents, for example, —H, a (optionally substituted) C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphoramidate groups include, but are not limited to, —OP(=O)(OCH$_2$CH$_3$)—N(CH$_3$)$_2$, —OP(=O)(OCH$_2$CH$_3$)—N(i-Pr)$_2$, and —OP(=O)(OCH$_2$CH$_2$CN)—N(i-Pr)$_2$.

Alkylene

C$_{3-12}$ alkylene: The term "C$_{3-12}$ alkylene", as used herein, pertains to a bidentate moiety obtained by removing two hydrogen atoms, either both from the same carbon atom, or one from each of two different carbon atoms, of a hydrocarbon compound having from 3 to 12 carbon atoms (unless otherwise specified), which may be aliphatic or alicyclic, and which may be saturated, partially unsaturated, or fully unsaturated. Thus, the term "alkylene" includes the subclasses alkenylene, alkynylene, cycloalkylene, etc., discussed below.

Examples of linear saturated C$_{3-12}$ alkylene groups include, but are not limited to, —(CH$_2$)$_n$— where n is an integer from 3 to 12, for example, —CH$_2$CH$_2$CH$_2$— (propylene), —CH$_2$CH$_2$CH$_2$CH$_2$— (butylene), —CH$_2$CH$_2$CH$_2$CH$_2$CH$_2$— (pentylene) and —CH$_2$CH$_2$CH$_2$CH—$_2$CH$_2$CH$_2$CH$_2$— (heptylene).

Examples of branched saturated C$_{3-12}$ alkylene groups include, but are not limited to, —CH(CH$_3$)CH$_2$—, —CH(CH$_3$)CH$_2$CH$_2$—, —CH(CH$_3$)CH$_2$CH$_2$CH$_2$—, —CH$_2$CH(CH$_3$)CH$_2$—, —CH$_2$CH(CH$_3$)CH$_2$CH$_2$—, —CH(CH$_2$CH$_3$)—, —CH(CH$_2$CH$_3$)CH$_2$—, and —CH$_2$CH(CH$_2$CH$_3$)CH$_2$—.

Examples of linear partially unsaturated C$_{3-12}$ alkylene groups (C$_{3-12}$ alkenylene, and alkynylene groups) include, but are not limited to, —CH=CH—CH$_2$—, —CH$_2$—CH=CH$_2$—, —CH=CH—CH$_2$—CH$_2$—, —CH=CH—CH$_2$—CH$_2$—CH$_2$—, —CH=CH—CH=CH—, —CH=CH—CH=CH—CH$_2$—, —CH=CH—CH$_2$—CH=CH—, —CH=CH—CH$_2$—CH$_2$—, —CH=CH—CH$_2$—CH=CH—, —CH=CH—CH$_2$—CH$_2$—CH=CH—, and —CH$_2$—C≡C—CH$_2$—.

Examples of branched partially unsaturated C$_{3-12}$ alkylene groups (C$_{3-12}$ alkenylene and alkynylene groups) include, but are not limited to, —C(CH$_3$)=CH—, —C(CH$_3$)=CH—CH$_2$—, —CH=CH—CH(CH$_3$)— and —C≡C—CH(CH$_3$)—.

Examples of alicyclic saturated C$_{3-12}$ alkylene groups (C$_{3-12}$ cycloalkylenes) include, but are not limited to, cyclopentylene (e.g. cyclopent-1,3-ylene), and cyclohexylene (e.g. cyclohex-1,4-ylene).

Examples of alicyclic partially unsaturated C$_{3-12}$ alkylene groups (C$_{3-12}$ cycloalkylenes) include, but are not limited to, cyclopentenylene (e.g. 4-cyclopenten-1,3-ylene), cyclohexenylene (e.g. 2-cyclohexen-1,4-ylene; 3-cyclohexen-1,2-ylene; 2,5-cyclohexadien-1,4-ylene).

Ligand Unit

The Ligand Unit may be of any kind, and include a protein, polypeptide, peptide and a non-peptidic agent that specifically binds to a target molecule. In some embodiments, the Ligand unit may be a protein, polypeptide or peptide. In some embodiments, the Ligand unit may be a cyclic polypeptide. These Ligand units can include antibodies or a fragment of an antibody that contains at least one target molecule-binding site, lymphokines, hormones, growth factors, or any other cell binding molecule or substance that can specifically bind to a target.

The terms "specifically binds" and "specific binding" refer to the binding of an antibody or other protein, polypeptide or peptide to a predetermined molecule (e.g., an antigen).

Typically, the antibody or other molecule binds with an affinity of at least about $1\times10^7$ M$^{-1}$, and binds to the predetermined molecule with an affinity that is at least two-fold greater than its affinity for binding to a non-specific molecule (e.g., BSA, casein) other than the predetermined molecule or a closely-related molecule.

Examples of Ligand units include those agents described for use in WO 2007/085930, which is incorporated herein.

In some embodiments, the Ligand unit is a Cell Binding Agent that binds to an extracellular target on a cell. Such a Cell Binding Agent can be a protein, polypeptide, peptide or a non-peptidic agent. In some embodiments, the Cell Binding Agent may be a protein, polypeptide or peptide. In some embodiments, the Cell Binding Agent may be a cyclic polypeptide. The Cell Binding Agent also may be antibody or an antigen-binding fragment of an antibody. Thus, in one embodiment, the present invention provides an antibody-drug conjugate (ADC).

Cell Binding Agent

A cell binding agent may be of any kind, and include peptides and non-peptides. These can include antibodies or a fragment of an antibody that contains at least one binding site, lymphokines, hormones, hormone mimetics, vitamins, growth factors, nutrient-transport molecules, or any other cell binding molecule or substance.

Peptides

In one embodiment, the cell binding agent is a linear or cyclic peptide comprising 4-30, preferably 6-20, contiguous amino acid residues. In this embodiment, it is preferred that one cell binding agent is linked to one monomer or dimer pyrrolobenzodiazepine compound.

In one embodiment the cell binding agent comprises a peptide that binds integrin $\alpha_v\beta_6$. The peptide may be selective for $\alpha_v\beta_6$ over XYS.

In one embodiment the cell binding agent comprises the A20FMDV-Cys polypeptide. The A20FMDV-Cys has the sequence: NAVPNLRGDLQVLAQKVARTC. Alternatively, a variant of the A20FMDV-Cys sequence may be used wherein one, two, three, four, five, six, seven, eight, nine or ten amino acid residues are substituted with another amino acid residue. Furthermore, the polypeptide may have the sequence NAVXXXXXXXXXXXXXXXRTC.

Antibodies

The term "antibody" herein is used in the broadest sense and specifically covers monoclonal antibodies, polyclonal antibodies, dimers, multimers, multispecific antibodies (e.g., bispecific antibodies), and antibody fragments, so long as they exhibit the desired biological activity (Miller et al (2003) *Jour. of Immunology* 170:4854-4861). Antibodies may be murine, human, humanized, chimeric, or derived from other species. An antibody is a protein generated by the immune system that is capable of recognizing and binding to a specific antigen. (Janeway, C., Travers, P., Walport, M., Shlomchik (2001) *Immuno Biology*, 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin can be of any type (e.g. IgG, IgE, IgM, IgD, and IgA), class (e.g. IgG1, IgG2, IgG3, IgG4, IgA1 and IgA2) or subclass of immunoglobulin molecule. The immunoglobulins can be derived from any species, including human, murine, or rabbit origin.

"Antibody fragments" comprise a portion of a full length antibody, generally the antigen binding or variable region thereof. Examples of antibody fragments include Fab, Fab', F(ab')$_2$, and scFv fragments; diabodies; linear antibodies; fragments produced by a Fab expression library, anti-idiotypic (anti-Id) antibodies, CDR (complementary determining region), and epitope-binding fragments of any of the above which immunospecifically bind to cancer cell antigens, viral antigens or microbial antigens, single-chain antibody molecules; and multispecific antibodies formed from antibody fragments.

The term "monoclonal antibody" as used herein refers to an antibody obtained from a population of substantially homogeneous antibodies, i.e. the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al (1975) *Nature* 256:495, or may be made by recombinant DNA methods (see, U.S. Pat. No. 4,816,567). The monoclonal antibodies may also be isolated from phage antibody libraries using the techniques described in Clackson et al (1991) *Nature*, 352:624-628; Marks et al (1991) *J. Mol. Biol.*, 222:581-597 or from transgenic mice carrying a fully human immunoglobulin system (Lonberg (2008) *Curr. Opinion* 20(4):450-459).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al (1984) *Proc. Natl. Acad. Sci. USA*, 81:6851-6855). Chimeric antibodies include "primatized" antibodies comprising variable domain antigen-binding sequences derived from a non-human primate (e.g. Old World Monkey or Ape) and human constant region sequences.

An "intact antibody" herein is one comprising a VL and VH domains, as well as a light chain constant domain (CL) and heavy chain constant domains, CH1, CH2 and CH3. The constant domains may be native sequence constant domains (e.g. human native sequence constant domains) or amino acid sequence variant thereof. The intact antibody may have one or more "effector functions" which refer to those biological activities attributable to the Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; and down regulation of cell surface receptors such as B cell receptor and BCR.

Depending on the amino acid sequence of the constant domain of their heavy chains, intact antibodies can be assigned to different "classes." There are five major classes of intact antibodies: IgA, IgD, IgE, IgG, and IgM, and several of these may be further divided into "subclasses"

(isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known.

Humanisation

Techniques to reduce the in vivo immunogenicity of a non-human antibody or antibody fragment include those termed "humanisation".

A "humanized antibody" refers to a polypeptide comprising at least a portion of a modified variable region of a human antibody wherein a portion of the variable region, preferably a portion substantially less than the intact human variable domain, has been substituted by the corresponding sequence from a non-human species and wherein the modified variable region is linked to at least another part of another protein, preferably the constant region of a human antibody. The expression "humanized antibodies" includes human antibodies in which one or more complementarity determining region ("CDR") amino acid residues and/or one or more framework region ("FW" or "FR") amino acid residues are substituted by amino acid residues from analogous sites in rodent or other non-human antibodies. The expression "humanized antibody" also includes an immunoglobulin amino acid sequence variant or fragment thereof that comprises an FR having substantially the amino acid sequence of a human immunoglobulin and a CDR having substantially the amino acid sequence of a non-human immunoglobulin.

"Humanized" forms of non-human (e.g., murine) antibodies are chimeric antibodies that contain minimal sequence derived from non-human immunoglobulin. Or, looked at another way, a humanized antibody is a human antibody that also contains selected sequences from non-human (e.g. murine) antibodies in place of the human sequences. A humanized antibody can include conservative amino acid substitutions or non-natural residues from the same or different species that do not significantly alter its binding and/or biologic activity. Such antibodies are chimeric antibodies that contain minimal sequence derived from non-human immunoglobulins.

There are a range of humanisation techniques, including 'CDR grafting', 'guided selection', 'deimmunization', 'resurfacing' (also known as 'veneering'), 'composite antibodies', 'Human String Content Optimisation' and framework shuffling.

CDR Grafting

In this technique, the humanized antibodies are human immunoglobulins (recipient antibody) in which residues from a complementary-determining region (CDR) of the recipient antibody are replaced by residues from a CDR of a non-human species (donor antibody) such as mouse, rat, camel, bovine, goat, or rabbit having the desired properties (in effect, the non-human CDRs are 'grafted' onto the human framework). In some instances, framework region (FR) residues of the human immunoglobulin are replaced by corresponding non-human residues (this may happen when, for example, a particular FR residue has significant effect on antigen binding).

Furthermore, humanized antibodies can comprise residues that are found neither in the recipient antibody nor in the imported CDR or framework sequences. These modifications are made to further refine and maximize antibody performance. Thus, in general, a humanized antibody will comprise all of at least one, and in one aspect two, variable domains, in which all or all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), or that of a human immunoglobulin.

Guided Selection

The method consists of combining the $V_H$ or $V_L$ domain of a given non-human antibody specific for a particular epitope with a human $V_H$ or $V_L$ library and specific human V domains are selected against the antigen of interest. This selected human VH is then combined with a VL library to generate a completely human VH×VL combination. The method is described in Nature Biotechnology (N.Y.) 12, (1994) 899-903.

Composite Antibodies

In this method, two or more segments of amino acid sequence from a human antibody are combined within the final antibody molecule. They are constructed by combining multiple human VH and VL sequence segments in combinations which limit or avoid human T cell epitopes in the final composite antibody V regions. Where required, T cell epitopes are limited or avoided by, exchanging V region segments contributing to or encoding a T cell epitope with alternative segments which avoid T cell epitopes. This method is described in US 2008/0206239 A1.

Deimmunization

This method involves the removal of human (or other second species) T-cell epitopes from the V regions of the therapeutic antibody (or other molecule). The therapeutic antibodies V-region sequence is analysed for the presence of MHC class II-binding motifs by, for example, comparison with databases of MHC-binding motifs (such as the "motifs" database hosted at www.wehi.edu.au). Alternatively, MHC class II-binding motifs may be identified using computational threading methods such as those devised by Altuvia et al. (J. Mol. Biol. 249 244-250 (1995)); in these methods, consecutive overlapping peptides from the V-region sequences are testing for their binding energies to MHC class II proteins. This data can then be combined with information on other sequence features which relate to successfully presented peptides, such as amphipathicity, Rothbard motifs, and cleavage sites for cathepsin B and other processing enzymes.

Once potential second species (e.g. human) T-cell epitopes have been identified, they are eliminated by the alteration of one or more amino acids. The modified amino acids are usually within the T-cell epitope itself, but may also be adjacent to the epitope in terms of the primary or secondary structure of the protein (and therefore, may not be adjacent in the primary structure). Most typically, the alteration is by way of substitution but, in some circumstances amino acid addition or deletion will be more appropriate.

All alterations can be accomplished by recombinant DNA technology, so that the final molecule may be prepared by expression from a recombinant host using well established methods such as Site Directed Mutagenesis. However, the use of protein chemistry or any other means of molecular alteration is also possible.

Resurfacing

This method involves:
(a) determining the conformational structure of the variable region of the non-human (e.g. rodent) antibody (or fragment thereof) by constructing a three-dimensional model of the non-human antibody variable region;
(b) generating sequence alignments using relative accessibility distributions from x-ray crystallographic structures of a sufficient number of non-human and human antibody variable region heavy and light chains to give a set of heavy and light chain framework positions wherein the alignment positions are identical in 98% of the sufficient number of non-human antibody heavy and light chains;

(c) defining for the non-human antibody to be humanized, a set of heavy and light chain surface exposed amino acid residues using the set of framework positions generated in step (b);

(d) identifying from human antibody amino acid sequences a set of heavy and light chain surface exposed amino acid residues that is most closely identical to the set of surface exposed amino acid residues defined in step (c), wherein the heavy and light chain from the human antibody are or are not naturally paired;

(e) substituting, in the amino acid sequence of the non-human antibody to be humanized, the set of heavy and light chain surface exposed amino acid residues defined in step (c) with the set of heavy and light chain surface exposed amino acid residues identified in step (d);

(f) constructing a three-dimensional model of the variable region of the non-human antibody resulting from the substituting specified in step (e);

(g) identifying, by comparing the three-dimensional models constructed in steps (a) and (f), any amino acid residues from the sets identified in steps (c) or (d), that are within 5 Angstroms of any atom of any residue of the complementarity determining regions of the non-human antibody to be humanized; and (h) changing any residues identified in step (g) from the human to the original non-human amino acid residue to thereby define a non-human antibody humanizing set of surface exposed amino acid residues; with the proviso that step (a) need not be conducted first, but must be conducted prior to step (g).

Superhumanization

The method compares the non-human sequence with the functional human germline gene repertoire. Those human genes encoding canonical structures identical or closely related to the non-human sequences are selected. Those selected human genes with highest homology within the CDRs are chosen as FR donors. Finally, the non-human CDRs are grafted onto these human FRs. This method is described in patent WO 2005/079479 A2.

Human String Content Optimization

This method compares the non-human (e.g. mouse) sequence with the repertoire of human germline genes and the differences are scored as Human String Content (HSC) that quantifies a sequence at the level of potential MHC/T-cell epitopes. The target sequence is then humanized by maximizing its HSC rather than using a global identity measure to generate multiple diverse humanized variants (described in Molecular Immunology, 44, (2007) 1986-1998).

Framework Shuffling

The CDRs of the non-human antibody are fused in-frame to cDNA pools encompassing all known heavy and light chain human germline gene frameworks. Humanised antibodies are then selected by e.g. panning of the phage displayed antibody library. This is described in *Methods* 36, 43-60 (2005).

Examples of cell binding agents include those agents described for use in WO 2007/085930, which is incorporated herein.

Tumour-associate antigens and cognate antibodies for use in embodiments of the present invention are listed below.

Figure 4:
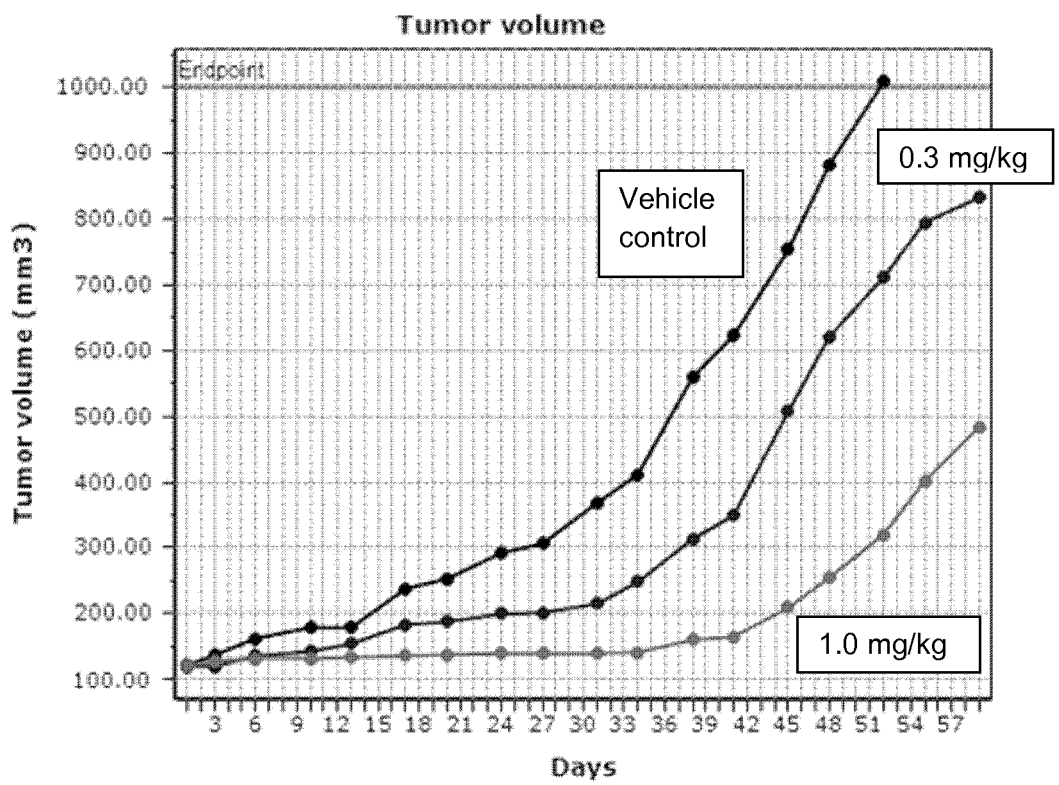
FIG. 4 shows the effect on volume of a JIMT-1 xenograft tumour following treatment with the same conjugate of the present invention as in FIG. 3.

Tumor-Associated Antigens and Cognate Antibodies (1) BMPR1B (Bone Morphogenetic Protein Receptor-Type IB)
Nucleotide
Genbank accession no. NM_001203
Genbank version no. NM_001203.2 GI:169790809
Genbank record update date: Sep. 23, 2012 02:06 PM
Polypeptide
Genbank accession no. NP_001194
Genbank version no. NP_001194.1 GI:4502431
Genbank record update date: Sep. 23, 2012 02:06 PM
Cross-References
ten Dijke, P., et al *Science* 264 (5155): 101-104 (1994), *Oncogene* 14 (11):1377-1382 (1997)); WO2004/063362 (claim 2); WO2003/042661 (Claim 12); US2003/134790-A1 (Page 38-39); WO2002/102235 (Claim 13; Page 296); WO2003/055443 (Page 91-92); WO2002/99122 (Example 2; Page 528-530); WO2003/029421 (Claim 6); WO2003/024392 (Claim 2; FIG. 112); WO2002/98358 (Claim 1; Page 183); WO2002/54940 (Page 100-101); WO2002/59377 (Page 349-350); WO2002/30268 (Claim 27; Page 376); WO2001/48204 (Example; FIG. 4); NP_001194 bone morphogenetic protein receptor, type IB/pid=NP_001194.1; MIM:603248; AY065994

Figure 3:
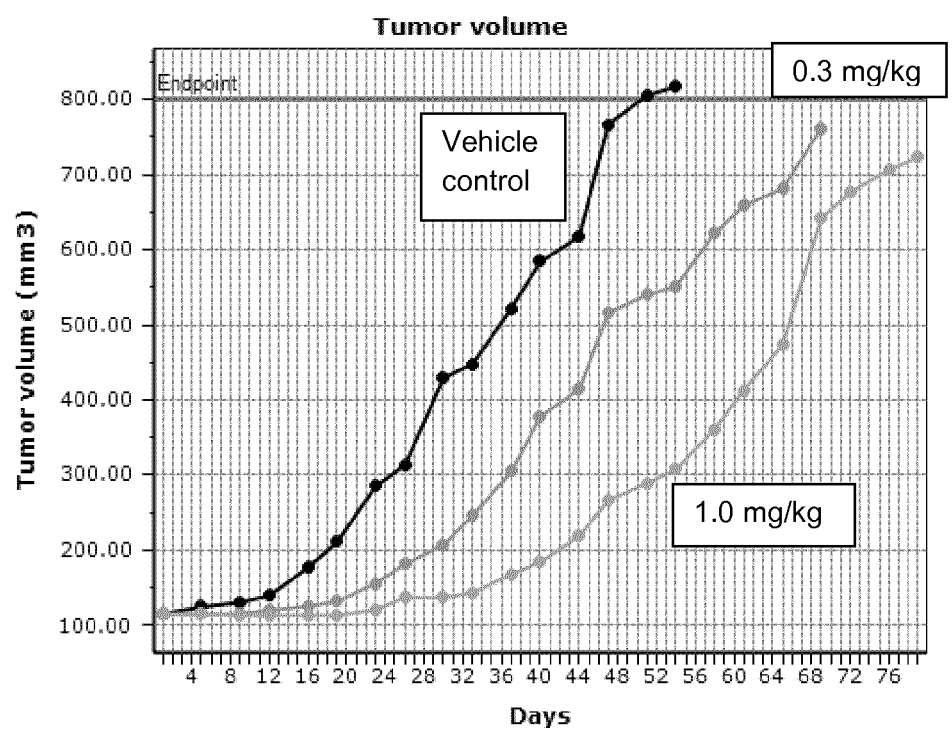
FIG. 3 shows the effect on volume of a NCI-N87 xenograft tumour following treatment with a different conjugate of the present invention.

(2) E16 (LAT1, SLC7A5)
Nucleotide
Genbank accession no. NM_003486
Genbank version no. NM_003486.5 GI:71979931
Genbank record update date: Jun. 27, 2012 12:06 PM
Polypeptide
Genbank accession no. NP_003477
Genbank version no. NP_003477.4 GI:71979932
Genbank record update date: Jun. 27, 2012 12:06 PM
Cross References
*Biochem. Biophys. Res. Commun.* 255 (2), 283-288 (1999), *Nature* 395 (6699):288-291 (1998), Gaugitsch, H. W., et al (1992) *J. Biol. Chem.* 267 (16):11267-11273); WO2004/048938 (Example 2); WO2004/032842 (Example IV); WO2003/042661 (Claim 12); WO2003/016475 (Claim 1); WO2002/78524 (Example 2); WO2002/99074 (Claim 19; Page 127-129); WO2002/86443 (Claim 27; Pages 222, 393); WO2003/003906 (Claim 10; Page 293); WO2002/64798 (Claim 33; Page 93-95); WO2000/14228 (Claim 5; Page 133-136); US2003/224454 (FIG. 3); WO2003/025138 (Claim 12; Page 150); NP_003477 solute carrier family 7 (cationic amino acid transporter, y+system), member 5/pid=NP_003477.3-*Homo sapiens*; MIM:600182; NM_015923.

Figure 2:
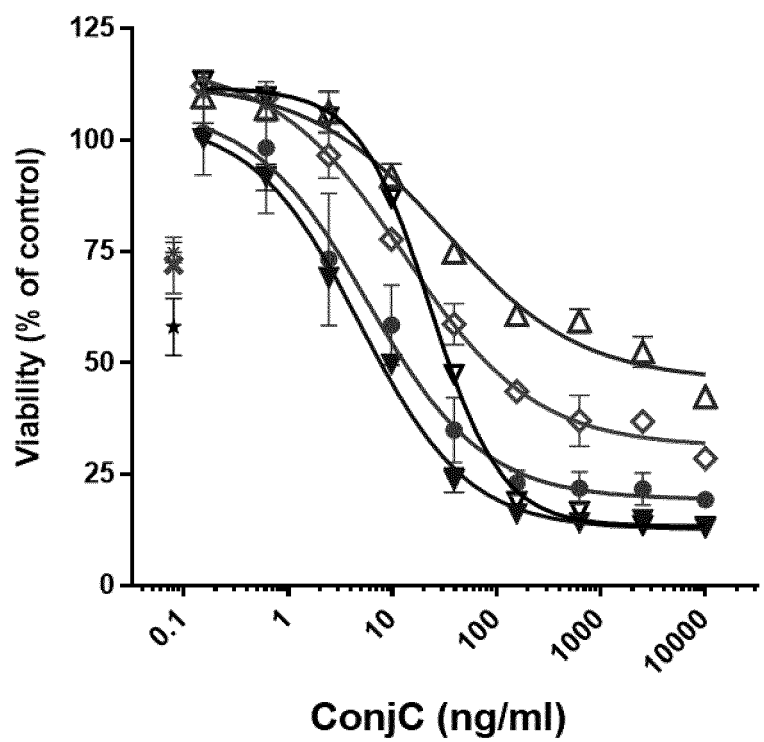
FIG. 2 shows the effect on viability of SKOV3 cells following incubation with a different conjugate of the present invention.

(3) STEAP1 (Six Transmembrane Epithelial Antigen of Prostate)
Nucleotide
Genbank accession no. NM_012449
Genbank version no. NM_012449.2 GI:22027487
Genbank record update date: Sep. 9, 2012 02:57 PM
Polypeptide
Genbank accession no. NP_036581
Genbank version no. NP_036581.1 GI:9558759
Genbank record update date: Sep. 9, 2012 02:57 PM
Cross References
*Cancer Res.* 61 (15), 5857-5860 (2001), Hubert, R. S., et al (1999) *Proc. Natl. Acad. Sci. U.S.A.* 96 (25):14523-14528); WO2004/065577 (Claim 6); WO2004/027049 (FIG. 1L); EP1394274 (Example 11); WO2004/016225 (Claim 2); WO2003/042661 (Claim 12); US2003/157089 (Example 5); US2003/185830 (Example 5); US2003/064397 (FIG. 2);

WO2002/89747 (Example 5; Page 618-619); WO2003/022995 (Example 9; FIG. 13A, Example 53; Page 173, Example 2; FIG. 2A); six transmembrane epithelial antigen of the prostate; MIM:604415.

(4) 0772P (CA125, MUC16)
Nucleotide
Genbank accession no. AF361486
Genbank version no. AF361486.3 GI:34501466
Genbank record update date: Mar. 11, 2010 07:56 AM
Polypeptide
Genbank accession no. AAK74120
Genbank version no. AAK74120.3 GI:34501467
Genbank record update date: Mar. 11, 2010 07:56 AM
Cross References
*J. Biol. Chem.* 276 (29):27371-27375 (2001)); WO2004/045553 (Claim 14); WO2002/92836 (Claim 6; FIG. 12); WO2002/83866 (Claim 15; Page 116-121); US2003/124140 (Example 16); 61:34501467;

(5) MPF (MPF, MSLN, SMR, Megakaryocyte Potentiating Factor, Mesothelin)
Nucleotide
Genbank accession no. NM_005823
Genbank version no. NM_005823.5 GI:293651528
Genbank record update date: Sep. 2, 2012 01:47 PM
Polypeptide
Genbank accession no. NP_005814
Genbank version no. NP 005814.2 GI:53988378
Genbank record update date: Sep. 2, 2012 01:47 PM
Cross References
Yamaguchi, N., et al *Biol. Chem.* 269 (2), 805-808 (1994), *Proc. Natl. Acad. Sci. U.S.A.* 96 (20):11531-11536 (1999), *Proc. Natl. Acad. Sci. U.S.A.* 93 (1):136-140 (1996), *J. Biol. Chem.* 270 (37):21984-21990 (1995)); WO2003/101283 (Claim 14); (WO2002/102235 (Claim 13; Page 287-288); WO2002/101075 (Claim 4; Page 308-309); WO2002/71928 (Page 320-321); WO94/10312 (Page 52-57); IM:601051.

(6) Napi3b (NAPI-3B, NPTIIb, SLC34A2, Solute Carrier Family 34 (Sodium Phosphate), Member 2, Type II Sodium-Dependent Phosphate Transporter 3b)
Nucleotide
Genbank accession no. NM_006424
Genbank version no. NM_006424.2 GI:110611905
Genbank record update date: Jul. 22, 2012 03:39 PM
Polypeptide
Genbank accession no. NP_006415
Genbank version no. NP_006415.2 GI:110611906
Genbank record update date: Jul. 22, 2012 03:39 PM
Cross References
*J. Biol. Chem.* 277 (22):19665-19672 (2002), *Genomics* 62 (2):281-284 (1999), Feild, J. A., et al (1999) *Biochem. Biophys. Res. Commun.* 258 (3):578-582); WO2004/022778 (Claim 2); EP1394274 (Example 11); WO2002/102235 (Claim 13; Page 326); EP0875569 (Claim 1; Page 17-19); WO2001/57188 (Claim 20; Page 329); WO2004/032842 (Example IV); WO2001/75177 (Claim 24; Page 139-140); MIM:604217.

(7) Sema 5b (FLJ10372, KIAA1445, Mm. 42015, SEMA58, SEMAG, Semaphorin 5b Hlog, Sema Domain, Seven Thrombospondin Repeats (Type 1 and Type 1-Like), Transmembrane Domain (TM) and Short Cytoplasmic Domain, (Semaphorin) 58)
Nucleotide
Genbank accession no. AB040878
Genbank version no. AB040878.1 GI:7959148
Genbank record update date: Aug. 2, 2006 05:40 PM
Polypeptide
Genbank accession no. BAA95969
Genbank version no. BAA95969.1 GI:7959149
Genbank record update date: Aug. 2, 2006 05:40 PM
Cross References
Nagase T., et al (2000) *DNA Res.* 7 (2):143-150); WO2004/000997 (Claim 1); WO2003/003984 (Claim 1); WO2002/06339 (Claim 1; Page 50); WO2001/88133 (Claim 1; Page 41-43, 48-58); WO2003/054152 (Claim 20); WO2003/101400 (Claim 11); Accession: Q9P283; Genew; HGNC: 10737

(8) PSCA hlg (2700050C12Rik, C530008O16Rik, RIKEN cDNA 2700050C12, RIKEN cDNA 2700050C12 gene)
Nucleotide
Genbank accession no. AY358628
Genbank version no. AY358628.1 GI:37182377
Genbank record update date: Dec. 1, 2009 04:15 AM
Polypeptide
Genbank accession no. AAQ88991
Genbank version no. AAQ88991.1 GI:37182378
Genbank record update date: Dec. 1, 2009 04:15 AM
Cross References
Ross et al (2002) *Cancer Res.* 62:2546-2553; US2003/129192 (Claim 2); US2004/044180 (Claim 12); US2004/044179 (Claim 11); US2003/096961 (Claim 11); US2003/232056 (Example 5); WO2003/105758 16 (Claim 12); US2003/206918 (Example 5); EP1347046 (Claim 1); WO2003/025148 (Claim 20); GI:37182378.

(9) ETBR (Endothelin Type B Receptor)
Nucleotide
Genbank accession no. AY275463
Genbank version no. AY275463.1 GI:30526094
Genbank record update date: Mar. 11, 2010 02:26 AM
Polypeptide
Genbank accession no. AAP32295
Genbank version no. AAP32295.1 GI:30526095
Genbank record update date: Mar. 11, 2010 02:26 AM
Cross References
Nakamuta M., et al *Biochem. Biophys. Res. Commun.* 177, 34-39, 1991; Ogawa Y., et al *Biochem. Biophys. Res. Commun.* 178, 248-255, 1991; Arai H., et al *Jpn. Circ. J.* 56, 1303-1307, 1992; Arai H., et al *J. Biol. Chem.* 268, 3463-3470, 1993; Sakamoto A., Yanagisawa M., et al *Biochem. Biophys. Res. Commun.* 178, 656-663, 1991; Elshourbagy N. A., et al *J. Biol. Chem.* 268, 3873-3879, 1993; Haendler B., et al *J. Cardiovasc. Pharmacol.* 20, s1-S4, 1992; Tsutsumi M., et al *Gene* 228, 43-49, 1999; Strausberg R. L., et al *Proc. Natl. Acad. Sci. U.S.A.* 99, 16899-16903, 2002; Bourgeois C., et al *J. Clin. Endocrinol. Metab.* 82, 3116-3123, 1997; Okamoto Y., et al *Biol. Chem.* 272, 21589-21596, 1997; Verheij J. B., et al *Am. J. Med. Genet.* 108, 223-225, 2002; Hofstra R. M. W., et al *Eur. J. Hum. Genet.* 5, 180-185, 1997; Puffenberger E. G., et al *Cell* 79, 1257-1266, 1994; Attie T., et al, *Hum. Mol. Genet.* 4, 2407-2409, 1995; Auricchio A., et al *Hum. Mol. Genet.* 5:351-354, 1996; Amiel J., et al *Hum. Mol. Genet.* 5, 355-357, 1996; Hofstra R. M. W., et al *Nat. Genet.* 12, 445-447, 1996; Svensson P. J., et al *Hum. Genet.* 103, 145-148, 1998; Fuchs S., et al *Mol. Med.* 7, 115-124, 2001; Pingault V., et al (2002) *Hum. Genet.* 111, 198-206; WO2004/045516 (Claim 1); WO2004/048938 (Example 2); WO2004/040000 (Claim 151); WO2003/087768 (Claim 1); WO2003/016475 (Claim 1); WO2003/016475 (Claim 1); WO2002/61087 (FIG. 1); WO2003/016494 (FIG. 6); WO2003/025138 (Claim 12; Page 144); WO2001/98351 (Claim 1; (Page 124-125); EP0522868 (Claim 8; FIG. 2); WO2001/77172 (Claim 1; Page 297-299); US2003/109676; U.S. Pat. No. 6,518,404 (FIG. 3); U.S. Pat. No. 5,773,223 (Claim 1a; Col 31-34); WO2004/001004.

(10) MSG783 (RNF124, Hypothetical Protein FLJ20315)
Nucleotide
Genbank accession no. NM_017763
Genbank version no. NM_017763.4 GI:167830482
Genbank record update date: Jul. 22, 2012 12:34 AM
Polypeptide
Genbank accession no. NP_060233
Genbank version no. NP_060233.3 GI:56711322
Genbank record update date: Jul. 22, 2012 12:34 AM
Cross References
WO2003/104275 (Claim 1); WO2004/046342 (Example 2); WO2003/042661 (Claim 12); WO2003/083074 (Claim 14; Page 61); WO2003/018621 (Claim 1); WO2003/024392 (Claim 2; FIG. 93); WO2001/66689 (Example 6); LocusID: 54894.

(11) STEAP2 (HGNC 8639, IPCA-1, PCANAP1, STAMP1, STEAP2, STMP, Prostate Cancer Associated Gene 1, Prostate Cancer Associated Protein 1, Six Transmembrane Epithelial Antigen of Prostate 2, Six Transmembrane Prostate Protein)
Nucleotide
Genbank accession no. AF455138
Genbank version no. AF455138.1 GI:22655487
Genbank record update date: Mar. 11, 2010 01:54 AM
Polypeptide
Genbank accession no. AAN04080
Genbank version no. AAN04080.1 GI:22655488
Genbank record update date: Mar. 11, 2010 01:54 AM
Cross References
Lab. Invest. 82 (11):1573-1582 (2002)); WO2003/087306; US2003/064397 (Claim 1; FIG. 1); WO2002/72596 (Claim 13; Page 54-55); WO2001/72962 (Claim 1; FIG. 4B); WO2003/104270 (Claim 11); WO2003/104270 (Claim 16); US2004/005598 (Claim 22); WO2003/042661 (Claim 12); US2003/060612 (Claim 12; FIG. 10); WO2002/26822 (Claim 23; FIG. 2); WO2002/16429 (Claim 12; FIG. 10); GI:22655488.

(12) TrpM4 (BR22450, FLJ20041, TRPM4, TRPM4B, Transient Receptor Potential Cation 5 Channel, Subfamily M, Member 4)
Nucleotide
Genbank accession no. NM_017636
Genbank version no. NM_017636.3 GI:304766649
Genbank record update date: Jun. 29, 2012 11:27 AM
Polypeptide
Genbank accession no. NP_060106
Genbank version no. NP_060106.2 GI:21314671
Genbank record update date: Jun. 29, 2012 11:27 AM
Cross References
Xu, X. Z., et al *Proc. Natl. Acad. Sci. U.S.A.* 98 (19):10692-10697 (2001), *Cell* 109 (3):397-407 (2002), *J. Biol. Chem.* 278 (33):30813-30820 (2003)); US2003/143557 (Claim 4); WO2000/40614 (Claim 14; Page 100-103); WO2002/10382 (Claim 1; FIG. 9A); WO2003/042661 (Claim 12); WO2002/30268 (Claim 27; Page 391); US2003/219806 (Claim 4); WO2001/62794 (Claim 14; FIGS. 1A-D); MIM:606936.

(13) CRIPTO (CR, CR1, CRGF, CRIPTO, TDGF1, Teratocarcinoma-Derived Growth Factor)
Nucleotide
Genbank accession no. NM_003212
Genbank version no. NM_003212.3 GI:292494881
Genbank record update date: Sep. 23, 2012 02:27 PM
Polypeptide
Genbank accession no. NP_003203
Genbank version no. NP_003203.1 GI:4507425
Genbank record update date: Sep. 23, 2012 02:27 PM
Cross References
Ciccodicola, A., et al *EMBO J.* 8 (7):1987-1991 (1989), *Am. J. Hum. Genet.* 49 (3):555-565 (1991)); US2003/224411 (Claim 1); WO2003/083041 (Example 1); WO2003/034984 (Claim 12); WO2002/88170 (Claim 2; Page 52-53); WO2003/024392 (Claim 2; FIG. 58); WO2002/16413 (Claim 1; Page 94-95, 105); WO2002/22808 (Claim 2; FIG. 1); U.S. Pat. No. 5,854,399 (Example 2; Col 17-18); U.S. Pat. No. 5,792,616 (FIG. 2); MIM:187395.

(14) CD21 (CR2 (Complement receptor 2) or C3DR (C3d/Epstein Barr virus receptor) or Hs. 73792)
Nucleotide
Genbank accession no M26004
Genbank version no. M26004.1 GI:181939
Genbank record update date: Jun. 23, 2010 08:47 AM
Polypeptide
Genbank accession no. AAA35786
Genbank version no. AAA35786.1 GI:181940
Genbank record update date: Jun. 23, 2010 08:47 AM
Cross References
Fujisaku et al (1989) *J. Biol. Chem.* 264 (4):2118-2125); Weis J. J., et al *J. Exp. Med.* 167, 1047-1066, 1988; Moore M., et al *Proc. Natl. Acad. Sci. U.S.A.* 84, 9194-9198, 1987; Barel M., et al *Mol. Immunol.* 35, 1025-1031, 1998; Weis J. J., et al *Proc. Natl. Acad. Sci. U.S.A.* 83, 5639-5643, 1986; Sinha S. K., et al (1993) *J. Immunol.* 150, 5311-5320; WO2004/045520 (Example 4); US2004/005538 (Example 1); WO2003/062401 (Claim 9); WO2004/045520 (Example 4); WO91/02536 (FIGS. 9.1-9.9); WO2004/020595 (Claim 1); Accession: P20023; Q13866; Q14212; EMBL; M26004; AAA35786.1.

(15) CD79b (CD79B, CD79β, IGb (immunoglobulin-associated beta), 829)
Nucleotide
Genbank accession no NM_000626
Genbank version no. NM_000626.2 GI:90193589
Genbank record update date: Jun. 26, 2012 01:53 PM
Polypeptide
Genbank accession no. NP_000617
Genbank version no. NP_000617.1 GI:11038674
Genbank record update date: Jun. 26, 2012 01:53 PM
Cross References
*Proc. Natl. Acad. Sci. U.S.A.* (2003) 100 (7):4126-4131, *Blood* (2002) 100 (9):3068-3076, Muller et al (1992) *Eur. J. Immunol.* 22 (6):1621-1625); WO2004/016225 (claim 2, FIG. 140); WO2003/087768, US2004/101874 (claim 1, page 102); WO2003/062401 (claim 9); WO2002/78524 (Example 2); US2002/150573 (claim 5, page 15); U.S. Pat. No. 5,644,033; WO2003/048202 (claim 1, pages 306 and 309); WO 99/58658, U.S. Pat. No. 6,534,482 (claim 13, FIGS. 17A/B); WO2000/55351 (claim 11, pages 1145-1146); MIM:147245

(16) FcRH2 (IFGP4, IRTA4, SPAP1A (SH2 Domain Containing Phosphatase Anchor Protein 51a), SPAP1B, SPAP1C)
Nucleotide
Genbank accession no NM_030764
Genbank version no. NM_030764.3 GI:227430280
Genbank record update date: Jun. 30, 2012 12:30 AM
Polypeptide
Genbank accession no. NP_110391
Genbank version no. NP_110391.2 GI:19923629
Genbank record update date: Jun. 30, 2012 12:30 AM
Cross References
AY358130); *Genome Res.* 13 (10):2265-2270 (2003), *Immunogenetics* 54 (2):87-95 (2002), *Blood* 99 (8):2662-2669 (2002), *Proc. Natl. Acad. Sci. U.S.A.* 98 (17)9772-9777 (2001), Xu, M. J., et al (2001) *Biochem. Biophys. Res.*

*Commun.* 280 (3):768-775; WO2004/016225 (Claim 2); WO2003/077836; WO2001/38490 (Claim 5; FIGS. 18D-1-18D-2); WO2003/097803 (Claim 12); WO2003/089624 (Claim 25): MIM:606509.

(17) HER2 (ErbB2)

Nucleotide

Genbank accession no M11730

Genbank version no. M11730.1 GI:183986

Genbank record update date: Jun. 23, 2010 08:47 AM

Polypeptide

Genbank accession no. AAA75493

Genbank version no. AAA75493.1 GI:306840

Genbank record update date: Jun. 23, 2010 08:47 AM

Cross References

Coussens L., et al *Science* (1985) 230(4730):1132-1139); Yamamoto T., et al *Nature* 319, 230-234, 1986; Semba K., et al *Proc. Natl. Acad. Sci. U.S.A.* 82, 6497-6501, 1985; Swiercz J. M., et al *J. Cell Biol.* 165, 869-880, 2004; Kuhns J. J., et al *J. Biol. Chem.* 274, 36422-36427, 1999; Cho H.-S., et al *Nature* 421, 756-760, 2003; Ehsani A., et al (1993) *Genomics* 15, 426-429; WO2004/048938 (Example 2); WO2004/027049 (FIG. 11); WO2004/009622; WO2003/081210; WO2003/089904 (Claim 9); WO2003/016475 (Claim 1); US2003/118592; WO2003/008537 (Claim 1); WO2003/055439 (Claim 29; FIGS. 1A-B); WO2003/025228 (Claim 37; FIG. 5C); WO2002/22636 (Example 13; Page 95-107); WO2002/12341 (Claim 68; FIG. 7); WO2002/13847 (Page 71-74); WO2002/14503 (Page 114-117); WO2001/53463 (Claim 2; Page 41-46); WO2001/41787 (Page 15); WO2000/44899 (Claim 52; FIG. 7); WO2000/20579 (Claim 3; FIG. 2); U.S. Pat. No. 5,869,445 (Claim 3; Col 31-38); WO9630514 (Claim 2; Page 56-61); EP1439393 (Claim 7); WO2004/043361 (Claim 7); WO2004/022709; WO2001/00244 (Example 3; FIG. 4); Accession: P04626; EMBL; M11767; AAA35808.1. EMBL; M11761; AAA35808.1

Antibodies

Abbott: US20110177095

For example, an antibody comprising CDRs having overall at least 80% sequence identity to CDRs having amino acid sequences of SEQ ID NO:3 (CDR-H1), SEQ ID NO:4 (CDR-H2), SEQ ID NO:5 (CDR-H3), SEQ ID NO:104 and/or SEQ ID NO:6 (CDR-L1), SEQ ID NO:7 (CDR-L2), and SEQ ID NO:8 (CDR-L3), wherein the anti-HER2 antibody or anti-HER2 binding fragment has reduced immunogenicity as compared to an antibody having a VH of SEQ ID NO:1 and a VL of SEQ ID NO:2.

Biogen: US20100119511

For example, ATCC accession numbers: PTA-10355, PTA-10356, PTA-10357, PTA-10358

For example, a purified antibody molecule that binds to HER2 comprising a all six CDR's from an antibody selected from the group consisting of BIIB71F10 (SEQ ID NOs:11, 13), BIIB69A09 (SEQ ID NOs:15, 17); BIIB67F10 (SEQ ID NOs:19, 21); BIIB67F11 (SEQ ID NOs:23, 25), BIIB66A12 (SEQ ID NOs:27, 29), BIIB66C01 (SEQ ID NOs:31, 33), BIIB65C10 (SEQ ID NOs:35, 37), BIIB65H09 (SEQ ID NOs:39, 41) and BIIB65B03 (SEQ ID NOs:43, 45), or CDRs which are identical or which have no more than two alterations from said CDRs.

Herceptin (Genentech)—U.S. Pat. No. 6,054,297; ATCC accession no. CRL-10463 (Genentech)

Pertuzumab (Genentech)

US20110117097 for example, see SEQ IDs No. 15&16, SEQ IDs No. 17&18, SEQ IDs No. 23&24 & ATCC accession numbers HB-12215, HB-12216, CRL 10463, HB-12697.

US20090285837

US20090202546 for example, ATCC accession numbers: HB-12215, HB-12216, CRL 10463, HB-12698.

US20060088523 for example, ATCC accession numbers: HB-12215, HB-12216 for example, an antibody comprising the variable light and variable heavy amino acid sequences in SEQ ID Nos. 3 and 4, respectively.

for example, an antibody comprising a light chain amino acid sequence selected from SEQ ID No. 15 and 23, and a heavy chain amino acid sequence selected from SEQ ID No. 16 and 24

US20060018899 for example, ATCC accession numbers: (7C2) HB-12215, (7F3) HB-12216, (4D5) CRL-10463, (2C4) HB-12697.

for example, an antibody comprising the amino acid sequence in SEQ ID No. 23, or a deamidated and/or oxidized variant thereof.

US2011/0159014 for example, an antibody having a light chain variable domain comprising the hypervariable regions of SEQ ID NO: 1".

For example, an antibody having a heavy chain variable domain comprising the hypervariable regions of SEQ ID NO: 2.

US20090187007

Glycotope: TrasGEX antibody http://www.glycotope.com/pipeline

For example, see International Joint Cancer Institute and Changhai Hospital Cancer Cent: HMTI-Fc Ab—Gao J., et al *BMB Rep.* 2009 Oct. 31; 42(10):636-41.

Symphogen: US20110217305

Union Stem Cell & Gene Engineering, China—Liu HQ., et al *Xi Bao Yu Fen Zi Mian Yi Xue Za Zhi*. 2010 May; 26(5):456-8.

(18) NCA (CEACAM6)

Nucleotide

Genbank accession no M18728

Genbank version no. M18728.1 GI:189084

Genbank record update date: Jun. 23, 2010 08:48 AM

Polypeptide

Genbank accession no. AAA59907

Genbank version no. AAA59907.1 GI:189085

Genbank record update date: Jun. 23, 2010 08:48 AM

Cross References

Barnett T., et al *Genomics* 3, 59-66, 1988; Tawaragi Y., et al *Biochem. Biophys. Res. Commun.* 150, 89-96, 1988; Strausberg R. L., et al *Proc. Natl. Acad. Sci. U.S.A.* 99:16899-16903, 2002; WO2004/063709; EP1439393 (Claim 7); WO2004/044178 (Example 4); WO2004/031238; WO2003/042661 (Claim 12); WO2002/78524 (Example 2); WO2002/86443 (Claim 27; Page 427); WO2002/60317 (Claim 2); Accession: P40199; Q14920; EMBL; M29541; AAA59915.1. EMBL; M18728.

(19) MDP (DPEP1)
Nucleotide
Genbank accession no BC017023
Genbank version no. BC017023.1 GI:16877538
Genbank record update date: Mar. 6, 2012 01:00 PM
Polypeptide
Genbank accession no. AAH17023
Genbank version no. AAH17023.1 GI: 6877539
Genbank record update date: Mar. 6, 2012 01:00 PM
Cross References
*Proc. Natl. Acad. Sci. U.S.A.* 99 (26):16899-16903 (2002)); WO2003/016475 (Claim 1); WO2002/64798 (Claim 33; Page 85-87); JP05003790 (FIG. 6-8); WO99/46284 (FIG. 9); MIM:179780.
(20) IL20R-alpha (IL20Ra, ZCYTOR7)
Nucleotide
Genbank accession no AF184971
Genbank version no. AF184971.1 GI:6013324
Genbank record update date: Mar. 10, 2010 10:00 PM
Polypeptide
Genbank accession no. AAF01320
Genbank version no. AAF01320.1 GI:6013325
Genbank record update date: Mar. 10, 2010 10:00 PM
Cross References
Clark H. F., et al *Genome Res.* 13, 2265-2270, 2003; Mungall A. J., et al *Nature* 425, 805-811, 2003; Blumberg H., et al *Cell* 104, 9-19, 2001; Dumoutier L., et al *J. Immunol.* 167, 3545-3549, 2001; Parrish-Novak J., et al *J. Biol. Chem.* 277, 47517-47523, 2002; Pletnev S., et al (2003) *Biochemistry* 42:12617-12624; Sheikh F., et al (2004) *J. Immunol.* 172, 2006-2010; EP1394274 (Example 11); US2004/005320 (Example 5); WO2003/029262 (Page 74-75); WO2003/002717 (Claim 2; Page 63); WO2002/22153 (Page 45-47); US2002/042366 (Page 20-21); WO2001/46261 (Page 57-59); WO2001/46232 (Page 63-65); WO98/37193 (Claim 1; Page 55-59); Accession: Q9UHF4; Q6UWA9; Q96SH8; EMBL; AF184971; AAF01320.1.
(21) Brevican (BCAN, BEHAB)
Nucleotide
Genbank accession no AF229053
Genbank version no. AF229053.1 GI:10798902
Genbank record update date: Mar. 11, 2010 12:58 AM
Polypeptide
Genbank accession no. AAG23135
Genbank version no. AAG23135.1 GI:10798903
Genbank record update date: Mar. 11, 2010 12:58 AM
Cross References
Gary S. C., et al *Gene* 256, 139-147, 2000; Clark H. F., et al *Genome Res.* 13, 2265-2270, 2003; Strausberg R. L., et al *Proc. Natl. Acad. Sci. U.S.A.* 99, 16899-16903, 2002; US2003/186372 (Claim 11); US2003/186373 (Claim 11); US2003/119131 (Claim 1; FIG. 52); US2003/119122 (Claim 1; FIG. 52); US2003/119126 (Claim 1); US2003/119121 (Claim 1; FIG. 52); US2003/119129 (Claim 1); US2003/119130 (Claim 1); US2003/119128 (Claim 1; FIG. 52); US2003/119125 (Claim 1); WO2003/016475 (Claim 1); WO2002/02634 (Claim 1)
(22) EphB2R (DRT, ERK, Hek5, EPHT3, Tyro5)
Nucleotide
Genbank accession no NM_004442
Genbank version no. NM_004442.6 GI:111118979
Genbank record update date: Sep. 8, 2012 04:43 PM
Polypeptide
Genbank accession no. NP_004433
Genbank version no. NP_004433.2 GI:21396504
Genbank record update date: Sep. 8, 2012 04:43 PM
Cross References
Chan, J. and Watt, V. M., Oncogene 6 (6), 1057-1061 (1991) Oncogene 10 (5):897-905 (1995), Annu. Rev. Neurosci. 21:309-345 (1998), Int. Rev. Cytol. 196:177-244 (2000)); WO2003042661 (Claim 12); WO200053216 (Claim 1; Page 41); WO2004065576 (Claim 1); WO2004020583 (Claim 9); WO2003004529 (Page 128-132); WO200053216 (Claim 1; Page 42); MIM:600997.
(23) ASLG659 (B7 h)
Nucleotide
Genbank accession no. AX092328
Genbank version no. AX092328.1 GI:13444478
Genbank record update date: Jan. 26, 2011 07:37 AM
Cross References
US2004/0101899 (Claim 2); WO2003104399 (Claim 11); WO2004000221 (FIG. 3); US2003/165504 (Claim 1); US2003/124140 (Example 2); US2003/065143 (FIG. 60); WO2002/102235 (Claim 13; Page 299); US2003/091580 (Example 2); WO2002/10187 (Claim 6; FIG. 10); WO2001/94641 (Claim 12; FIG. 7b); WO2002/02624 (Claim 13; FIGS. 1A-1B); US2002/034749 (Claim 54; Page 45-46); WO2002/06317 (Example 2; Page 320-321, Claim 34; Page 321-322); WO2002/71928 (Page 468-469); WO2002/02587 (Example 1; FIG. 1); WO2001/40269 (Example 3; Pages 190-192); WO2000/36107 (Example 2; Page 205-207); WO2004/053079 (Claim 12); WO2003/004989 (Claim 1); WO2002/71928 (Page 233-234, 452-453); WO 01/16318.
(24) PSCA (Prostate Stem Cell Antigen Precursor)
Nucleotide
Genbank accession no AJ297436
Genbank version no. AJ297436.1 GI:9367211
Genbank record update date: Feb. 1, 2011 11:25 AM
Polypeptide
Genbank accession no. CAB97347
Genbank version no. CAB97347.1 GI:9367212
Genbank record update date: Feb. 1, 2011 11:25 AM
Cross References
Reiter R. E., et al *Proc. Natl. Acad. Sci. U.S.A.* 95, 1735-1740, 1998; Gu Z., et al *Oncogene* 19, 1288-1296, 2000; *Biochem. Biophys. Res. Commun.* (2000) 275(3):783-788; WO2004/022709; EP1394274 (Example 11); US2004/018553 (Claim 17); WO2003/008537 (Claim 1); WO2002/81646 (Claim 1; Page 164); WO2003/003906 (Claim 10; Page 288); WO2001/40309 (Example 1; FIG. 17); US2001/055751 (Example 1; FIG. 1b); WO2000/32752 (Claim 18; FIG. 1); WO98/51805 (Claim 17; Page 97); WO98/51824 (Claim 10; Page 94); WO98/40403 (Claim 2; FIG. 1B); Accession: 043653; EMBL; AF043498; AAC39607.1
(25) GEDA
Nucleotide
Genbank accession no AY260763
Genbank version no. AY260763.1 GI:30102448
Genbank record update date: Mar. 11, 2010 02:24 AM
Polypeptide
Genbank accession no. AAP14954
Genbank version no. AAP14954.1 GI:30102449
Genbank record update date: Mar. 11, 2010 02:24 AM
Cross References
AP14954 lipoma HMGIC fusion-partnerlike protein/pid=AAP14954.1-*Homo sapiens* (human); WO2003/054152 (Claim 20); WO2003/000842 (Claim 1); WO2003/023013 (Example 3, Claim 20); US2003/194704 (Claim 45); GI:30102449;

(26) BAFF-R (B Cell-Activating Factor Receptor, BLyS Receptor 3, BR3)
Nucleotide
Genbank accession no AF116456
Genbank version no. AF116456.1 GI:4585274
Genbank record update date: Mar. 10, 2010 09:44 PM
Polypeptide
Genbank accession no. AAD25356
Genbank version no. AAD25356.1 GI:4585275
Genbank record update date: Mar. 10, 2010 09:44 PM
Cross References
BAFF receptor/pid=NP_443177.1-*Homo sapiens*: Thompson, J. S., et al *Science* 293 (5537), 2108-2111 (2001); WO2004/058309; WO2004/011611; WO2003/045422 (Example; Page 32-33); WO2003/014294 (Claim 35; FIG. 6B); WO2003/035846 (Claim 70; Page 615-616); WO2002/94852 (Col 136-137); WO2002/38766 (Claim 3; Page 133); WO2002/24909 (Example 3; FIG. 3); MIM:606269; NP_443177.1; NM_052945_1; AF132600

(27) CD22 (B-Cell Receptor CD22-Bisoform, BL-CAM, Lyb-8, Lyb8, SIGLEC-2, FLJ22814)
Nucleotide
Genbank accession no AK026467
Genbank version no. AK026467.1 GI:10439337
Genbank record update date: Sep. 11, 2006 11:24 PM
Polypeptide
Genbank accession no. BAB15489
Genbank version no. BAB15489.1 GI:10439338
Genbank record update date: Sep. 11, 2006 11:24 PM
Cross References
Wilson et al (1991) *J. Exp. Med.* 173:137-146; WO2003/072036 (Claim 1; FIG. 1); IM:107266; NP_001762.1; NM_0017711.

(27a) CD22 (CD22 Molecule)
Nucleotide
Genbank accession no X52785
Genbank version no. X52785.1 GI:29778
Genbank record update date: Feb. 2, 2011 10:09 AM
Polypeptide
Genbank accession no. CAA36988
Genbank version no. CAA36988.1 GI:29779
Genbank record update date: Feb. 2, 2011 10:09 AM
Cross References
Stamenkovic I. et al., *Nature* 345 (6270), 74-77 (1990)
Other Information
Official Symbol: CD22
Other Aliases: SIGLEC-2, SIGLEC2
Other Designations: B-cell receptor CD22; B-lymphocyte cell adhesion molecule; BL-CAM; CD22 antigen; T-cell surface antigen Leu-14; sialic acid binding Ig-like lectin 2; sialic acid-binding Ig-like lectin 2
Antibodies
G5/44 (Inotuzumab): DiJoseph J F., et al *Cancer. Immunol Immunother.* 2005 January; 54(1):11-24.
Epratuzumab-Goldenberg D M., et al *Expert Rev Anticancer Ther.* 6(10): 1341-53, 2006.

(28) CD79a (CD79A, CD79alpha), Immunoglobulin-Associated Alpha, a B Cell-Specific Protein that Covalently Interacts with Ig Beta (CD79B) and Forms a Complex on the Surface with Ig M Molecules, Transduces a Signal Involved in B-Cell Differentiation), pI: 4.84, MW: 25028 TM: 2 [P] *Gene Chromosome:* 19q13.2).
Nucleotide
Genbank accession no NM_001783
Genbank version no. NM_001783.3 GI:90193587
Genbank record update date: Jun. 26, 2012 01:48 PM
Polypeptide
Genbank accession no. NP_001774
Genbank version no. NP_001774.1 GI:4502685
Genbank record update date: Jun. 26, 2012 01:48 PM
Cross References
WO2003/088808, US2003/0228319; WO2003/062401 (claim 9); US2002/150573 (claim 4, pages 13-14); WO99/58658 (claim 13, FIG. 16); WO92/07574 (FIG. 1); U.S. Pat. No. 5,644,033; Ha et al (1992) *J. Immunol.* 148(5):1526-1531; Müller et al (1992) *Eur. J. Immunol.* 22:1621-1625; Hashimoto et al (1994) *Immunogenetics* 40(4):287-295; Preud'homme et al (1992) *Clin. Exp. Immunol.* 90(1):141-146; Yu et al (1992) *J. Immunol.* 148(2) 633-637; Sakaguchi et al (1988) *EMBO J.* 7(11):3457-3464

(29) CXCR5 (Burkitt's Lymphoma Receptor 1, a G Protein-Coupled Receptor that is Activated by the CXCL13 Chemokine, Functions in Lymphocyte Migration and Humoral Defense, Plays a Role in HIV-2 Infection and Perhaps Development of AIDS, Lymphoma, Myeloma, and Leukemia); 372 aa, pI: 8.54 MW: 41959 TM: 7 [P] *Gene Chromosome:* 11q23.3,
Nucleotide
Genbank accession no NM_001716
Genbank version no. NM_001716.4 GI:342307092
Genbank record update date: Sep. 30, 2012 01:49 PM
Polypeptide
Genbank accession no. NP_001707
Genbank version no. NP_001707.1 GI:4502415
Genbank record update date: Sep. 30, 2012 01:49 PM
Cross References
WO2004/040000; WO2004/015426; US2003/105292 (Example 2); U.S. Pat. No. 6,555,339 (Example 2); WO2002/61087 (FIG. 1); WO2001/57188 (Claim 20, page 269); WO2001/72830 (pages 12-13); WO2000/22129 (Example 1, pages 152-153, Example 2, pages 254-256); WO99/28468 (claim 1, page 38); U.S. Pat. No. 5,440,021 (Example 2, col 49-52); WO94/28931 (pages 56-58); WO92/17497 (claim 7, FIG. 5); Dobner et al (1992) *Eur. J. Immunol.* 22:2795-2799; Barella et al (1995) *Biochem. J.* 309:773-779

(30) HLA-DOB (Beta Subunit of MHC Class II Molecule (La Antigen) that Binds Peptides and Presents them to CD4+ T Lymphocytes); 273 aa, pI: 6.56, MW: 30820. TM: 1 [P] *Gene Chromosome:* 6p21.3)
Nucleotide
Genbank accession no NM_002120
Genbank version no. NM_002120.3 GI:118402587
Genbank record update date: Sep. 8, 2012 04:46 PM
Polypeptide
Genbank accession no. NP 002111
Genbank version no. NP_002111.1 GI:4504403
Genbank record update date: Sep. 8, 2012 04:46 PM
Cross References
Tonnelle et al (1985) *EMBO J.* 4(11):2839-2847; Jonsson et al (1989) *Immunogenetics* 29(6):411-413; Beck et al (1992) *J. Mol. Biol.* 228:433-441; Strausberg et al (2002) *Proc. Natl. Acad. Sci USA* 99:16899-16903; Servenius et al (1987) *J. Biol. Chem.* 262:8759-8766; Beck et al (1996) *J. Mol. Biol.* 255:1-13; Naruse et al (2002) *Tissue Antigens* 59:512-519; WO99/58658 (claim 13, FIG. 15); U.S. Pat. No. 6,153,408 (Col 35-38); U.S. Pat. No. 5,976,551 (col 168-170); U.S. Pat. No. 6,011,146 (col 145-146); Kasahara et al (1989) *Immunogenetics* 30(1):66-68; Larhammar et al (1985) *J. Biol. Chem.* 260(26):14111-14119

(31) P2X5 (Purinergic Receptor P2X Ligand-Gated Ion Channel 5, an Ion Channel Gated by Extracellular ATP, May be Involved in Synaptic Transmission and Neurogenesis, Deficiency May Contribute to the Pathophysiology of Idiopathic Detrusor Instability); 422 Aa), pI: 7.63, MW: 47206 TM: 1 [P] *Gene Chromosome:* 17p13.3).
Nucleotide
Genbank accession no NM_002561
Genbank version no. NM_002561.3 GI:325197202
Genbank record update date: Jun. 27, 2012 12:41 AM
Polypeptide
Genbank accession no. NP 002552
Genbank version no. NP_002552.2 GI:28416933
Genbank record update date: Jun. 27, 2012 12:41 AM
Cross References
Le et al (1997) *FEBS Lett.* 418(1-2):195-199; WO2004/047749; WO2003/072035 (claim 10); Touchman et al (2000) *Genome Res.* 10:165-173; WO2002/22660 (claim 20); WO2003/093444 (claim 1); WO2003/087768 (claim 1); WO2003/029277 (page 82)

(32) CD72 (B-Cell Differentiation Antigen CD72, Lyb-2); 359 Aa, pI: 8.66, MW: 40225, TM: 1 5 [P] *Gene Chromosome:* 9p13.3).
Nucleotide
Genbank accession no NM_001782
Genbank version no. NM_001782.2 GI:194018444
Genbank record update date: Jun. 26, 2012 01:43 PM
Polypeptide
Genbank accession no. NP_001773
Genbank version no. NP_001773.1 GI:4502683
Genbank record update date: Jun. 26, 2012 01:43 PM
Cross References
WO2004042346 (claim 65); WO2003/026493 (pages 51-52, 57-58); WO2000/75655 (pages 105-106); Von Hoegen et al (1990) *J. Immunol.* 144(12):4870-4877; Strausberg et al (2002) *Proc. Natl. Acad. Sci USA* 99:16899-16903.

(33) LY64 (Lymphocyte Antigen 64 (RP105), Type I Membrane Protein of the Leucine Rich Repeat (LRR) Family, Regulates B-Cell Activation and Apoptosis, Loss of Function is Associated with Increased Disease Activity in Patients with Systemic Lupus Erythematosis); 661 aa, pI: 6.20, MW: 74147 TM: 1 [P] *Gene Chromosome:* 5q12).
Nucleotide
Genbank accession no NM_005582
Genbank version no. NM_005582.2 GI:167555126
Genbank record update date: Sep. 2, 2012 01:50 PM
Polypeptide
Genbank accession no. NP 005573
Genbank version no. NP_005573.2 GI:167555127
Genbank record update date: Sep. 2, 2012 01:50 PM
Cross References
US2002/193567; WO97/07198 (claim 11, pages 39-42); Miura et al (1996) *Genomics* 38(3):299-304; Miura et al (1998) *Blood* 92:2815-2822; WO2003/083047; WO97/44452 (claim 8, pages 57-61); WO2000/12130 (pages 24-26).

(34) FcRH1 (Fc Receptor-Like Protein 1, a Putative Receptor for the Immunoglobulin Fc Domain that Contains C2 Type Ig-Like and ITAM Domains, May have a Role in B-Lymphocyte Differentiation); 429 aa, pI: 5.28, MW: 46925 TM: 1 [P] *Gene Chromosome:* 1q21-1q22)
Nucleotide
Genbank accession no NM_052938
Genbank version no. NM_052938.4 GI:226958543
Genbank record update date: Sep. 2, 2012 01:43 PM
Polypeptide
Genbank accession no. NP_443170
Genbank version no. NP_443170.1 GI:16418419
Genbank record update date: Sep. 2, 2012 01:43 PM
Cross References
WO2003/077836; WO2001/38490 (claim 6, FIGS. 18E-1-18-E-2); Davis et al (2001) *Proc. Natl. Acad. Sci USA* 98(17):9772-9777; WO2003/089624 (claim 8); EP1347046 (claim 1); WO2003/089624 (claim 7).

(35) IRTA2 (Immunoglobulin Superfamily Receptor Translocation Associated 2, a Putative Immunoreceptor with Possible Roles in B Cell Development and Lymphoma Genesis; Deregulation of the Gene by Translocation Occurs in Some B Cell Malignancies); 977 aa, pI: 6.88, MW: 106468, TM: 1 [P] *Gene Chromosome:* 1q21)
Nucleotide
Genbank accession no AF343662
Genbank version no. AF343662.1 GI:13591709
Genbank record update date: Mar. 11, 2010 01:16 AM
Polypeptide
Genbank accession no. AAK31325
Genbank version no. AAK31325.1 GI:13591710
Genbank record update date: Mar. 11, 2010 01:16 AM
Cross References
AF343663, AF343664, AF343665, AF369794, AF397453, AK090423, AK090475, AL834187, AY358085; Mouse: AK089756, AY158090, AY506558; NP_112571.1; WO2003/024392 (claim 2, FIG. 97); Nakayama et al (2000) *Biochem. Biophys. Res. Commun.* 277(1):124-127; WO2003/077836; WO2001/38490 (claim 3, FIG. 18B-1-18B-2).

(36) TENB2 (TMEFF2, Tomoregulin, TPEF, HPP1, TR, Putative Transmembrane Proteoglycan, Related to the EGF/Heregulin Family of Growth Factors and Follistatin); 374 aa)
Nucleotide
Genbank accession no AF179274
Genbank version no. AF179274.2 GI:12280939
Genbank record update date: Mar. 11, 2010 01:05 AM
Polypeptide
Genbank accession no. AAD55776
Genbank version no. AAD55776.2 GI:12280940
Genbank record update date: Mar. 11, 2010 01:05 AM
Cross References
NCBI Accession: AAD55776, AAF91397, AAG49451, NCBI RefSeq: NP_057276; NCBI Gene: 23671; OMIM: 605734; SwissProt Q9UIK5; AY358907, CAF85723, CQ782436; WO2004/074320; JP2004113151; WO2003/042661; WO2003/009814; EP1295944 (pages 69-70); WO2002/30268 (page 329); WO2001/90304; US2004/249130; US2004/022727; WO2004/063355; US2004/197325; US2003/232350; US2004/005563; US2003/124579; Horie et al (2000) *Genomics* 67:146-152; Uchida et al (1999) *Biochem. Biophys. Res. Commun.* 266:593-602; Liang et al (2000) *Cancer Res.* 60:4907-12; Glynne-Jones et al (2001) *Int J Cancer.* October 15; 94(2):178-84.

(37) PSMA—FOLH1 (Folate Hydrolase (Prostate-Specific Membrane Antigen) 1)
Nucleotide
Genbank accession no M99487
Genbank version no. M99487.1 GI:190663
Genbank record update date: Jun. 23, 2010 08:48 AM
Polypeptide
Genbank accession no. AAA60209
Genbank version no. AAA60209.1 GI:190664
Genbank record update date: Jun. 23, 2010 08:48 AM Cross References
Israeli R. S., et al *Cancer Res.* 53 (2), 227-230 (1993)
Other Information
Official Symbol: FOLH1
Other Aliases: GIG27, FGCP, FOLH, GCP2, GCPII, NAALAD1, NAALAdase, PSM, PSMA, mGCP
Other Designations: N-acetylated alpha-linked acidic dipeptidase 1; N-acetylated-alpha-linked acidic dipeptidase I; NAALADase I; cell growth-inhibiting gene 27 protein; folylpoly-gamma-glutamate carboxypeptidase; glutamate carboxylase II; glutamate carboxypeptidase 2; glutamate carboxypeptidase II; membrane glutamate carboxypeptidase; prostate specific membrane antigen variant F; pteroyl-poly-gamma-glutamate carboxypeptidase
Antibodies
U.S. Pat. No. 7,666,425:
Antibodies produces by Hybridomas having the following ATCC references: ATCC accession No. HB-12101, ATCC accession No. HB-12109, ATCC accession No. HB-12127 and ATCC accession No. HB-12126.
Proscan: a monoclonal antibody selected from the group consisting of 8H12, 3E11, 17G1, 2964, 30C1 and 20F2 (U.S. Pat. No. 7,811,564; Moffett S., et al Hybridoma (Larchmt). 2007 December; 26(6):363-72).
Cytogen: monoclonal antibodies 7E11-05 (ATCC accession No. HB 10494) and 9H10-A4 (ATCC accession No. H611430)—U.S. Pat. No. 5,763,202
GlycoMimetics: NUH2—ATCC accession No. HB 9762 (U.S. Pat. No. 7,135,301)
Human Genome Science: HPRAJ70-ATCC accession No. 97131 (U.S. Pat. No. 6,824,993); Amino acid sequence encoded by the cDNA clone (HPRAJ70) deposited as American Type Culture Collection ("ATCC") Deposit No. 97131
Medarex: Anti-PSMA antibodies that lack fucosyl residues—U.S. Pat. No. 7,875,278
Mouse anti-PSMA antibodies include the 3F5.4G6, 3D7.1.1, 4E10-1.14, 3E11, 4D8, 3E6, 3C9, 2C7, 1G3, 3C4, 3C6, 4D4, 1G9, 5C869, 3G6, 4C8B9, and monoclonal antibodies. Hybridomas secreting 3F5.4G6, 3D7.1.1, 4E10-1.14, 3E11, 4D8, 3E6, 3C9, 2C7, 1G3, 3C4, 3C6, 4D4, 1G9, 5C8B9, 3G6 or 4C8B9 have been publicly deposited and are described in U.S. Pat. No. 6,159,508. Relevant hybridomas have been publicly deposited and are described in U.S. Pat. No. 6,107,090. Moreover, humanized anti-PSMA antibodies, including a humanized version of J591, are described in further detail in PCT Publication WO 02/098897.
Other mouse anti-human PSMA antibodies have been described in the art, such as mAb 107-1A4 (Wang, S. et al. (2001) Int. J. Cancer 92:871-876) and mAb 2C9 (Kato, K. et al. (2003) Int. J. Urol. 10:439-444).
Examples of human anti-PSMA monoclonal antibodies include the 4A3, 7F12, 8C12, 8A11, 16F9, 2A10, 2C6, 2F5 and 1C3 antibodies, isolated and structurally characterized as originally described in PCT Publications WO 01/09192 and WO 03/064606 and in U.S. Provisional Application Ser. No. 60/654,125, entitled "Human Monoclonal Antibodies to Prostate Specific Membrane Antigen (PSMA)", filed on Feb. 18, 2005. The V.sub.H amino acid sequences of 4A3, 7F12, 8C12, 8A11, 16F9, 2A10, 2C6, 2F5 and 1C3 are shown in SEQ ID NOs: 1-9, respectively. The V.sub.L amino acid sequences of 4A3, 7F12, 8C12, 8A11, 16F9, 2A10, 2C6, 2F5 and 1C3 are shown in SEQ ID NOs: 10-18, respectively. Other human anti-PSMA antibodies include the antibodies disclosed in PCT Publication WO 03/034903 and US Application No. 2004/0033229.

NW Biotherapeutics: A hybridoma cell line selected from the group consisting of 3F5.4G6 having ATCC accession number HB12060, 3D7-1.1. having ATCC accession number HB12309, 4E10-1.14 having ATCC accession number HB12310, 3E11 (ATCC HB12488), 4D8 (ATCC HB12487), 3E6 (ATCC HB12486), 3C9 (ATCC HB12484), 2C7 (ATCC HB12490), 1G3 (ATCC HB12489), 3C4 (ATCC HB12494), 3C6 (ATCC HB12491), 4D4 (ATCC HB12493), 1G9 (ATCC HB12495), 5C8B9 (ATCC HB12492) and 3G6 (ATCC HB12485)—see U.S. Pat. No. 6,150,508
PSMA Development Company/Progenics/Cytogen—Seattle Genetics: mAb 3.9, produced by the hybridoma deposited under ATCC Accession No. PTA-3258 or mAb 10.3, produced by the hybridoma deposited under ATCC Accession No. PTA-3347—U.S. Pat. No. 7,850,971
PSMA Development Company—Compositions of PSMA antibodies (US 20080286284, Table 1)
This application is a divisional of U.S. patent application Ser. No. 10/395,894, filed on Mar. 21, 2003 (U.S. Pat. No. 7,850,971)
University Hospital Freiburg, Germany—mAbs 3/A12, 3/E7, and 3/F11 (Wolf P., et al *Prostate.* 2010 Apr. 1; 70(5):562-9).
(38) SST (Somatostatin Receptor; Note that there are 5 Subtypes)
(38.1) SSTR2 (Somatostatin Receptor 2)
Nucleotide
Genbank accession no NM_001050
Genbank version no. NM_001050.2 GI:44890054
Genbank record update date: Aug. 19, 2012 01:37 PM
Polypeptide
Genbank accession no. NP_001041
Genbank version no. NP_001041.1 GI:4557859
Genbank record update date: Aug. 19, 2012 01:37 PM
Cross References
Yamada Y., et al *Proc. Natl. Acad. Sci. U.S.A.* 89 (1), 251-255 (1992); Susini C., et al *Ann Oncol.* 2006 December; 17(12):1733-42
Other Information
Official Symbol: SSTR2
Other Designations: SRIF-1; SS2R; somatostatin receptor type 2
(38.2) SSTR5 (Somatostatin Receptor 5)
Nucleotide
Genbank accession no D16827
Genbank version no. D16827.1 GI:487683
Genbank record update date: Aug. 1, 2006 12:45 PM
Polypeptide
Genbank accession no. BAA04107
Genbank version no. BAA04107.1 GI:487684
Genbank record update date: Aug. 1, 2006 12:45 PM
Cross References
Yamada, Y., et al *Biochem. Biophys. Res. Commun.* 195 (2), 844-852 (1993)
Other Information
Official Symbol: SSTR5
Other Aliases: SS-5-R
Other Designations: Somatostatin receptor subtype 5; somatostatin receptor type 5

(38.3) SSTR1
(38.4) SSTR3
(38.5) SSTR4
AvB6—Both Subunits (39+40)
(39) ITGAV (Integrin, Alpha V;
Nucleotide
Genbank accession no M14648 J02826 M18365
Genbank version no. M14648.1 GI:340306
Genbank record update date: Jun. 23, 2010 08:56 AM
Polypeptide
Genbank accession no. AAA36808
Genbank version no. AAA36808.1 GI:340307
Genbank record update date: Jun. 23, 2010 08:56 AM
Cross References
Suzuki S., et al *Proc. Natl. Acad. Sci. U.S.A.* 83 (22), 8614-8618 (1986)
Other Information
Official Symbol: ITGAV
Other Aliases: CD51, MSK8, VNRA, VTNR
Other Designations: antigen identified by monoclonal antibody L230; integrin alpha-V; integrin alphaVbeta3; integrin, alpha V (vitronectin receptor, alpha polypeptide, antigen CD51); vitronectin receptor subunit alpha
(40) ITGB6 (Integrin, Beta 6)
Nucleotide
Genbank accession no NM_000888
Genbank version no. NM_000888.3 GI:9966771
Genbank record update date: Jun. 27, 2012 12:46 AM
Polypeptide
Genbank accession no. NP_000879
Genbank version no. NP_000879.2 GI:9625002
Genbank record update date: Jun. 27, 2012 12:46 AM
Cross References
Sheppard D. J., et al *Biol. Chem.* 265 (20), 11502-11507 (1990)
Other Information
Official Symbol: ITGB6
Other Designations: integrin beta-6
Antibodies
Biogen: U.S. Pat. No. 7,943,742—Hybridoma clones 6.3G9 and 6.8G6 were deposited with the ATCC, accession numbers ATCC PTA-3649 and -3645, respectively.
Biogen: U.S. Pat. No. 7,465,449—In some embodiments, the antibody comprises the same heavy and light chain polypeptide sequences as an antibody produced by hybridoma 6.1A8, 6.3G9, 6.8G6, 6.2B1, 6.2B10, 6.2A1, 6.2E5, 7.1G10, 7.7G5, or 7.1C5.
Centocor (J&J): U.S. Pat. Nos. 7,550,142; 7,163,681
  For example in U.S. Pat. No. 7,550,142—an antibody having human heavy chain and human light chain variable regions comprising the amino acid sequences shown in SEQ ID NO: 7 and SEQ ID NO: 8.
Seattle Genetics: 15H3 (Ryan M C., et al Cancer Res Apr. 15, 2012; 72(8 Supplement): 4630)
(41) CEACAM5 (Carcinoembryonic Antigen-Related Cell Adhesion Molecule 5)
Nucleotide
Genbank accession no M17303
Genbank version no. M17303.1 GI:178676
Genbank record update date: Jun. 23, 2010 08:47 AM
Polypeptide
Genbank accession no. AA659513
Genbank version no. AA659513.1 GI:178677
Genbank record update date: Jun. 23, 2010 08:47 AM
Cross References
Beauchemin N., et al *Mol. Cell. Biol.* 7 (9), 3221-3230 (1987)
Other Information
Official Symbol: CEACAM5
Other Aliases: CD66e, CEA
Other Designations: meconium antigen 100
Antibodies
AstraZeneca-MedImmune:US 20100330103; US20080057063;
  US20020142359
    for example an antibody having complementarity determining regions (CDRs) with the following sequences: heavy chain; CDR1—DNYMH, CDR2—WIDPENGDTE YAPKFRG, CDR3—LIYAGYLAMD Y; and light chain CDR1—SASSSVTYMH, CDR2—STSNLAS, CDR3—QQRSTYPLT.
    Hybridoma 806.077 deposited as European Collection of Cell Cultures (ECACC) deposit no. 96022936.
Research Corporation Technologies, Inc.: U.S. Pat. No. 5,047,507
Bayer Corporation: U.S. Pat. No. 6,013,772
BioAlliance: U.S. Pat. Nos. 7,982,017; 7,674,605
  U.S. Pat. No. 7,674,605
    an antibody comprising the heavy chain variable region sequence from the amino acid sequence of SEQ ID NO: 1, and the light chain variable region sequence from the amino acid sequence of SEQ ID NO:2.
    an antibody comprising the heavy chain variable region sequence from the amino acid sequence of SEQ ID NO:5, and the light chain variable region sequence from the amino acid sequence of SEQ ID NO:6.
Celltech Therapeutics Limited: U.S. Pat. No. 5,877,293
The Dow Chemical Company: U.S. Pat. Nos. 5,472,693; 6,417,337; 6,333,405
  U.S. Pat. No. 5,472,693—for example, ATCC No. CRL-11215
  U.S. Pat. No. 6,417,337—for example, ATCC CRL-12208
  U.S. Pat. No. 6,333,405—for example, ATCC CRL-12208
Immunomedics, Inc: U.S. Pat. Nos. 7,534,431; 7,230,084; 7,300,644; 6,730,300;
  US20110189085
    an antibody having CDRs of the light chain variable region comprise: CDR1 comprises KASQDVGTSVA (SEQ ID NO: 20); CDR2 comprises WTSTRHT (SEQ ID NO: 21); and CDR3 comprises QQYSLYRS (SEQ ID NO: 22); and the CDRs of the heavy chain variable region of said anti-CEA antibody comprise: CDR1 comprises TYWMS (SEQ ID NO: 23); CDR2 comprises EIHPDSSTINYAPSLKD (SEQ ID NO: 24); and CDR3 comprises LYFGFPWFAY (SEQ ID NO: 25).
  US20100221175; US20090092598; US20070202044; US20110064653; US20090185974; US20080069775.
(42) MET (Met Proto-Oncogene; Hepatocyte Growth Factor Receptor)
Nucleotide
Genbank accession no M35073
Genbank version no. M35073.1 GI:187553
Genbank record update date: Mar. 6, 2012 11:12 AM
Polypeptide
Genbank accession no. AAA59589
Genbank version no. AAA59589.1 GI:553531
Genbank record update date: Mar. 6, 2012 11:12 AM Cross References
Dean M., et al *Nature* 318 (6044), 385-388 (1985)
Other Information
Official Symbol: MET
Other Aliases: AUTS9, HGFR, RCCP2, c-Met
Other Designations: HGF Receptor; HGF/SF Receptor; SF Receptor; Hepatocyte Growth Factor Receptor; Met Proto-Oncogene Tyrosine Kinase; Proto-Oncogene c-Met; Scatter Factor receptor; tyrosine-protein kinase Met
Antibodies
Abgenix/Pfizer: US20100040629
  for example, the antibody produced by hybridoma 13.3.2 having American Type Culture Collection (ATCC) accession number PTA-5026; the antibody produced by hybridoma 9.1.2 having ATCC accession number PTA-5027; the antibody produced by hybridoma 8.70.2 having ATCC accession number PTA-5028; or the antibody produced by hybridoma 6.90.3 having ATCC accession number PTA-5029.
Amgen/Pfizer: US20050054019
  for example, an antibody comprising a heavy chain having the amino acid sequences set forth in SEQ ID NO: 2 where X2 is glutamate and X4 is serine and a light chain having the amino acid sequence set forth in SEQ ID NO: 4 where X8 is alanine, without the signal sequences; an antibody comprising a heavy chain having the amino acid sequences set forth in SEQ ID NO: 6 and a light chain having the amino acid sequence set forth in SEQ ID NO: 8, without the signal sequences; an antibody comprising a heavy chain having the amino acid sequences set forth in SEQ ID NO: and a light chain having the amino acid sequence set forth in SEQ ID NO: 12, without the signal sequences; or an antibody comprising a heavy chain having the amino acid sequences set forth in SEQ ID NO: 14 and a light chain having the amino acid sequence set forth in SEQ ID NO: 16, without the signal sequences.
Agouron Pharmaceuticals (Now Pfizer): US20060035907
Eli Lilly: US20100129369
Genentech: U.S. Pat. No. 5,686,292; US20100028337; US20100016241; US20070129301; US20070098707; US20070092520, US20060270594; US20060134104; US20060035278; US20050233960; US20050037431
  U.S. Pat. No. 5,686,292—for example, ATCC HB-11894 and ATCC HB-11895
  US 20100016241—for example, ATCC HB-11894 (hybridoma 1A3.3.13) or HB-11895 (hybridoma 5D5.11.6)
National Defense Medical Center, Taiwan: Lu R M., et al *Biomaterials*. 2011 April; 32(12):3265-74.
Novartis: US20090175860
  for example, an antibody comprising the sequences of CDR1, CDR2 and CDR3 of heavy chain 4687, wherein the sequences of CDR1, CDR2, and CDR3 of heavy chain 4687 are residues 26-35, 50-65, and 98-102, respectively, of SEQ ID NO: 58; and the sequences of CDR1, CDR2, and CDR3 of light chain 5097, wherein the sequences of CDR1, CDR2, and CDR3 of light chain 5097 are residues 24-39, 55-61, and 94-100 of SEQ ID NO: 37.
Pharmacia Corporation: US20040166544
Pierre Fabre: US20110239316, US20110097262, US20100115639
Sumsung: US 20110129481—for example a monoclonal antibody produced from a hybridoma cell having accession number KCLRF-BP-00219 or accession number of KCLRF-BP-00223.
Samsung: US 20110104176—for example an antibody produced by a hybridoma cell having Accession Number: KCLRF-BP-00220.
University of Turin Medical School: DN-30 Pacchiana G., et al *J Biol Chem.* 2010 Nov. 12; 285(46):36149-57
Van Andel Research Institute: Jiao Y., et al *Mol Biotechnol.* 2005 September; 31(1):41-54.
(43) MUC1 (Mucin 1, Cell Surface Associated)
Nucleotide
Genbank accession no J05581
Genbank version no. J05581.1 GI:188869
Genbank record update date: Jun. 23, 2010 08:48 AM
Polypeptide
Genbank accession no. AAA59876
Genbank version no. AAA59876.1 GI:188870
Genbank record update date: Jun. 23, 2010 08:48 AM
Cross References
Gendler S. J., et al *J. Biol. Chem.* 265 (25), 15286-15293 (1990)
Other Information
Official Symbol: MUC1
Other Aliases: RP11-263K19.2, CD227, EMA, H23AG, KL-6, MAM6, MUC-1, MUC-1/SEC, MUC-1/X, MUC1/ZD, PEM, PEMT, PUM
Other Designations: DF3 antigen; H23 antigen; breast carcinoma-associated antigen DF3; carcinoma-associated mucin; episialin; krebs von den Lungen-6; mucin 1, transmembrane; mucin-1; peanut-reactive urinary mucin; polymorphic epithelial mucin; tumor associated epithelial mucin; tumor-associated epithelial membrane antigen; tumor-associated mucin
Antibodies
AltaRex—Quest Pharma Tech: U.S. Pat. No. 6,716,966—for example an Alt-1 antibody produced by the hybridoma ATCC No PTA-975.
AltaRex—Quest Pharma Tech: U.S. Pat. No. 7,147,850
CRT: 5E5—Sorensen A L., et al *Glycobiology* vol. 16 no. 2 pp. 96-107, 2006; HMFG2—Burchell J., et al *Cancer Res.,* 47, 5476-5482 (1987); see WO2015/159076
Glycotope GT-MAB: GT-MAB 2.5-GEX (Website: http://www.glycotope.com/pipeline/pankomab-gex)
Immunogen: U.S. Pat. No. 7,202,346
  for example, antibody MJ-170: hybridoma cell line MJ-170 ATCC accession no. PTA-5286Monoclonal antibody MJ-171: hybridoma cell line MJ-171 ATCC accession no. PTA-5287; monoclonal antibody MJ-172: hybridoma cell line MJ-172 ATCC accession no. PTA-5288; or monoclonal antibody MJ-173: hybridoma cell line MJ-173 ATCC accession no. PTA-5302
Immunomedics: U.S. Pat. No. 6,653,104
Ramot Tel Aviv Uni: U.S. Pat. No. 7,897,351
Regents Uni. CA: U.S. Pat. No. 7,183,388; US20040005647; US20030077676.
Roche GlycArt: U.S. Pat. No. 8,021,856
Russian National Cancer Research Center: Imuteran-Ivanov P K., et al *Biotechnol J.* 2007 July; 2(7):863-70
Technische Univ Braunschweig: (11136, HT186-B7, HT186-D11, HT186-G2, HT200-3A-C1, HT220-M-D1, HT220-M-G8)—Thie H., et al *PLoS One.* 2011 Jan. 14; 6(1):e15921 (44) CA9 (Carbonic anhydrase IX)
Nucleotide
Genbank accession no. X66839
Genbank version no. X66839.1 GI:1000701
Genbank record update date: Feb. 2, 2011 10:15 AM Polypeptide
Genbank accession no. CAA47315
Genbank version no. CAA47315.1 GI:1000702
Genbank record update date: Feb. 2, 2011 10:15 AM
Cross References
Pastorek J., et al *Oncogene* 9 (10), 2877-2888 (1994)
Other Information
Official Symbol: CA9
Other Aliases: CAIX, MN
Other Designations: CA-IX; P54/58N; RCC-associated antigen G250; RCC-associated protein G250; carbonate dehydratase IX; carbonic anhydrase 9; carbonic dehydratase; membrane antigen MN; pMW1; renal cell carcinoma-associated antigen G250
Antibodies
Abgenix/Amgen: US20040018198
Affibody: Anti-CAIX Affibody molecules
 (http://www.affibody.com/en/Product-Portfolio/Pipeline/)
Bayer: U.S. Pat. No. 7,462,696
Bayer/Morphosys: 3ee9 mAb—Petrul H M., et al *Mol Cancer Ther.* 2012 February; 11(2):340-9
Harvard Medical School: Antibodies G10, G36, G37, G39, G45, G57, G106, G119, G6, G27, G40 and G125. Xu C., et al *PLoS One.* 2010 Mar. 10; 5(3):e9625
Institute of Virology, Slovak Academy of Sciences (Bayer)—U.S. Pat. No. 5,955,075
 for example, M75—ATCC Accession No. HB 11128 or MN12—ATCC Accession No. HB 11647
Institute of Virology, Slovak Academy of Sciences: U.S. Pat. No. 7,816,493
 for example the M75 monoclonal antibody that is secreted from the hybridoma VU-M75, which was deposited at the American Type Culture Collection under ATCC No. HB 11128; or the V/10 monoclonal antibody secreted from the hybridoma V/10-VU, which was deposited at the International Depository Authority of the Belgian Coordinated Collection of Microorganisms (BCCM) at the Laboratorium voor Moleculaire Bioloqie-Plasmidencollectie (LMBP) at the Universeit Gent in Gent, Belgium, under Accession No. LMBP 6009CB.
Institute of Virology, Slovak Academy of Sciences US20080177046; US20080176310; US20080176258; US20050031623
Novartis: US20090252738
Wilex: U.S. Pat. No. 7,691,375—for example the antibody produced by the hybridoma cell line DSM ASC 2526.
Wilex: US20110123537; Rencarex: Kennett R H., et al *Curr Opin Mol Ther.* 2003 February; 5(1):70-5
Xencor: US20090162382
(45) EGFRvIII (Epidermal Growth Factor Receptor (EGFR), Transcript Variant 3,
Nucleotide
Genbank accession no. NM_201283
Genbank version no. NM_201283.1 GI:41327733
Genbank record update date: Sep. 30, 2012 01:47 PM
Polypeptide
Genbank accession no. NP_958440
Genbank version no. NP_958440.1 GI:41327734
Genbank record update date: Sep. 30, 2012 01:47 PM
Cross-References
Batra S K., et al *Cell Growth Differ* 1995; 6:1251-1259.
Antibodies:
U.S. Pat. Nos. 7,628,986 and 7,736,644 (Amgen)
 For example, a heavy chain variable region amino acid sequence selected from the group consisting of SEQ ID NO: 142 and variants & a light chain variable region amino acid sequence selected from the group consisting of: SEQ ID NO: 144 and variants.
US20100111979 (Amgen)
 For example, an antibody comprising a heavy chain amino acid sequence comprising:
 CDR1 consisting of a sequence selected from the group consisting of the amino acid sequences for the CDR1 region of antibodies 13.1.2 (SEQ ID NO: 138), 131 (SEQ ID NO: 2), 170 (SEQ ID NO: 4), 150 (SEQ ID NO: 5), 095 (SEQ ID NO: 7), 250 (SEQ ID NO: 9), 139 (SEQ ID NO: 10), 211 (SEQ ID NO: 12), 124 (SEQ ID NO: 13), 318 (SEQ ID NO: 15), 342 (SEQ ID NO: 16), and 333 (SEQ ID NO: 17); CDR2 consisting of a sequence selected from the group consisting of the amino acid sequences for the CDR2 region of antibodies 13.1.2 (SEQ ID NO: 138), 131 (SEQ ID NO: 2), 170 (SEQ ID NO: 4), 150 (SEQ ID NO: 5), 095 (SEQ ID NO: 7), 250 (SEQ ID NO: 9), 139 (SEQ ID NO: 10), 211 (SEQ ID NO: 12), 124 (SEQ ID NO: 13), 318 (SEQ ID NO: 15), 342 (SEQ ID NO: 16), and 333 (SEQ ID NO: 17); and
 CDR3 consisting of a sequence selected from the group consisting of the amino acid sequences for the CDR3 region of antibodies 13.1.2 (SEQ ID NO: 138), 131 (SEQ ID NO: 2), 170 (SEQ ID NO: 4), 150 (SEQ ID NO: 5), 095 (SEQ ID NO: 7), 250 (SEQ ID NO: 9), 139 (SEQ ID NO: 10), 211 (SEQ ID NO: 12), 124 (SEQ ID NO: 13), 318 (SEQ ID NO: 15), 342 (SEQ ID NO: 16), and 333 (SEQ ID NO: 17).
US20090240038 (Amgen)
 For example, an antibody having at least one of the heavy or light chain polypeptides comprises an amino acid sequence that is at least 90% identical to the amino acid sequence selected from the group consisting of: SEQ ID NO: 2, SEQ ID NO: 19, SEQ ID NO: 142, SEQ ID NO: 144, and any combination thereof.
US20090175887 (Amgen)
 For example, an antibody having a heavy chain amino acid sequence selected from the group consisting of the heavy chain amino acid sequence of antibody 13.1.2 (SEQ ID NO: 138), 131 (SEQ ID NO: 2), 170 (SEQ ID NO: 4), 150 (SEQ ID NO: 5), 095 (SEQ ID NO: 7), 250 (SEQ ID NO: 9), 139 (SEQ ID NO: 10), 211 (SEQ ID NO: 12), 124 (SEQ ID NO: 13), 318 (SEQ ID NO: 15), 342 (SEQ ID NO: 16), and 333 (SEQ ID NO: 17).
US20090156790 (Amgen)
 For example, antibody having heavy chain polypeptide and a light chain polypeptide, wherein at least one of the heavy or light chain polypeptides comprises an amino acid sequence that is at least 90% identical to the amino acid sequence selected from the group consisting of: SEQ ID NO: 2, SEQ ID NO: 19, SEQ ID NO: 142, SEQ ID NO: 144, and any combination thereof.
US20090155282, US20050059087 and US20050053608 (Amgen)
 For example, an antibody heavy chain amino acid sequence selected from the group consisting of the heavy chain amino acid sequence of antibody 13.1.2 (SEQ ID NO: 138), 131 (SEQ ID NO: 2), 170 (SEQ ID NO: 4), 150 (SEQ ID NO: 5), 095 (SEQ ID NO: 7), 250 (SEQ ID NO: 9), 139 (SEQ ID NO: 10), 211 (SEQ ID NO: 12), 124 (SEQ ID NO: 13), 318 (SEQ ID NO: 15), 342 (SEQ ID NO: 16), and 333 (SEQ ID NO: 17).
MR1-1 (U.S. Pat. No. 7,129,332; Duke)
 For example, a variant antibody having the sequence of SEQ ID NO. 18 with the substitutions S98P-T99Y in the CDR3 VH, and F92W in CDR3 VL.

L8A4, H10, Y10 (Wikstrand C J., et al *Cancer Res.* 1995 Jul. 15; 55(14):3140-8; Duke)

US20090311803 (Harvard University)
  For example, SEQ ID NO:9 for antibody heavy chain variable region, and SEQ ID NO: 3 for light chain variable region amino acid sequences US20070274991 (EMD72000, also known as matuzumab; Harvard University)
  For example, SEQ ID NOs: 3 & 9 for light chain and heavy chain respectively U.S. Pat. No. 6,129,915 (Schering)
  For example, SEQ. ID NOs: 1, 2, 3, 4, 5 and 6.

mAb CH12—Wang H., et al *FASEB J.* 2012 January; 26(1):73-80 (Shanghai Cancer Institute).
  RAbDMvIII—Gupta P., et al *BMC Biotechnol.* 2010 Oct. 7; 10:72 (Stanford University Medical Center).

mAb Ua30—Ohman L., et al *Tumour Biol.* 2002 March-April; 23(2):61-9 (Uppsala University).

Han D G., et al *Nan Fang Yi Ke Da Xue Xue Bao.* 2010 January; 30(1):25-9 (Xi'an Jiaotong University).

(46) Cd33 (Cd33 Molecule)
Nucleotide
Genbank accession no. M_23197
Genbank version no. NM_23197.1 GI:180097
Genbank record update date: Jun. 23, 2010 08:47 AM
Polypeptide
Genbank accession no. AAA51948
Genbank version no. AAA51948.1 GI:188098
Genbank record update date: Jun. 23, 2010 08:47 AM
Cross-References
Simmons D., et al *J. Immunol.* 141 (8), 2797-2800 (1988)
Other Information
Official Symbol: CD33
Other Aliases: SIGLEC-3, SIGLEC3, p67
Other Designations: CD33 antigen (gp67); gp67; myeloid cell surface antigen CD33; sialic acid binding Ig-like lectin 3; sialic acid-binding Ig-like lectin
Antibodies
H195 (Lintuzumab)—Raza A., et al *Leuk Lymphoma.* 2009 August; 50(8):1336-44; U.S. Pat. No. 6,759,045 (Seattle Genetics/Immunomedics)
mAb OKT9: Sutherland, D. R. et al. *Proc Natl Acad Sci USA* 78(7): 4515-4519 1981, Schneider, C., et al *J Biol Chem* 257, 8516-8522 (1982)
mAb E6: Hoogenboom, H. R., et al *J Immunol* 144, 3211-3217 (1990)
U.S. Pat. No. 6,590,088 (Human Genome Sciences)
  For example, SEQ ID NOs: 1 and 2 and ATCC accession no. 97521
U.S. Pat. No. 7,557,189 (Immunogen)
  For example, an antibody or fragment thereof comprising a heavy chain variable region which comprises three CDRs having the amino acid sequences of SEQ ID NOs:1-3 and a light chain variable region comprising three CDRs having the amino acid sequences of SEQ ID NOs:4-6.

(47) CD19 (CD19 Molecule)
Nucleotide
Genbank accession no. NM_001178098
Genbank version no. NM_001178098.1 GI:296010920
Genbank record update date: Sep. 10, 2012 12:43 AM
Polypeptide
Genbank accession no. NP_001171569
Genbank version no. NP_001171569.1 GI:296010921
Genbank record update date: Sep. 10, 2012 12:43 AM
Cross-References
Tedder T F., et al *J. Immunol.* 143 (2): 712-7 (1989)
Other Information
Official Symbol: CD19
Other Aliases: B4, CVID3
Other Designations: B-lymphocyte antigen CD19; B-lymphocyte surface antigen B4; T-cell surface antigen Leu-12; differentiation antigen CD19
Antibodies
Immunogen: HuB4—Al-Katib A M., et al *Clin Cancer Res.* 2009 Jun. 15; 15(12):4038-45.
4G7: Kügler M., et al *Protein Eng Des Sel.* 2009 March; 22(3):135-47
  For example, sequences in FIG. 3 of of Knappik, A. et al. *J Mol Biol* 2000 February; 296(1):57-86
AstraZeneca/MedImmune: MEDI-551—Herbst R., et al *J Pharmacol Exp Ther.* 2010 October; 335(1):213-22
Glenmark Pharmaceuticals: GBR-401—Hou S., et al *Mol Cancer Ther* November 2011 (Meeting Abstract Supplement) C164
U.S. Pat. No. 7,109,304 (Immunomedics)
  For example, an antibody comprising the sequence of hA19Vk (SEQ ID NO:7) and the sequence of hA19VH (SEQ ID NO:10)
U.S. Pat. No. 7,902,338 (Immunomedics)
  For example, an antibody or antigen-binding fragment thereof that comprises the light chain complementarity determining region CDR sequences CDR1 of SEQ ID NO: 16 (KASQSVDYDGDSYLN); CDR2 of SEQ ID NO: 17 (DASNLVS); and CDR3 of SEQ ID NO: 18 (QQSTEDPWT) and the heavy chain CDR sequences CDR1 of SEQ ID NO: 19 (SYWMN); CDR2 of SEQ ID NO: 20 (QIWPGDGDTNYNGKFKG) and CDR3 of SEQ ID NO: 21 (RETTTVGRYYYAMDY) and also comprises human antibody framework (FR) and constant region sequences with one or more framework region amino acid residues substituted from the corresponding framework region sequences of the parent murine antibody, and wherein said substituted FR residues comprise the substitution of serine for phenylalanine at Kabat residue 91 of the heavy chain variable region.
Medarex: MDX-1342—Cardarelli P M., et al *Cancer Immunol Immunother.* 2010 February; 59(2):257-65.
MorphoSys/Xencor: MOR-208/XmAb-5574—Zalevsky J., et al *Blood.* 2009 Apr. 16; 113(16):3735-43
U.S. Pat. No. 7,968,687 (Seattle Genetics)
  An antibody or antigen-binding fragment comprising a heavy chain variable domain comprising the amino acid sequence of SEQ ID NO:9 and a light chain variable domain comprising the amino acid sequence of SEQ ID NO: 24.
4G7 chim—Lang P., et al *Blood.* 2004 May 15; 103(10):3982-5 (University of Tübingen)
  For example, FIG. 6 and SEQ ID No: 80 of US20120082664
Zhejiang University School of Medicine: 2E8—Zhang J., et al *J Drug Target.* 2010 November; 18(9):675-8

(48) IL2RA (Interleukin 2 Receptor, Alpha); NCBI Reference Sequence: NM_000417.2);
Nucleotide
Genbank accession no. NM_000417
Genbank version no. NM_000417.2 GI:269973860
Genbank record update date: Sep. 9, 2012 04:59 PM
Polypeptide
Genbank accession no. NP_000408
Genbank version no. NP_000408.1 GI:4557667
Genbank record update date: Sep. 9, 2012 04:59 PM Cross-References
Kuziel W. A., et al *J. Invest. Dermatol.* 94 (6 SUPPL), 27S-32S (1990)
Other Information
Official Symbol: IL2RA
Other Aliases: RP11-536K7.1, CD25, IDDM10, IL2R, TCGFR
Other Designations: FIL-2 receptor subunit alpha; IL-2-RA; IL-2R subunit alpha; IL2-RA; TAC antigen; interleukin-2 receptor subunit alpha; p55
Antibodies
U.S. Pat. No. 6,383,487 (Novartis/UCL: Baxilisimab [Simulect])
U.S. Pat. No. 6,521,230 (Novartis/UCL: Baxilisimab [Simulect])
  For example, an antibody having an antigen binding site comprises at least one domain which comprises CDR1 having the amino acid sequence in SEQ. ID. NO: 7, CDR2 having the amino acid sequence in SEQ. ID. NO: 8, and CDR3 having the amino acid sequence in SEQ. ID. NO: 9; or said CDR1, CDR2 and CDR3 taken in sequence as a whole comprise an amino acid sequence which is at least 90% identical to SEQ. ID. NOs: 7, 8 and 9 taken in sequence as a whole.
Daclizumab—Rech A J., et al *Ann NY Acad Sci.* 2009 September; 1174:99-106 (Roche)
(49) AXL (AXL Receptor Tyrosine Kinase)
Nucleotide
Genbank accession no. M76125
Genbank version no. M76125.1 GI:292869
Genbank record update date: Jun. 23, 2010 08:53 AM
Polypeptide
Genbank accession no. AAA61243
Genbank version no. AAA61243.1 GI:29870
Genbank record update date: Jun. 23, 2010 08:53 AM
Cross-References
O'Bryan J. P., et al *Mol. Cell. Biol.* 11 (10), 5016-5031 (1991); Bergsagel P. L., et al *J. Immunol.* 148 (2), 590-596 (1992)
Other Information
Official Symbol: AXL
Other Aliases: JTK11, UFO
Other Designations: AXL oncogene; AXL transforming sequence/gene; oncogene AXL; tyrosine-protein kinase receptor UFO
Antibodies
YW327.652—Ye X., et al *Oncogene.* 2010 Sep. 23; 29(38): 5254-64. (Genentech)
Bergen Bio: BGB324 (http://www.bergenbio.com/BGB324)
(50) CD30—TNFRSF8 (Tumor Necrosis Factor Receptor Superfamily, Member 8)
Nucleotide
Genbank accession no. M83554
Genbank version no. M83554.1 GI:180095
Genbank record update date: Jun. 23, 2010 08:53 AM
Polypeptide
Genbank accession no. AAA51947
Genbank version no. AAA51947.1 GI:180096
Genbank record update date: Jun. 23, 2010 08:53 AM
Cross-References
Durkop H., et al *Cell* 68 (3), 421-427 (1992)
Other Information
Official Symbol: TNFRSF8
Other Aliases: CD30, D1S166E, Ki-1
Other Designations: CD30L receptor; Ki-1 antigen; cytokine receptor CD30; lymphocyte activation antigen CD30; tumor necrosis factor receptor superfamily member 8

(51) BCMA (B-Cell Maturation Antigen)—TNFRSF17 (Tumor Necrosis Factor Receptor Superfamily, Member 17)
Nucleotide
Genbank accession no. Z29574
Genbank version no. Z29574.1 GI:471244
Genbank record update date: Feb. 2, 2011 10:40 AM
Polypeptide
Genbank accession no. CAA82690
Genbank version no. CAA82690.1 GI:471245
Genbank record update date: Feb. 2, 2011 10:40 AM
Cross-References
Laabi Y., et al *Nucleic Acids Res.* 22 (7), 1147-1154 (1994)
Other Information
Official Symbol: TNFRSF17
Other Aliases: BCM, BCMA, CD269
Other Designations: B cell maturation antigen; B-cell maturation factor; B-cell maturation protein; tumor necrosis factor receptor superfamily member 17
(52) CT Ags—CTA (Cancer Testis Antigens)
Cross-References
Fratta E., et al. *Mol Oncol.* 2011 April; 5(2):164-82; Lim S H., at al *Am J Blood Res.* 2012; 2(1):29-35.
(53) CD174 (Lewis Y)—FUT3 (Fucosyltransferase 3 (Galactoside 3(4)-L-fucosyltransferase, Lewis Blood Group)
Nucleotide
Genbank accession no. NM000149
Genbank version no. NM000149.3 GI:148277008
Genbank record update date: Jun. 26, 2012 04:49 PM
Polypeptide
Genbank accession no. NP_000140
Genbank version no. NP_000140.1 GI:4503809
Genbank record update date: Jun. 26, 2012 04:49 PM
Cross-References
Kukowska-Latallo, J. F., et al *Genes Dev.* 4 (8), 1288-1303 (1990)
Other Information
Official Symbol: FUT3
Other Aliases: CD174, FT3B, FucT-III, LE, Les
Other Designations: Lewis FT; alpha-(1,3/1,4)-fucosyltransferase; blood group Lewis alpha-4-fucosyltransferase; fucosyltransferase III; galactoside 3(4)-L-fucosyltransferase
(54) CLEC14A (C-Type Lectin Domain Family 14, Member A; Genbank Accession No. NM175060)
Nucleotide
Genbank accession no. NM175060
Genbank version no. NM175060.2 GI:371123930
Genbank record update date: Apr. 1, 2012 03:34 PM
Polypeptide
Genbank accession no. NP_778230
Genbank version no. NP_778230.1 GI:28269707
Genbank record update date: Apr. 1, 2012 03:34 PM
Other Information
Official Symbol: CLEC14A
Other Aliases: UNQ236/PRO269, C14orf27, CEG1, EGFR-5
Other Designations: C-type lectin domain family 14 member A; CIECT and EGF-like domain containing protein; epidermal growth factor receptor 5
(55) GRP78—HSPA5 (Heat Shock 70 kDa Protein 5 (Glucose-Regulated Protein, 78 kDa)
Nucleotide
Genbank accession no. NM005347
Genbank version no. NM005347.4 GI:305855105
Genbank record update date: Sep. 30, 2012 01:42 PM Polypeptide
Genbank accession no. NP_005338
Genbank version no. NP_005338.1 GI:16507237
Genbank record update date: Sep. 30, 2012 01:42 PM
Cross-References
Ting J., et al DNA 7 (4), 275-286 (1988)
Other Information
Official Symbol: HSPA5
Other Aliases: BIP, GRP78, MIF2
Other Designations: 78 kDa glucose-regulated protein; endoplasmic reticulum lumenal Ca(2+)-binding protein grp78; immunoglobulin heavy chain-binding protein

(56) CD70 (CD70 Molecule) L08096
Nucleotide
Genbank accession no. L08096
Genbank version no. L08096.1 GI:307127
Genbank record update date: Jun. 23, 2012 08:54 AM
Polypeptide
Genbank accession no. AAA36175
Genbank version no. AAA36175.1 GI:307128
Genbank record update date: Jun. 23, 2012 08:54 AM
Cross-References
Goodwin R. G., et al Cell 73 (3), 447-456 (1993)
Other Information
Official Symbol: CD70
Other Aliases: CD27L, CD27LG, TNFSF7
Other Designations: CD27 ligand; CD27-L; CD70 antigen; Ki-24 antigen; surface antigen CD70; tumor necrosis factor (ligand) superfamily, member 7; tumor necrosis factor ligand superfamily member 7
Antibodies
MDX-1411 against CD70 (Medarex)
h1F6 (Oflazoglu, E., et al, Clin Cancer Res. 2008 Oct. 1; 14(19):6171-80; Seattle Genetics)
  For example, see US20060083736 SEQ ID NOs: 1, 2, 11 and 12 and FIG. 1.

(57) Stem Cell Specific Antigens. For Example:
  5T4 (see entry (63) below)
  CD25 (see entry (48) above)
  CD32
    Polypeptide
      Genbank accession no. ABK42161
      Genbank version no. ABK42161.1 GI:117616286
      Genbank record update date: Jul. 25, 2007 03:00 PM
  LGR5/GPR49
    Nucleotide
      Genbank accession no. NM_003667
      Genbank version no. NM_003667.2 GI:24475886
      Genbank record update date: Jul. 22, 2012 03:38 PM
    Polypeptide
      Genbank accession no. NP_003658
      Genbank version no. NP_003658.1 GI:4504379
      Genbank record update date: Jul. 22, 2012 03:38 PM
  Prominin/CD133
    Nucleotide
      Genbank accession no. NM_006017
      Genbank version no. NM_006017.2 GI:224994187
      Genbank record update date: Sep. 30, 2012 01:47 PM
    Polypeptide
      Genbank accession no. NP_006008
      Genbank version no. NP_006008.1 GI:5174387
      Genbank record update date: Sep. 30, 2012 01:47 PM

(58) ASG-5
Cross-References
(Smith L. M., et. al AACR 2010 Annual Meeting (abstract #2590); Gudas J. M., et. al. AACR 2010 Annual Meeting (abstract #4393)
Antibodies
Anti-AGS-5 Antibody: M6.131 (Smith, L. M., et. al AACR 2010 Annual Meeting (abstract #2590)

(59) ENPP3 (Ectonucleotide pyrophosphatase/phosphodiesterase 3)
Nucleotide
Genbank accession no. AF005632
Genbank version no. AF005632.2 GI:4432589
Genbank record update date: Mar. 10, 2010 09:41 PM
Polypeptide
Genbank accession no. AAC51813
Genbank version no. AAC51813.1 GI:2465540
Genbank record update date: Mar. 10, 2010 09:41 PM
Cross-References
Jin-Hua P., et al Genomics 45 (2), 412-415 (1997)
Other Information
Official Symbol: ENPP3
Other Aliases: RP5-988G15.3, B10, CD203c, NPP3, PD-IBETA, PDNP3
Other Designations: E-NPP 3; dJ1005H11.3 (phosphodiesterase I/nucleotide pyrophosphatase 3); dJ914N13.3 (phosphodiesterase I/nucleotide pyrophosphatase 3); ectonucleotide pyrophosphatase/phosphodiesterase family member 3; gp130RB13-6; phosphodiesterase I beta; phosphodiesterase I/nucleotide pyrophosphatase 3; phosphodiesterase-I beta

(60) PRR4 (Proline Rich 4 (Lacrimal))
Nucleotide
Genbank accession no. NM_007244
Genbank version no. NM_007244.2 GI:154448885
Genbank record update date: Jun. 28, 2012 12:39 PM
Polypeptide
Genbank accession no. NP_009175
Genbank version no. NP_009175.2 GI:154448886
Genbank record update date: Jun. 28, 2012 12:39 PM
Cross-References
Dickinson D. P., et al Invest. Ophthalmol. Vis. Sci. 36 (10), 2020-2031 (1995)
Other Information
Official Symbol: PRR4
Other Aliases: LPRP, PROL4
Other Designations: lacrimal proline-rich protein; nasopharyngeal carcinoma-associated proline-rich protein 4; proline-rich polypeptide 4; proline-rich protein 4

(61) GCC—GUCY2C (Guanylate Cyclase 2C (Heat Stable Enterotoxin Receptor)
Nucleotide
Genbank accession no. NM_004963
Genbank version no. NM_004963.3 GI:222080082
Genbank record update date: Sep. 2, 2012 01:50 PM
Polypeptide
Genbank accession no. NP_004954
Genbank version no. NP_004954.2 GI:222080083
Genbank record update date: Sep. 2, 2012 01:50 PM
Cross-References
De Sauvage F. J., et al J. Biol. Chem. 266 (27), 17912-17918 (1991); Singh S., et al Biochem. Biophys. Res. Commun. 179 (3), 1455-1463 (1991)
Other Information
Official Symbol: GUCY2C
Other Aliases: DIAR6, GUC2C, MUCIL, STAR
Other Designations: GC-C; STA receptor; guanylyl cyclase C; hSTAR; heat-stable enterotoxin receptor; intestinal guanylate cyclase

(62) Liv-1—SLC39A6 (Solute Carrier Family 39 (Zinc Transporter), Member 6)
Nucleotide
Genbank accession no. U41060
Genbank version no. U41060.2 GI:12711792
Genbank record update date: Nov. 30, 2009 04:35 PM
Polypeptide
Genbank accession no. AAA96258
Genbank version no. AAA96258.2 GI:12711793
Genbank record update date: Nov. 30, 2009 04:35 PM
Cross-References
Taylor K M., et al *Biochim Biophys Acta.* 2003 Apr. 1; 1611(1-2):16-30
Other Information
Official Symbol: SLC39A6
Other Aliases: LIV-1
Other Designations: LIV-1 protein, estrogen regulated; ZIP-6; estrogen-regulated protein LIV-1; solute carrier family 39 (metal ion transporter), member 6; solute carrier family 39 member 6; zinc transporter ZIP6; zrt- and Irt-like protein 6
(63) 5T4, Trophoblast Glycoprotein, TPBG-TPBG (Trophoblast Glycoprotein)
Nucleotide
Genbank accession no. AJ012159
Genbank version no. AJ012159.1 GI:3805946
Genbank record update date: Feb. 1, 2011 10:27 AM
Polypeptide
Genbank accession no. CAA09930
Genbank version no. CAA09930.1 GI:3805947
Genbank record update date: Feb. 1, 2011 10:27 AM
Cross-References
King K. W., et al *Biochim. Biophys. Acta* 1445 (3), 257-270 (1999)
Other Information
   Official Symbol: TPBG
   Other Aliases: 5T4, 5T4AG, M6P1
   Other Designations: 5T4 oncofetal antigen; 5T4 oncofetal trophoblast glycoprotein; 5T4 oncotrophoblast glycoprotein
   See WO2015/155345
(64) CD56—NCMA1 (Neural Cell Adhesion Molecule 1)
Nucleotide
Genbank accession no. NM_000615
Genbank version no. NM_000615.6 GI:336285433
Genbank record update date: Sep. 23, 2012 02:32 PM
Polypeptide
Genbank accession no. NP_000606
Genbank version no. NP_000606.3 GI:94420689
Genbank record update date: Sep. 23, 2012 02:32 PM
Cross-References
Dickson, G., et al, *Cell* 50 (7), 1119-1130 (1987)
Other Information
Official Symbol: NCAM1
Other Aliases: CD56, MSK39, NCAM
Other Designations: antigen recognized by monoclonal antibody 5.1H11; neural cell adhesion molecule, NCAM
Antibodies
Immunogen: HuN901 (Smith S V., et al *Curr Opin Mol Ther.* 2005 August; 7(4):394-401)
   For example, see humanized from murine N901 antibody. See FIGS. 1b and 1e of Roguska, M. A., et al. *Proc Natl Acad Sci USA* February 1994; 91:969-973.
(65) CanAg (Tumor Associated Antigen CA242)
Cross-References
Haglund C., et al *Br J Cancer* 60:845-851, 1989; Baeckstrom D., et al *J Biol Chem* 266:21537-21547, 1991
Antibodies
huC242 (Tolcher A W et al., *J Clin Oncol.* 2003 Jan. 15; 21(2):211-22; Immunogen)
   For example, see US20080138898A1 SEQ ID NO: 1 and 2
(66) FOLR1 (Folate Receptor 1)
Nucleotide
Genbank accession no. J05013
Genbank version no. J05013.1 GI:182417
Genbank record update date: Jun. 23, 2010 08:47 AM
Polypeptide
Genbank accession no. AAA35823
Genbank version no. AAA35823.1 GI:182418
Genbank record update date: Jun. 23, 2010 08:47 AM
Cross-References
Elwood P. C., et al *J. Biol. Chem.* 264 (25), 14893-14901 (1989)
Other Information
Official Symbol: FOLR1
Other Aliases: FBP, FOLR
Other Designations: FR-alpha; KB cells FBP; adult folate-binding protein; folate binding protein; folate receptor alpha; folate receptor, adult; ovarian tumor-associated antigen MOv18
Antibodies
M9346A—Whiteman K R., et al *Cancer Res* Apr. 15, 2012; 72(8 Supplement): 4628 (Immunogen)
(67) GPNMB (Glycoprotein (Transmembrane) Nmb)
Nucleotide
Genbank accession no. X76534
Genbank version no. X76534.1 GI:666042
Genbank record update date: Feb. 2, 2011 10:10 AM
Polypeptide
Genbank accession no. CAA54044
Genbank version no. CAA54044.1 GI:666043
Genbank record update date: Feb. 2, 2011 10:10 AM
Cross-References
Weterman M. A., et al *Int. J. Cancer* 60 (1), 73-81 (1995)
Other Information
Official Symbol: GPNMB
Other Aliases: UNQ1725/PRO9925, HGFIN, NMB
Other Designations: glycoprotein NMB; glycoprotein nmb-like protein; osteoactivin; transmembrane glycoprotein HGFIN; transmembrane glycoprotein NMB
Antibodies
Celldex Therapeutics: CR011 (Tse K F., et al *Clin Cancer Res.* 2006 Feb. 15; 12(4):1373-82)
   For example, see EP1827492B1 SEQ ID NO: 22, 24, 26, 31, 33 and 35
(68) TIM-1—HAVCR1 (Hepatitis a Virus Cellular Receptor 1)
Nucleotide
Genbank accession no. AF043724
Genbank version no. AF043724.1 GI:2827453
Genbank record update date: Mar. 10, 2010 06:24 PM
Polypeptide
Genbank accession no. AAC39862
Genbank version no. AAC39862.1 GI:2827454
Genbank record update date: Mar. 10, 2010 06:24 PM
Cross-References
Feigelstock D., et al *J. Virol.* 72 (8), 6621-6628 (1998)
Other Information
Official Symbol: HAVCR1
Other Aliases: HAVCR, HAVCR-1, KIM-1, KIM1, TIM, TIM-1, TIM1, TIMD-1, TIMD1
Other Designations: T cell immunoglobin domain and mucin domain protein 1; T-cell membrane protein 1; kidney injury molecule 1

(69) RG-1/Prostate Tumor Target Mindin—Mindin/RG-1
Cross-References
Parry R., et al *Cancer Res.* 2005 Sep. 15; 65(18):8397-405
(70) B7-H4—VTCN1 (V-set domain containing T cell activation inhibitor 1
Nucleotide
Genbank accession no. BX648021
Genbank version no. BX648021.1 GI:34367180
Genbank record update date: Feb. 2, 2011 08:40 AM
Cross-References
Sica G L., et al *Immunity.* 2003 June; 18(6):849-61
Other Information
Official Symbol: VTCN1
Other Aliases: RP11-229A19.4, B7-H4, B7H4, B7S1, B7X, B7 h.5, PRO1291, VCTN1
Other Designations: B7 family member, H4; B7 superfamily member 1; T cell costimulatory molecule B7x; T-cell costimulatory molecule B7x; V-set domain-containing T-cell activation inhibitor 1; immune costimulatory protein B7-H4
(71) PTK7 (PTK7 Protein Tyrosine Kinase 7)
Nucleotide
Genbank accession no. AF447176
Genbank version no. AF447176.1 GI:17432420
Genbank record update date: Nov. 28, 2008 01:51 PM
Polypeptide
Genbank accession no. AAL39062
Genbank version no. AAL39062.1 GI:17432421
Genbank record update date: Nov. 28, 2008 01:51 PM
Cross-References
Park S. K., et al *J. Biochem.* 119 (2), 235-239 (1996)
Other Information
Official Symbol: PTK7
Other Aliases: CCK-4, CCK4
Other Designations: colon carcinoma kinase 4; inactive tyrosine-protein kinase 7; pseudo tyrosine kinase receptor 7; tyrosine-protein kinase-like 7
(72) CD37 (CD37 Molecule)
Nucleotide
Genbank accession no. NM_001040031
Genbank version no. NM_001040031.1 GI:91807109
Genbank record update date: Jul. 29, 2012 02:08 PM
Polypeptide
Genbank accession no. NP_001035120
Genbank version no. NP_001035120.1 GI:91807110
Genbank record update date: Jul. 29, 2012 02:08 PM
Cross-References
Schwartz-Albiez R., et al *J. Immunol.* 140 (3), 905-914 (1988)
Other Information
Official Symbol: CD37
Other Aliases: GP52-40, TSPAN26
Other Designations: CD37 antigen; cell differentiation antigen 37; leukocyte antigen CD37; leukocyte surface antigen CD37; tetraspanin-26; tspan-26
Antibodies
Boehringer Ingelheim: mAb 37.1 (Heider K H., et al *Blood.* 2011 Oct. 13; 118(15):4159-68)
Trubion: CD37-SMIP (G28-1 scFv-Ig) ((Zhao X., et al *Blood.* 2007; 110: 2569-2577)
    For example, see US20110171208A1 SEQ ID NO: 253
Immunogen: K7153A (Deckert J., et al *Cancer Res* Apr. 15, 2012; 72(8 Supplement): 4625)
(73) CD138—SDC1 (Syndecan 1)
Nucleotide
Genbank accession no. AJ551176
Genbank version no. AJ551176.1 GI:29243141
Genbank record update date: Feb. 1, 2011 12:09 PM
Polypeptide
Genbank accession no. CAD80245
Genbank version no. CAD80245.1 GI:29243142
Genbank record update date: Feb. 1, 2011 12:09 PM
Cross-References
O'Connell F P., et al *Am J Clin Pathol.* 2004 February; 121(2):254-63
Other Information
Official Symbol: SDC1
Other Aliases: CD138, SDC, SYND1, syndecan
Other Designations: CD138 antigen; heparan sulfate proteoglycan fibroblast growth factor receptor; syndecan proteoglycan 1; syndecan-1
Antibodies
Biotest: chimerized MAb (nBT062)—(Jagannath S., et al Poster ASH #3060, 2010; WIPO Patent Application WO/2010/128087)
    For example, see US20090232810 SEQ ID NO: 1 and 2
Immunogen: B-B4 (Tassone P., et al *Blood* 104_3688-3696)
    For example, see US20090175863A1 SEQ ID NO: 1 and 2
(74) CD74 (CD74 Molecule, Major Histocompatibility Complex, Class II Invariant Chain)
Nucleotide
Genbank accession no. NM_004355
Genbank version no. NM_004355.1 GI:343403784
Genbank record update date: Sep. 23, 2012 02:30 PM
Polypeptide
Genbank accession no. NP_004346
Genbank version no. NP_004346.1 GI:10835071
Genbank record update date: Sep. 23, 2012 02:30 PM
Cross-References
Kudo, J., et al *Nucleic Acids Res.* 13 (24), 8827-8841 (1985)
Other Information
Official Symbol: CD74
Other Aliases: DHLAG, HLADG, II, Ia-GAMMA
Other Designations: CD74 antigen (invariant polypeptide of major histocompatibility complex, class II antigen-associated); HLA class II histocompatibility antigen gamma chain; HLA-DR antigens-associated invariant chain; HLA-DR-gamma; Ia-associated invariant chain; MHC HLA-DR gamma chain; gamma chain of class II antigens; p33
Antibodies
Immunomedics: hLL1 (Milatuzumab,)—Berkova Z., et al *Expert Opin Investig Drugs.* 2010 January; 19(1):141-9)
    For example, see US20040115193 SEQ ID NOs: 19, 20, 21, 22, 23 and 24
Genmab: HuMax-CD74 (see website)
(75) Claudins—CLs (Claudins)
Cross-References
Offner S., et al *Cancer Immunol Immunother.* 2005 May; 54(5):431-45, Suzuki H., et al *Ann N Y Acad Sci.* 2012 July; 1258:65-70)
In humans, 24 members of the family have been described—see literature reference.
(76) EGFR (Epidermal Growth Factor Receptor)
Nucleotide
Genbank accession no. NM_005228
Genbank version no. NM_005228.3 GI:41927737
Genbank record update date: Sep. 30, 2012 01:47 PM
Polypeptide
Genbank accession no. NP_005219
Genbank version no. NP_005219.2 GI:29725609
Genbank record update date: Sep. 30, 2012 01:47 PM Cross-References
Dhomen N S., et al *Crit Rev Oncog.* 2012; 17(1):31-50
Other Information
Official Symbol: EGFR
Other Aliases: ERBB, ERBB1, HER1, PIG61, mENA
Other Designations: avian erythroblastic leukemia viral (v-erb-b) oncogene homolog; cell growth inhibiting protein 40; cell proliferation-inducing protein 61; proto-oncogene c-ErbB-1; receptor tyrosine-protein kinase erbB-1
Antibodies
BMS: Cetuximab (Erbitux)—Broadbridge Vt., et al *Expert Rev Anticancer Ther.* 2012 May; 12(5):555-65.
  For example, see U.S. Pat. No. 6,217,866—ATTC deposit No. 9764.
Amgen: Panitumumab (Vectibix)—Argiles G., et al *Future Oncol.* 2012 April; 8(4):373-89
  For example, see U.S. Pat. No. 6,235,883 SEQ ID NOs: 23-38.
Genmab: Zalutumumab—Rivera F., et al *Expert Opin Biol Ther.* 2009 May; 9(5):667-74.
YM Biosciences: Nimotuzumab—Ramakrishnan M S., et al MAbs. 2009 January-February; 1(1):41-8.
  For example, see U.S. Pat. No. 5,891,996 SEQ ID NOs: 27-34.
(77) Her3 (ErbB3)—ERBB3 (v-Erb-b2 Erythroblastic Leukemia Viral Oncogene Homolog 3 (Avian))
Nucleotide
Genbank accession no. M34309
Genbank version no. M34309.1 GI:183990
Genbank record update date: Jun. 23, 2010 08:47 PM
Polypeptide
Genbank accession no. AAA35979
Genbank version no. AAA35979.1 GI:306841
Genbank record update date: Jun. 23, 2010 08:47 PM
Cross-References
Plowman, G. D., et al., *Proc. Natl. Acad. Sci. U.S.A.* 87 (13), 4905-4909 (1990)
Other Information
Official Symbol: ERBB3
Other Aliases: ErbB-3, HER3, LCCS2, MDA-BF-1, c-erbB-3, c-erbB3, erbB3-S, p180-ErbB3, p45-sErbB3, p85-sErbB3
Other Designations: proto-oncogene-like protein c-ErbB-3; receptor tyrosine-protein kinase erbB-3; tyrosine kinase-type cell surface receptor HER3
Antibodies
Merimack Pharma: MM-121 (Schoeberl B., et al *Cancer Res.* 2010 Mar. 15; 70(6):2485-2494)
  For example, see US2011028129 SEQ ID NOs: 1, 2, 3, 4, 5, 6, 7 and 8.
(78) RON—MST1R (Macrophage Stimulating 1 Receptor (c-Met-Related Tyrosine Kinase))
Nucleotide
Genbank accession no. X70040
Genbank version no. X70040.1 GI:36109
Genbank record update date: Feb. 2, 2011 10:17 PM
Polypeptide
Genbank accession no. CCA49634
Genbank version no. CCA49634.1 GI:36110
Genbank record update date: Feb. 2, 2011 10:17 PM
Cross-References
Ronsin C., et al *Oncogene* 8 (5), 1195-1202 (1993)
Other Information
Official Symbol: MST1R
Other Aliases: CD136, CDw136, PTK8, RON
Other Designations: MSP receptor; MST1R variant RON30; MST1R variant RON62; PTK8 protein tyrosine kinase 8; RON variant E2E3; c-met-related tyrosine kinase; macrophage-stimulating protein receptor; p185-Ron; soluble RON variant 1; soluble RON variant 2; soluble RON variant 3; soluble RONvariant 4
(79) EPHA2 (EPH Receptor A2)
Nucleotide
Genbank accession no. BC037166
Genbank version no. BC037166.2 GI:33879863
Genbank record update date: Mar. 6, 2012 01:59 PM
Polypeptide
Genbank accession no. AAH37166
Genbank version no. AAH37166.1 GI:22713539
Genbank record update date: Mar. 6, 2012 01:59 PM
Cross-References
Strausberg R. L., et al *Proc. Natl. Acad. Sci. U.S.A.* 99 (26), 16899-16903 (2002)
Other Information
Official Symbol: EPHA2
Other Aliases: ARCC2, CTPA, CTPP1, ECK
Other Designations: ephrin type-A receptor 2; epithelial cell receptor protein tyrosine kinase; soluble EPHA2 variant 1; tyrosine-protein kinase receptor ECK
Antibodies
Medimmune: 1C1 (Lee J W., et al *Clin Cancer Res.* 2010 May 1; 16(9):2562-2570)
  For example, see US20090304721A1 FIGS. 7 and 8.
(80) CD20—MS4A1 (Membrane-Spanning 4-Domains, Subfamily A, Member 1)
Nucleotide
Genbank accession no. M27394
Genbank version no. M27394.1 GI:179307
Genbank record update date: Nov. 30, 2009 11:16 AM
Polypeptide
Genbank accession no. AAA35581
Genbank version no. AAA35581.1 GI:179308
Genbank record update date: Nov. 30, 2009 11:16 AM
Cross-References
Tedder T. F., et al *Proc. Natl. Acad. Sci. U.S.A.* 85 (1), 208-212 (1988)
Other Information
Official Symbol: MS4A1
Other Aliases: B1, Bp35, CD20, CVID5, LEU-16, MS4A2, S7
Other Designations: B-lymphocyte antigen CD20; B-lymphocyte cell-surface antigen B1; CD20 antigen; CD20 receptor; leukocyte surface antigen Leu-16
Antibodies
Genentech/Roche: Rituximab—Abdulla N E., et al *BioDrugs.* 2012 Apr. 1; 26(2):71-82.
  For example, see U.S. Pat. No. 5,736,137, ATCC deposit No. HB-69119.
GSK/Genmab: Ofatumumab—Nightingale G., et al Ann Pharmacother. 2011 October; 45(10):1248-55.
  For example, see US20090169550A1 SEQ ID NOs: 2, 4 and 5.
Immunomedics: Veltuzumab—Goldenberg D M., et al *Leuk Lymphoma.* 2010 May; 51(5):747-55.
  For example, see U.S. Pat. No. 7,919,273B2 SEQ ID NOs: 1, 2, 3, 4, 5 and 6.
(81) Tenascin C—TNC (Tenascin C)
Nucleotide
Genbank accession no. NM_002160
Genbank version no. NM_002160.3 GI:340745336
Genbank record update date: Sep. 23, 2012 02:33 PM
Polypeptide
Genbank accession no. NP_002151
Genbank version no. NP_002151.2 GI:153946395

Genbank record update date: Sep. 23, 2012 02:33 PM
Cross-References
Nies D. E., et al *J. Biol. Chem.* 266 (5), 2818-2823 (1991);
Sin A., et al *Nucleic Acids Res.* 19 (3), 525-531 (1991)
Other Information
Official Symbol: TNC
Other Aliases: 150-225, GMEM, GP, HXB, JI, TN, TN-C
Other Designations: GP 150-225; cytotactin; glioma-associated-extracellular matrix antigen; hexabrachion (tenascin); myotendinous antigen; neuronectin; tenascin; tenascin-C isoform 14/AD1/16
Antibodies
Philogen: G11 (von Lukowicz T., et al *J Nucl Med.* 2007 April; 48(4):582-7) and F16 (Pedretti M., et al Lung Cancer. 2009 April; 64(1):28-33)
   For example, see U.S. Pat. No. 7,968,685 SEQ ID NOs: 29, 35, 45 and 47.
(82) FAP (Fibroblast Activation Protein, Alpha)
Nucleotide
Genbank accession no. U09278
Genbank version no. U09278.1 GI:1888315
Genbank record update date: Jun. 23, 2010 09:22 AM
Polypeptide
Genbank accession no. AAB49652
Genbank version no. AAB49652.1 GI:1888316
Genbank record update date: Jun. 23, 2010 09:22 AM
Cross-References
Scanlan, M. J., et al *Proc. Natl. Acad. Sci. U.S.A.* 91 (12), 5657-5661 (1994)
Other Information
Official Symbol: FAP
Other Aliases: DPPIV, FAPA
Other Designations: 170 kDa melanoma membrane-bound gelatinase; integral membrane serine protease; seprase
(83) DKK-1 (Dickkopf 1 Homolog (*Xenopus laevis*)
Nucleotide
Genbank accession no. NM_012242
Genbank version no. NM_012242.2 GI:61676924
Genbank record update date: Sep. 30, 2012 01:48 PM
Polypeptide
Genbank accession no. NP_036374
Genbank version no. NP_036374.1 GI:7110719
Genbank record update date: Sep. 30, 2012 01:48 PM
Cross-References
Fedi P. et al *J. Biol. Chem.* 274 (27), 19465-19472 (1999)
Other Information
Official Symbol: DKK1
Other Aliases: UNQ492/PRO1008, DKK-1, SK
Other Designations: dickkopf related protein-1; dickkopf-1 like; dickkopf-like protein 1; dickkopf-related protein 1; hDkk-1
Antibodies
Novartis: BHQ880 (Fulciniti M., et al *Blood.* 2009 Jul. 9; 114(2):371-379)
   For example, see US20120052070A1 SEQ ID NOs: 100 and 108.
(84) Cd52 (Cd52 Molecule)
Nucleotide
Genbank accession no. NM_001803
Genbank version no. NM_001803.2 GI:68342029
Genbank record update date: Sep. 30, 2012 01:48 PM
Polypeptide
Genbank accession no. NP_001794
Genbank version no. NP_001794.2 GI:68342030
Genbank record update date: Sep. 30, 2012 01:48 PM
Cross-References
Xia M. Q., et al *Eur. J. Immunol.* 21 (7), 1677-1684 (1991)
Other Information
Official Symbol: CD52
Other Aliases: CDW52
Other Designations: CAMPATH-1 antigen; CD52 antigen (CAMPATH-1 antigen); CDW52 antigen (CAMPATH-1 antigen); cambridge pathology 1 antigen; epididymal secretory protein E5; he5; human epididymis-specific protein 5
Antibodies
Alemtuzumab (Campath)—Skoetz N., et al *Cochrane Database Syst Rev.* 2012 Feb. 15; 2:CD008078.
   For example, see Drugbank Acc. No. DB00087 (BIOD00109, BTD00109)
(85) CS1—SLAMF7 (SLAM family member 7)
Nucleotide
Genbank accession no. NM_021181
Genbank version no. NM_021181.3 GI:1993571
Genbank record update date: Jun. 29, 2012 11:24 AM
Polypeptide
Genbank accession no. NP_067004
Genbank version no. NP_067004.3 GI:19923572
Genbank record update date: Jun. 29, 2012 11:24 AM
Cross-References
Boles K. S., et al *Immunogenetics* 52 (3-4), 302-307 (2001)
Other Information
Official Symbol: SLAMF7
Other Aliases: UNQ576/PRO1138, 19A, CD319, CRACC, CS1
Other Designations: 19A24 protein; CD2 subset 1; CD2-like receptor activating cytotoxic cells; CD2-like receptor-activating cytotoxic cells; membrane protein FOAP-12; novel LY9 (lymphocyte antigen 9) like protein; protein 19A
Antibodies
BMS: elotuzumab/HuLuc63 (Benson D M., et al *J Clin Oncol.* 2012 Jun. 1; 30(16):2013-2015)
   For example, see US20110206701 SEQ ID NOs: 9, 10, 11, 12, 13, 14, 15 and 16.
(86) Endoglin—ENG (Endoglin)
Nucleotide
Genbank accession no. AF035753
Genbank version no. AF035753.1 GI:3452260
Genbank record update date: Mar. 10, 2010 06:36 PM
Polypeptide
Genbank accession no. AAC32802
Genbank version no. AAC32802.1 GI:3452261
Genbank record update date: Mar. 10, 2010 06:36 PM
Cross-References
Rius C., et al *Blood* 92 (12), 4677-4690 (1998)
Official Symbol: ENG
Other Information
Other Aliases: RP11-228B15.2, CD105, END, HHT1, ORW, ORW1
Other Designations: CD105 antigen
(87) Annexin A1—ANXA1 (Annexin A1)
Nucleotide
Genbank accession no. X05908
Genbank version no. X05908.1 GI:34387
Genbank record update date: Feb. 2, 2011 10:02 AM
Polypeptide
Genbank accession no. CCA29338
Genbank version no. CCA29338.1 GI:34388
Genbank record update date: Feb. 2, 2011 10:02 AM
Cross-References
Wallner B. P., et al *Nature* 320 (6057), 77-81 (1986)

Other Information
Official Symbol: ANXA1
Other Aliases: RP11-71A24.1, ANX1, LPC1
Other Designations: annexin I (lipocortin I); annexin-1; calpactin II; calpactin-2; chromobindin-9; lipocortin I; p35; phospholipase A2 inhibitory protein
(88) V-CAM (CD106)—VCAM1 (Vascular Cell Adhesion Molecule 1)
Nucleotide
Genbank accession no. M60335
Genbank version no. M60335.1 GI:340193
Genbank record update date: Jun. 23, 2010 08:56 AM
Polypeptide
Genbank accession no. AAA61269
Genbank version no. AAA61269.1 GI:340194
Genbank record update date: Jun. 23, 2010 08:56 AM
Cross-References
Hession C., et al *J. Biol. Chem.* 266 (11), 6682-6685 (1991)
Other Information
Official Symbol VCAM1
Other Aliases: CD106, INCAM-100
Other Designations: CD106 antigen; vascular cell adhesion protein 1
Antibody Sequences

```
Anti-Integrin avB6
RHAB6.2
QVQLVQSGSELKKPGASVKISCKASGFAFTDSYMHWVRQAPGQGLEWMGWIDPENGDT
EYAPKFQGRFVFSLDTSVSTAYLQISSLKAEDTAVYYCTRGTPTAVPNLRGDLQVLAQKVA
GPYPFDYWGQGTLVTVSS RHCB6.2
QVQLVQSGAEVKKPGASVKVSCKASGYTFIDSYMHWVRQAPGQRLEWMGWIDPENGDT
EYAPKFQGRVTITTDTSASTAYMELSSLRSEDTAVYYCARGTPTAVPNLRGDLQVLAQKV
AGPYPFDYWGQGTLVTVSS RHF
QVQLVQSGAEVKKPGASVKVSCKASGFNFIDSYMHWVRQAPGQRLEWMGWIDPENGD
TEYAPKFQGRVTFTTDTSASTAYMELSSLRSEDTAVYYCNEGTPTGPYYFDYWGQGTLV
TVSS RHFB6
QVQLVQSGAEVKKPGASVKVSCKASGFNFIDSYMHWVRQAPGQRLEWMGWIDPENGD
TEYAPKFQGRVTFTTDTSASTAYMELSSLRSEDTAVYYCNEGTPTAVPNLRGDLQVLAQK
VAGPYYFDYWGQGTLVTVSS RHAY100bP
QVQLVQSGSELKKPGASVKISCKASGFAFTDSYMHWVRQAPGQGLEWMGWIDPENGDT
EYAPKFQGRFVFSLDTSVSTAYLQISSLKAEDTAVYYCTRGTPTGPYPFDYWGQGTLVTV
SS RKF
ENVLTQSPGTLSLSPGERATLSCSASSSVSYMHWFQQKPGQAPRLLIYSTSNLASGIPDR
FSGSGSGTDFTLTISRLEPEDFAVYYCQQRSSYPLTFGGGTKVEIK RKFL36L50
ENVLTQSPGTLSLSPGERATLSCSASSSVSYMHWLQQKPGQAPRLLIYLTSNLASGIPDR
FSGSGSGTDFTLTISRLEPEDFAVYYCQQRSSYPLTFGGGTKVEIK RKC
EIVLTQSPGTLSLSPGERATLSCSASSSVSYMHWFQQKPGQAPRLLIYSTSNLASGIPDRF
SGSGSGTDFTLTISRLEPEDFAVYYCQQRSSYPLTFGGGTKVEIK Anti-CD33
CD33 Hum195 VH
QVQLVQSGAEVKKPGSSVKVSCKASGYTFTDYNMHWVRQAPGQGLEWIGYIYPYNGGT
GYNQKFKSKATITADESTNTAYMELSSLRSEDTAVYYCARGRPAMDYWGQGTLVTVSS CD33 Hum195 VK
DIQMTQSPSSLSASVGDRVTITCRASESVDNYGISFMNWFQQKPGKAPKLLIYAASNQGS
GVPSRFSGSGSGTDFTLTISSLQPDDFATYYCQQSKEVPWTFGQGTKVEIK Anti-CD19
CD19 B4 resurfaced VH
QVQLVQPGAEVVKPGASVKLSCKTSGYTFTSNWMHWVKQRPGQGLEWIGEIDPSDSYT
NYNQNFKGKAKLTVDKSTSTAYMEVSSLRSDDTAVYYCARGSNPYYYAMDYWGQGTSV
TVSS CD19 B4 resurfaced VK
EIVLTQSPAIMSASPGERVTMTCSASSGVNYMHWYQQKPGTSPRRWIYDTSKLASGVPA
RFSGSGSGTSYSLTISSMEPEDAATYYCHQRGSYTFGGGTKLEIK Anti-Her2
Herceptin VH chain
EVQLVESGGGLVQPGGSLRLSCAASGFNIKDTYIHWVRQAPGKGLEWVARIYPTNGYTR
YADSVKGRFTISADTSKNTAYLQMNSLRAEDTAVYYCSRWGGDGFYAMDYWGQGTLVT
VSS
```

-continued

Herceptin VL chain
DIQMTQSPSSLSASVGDRVTITCRASQDVNTAVAWYQQKPGKAPKLLIYSASFLYSGVPS
RFSGSRSGTDFTLTISSLQPEDFATYYCQQHYTTPPTFGQGTKVEIK Anti-CD25
Simulect VK (also known as Basiliximab)
QIVSTQSPAIMSASPGEKVTMTCSASSSRSYMQWYQQKPGTSPKRWIYDTSKLASGVPA
RFSGSGSGTSYSLTISSMEAEDAATYYCHQRSSYTFGGGTKLEIK Simulect VH
QLQQSGTVLARPGASVKMSCKASGYSFTRYWMHWIKQRPGQGLEWIGAIYPGNSDTSY
NQKFEGKAKLTAVTSASTAYMELSSLTHEDSAVYYCSRDYGYYFDFWGQGTTLTVSS Anti-PSMA
Deimmunised VH '1
EVQLVQSGPEVKKPGATVKISCKTSGYTFTEYTIHWVKQAPGKGLEWIGNINPNNGGTTY
NQKFEDKATLTVDKSTDTAYMELSSLRSEDTAVYYCAAGWNFDYWGQGTLLTVSS Deimmunised VK '1
DIQMTQSPSSLSTSVGDRVTLTCKASQDVGTAVDWYQQKPGPSPKLLIYWASTRHTGIPS
RFSGSGSGTDFTLTISSLQPEDFADYYCQQYNSYPLTFGPGTKVDIK Deimmunised VH1 '5
EVKLVESGGGLVQPGGSMKLSCVASGFTFSNYWMNWVRQAPGKGLEWVAEIRSQSNN
FATHYAESVKGRVTISRDDSKSIVYLQMNNLRAEDTGVYYCTRRWNNFWGQGTTVTVSS Deimmunised VH2 '5
EVKLVESGGGLVQPGGSLKLSCVASGFTFSNYWMNWVRQAPGKGLEWVAEIRSQSNNF
ATHYAESVKGRVTISRDDSKSIVYLQMNNLRAEDTAVYYCTRRWNNFWGQGTTVTVSS Deimmunised VH3 '5
EVQLVESGGGLVQPGGSLKLSCVASGFTFSNYWMNWVRQAPGKGLEWVAEIRSQSNNF
ATHYAESVKGRVTISRDDSKSIVYLQMNNLRAEDTAVYYCTRRWNNFWGQGTTVTVSS Deimmunised VH4 '5
EVQLVESGGGLVQPGGSLKLSCVASGFTFSNYWMNWVRQAPGKGLEWVAEIRSQSNNF
ATHYAESVKGRFTISRDDSKSIVYLQMNNLRAEDTAVYYCTRRWNNFWGQGTTVTVSS Deimmunised VK1 '5
NIVMTQFPSSMSASVGDRVTITCKASENVGTYVSWYQQKPDQSPKMLIYGASNRFTGVP
DRFTGSGSATDFTLTISSLQTEDLADYYCGQSYTFPYTFGQGTKLEMK Deimmunised VK2 '5
NIVMTQFPSSMSASVGDRVTITCKASENVGTYVSWYQQKPDQSPKMLIYGASNRFTGVP
DRFSGSGSGTDFTLTISSLQAEDLADYYCGQSYTFPYTFGQGTKLEIK Deimmunised VK3 '5
NIQMTQFPSAMSASVGDRVTITCKASENVGTYVSWYQQKPDQSPKMLIYGASNRFTGVP
DRFSGSGSGTDFTLTISSLQAEDLADYYCGQSYTFPYTFGQGTKLEIK Deimmunised VK4 '5
NIQMTQFPSAMSASVGDRVTITCKASENVGTYVSWYQQKPDQSPKMLIYGASNRFTGVP
DRFSGSGSGTDFTLTISSLQAEDEADYYCGQSYTFPYTFGQGTKLEIK Deimmunised VK DI '5
NIVMTQFPKSMSASAGERMTLTCKASENVGTYVSWYQQKPTQSPKMLIYGASNRFTGVP
DRFSGSGSGTDFILTISSVQAEDLVDYYCGQSYTFPYTFGGGTKLEMK Deimmunised VH DI '5
EVKLEESGGGLVQPGGSMKISCVASGFTFSNYWMNWVRQSPEKGLEWVAEIRSQSNNF
ATHYAESVKGRVIISRDDSKSSVYLQMNSLRAEDTAVYYCTRRWNNFWGQGTTVTVSS Humanised RHA '5
EVQLVESGGGLVQPGGSLKLSCAASGFTFSNYWMNWVRQASGKGLEWVGEIRSQSNNF
ATHYAESVKGRFTISRDDSKNTAYLQMNSLKTEDTAVYYCTRRWNNFWGQGTTVTVSS Humanised RHB '5
EVKLVESGGGLVQPGGSLKLSCAASGFTFSNYWMNWVRQASGKGLEWVAEIRSQSNNF
ATHYAESVKGRVIISRDDSKNTVYLQMNSLRTEDTAVYYCTRRWNNFWGQGTTVTVSS Humanised RHC '5
EVQLVESGGGLVQPGGSLKLSCAASGFTFSNYWMNWVRQASGKGLEWVAEIRSQSNNF
ATHYAESVKGRVIISRDDSKNTVYLQMNSLRTEDTAVYYCTRRWNNFWGQGTTVTVSS Humanised RHD '5
EVKLVESGGGLVQPGGSLKLSCAASGFTFSNYWMNWVRQASGKGLEWVGEIRSQSNNF
ATHYAESVKGRVIISRDDSKNTVYLQMNSLRTEDTAVYYCTRRWNNFWGQGTTVTVSS Humanised RHE '5
EVKLVESGGGLVQPGGSLKLSCAASGFTFSNYWMNWVRQASGKGLEWVAEIRSQSNNF
ATHYAESVKGRFTISRDDSKNTVYLQMNSLRTEDTAVYYCTRRWNNFWGQGTTVTVSS -continued

```
Humanised RHF '5
EVKLVESGGGLVQPGGSLKLSCAASGFTFSNYWMNWVRQASGKGLEWVAEIRSQSNNF
ATHYAESVKGRVIISRDDSKNTAYLQMNSLRTEDTAVYYCTRRWNNFWGQGTTVTVSS Humanised RHG '5
EVKLVESGGGLVQPGGSLKLSCAASGFTFSNYWMNWVRQASGKGLEWVAEIRSQSNNF
ATHYAESVKGRVIISRDDSKNTAYLQMNSLRTEDTAVYYCTRRWNNFWGQGTTVTVSS Humanised RKA '5
DIQMTQSPSSVSASVGDRVTITCKASENVGTYVSWYQQKPGTAPKLLIYGASNRFTGVPS
RFSGSGSATDFTLTINNLQPEDFATYYCGQSYTFPYTFGQGTKVEIK Humanised RKB '5
DIQMTQSPSSVSASVGDRVTITCKASENVGTYVSWYQQKPGTAPKLLIYGASNRFTGVPS
RFSGSGSATDFTLTINNLQPEDFATYYCGQSYTFPYTFGQGTKVEIK Humanised RKC '5
DIQMTQSPSSVSASVGDRVTITCKASENVGTYVSWYQQKPGTAPKMLIYGASNRFTGVPS
RFSGSGSATDFTLTINNLQPEDFATYYCGQSYTFPYTFGQGTKVEIK Humanised RKD '5
DIQMTQSPSSVSASVGDRVTITCKASENVGTYVSWYQQKPGTAPKMLIYGASNRFTGVPS
RFSGSGSATDFTLTINNLQPEDFATYYCGQSYTFPYTFGQGTKVEIK Humanised RKE '5
NIVMTQSPSSVSASVGDRVTITCKASENVGTYVSWYQQKPGTAPKLLIYGASNRFTGVPD
RFTGSGSATDFILTINNLQPEDFATYYCGQSYTFPYTFGQGTKVEIK Humanised RKF '5
NIVMTQSPSSVSASVGDRVTITCKASENVGTYVSWYQQKPGTAPKMLIYGASNRFTGVPS
RFSGSGSATDFILTINNLQPEDFATYYCGQSYTFPYTFGQGTKVEIK Humanised RKG '5
NIVMTQSPSSVSASVGDRVTITCKASENVGTYVSWYQQKPGTAPKMLIYGASNRFTGVPD
RFTGSGSATDFTLTINNLQPEDFATYYCGQSYTFPYTFGQGTKVEIK
```

The parent antibody may also be a fusion protein comprising an albumin-binding peptide (ABP) sequence (Dennis et al. (2002) "Albumin Binding As A General Strategy For Improving The Pharmacokinetics Of Proteins" *J Biol Chem.* 277:35035-35043; WO 01/45746). Antibodies of the invention include fusion proteins with ABP sequences taught by: (i) Dennis et al (2002) *J Biol Chem.* 277:35035-35043 at Tables III and IV, page 35038; (ii) US 2004/0001827 at [0076]; and (iii) WO 01/45746 at pages 12-13, and all of which are incorporated herein by reference.

In one embodiment, the antibody has been raised to target specific the tumour related antigen $\alpha_v\beta_6$.

The cell binding agent may be labelled, for example to aid detection or purification of the agent either prior to incorporation as a conjugate, or as part of the conjugate. The label may be a biotin label. In another embodiment, the cell binding agent may be labelled with a radioisotope.

Connection of Linker Unit to Ligand Unit

The Ligand unit is connected to the Linker unit through a disulfide bond.

In one embodiment, the connection between the Ligand unit and the Drug Linker is formed between a thiol group of a cysteine residue of the Ligand unit and a maleimide group of the Drug Linker unit.

The cysteine residues of the Ligand unit may be available for reaction with the functional group of the Linker unit to form a connection. In other embodiments, for example where the Ligand unit is an antibody, the thiol groups of the antibody may participate in interchain disulfide bonds. These interchain bonds may be converted to free thiol groups by e.g. treatment of the antibody with DTT prior to reaction with the functional group of the Linker unit.

In some embodiments, the cysteine residue is an introduced into the heavy or light chain of an antibody. Positions for cysteine insertion by substitution in antibody heavy or light chains include those described in Published U.S. Application No. 2007-0092940 and International Patent Publication WO2008070593, which are incorporated herein.

Methods of Treatment

The compounds of the present invention may be used in a method of therapy. Also provided is a method of treatment, comprising administering to a subject in need of treatment a therapeutically-effective amount of a conjugate of formula II. The term "therapeutically effective amount" is an amount sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage, is within the responsibility of general practitioners and other medical doctors.

A conjugate may be administered alone or in combination with other treatments, either simultaneously or sequentially dependent upon the condition to be treated. Examples of treatments and therapies include, but are not limited to, chemotherapy (the administration of active agents, including, e.g. drugs; surgery; and radiation therapy.

Pharmaceutical compositions according to the present invention, and for use in accordance with the present invention, may comprise, in addition to the active ingredient, i.e. a conjugate of formula I, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous, or intravenous.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such a gelatin.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

The Conjugates can be used to treat proliferative disease and autoimmune disease. The term "proliferative disease" pertains to an unwanted or uncontrolled cellular proliferation of excessive or abnormal cells which is undesired, such as, neoplastic or hyperplastic growth, whether in vitro or in vivo.

Examples of proliferative conditions include, but are not limited to, benign, pre-malignant, and malignant cellular proliferation, including but not limited to, neoplasms and tumours (e.g., histocytoma, glioma, astrocyoma, osteoma), cancers (e.g. lung cancer, small cell lung cancer, gastrointestinal cancer, bowel cancer, colon cancer, breast carinoma, ovarian carcinoma, prostate cancer, testicular cancer, liver cancer, kidney cancer, bladder cancer, pancreatic cancer, brain cancer, sarcoma, osteosarcoma, Kaposi's sarcoma, melanoma), leukemias, psoriasis, bone diseases, fibroproliferative disorders (e.g. of connective tissues), and atherosclerosis. Other cancers of interest include, but are not limited to, haematological; malignancies such as leukemias and lymphomas, such as non-Hodgkin lymphoma, and subtypes such as DLBCL, marginal zone, mantle zone, and follicular, Hodgkin lymphoma, AML, and other cancers of B or T cell origin.

Examples of autoimmune disease include the following: rheumatoid arthritis, autoimmune demyelinative diseases (e.g., multiple sclerosis, allergic encephalomyelitis), psoriatic arthritis, endocrine ophthalmopathy, uveoretinitis, systemic lupus erythematosus, myasthenia gravis, Graves' disease, glomerulonephritis, autoimmune hepatological disorder, inflammatory bowel disease (e.g., Crohn's disease), anaphylaxis, allergic reaction, Sjögren's syndrome, type I diabetes mellitus, primary biliary cirrhosis, Wegener's granulomatosis, fibromyalgia, polymyositis, dermatomyositis, multiple endocrine failure, Schmidt's syndrome, autoimmune uveitis, Addison's disease, adrenalitis, thyroiditis, Hashimoto's thyroiditis, autoimmune thyroid disease, pernicious anemia, gastric atrophy, chronic hepatitis, lupoid hepatitis, atherosclerosis, subacute cutaneous lupus erythematosus, hypoparathyroidism, Dressler's syndrome, autoimmune thrombocytopenia, idiopathic thrombocytopenic purpura, hemolytic anemia, pemphigus vulgaris, pemphigus, dermatitis herpetiformis, alopecia arcata, pemphigoid, scleroderma, progressive systemic sclerosis, CREST syndrome (calcinosis, Raynaud's phenomenon, esophageal dysmotility, sclerodactyly, and telangiectasia), male and female autoimmune infertility, ankylosing spondolytis, ulcerative colitis, mixed connective tissue disease, polyarteritis nedosa, systemic necrotizing vasculitis, atopic dermatitis, atopic rhinitis, Goodpasture's syndrome, Chagas' disease, sarcoidosis, rheumatic fever, asthma, recurrent abortion, anti-phospholipid syndrome, farmer's lung, erythema multiforme, post cardiotomy syndrome, Cushing's syndrome, autoimmune chronic active hepatitis, bird-fancier's lung, toxic epidermal necrolysis, Alport's syndrome, alveolitis, allergic alveolitis, fibrosing alveolitis, interstitial lung disease, erythema nodosum, pyoderma gangrenosum, transfusion reaction, Takayasu's arteritis, polymyalgia rheumatica, temporal arteritis, schistosomiasis, giant cell arteritis, ascariasis, aspergillosis, Sampter's syndrome, eczema, lymphomatoid granulomatosis, Behcet's disease, Caplan's syndrome, Kawasaki's disease, dengue, encephalomyelitis, endocarditis, endomyocardial fibrosis, endophthalmitis, erythema elevatum et diutinum, psoriasis, erythroblastosis fetalis, eosinophilic faciitis, Shulman's syndrome, Felty's syndrome, filariasis, cyclitis, chronic cyclitis, heterochronic cyclitis, Fuch's cyclitis, IgA nephropathy, Henoch-Schonlein purpura, graft versus host disease, transplantation rejection, cardiomyopathy, Eaton-Lambert syndrome, relapsing polychondritis, cryoglobulinemia, Waldenstrom's macroglobulemia, Evan's syndrome, and autoimmune gonadal failure.

In some embodiments, the autoimmune disease is a disorder of B lymphocytes (e.g., systemic lupus erythematosus, Goodpasture's syndrome, rheumatoid arthritis, and type I diabetes), Th1-lymphocytes (e.g., rheumatoid arthritis, multiple sclerosis, psoriasis, Sjögren's syndrome, Hashimoto's thyroiditis, Graves' disease, primary biliary cirrhosis, Wegener's granulomatosis, tuberculosis, or graft versus host disease), or Th2-lymphocytes (e.g., atopic dermatitis, systemic lupus erythematosus, atopic asthma, rhinoconjunctivitis, allergic rhinitis, Omenn's syndrome, systemic sclerosis, or chronic graft versus host disease). Generally, disorders involving dendritic cells involve disorders of Th1-lymphocytes or Th2-lymphocytes. In some embodiments, the autoimmune disorder is a T cell-mediated immunological disorder.

In some embodiments, the amount of the Conjugate administered ranges from about 0.01 to about 10 mg/kg per dose. In some embodiments, the amount of the Conjugate administered ranges from about 0.01 to about 5 mg/kg per dose. In some embodiments, the amount of the Conjugate administered ranges from about 0.05 to about 5 mg/kg per dose. In some embodiments, the amount of the Conjugate administered ranges from about 0.1 to about 5 mg/kg per dose. In some embodiments, the amount of the Conjugate administered ranges from about 0.1 to about 4 mg/kg per dose. In some embodiments, the amount of the Conjugate administered ranges from about 0.05 to about 3 mg/kg per dose. In some embodiments, the amount of the Conjugate administered ranges from about 0.1 to about 3 mg/kg per dose. In some embodiments, the amount of the Conjugate administered ranges from about 0.1 to about 2 mg/kg per dose.

Drug Loading

The drug loading (p) is the average number of PBD drugs per cell binding agent, e.g. antibody. Where the compounds of the invention are bound to cysteines, drug loading may range from 1 to 8 drugs (D) per cell binding agent, i.e. where 1, 2, 3, 4, 5, 6, 7, and 8 drug moieties are covalently attached to the cell binding agent. Compositions of conjugates include collections of cell binding agents, e.g. antibodies, conjugated with a range of drugs, from 1 to 8. Where the compounds of the invention are bound to lysines, drug loading may range from 1 to 80 drugs (D) per cell binding agent, although an upper limit of 40, 20, 10 or 8 may be preferred. Compositions of conjugates include collections of cell binding agents, e.g. antibodies, conjugated with a range of drugs, from 1 to 80, 1 to 40, 1 to 20, 1 to 10 or 1 to 8.

The average number of drugs per antibody in preparations of ADC from conjugation reactions may be characterized by conventional means such as UV, reverse phase HPLC, HIC, mass spectroscopy, ELISA assay, and electrophoresis. The quantitative distribution of ADC in terms of p may also be determined. By ELISA, the averaged value of p in a particular preparation of ADC may be determined (Hamblett et al (2004) Clin. Cancer Res. 10:7063-7070; Sanderson et al (2005) Clin. Cancer Res. 11:843-852). However, the distribution of p (drug) values is not discernible by the antibody-antigen binding and detection limitation of ELISA. Also, ELISA assay for detection of antibody-drug conjugates does not determine where the drug moieties are attached to the antibody, such as the heavy chain or light chain fragments, or the particular amino acid residues. In some instances, separation, purification, and characterization of homogeneous ADC where p is a certain value from ADC with other drug loadings may be achieved by means such as reverse phase HPLC or electrophoresis. Such techniques are also applicable to other types of conjugates.

For some antibody-drug conjugates, p may be limited by the number of attachment sites on the antibody. For example, an antibody may have only one or several cysteine thiol groups, or may have only one or several sufficiently reactive thiol groups through which a linker may be attached. Higher drug loading, e.g. p>5, may cause aggregation, insolubility, toxicity, or loss of cellular permeability of certain antibody-drug conjugates.

Typically, fewer than the theoretical maximum of drug moieties are conjugated to an antibody during a conjugation reaction. An antibody may contain, for example, many lysine residues that do not react with the Drug Linker. Only the most reactive lysine groups may react with an amine-reactive linker reagent. Also, only the most reactive cysteine thiol groups may react with a thiol-reactive linker reagent. Generally, antibodies do not contain many, if any, free and reactive cysteine thiol groups which may be linked to a drug moiety. Most cysteine thiol residues in the antibodies of the compounds exist as disulfide bridges and must be reduced with a reducing agent such as dithiothreitol (DTT) or TCEP, under partial or total reducing conditions. The loading (drug/antibody ratio) of an ADC may be controlled in several different manners, including: (i) limiting the molar excess of Drug Linker relative to antibody, (ii) limiting the conjugation reaction time or temperature, and (iii) partial or limiting reductive conditions for cysteine thiol modification.

Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by engineering one, two, three, four, or more cysteine residues (e.g., preparing mutant antibodies comprising one or more non-native cysteine amino acid residues). U.S. Pat. No. 7,521,541 teaches engineering antibodies by introduction of reactive cysteine amino acids.

Cysteine amino acids may be engineered at reactive sites in an antibody and which do not form intrachain or intermolecular disulfide linkages (Junutula, et al., 2008b Nature Biotech., 26(8):925-932; Dornan et al (2009) Blood 114 (13):2721-2729; U.S. Pat. Nos. 7,521,541; 7,723,485; WO2009/052249). The engineered cysteine thiols may react with linker reagents or the drug-linker reagents of the present invention which have thiol-reactive, electrophilic groups such as maleimide or alpha-halo amides to form ADC with cysteine engineered antibodies and the PBD drug moieties. The location of the drug moiety can thus be designed, controlled, and known. The drug loading can be controlled since the engineered cysteine thiol groups typically react with thiol-reactive linker reagents or drug-linker reagents in high yield. Engineering an IgG antibody to introduce a cysteine amino acid by substitution at a single site on the heavy or light chain gives two new cysteines on the symmetrical antibody. A drug loading near 2 can be achieved with near homogeneity of the conjugation product ADC.

Where more than one nucleophilic or electrophilic group of the antibody reacts with a drug-linker intermediate, or linker reagent followed by drug moiety reagent, then the resulting product is a mixture of ADC compounds with a distribution of drug moieties attached to an antibody, e.g. 1, 2, 3, etc. Liquid chromatography methods such as polymeric reverse phase (PLRP) and hydrophobic interaction (HIC) may separate compounds in the mixture by drug loading value. Preparations of ADC with a single drug loading value (p) may be isolated, however, these single loading value ADCs may still be heterogeneous mixtures because the drug moieties may be attached, via the linker, at different sites on the antibody.

Thus the antibody-drug conjugate compositions of the invention include mixtures of antibody-drug conjugate compounds where the antibody has one or more PBD drug moieties and where the drug moieties may be attached to the antibody at various amino acid residues.

In one embodiment, the average number of dimer pyrrolobenzodiazepine groups per cell binding agent is in the range 1 to 20. In some embodiments the range is selected from 1 to 8, 2 to 8, 2 to 6, 2 to 4, and 4 to 8.

In some embodiments, there is one dimer pyrrolobenzodiazepine group per cell binding agent.

General Synthetic Routes

The synthesis of PBD compounds is extensively discussed in the following references, which discussions are incorporated herein by reference:

a) WO 00/12508 (pages 14 to 30);

b) WO 2005/023814 (pages 3 to 10);

c) WO 2004/043963 (pages 28 to 29); and d) WO 2005/085251 (pages 30 to 39).

Synthesis Route

Compounds of the present invention of formula I:

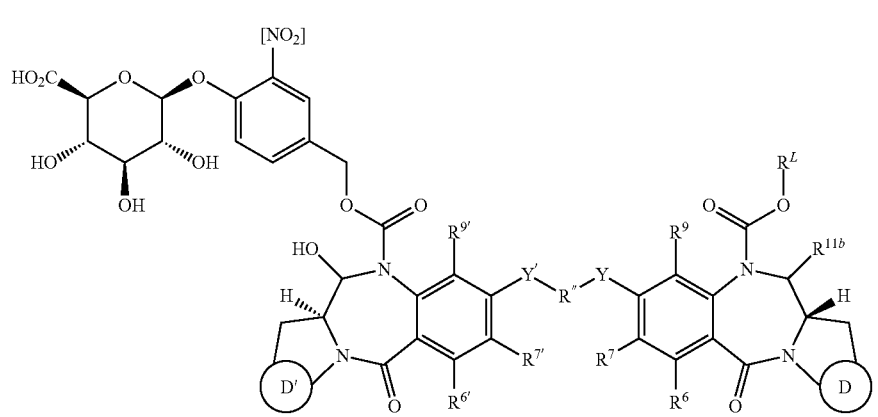

I can be synthesised from a compound of Formula II:

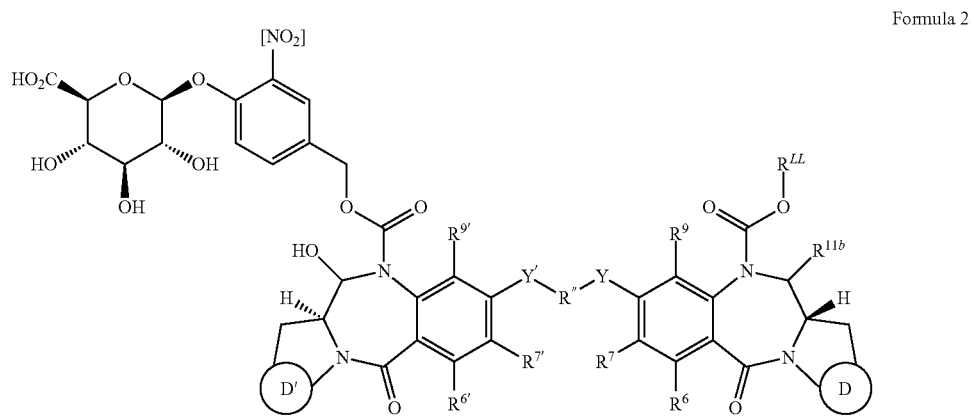

Formula 2 where $R^2$, $R^6$, $R^7$, $R^9$, $R^{6'}$, $R^{7'}$, $R^{9'}$, $R^{11b}$, $R^{12}$, Y, Y' and R" are as defined for compounds of formula I, and $R^{LL}$ is a precursor of $R^L$—this method is particularly applicable to compounds of formula I where $R^L$ is of formula IIIa. For these compounds, $R^{LL}$ will typically be a portion of $R^L$, such as a group of formula IIIa':

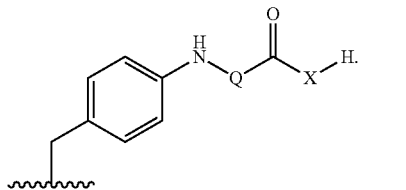

IIIa'

In such as case, the reaction involves adding the group G.

The compounds of Formula 2 may be made by deprotecting compounds of Formula 3:

Formula 3

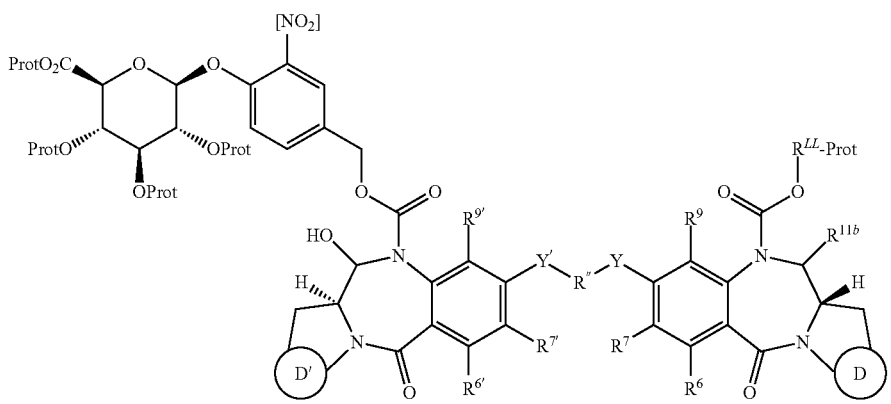

where $R^2$, $R^6$, $R^7$, $R^9$, $R^{6'}$, $R^{7'}$, $R^{9'}$, $R^{11b}$, $R^{12}$, Y, Y' and R" are as defined for compounds of formula I, $R^{LL\text{-}Prot}$ is a protected version of $R^{LL}$, and the Prot represents an appropriate carboxy/hydroxy protecting group.

Compounds of formula 3 may be made by ring-closure of compounds of Formula 4:

Formula 4

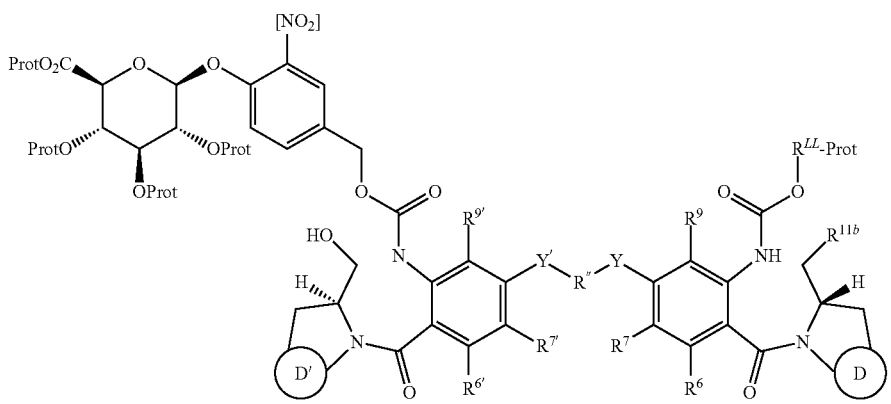

where the ring closure is carried out by oxidation, e.g. Swern.

Compounds of formula 4 can be synthesised from compounds of formula 5:

Formula 5

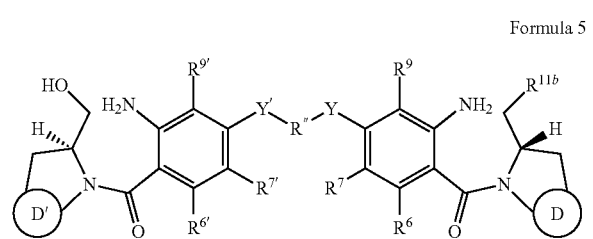

by step-wise addition of the two amino protecting groups. Step-wise addition can be achieved by simple protection of one amino group (e.g. by Fmoc), followed by installation of a desired protecting group at the other amino group. This can be followed by removal of the simple protecting group, and then installation of the other desired amino protecting group.

Compounds of formula I where $R^L$ is of formula IIIb, may be synthesised in a similar manner, although the complete $R^L$ group may be installed starting from a compound of Formula 5, rather than with the use of a protected precursor.

Compounds of Formula 5 can be synthesised by known methods, such as those disclosed in WO 2011/130598.

Synthesis of Drug Conjugates

Conjugates can be prepared as previously described. Antibodies can be conjugated to the Drug Linker compound as described in Doronina et al., Nature Biotechnology, 2003, 21, 778-784). Briefly, antibodies (4-5 mg/mL) in PBS containing 50 mM sodium borate at pH 7.4 are reduced with tris(carboxyethyl)phosphine hydrochloride (TCEP) at 37° C. The progress of the reaction, which reduces interchain disulfides, is monitored by reaction with 5,5'-dithiobis(2-nitrobenzoic acid) and allowed to proceed until the desired level of thiols/mAb is achieved. The reduced antibody is then cooled to 0° C. and alkylated with 1.5 equivalents of maleimide drug-linker per antibody thiol. After 1 hour, the reaction is quenched by the addition of 5 equivalents of N-acetyl cysteine. Quenched drug-linker is removed by gel filtration over a PD-10 column. The ADC is then sterile-filtered through a 0.22 μm syringe filter. Protein concentration can be determined by spectral analysis at 280 nm and 329 nm, respectively, with correction for the contribution of drug absorbance at 280 nm. Size exclusion chromatography can be used to determine the extent of antibody aggregation, and RP-HPLC can be used to determine the levels of remaining NAC-quenched drug-linker.

Further Preferences

The following preferences may apply to all aspects of the invention as described above, or may relate to a single aspect. The preferences may be combined together in any combination.

In some embodiments, the $NO_2$ group is present. In other embodiments, the $NO_2$ is absent.

In some embodiments, $R^{6'}$, $R^{7'}$, $R^{9'}$, and Y' are selected from the same groups as $R^6$, $R^7$, $R^9$, and Y respectively. In some of these embodiments, $R^{6'}$, $R^{7'}$, $R^{9'}$, and Y' are the same as $R^6$, $R^7$, $R^9$, and Y respectively.

In some embodiments, $R^{12}$ is the same as $R^2$.

Dimer Link

In some embodiments, Y and Y' are both O.

In some embodiments, R" is a $C_{3-7}$ alkylene group with no substituents. In some of these embodiments, R" is a $C_3$, $C_5$ or $C_7$ alkylene. In particular, R" may be a $C_3$ or $C_5$ alkylene.

In other embodiments, R" is a group of formula:

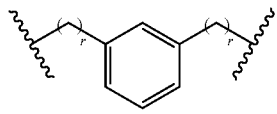

where r is 1 or 2.

$R^6$ to $R^9$

In some embodiments, $R^9$ is H.

In some embodiments, $R^6$ is selected from H, OH, OR, SH, $NH_2$, nitro and halo, and may be selected from H or halo. In some of these embodiments $R^6$ is H.

In some embodiments, $R^7$ is selected from H, OH, OR, SH, SR, $NH_2$, NHR, NRR', and halo. In some of these embodiments $R^7$ is selected from H, OH and OR, where R is selected from optionally substituted $C_{1-7}$ alkyl, $C_{3-10}$ heterocyclyl and $C_{5-10}$ aryl groups. R may be more preferably a $C_{1-4}$ alkyl group, which may or may not be substituted. A substituent of interest is a $C_{5-6}$ aryl group (e.g. phenyl). Particularly preferred substituents at the 7-positions are OMe and $OCH_2Ph$. Other substituents of particular interest are dimethylamino (i.e. —$NMe_2$); —$(OC_2H_4)_qOMe$, where q is from 0 to 2; nitrogen-containing $C_6$ heterocyclyls, including morpholino, piperidinyl and N-methyl-piperazinyl.

These embodiments and preferences apply to $R^{9'}$, $R^{6'}$ and $R^{7'}$ respectively.

D and D'

In some embodiments, D and D' are D1 and D'1 respectively.

In some embodiments, D and D' are D2 and D'2 respectively.

$R^2$

When there is a double bond present between C2 and C3, $R^2$ is selected from:

(a) $C_{5-10}$ aryl group, optionally substituted by one or more substituents selected from the group comprising: halo, nitro, cyano, ether, $C_{1-7}$ alkyl, $C_{3-7}$ heterocyclyl and bis-oxy-$C_{1-3}$ alkylene;

(b) $C_{1-5}$ saturated aliphatic alkyl;
(c) $C_{3-6}$ saturated cycloalkyl;

wherein each of $R^{11}$, $R^{12}$ and $R^{13}$ are independently selected from H, $C_{1-3}$ saturated alkyl, $C_{2-3}$ alkenyl, $C_{2-3}$ alkynyl and cyclopropyl, where the total number of carbon atoms in the $R^2$ group is no more than 5;

wherein one of $R^{15a}$ and $R^{15b}$ is H and the other is selected from: phenyl, which phenyl is optionally substituted by a group selected from halo methyl, methoxy; pyridyl; and thiophenyl; and

where $R^{14}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo methyl, methoxy; pyridyl; and thiophenyl.

When $R^2$ is a $C_{5-10}$ aryl group, it may be a $C_{5-7}$ aryl group. A $C_{5-7}$ aryl group may be a phenyl group or a $C_{5-7}$ heteroaryl group, for example furanyl, thiophenyl and pyridyl. In some embodiments, $R^2$ is preferably phenyl. In other embodiments, $R^2$ is preferably thiophenyl, for example, thiophen-2-yl and thiophen-3-yl.

When $R^2$ is a $C_{5-10}$ aryl group, it may be a $C_{8-10}$ aryl, for example a quinolinyl or isoquinolinyl group. The quinolinyl or isoquinolinyl group may be bound to the PBD core through any available ring position. For example, the quinolinyl may be quinolin-2-yl, quinolin-3-yl, quinolin-4yl, quinolin-5-yl, quinolin-6-yl, quinolin-7-yl and quinolin-8-yl. Of these quinolin-3-yl and quinolin-6-yl may be preferred. The isoquinolinyl may be isoquinolin-1-yl, isoquinolin-3-yl, isoquinolin-4yl, isoquinolin-5-yl, isoquinolin-6-yl, isoquinolin-7-yl and isoquinolin-8-yl. Of these isoquinolin-3-yl and isoquinolin-6-yl may be preferred.

When $R^2$ is a $C_{5-10}$ aryl group, it may bear any number of substituent groups. It preferably bears from 1 to 3 substituent groups, with 1 and 2 being more preferred, and singly substituted groups being most preferred. The substituents may be any position.

Where $R^2$ is $C_{5-7}$ aryl group, a single substituent is preferably on a ring atom that is not adjacent the bond to the remainder of the compound, i.e. it is preferably β or γ to the bond to the remainder of the compound. Therefore, where the $C_{5-7}$ aryl group is phenyl, the substituent is preferably in the meta- or para-positions, and more preferably is in the para-position.

Where $R^2$ is a $C_{8-10}$ aryl group, for example quinolinyl or isoquinolinyl, it may bear any number of substituents at any position of the quinoline or isoquinoline rings. In some embodiments, it bears one, two or three substituents, and these may be on either the proximal and distal rings or both (if more than one substituent).

$R^2$ Substituents, when $R^2$ is a $C_{5-10}$ Aryl Group

If a substituent on $R^2$ when $R^2$ is a $C_{5-10}$ aryl group is halo, it is preferably F or Cl, more preferably Cl.

If a substituent on $R^2$ when $R^2$ is a $C_{5-10}$ aryl group is ether, it may in some embodiments be an alkoxy group, for example, a $C_{1-7}$ alkoxy group (e.g. methoxy, ethoxy) or it may in some embodiments be a $C_{5-7}$ aryloxy group (e.g phenoxy, pyridyloxy, furanyloxy). The alkoxy group may itself be further substituted, for example by an amino group (e.g. dimethylamino).

If a substituent on $R^2$ when $R^2$ is a $C_{5-10}$ aryl group is $C_{1-7}$ alkyl, it may preferably be a $C_{1-4}$ alkyl group (e.g. methyl, ethyl, propyl, butyl).

If a substituent on $R^2$ when $R^2$ is a $C_{5-10}$ aryl group is $C_{3-7}$ heterocyclyl, it may in some embodiments be $C_6$ nitrogen containing heterocyclyl group, e.g. morpholino, thiomorpholino, piperidinyl, piperazinyl. These groups may be bound to the rest of the PBD moiety via the nitrogen atom. These groups may be further substituted, for example, by $C_{1-4}$ alkyl groups. If the $C_6$ nitrogen containing heterocyclyl group is piperazinyl, the said further substituent may be on the second nitrogen ring atom.

If a substituent on $R^2$ when $R^2$ is a $C_{5-10}$ aryl group is bis-oxy-$C_{1-3}$ alkylene, this is preferably bis-oxy-methylene or bis-oxy-ethylene.

If a substituent on $R^2$ when $R^2$ is a $C_{5-10}$ aryl group is ester, this is preferably methyl ester or ethyl ester.

Particularly preferred substituents when $R^2$ is a $C_{5-10}$ aryl group include methoxy, ethoxy, fluoro, chloro, cyano, bis-oxy-methylene, methyl-piperazinyl, morpholino and methyl-thiophenyl. Other particularly preferred substituents for $R^2$ are dimethylaminopropyloxy and carboxy.

Particularly preferred substituted $R^2$ groups when $R^2$ is a $C_{5-10}$ aryl group include, but are not limited to, 4-methoxyphenyl, 3-methoxyphenyl, 4-ethoxy-phenyl, 3-ethoxy-phenyl, 4-fluoro-phenyl, 4-chloro-phenyl, 3,4-bisoxymethylene-phenyl, 4-methylthiophenyl, 4-cyanophenyl, 4-phenoxyphenyl, quinolin-3-yl and quinolin-6-yl, isoquinolin-3-yl and isoquinolin-6-yl, 2-thienyl, 2-furanyl, methoxynaphthyl, and naphthyl. Another possible substituted $R^{12}$ group is 4-nitrophenyl. $R^{12}$ groups of particular interest include 4-(4-methylpiperazin-1-yl)phenyl and 3,4-bisoxymethylene-phenyl.

When $R^2$ is $C_{1-5}$ saturated aliphatic alkyl, it may be methyl, ethyl, propyl, butyl or pentyl. In some embodiments, it may be methyl, ethyl or propyl (n-pentyl or isopropyl). In some of these embodiments, it may be methyl. In other embodiments, it may be butyl or pentyl, which may be linear or branched.

When $R^2$ is $C_{3-6}$ saturated cycloalkyl, it may be cyclopropyl, cyclobutyl, cyclopentyl or cyclohexyl. In some embodiments, it may be cyclopropyl.

When $R^2$ is

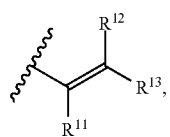

each of $R^{11}$, $R^{12}$ and $R^{13}$ are independently selected from H, $C_{1-3}$ saturated alkyl, $C_{2-3}$ alkenyl, $C_{2-3}$ alkynyl and cyclopropyl, where the total number of carbon atoms in the $R^2$ group is no more than 5. In some embodiments, the total number of carbon atoms in the $R^2$ group is no more than 4 or no more than 3.

In some embodiments, one of $R^{11}$, $R^{12}$ and $R^{13}$ is H, with the other two groups being selected from H, $C_{1-3}$ saturated alkyl, $C_{2-3}$ alkenyl, $C_{2-3}$ alkynyl and cyclopropyl.

In other embodiments, two of $R^{11}$, $R^{12}$ and $R^{13}$ are H, with the other group being selected from H, $C_{1-3}$ saturated alkyl, $C_{2-3}$ alkenyl, $C_{2-3}$ alkynyl and cyclopropyl.

In some embodiments, the groups that are not H are selected from methyl and ethyl. In some of these embodiments, the groups that re not H are methyl.

In some embodiments, $R^{11}$ is H.

In some embodiments, $R^{12}$ is H.

In some embodiments, $R^{13}$ is H.

In some embodiments, $R^{11}$ and $R^{12}$ are H.

In some embodiments, $R^{11}$ and $R^{13}$ are H.

In some embodiments, $R^{12}$ and $R^{13}$ are H.

An $R^2$ group of particular interest is:

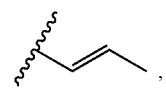

When $R^2$ is

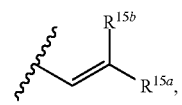

one of $R^{15a}$ and $R^{15b}$ is H and the other is selected from: phenyl, which phenyl is optionally substituted by a group selected from halo, methyl, methoxy; pyridyl; and thiophenyl. In some embodiments, the group which is not H is optionally substituted phenyl. If the phenyl optional substituent is halo, it is preferably fluoro. In some embodiment, the phenyl group is unsubstituted.

When $R^2$ is

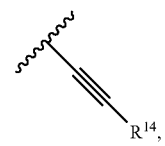

$R^{14}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo methyl, methoxy; pyridyl; and thiophenyl. If the phenyl optional substituent is halo, it is preferably fluoro. In some embodiment, the phenyl group is unsubstituted. In some embodiments, $R^{14}$ is selected from H, methyl, ethyl, ethenyl and ethynyl. In some of these embodiments, $R^{14}$ is selected from H and methyl.

When there is a single bond present between C2 and C3, $R^2$ is H or

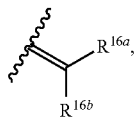

where $R^{16a}$ and $R^{16b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{16a}$ and $R^{16b}$ is H, the other is selected from nitrile and a $C_{1-4}$ alkyl ester.

In some embodiments, $R^2$ is H.

In some embodiments, $R^2$ is

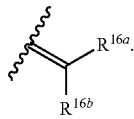

In some embodiments, it is preferred that $R^{16a}$ and $R^{16b}$ are both H.

In other embodiments, it is preferred that $R^{16a}$ and $R^{16b}$ are both methyl.

In further embodiments, it is preferred that one of $R^{16a}$ and $R^{16b}$ is H, and the other is selected from $C_{1-4}$ saturated alkyl, $C_{2-3}$ alkenyl, which alkyl and alkenyl groups are optionally substituted. In these further embodiment, it may be further preferred that the group which is not H is selected from methyl and ethyl.

$R^{12}$

When there is a double bond present between C2' and C3', $R^{12}$ is selected from:

(a) $C_{5-10}$ aryl group, optionally substituted by one or more substituents selected from the group comprising: halo, nitro, cyano, ether, $C_{1-7}$ alkyl, $C_{3-7}$ heterocyclyl and bis-oxy-$C_{1-3}$ alkylene;

(b) $C_{1-5}$ saturated aliphatic alkyl;

(c) $C_{3-6}$ saturated cycloalkyl;

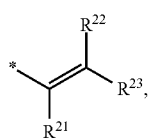 (d)

wherein each of $R^{21}$, $R^{22}$ and $R^{23}$ are independently selected from H, $C_{1-3}$ saturated alkyl, $C_{2-3}$ alkenyl, $C_{2-3}$ alkynyl and cyclopropyl, where the total number of carbon atoms in the $R^{12}$ group is no more than 5;

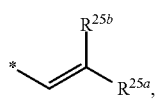 (e)

wherein one of $R^{25a}$ and $R^{25b}$ is H and the other is selected from: phenyl, which phenyl is optionally substituted by a group selected from halo methyl, methoxy; pyridyl; and thiophenyl; and

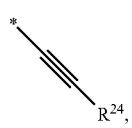 (f)

where $R^{24}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo methyl, methoxy; pyridyl; and thiophenyl.

When $R^{12}$ is a $C_{5-10}$ aryl group, it may be a $C_{5-7}$ aryl group. A $C_{5-7}$ aryl group may be a phenyl group or a $C_{5-7}$ heteroaryl group, for example furanyl, thiophenyl and pyridyl. In some embodiments, $R^{12}$ is preferably phenyl. In other embodiments, $R^{12}$ is preferably thiophenyl, for example, thiophen-2-yl and thiophen-3-yl.

When $R^{12}$ is a $C_{5-10}$ aryl group, it may be a $C_{8-10}$ aryl, for example a quinolinyl or isoquinolinyl group. The quinolinyl or isoquinolinyl group may be bound to the PBD core through any available ring position. For example, the quinolinyl may be quinolin-2-yl, quinolin-3-yl, quinolin-4yl, quinolin-5-yl, quinolin-6-yl, quinolin-7-yl and quinolin-8-yl. Of these quinolin-3-yl and quinolin-6-yl may be preferred. The isoquinolinyl may be isoquinolin-1-yl, isoquinolin-3-yl, isoquinolin-4yl, isoquinolin-5-yl, isoquinolin-6-yl, isoquinolin-7-yl and isoquinolin-8-yl. Of these isoquinolin-3-yl and isoquinolin-6-yl may be preferred.

When $R^{12}$ is a $C_{5-10}$ aryl group, it may bear any number of substituent groups. It preferably bears from 1 to 3 substituent groups, with 1 and 2 being more preferred, and singly substituted groups being most preferred. The substituents may be any position.

Where $R^{12}$ is $C_{5-7}$ aryl group, a single substituent is preferably on a ring atom that is not adjacent the bond to the remainder of the compound, i.e. it is preferably β or γ to the bond to the remainder of the compound. Therefore, where the $C_{5-7}$ aryl group is phenyl, the substituent is preferably in the meta- or para-positions, and more preferably is in the para-position.

Where $R^{12}$ is a $C_{8-10}$ aryl group, for example quinolinyl or isoquinolinyl, it may bear any number of substituents at any position of the quinoline or isoquinoline rings. In some embodiments, it bears one, two or three substituents, and these may be on either the proximal and distal rings or both (if more than one substituent).

$R^{12}$ Substituents, when $R^{12}$ is a $C_{5-10}$ Aryl Group

If a substituent on $R^{12}$ when $R^{12}$ is a $C_{5-10}$ aryl group is halo, it is preferably F or Cl, more preferably Cl.

If a substituent on $R^{12}$ when $R^{12}$ is a $C_{5-10}$ aryl group is ether, it may in some embodiments be an alkoxy group, for example, a $C_{1-7}$ alkoxy group (e.g. methoxy, ethoxy) or it may in some embodiments be a $C_{5-7}$ aryloxy group (e.g phenoxy, pyridyloxy, furanyloxy). The alkoxy group may itself be further substituted, for example by an amino group (e.g. dimethylamino).

If a substituent on $R^{12}$ when $R^{12}$ is a $C_{5-10}$ aryl group is $C_{1-7}$ alkyl, it may preferably be a $C_{1-4}$ alkyl group (e.g. methyl, ethyl, propyl, butyl).

If a substituent on $R^{12}$ when $R^{12}$ is a $C_{5-10}$ aryl group is $C_{3-7}$ heterocyclyl, it may in some embodiments be $C_6$ nitrogen containing heterocyclyl group, e.g. morpholino, thiomorpholino, piperidinyl, piperazinyl. These groups may be bound to the rest of the PBD moiety via the nitrogen atom. These groups may be further substituted, for example, by $C_{1-4}$ alkyl groups. If the $C_6$ nitrogen containing heterocyclyl group is piperazinyl, the said further substituent may be on the second nitrogen ring atom.

If a substituent on $R^{12}$ when $R^{12}$ is a $C_{5-10}$ aryl group is bis-oxy-$C_{1-3}$ alkylene, this is preferably bis-oxy-methylene or bis-oxy-ethylene.

If a substituent on $R^{12}$ when $R^{12}$ is a $C_{5-10}$ aryl group is ester, this is preferably methyl ester or ethyl ester.

Particularly preferred substituents when $R^{12}$ is a $C_{5-10}$ aryl group include methoxy, ethoxy, fluoro, chloro, cyano, bis-oxy-methylene, methyl-piperazinyl, morpholino and methyl-thiophenyl. Other particularly preferred substituents for $R^{12}$ are dimethylaminopropyloxy and carboxy.

Particularly preferred substituted $R^{12}$ groups when $R^{12}$ is a $C_{5-10}$ aryl group include, but are not limited to, 4-methoxyphenyl, 3-methoxyphenyl, 4-ethoxy-phenyl, 3-ethoxy-phenyl, 4-fluoro-phenyl, 4-chloro-phenyl, 3,4-bisoxymethylene-phenyl, 4-methylthiophenyl, 4-cyanophenyl, 4-phenoxyphenyl, quinolin-3-yl and quinolin-6-yl, isoquinolin-3-yl and isoquinolin-6-yl, 2-thienyl, 2-furanyl, methoxynaphthyl, and naphthyl. Another possible substituted $R^{12}$ group is 4-nitrophenyl. $R^{12}$ groups of particular interest include 4-(4-methylpiperazin-1-yl)phenyl and 3,4-bisoxymethylene-phenyl.

When $R^{12}$ is $C_{1-5}$ saturated aliphatic alkyl, it may be methyl, ethyl, propyl, butyl or pentyl. In some embodiments, it may be methyl, ethyl or propyl (n-pentyl or isopropyl). In some of these embodiments, it may be methyl. In other embodiments, it may be butyl or pentyl, which may be linear or branched.

When $R^{12}$ is $C_{3-6}$ saturated cycloalkyl, it may be cyclopropyl, cyclobutyl, cyclopentyl or cyclohexyl. In some embodiments, it may be cyclopropyl.

When $R^{12}$ is

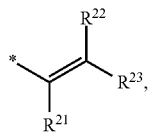

each of $R^{21}$, $R^{22}$ and $R^{23}$ are independently selected from H, $C_{1-3}$ saturated alkyl, $C_{2-3}$ alkenyl, $C_{2-3}$ alkynyl and cyclopropyl, where the total number of carbon atoms in the $R^{12}$ group is no more than 5. In some embodiments, the total number of carbon atoms in the $R^{12}$ group is no more than 4 or no more than 3.

In some embodiments, one of $R^{21}$, $R^{22}$ and $R^{23}$ is H, with the other two groups being selected from H, $C_{1-3}$ saturated alkyl, $C_{2-3}$ alkenyl, $C_{2-3}$ alkynyl and cyclopropyl.

In other embodiments, two of $R^{21}$, $R^{22}$ and $R^{23}$ are H, with the other group being selected from H, $C_{1-3}$ saturated alkyl, $C_{2-3}$ alkenyl, $C_{2-3}$ alkynyl and cyclopropyl.

In some embodiments, the groups that are not H are selected from methyl and ethyl. In some of these embodiments, the groups that re not H are methyl.

In some embodiments, $R^{21}$ is H.
In some embodiments, $R^{22}$ is H.
In some embodiments, $R^{23}$ is H.
In some embodiments, $R^{21}$ and $R^{22}$ are H.

In some embodiments, $R^{21}$ and $R^{23}$ are H.
In some embodiments, $R^{22}$ and $R^{23}$ are H.
An $R^{12}$ group of particular interest is:

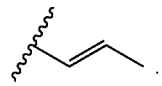

When $R^{12}$ is

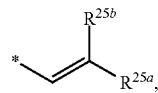

one of $R^{25a}$ and $R^{25b}$ is H and the other is selected from: phenyl, which phenyl is optionally substituted by a group selected from halo, methyl, methoxy; pyridyl; and thiophenyl. In some embodiments, the group which is not H is optionally substituted phenyl. If the phenyl optional substituent is halo, it is preferably fluoro. In some embodiment, the phenyl group is unsubstituted.

When $R^{12}$ is

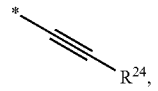

$R^{24}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo methyl, methoxy; pyridyl; and thiophenyl. If the phenyl optional substituent is halo, it is preferably fluoro. In some embodiment, the phenyl group is unsubstituted.

In some embodiments, $R^{24}$ is selected from H, methyl, ethyl, ethenyl and ethynyl. In some of these embodiments, $R^{24}$ is selected from H and methyl.

When there is a single bond present between C2' and C3', $R^{12}$ is H or

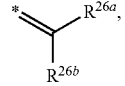

where $R^{26a}$ and $R^{26b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{26a}$ and $R^{26b}$ is H, the other is selected from nitrile and a $C_{1-4}$ alkyl ester.

In some embodiments, $R^{12}$ is H.
In some embodiments, $R^{12}$ is

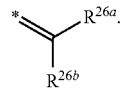

In some embodiments, it is preferred that $R^{26a}$ and $R^{26b}$ are both H.

In other embodiments, it is preferred that $R^{26a}$ and $R^{26b}$ are both methyl.

In further embodiments, it is preferred that one of $R^{26a}$ and $R^{26b}$ is H, and the other is selected from $C_{1-4}$ saturated alkyl, $C_{2-3}$ alkenyl, which alkyl and alkenyl groups are optionally substituted. In these further embodiment, it may be further preferred that the group which is not H is selected from methyl and ethyl.

$R^{11b}$

In some embodiments, $R^{11b}$ is OH.

In some embodiments, $R^{11b}$ is $OR^A$, where $R^A$ is $C_{1-4}$ alkyl. In some of these embodiments, $R^A$ is methyl.

In some embodiments of the first aspect of the present invention are of formula Ia-1, Ia-2 or Ia-3:

where $R^{2a}$ and $R^{12a}$ are the same and are selected from:

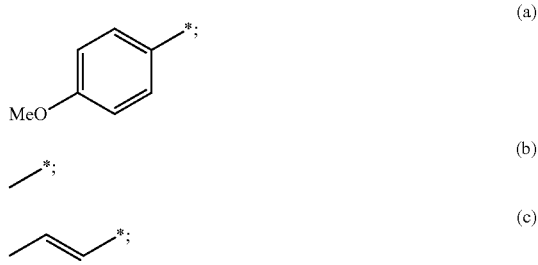

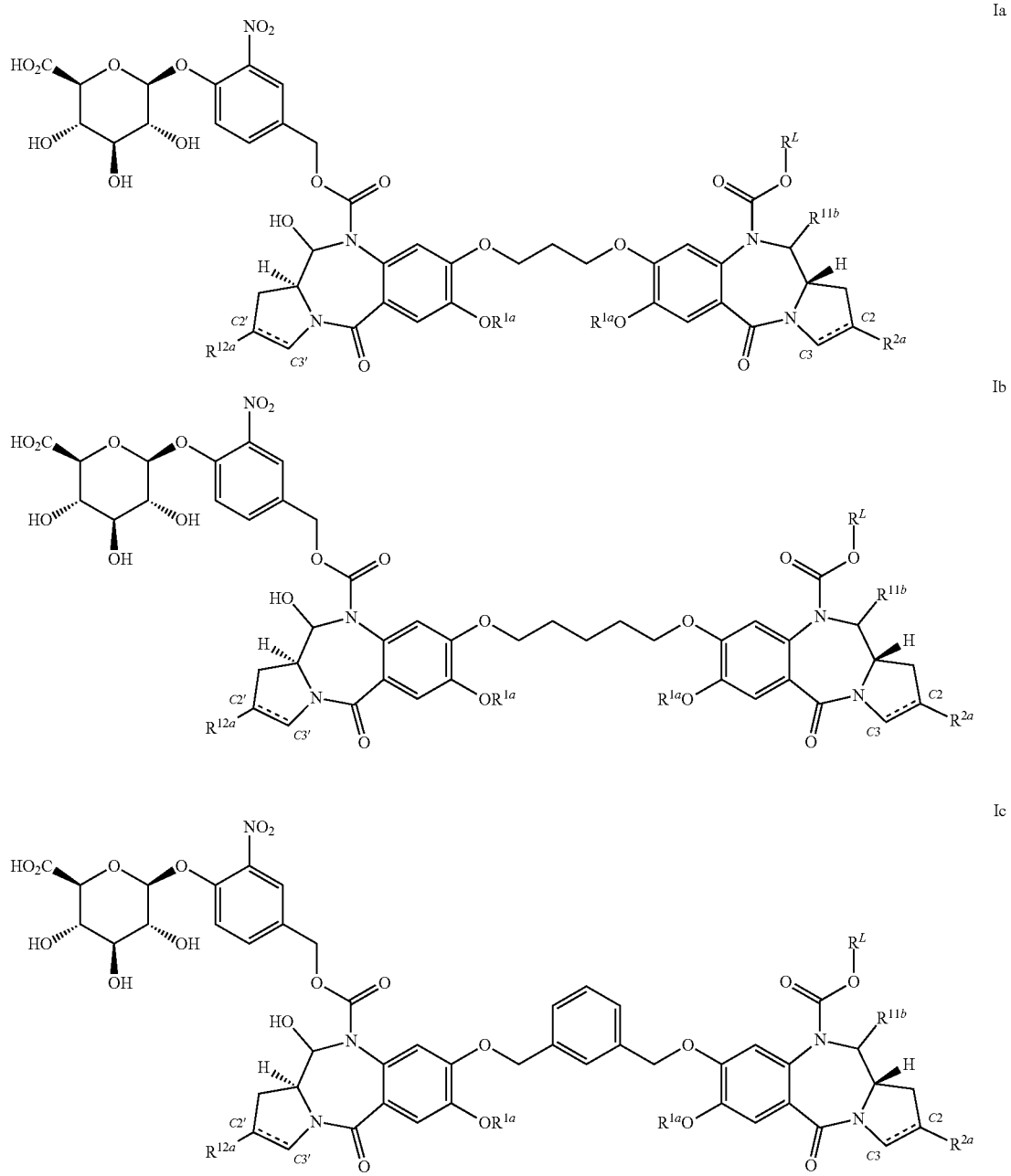

-continued (d) 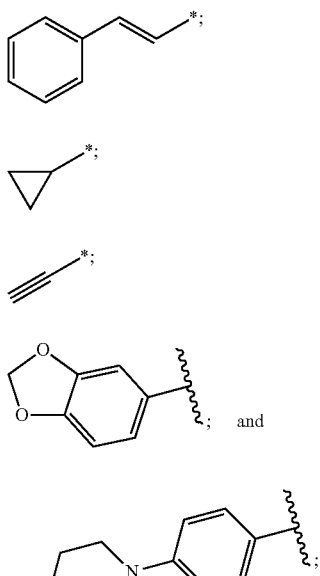

(e) 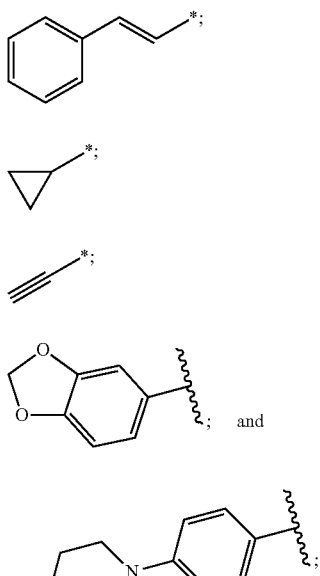

(f) 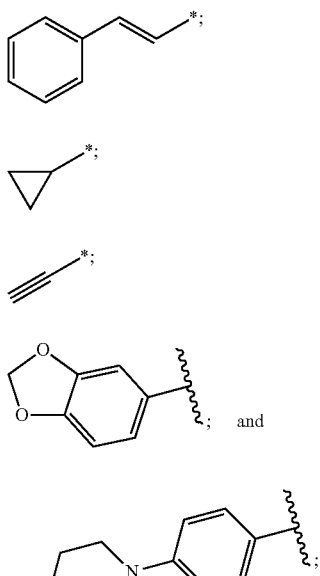

(g) 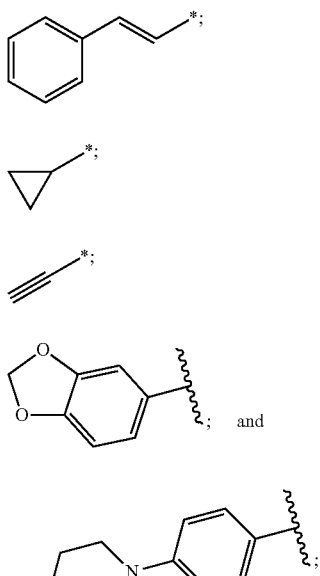; and (h) 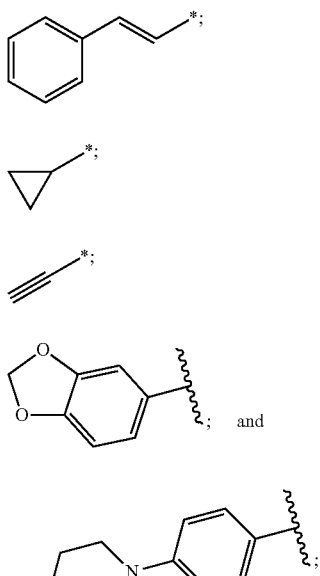;

$R^{1a}$ is selected from methyl and benzyl;

$R^L$ and $R^{11b}$ are as defined above.

In some embodiments of the present invention both $R^2$ and $R^{12}$ comprise no more than 3 carbon atoms.

Thus in these embodiments where there is a double bond present between C2 and C3, $R^2$ may be selected from:

(i) Methyl;

(ii) Ethyl;

(iii) Propyl;

(iv) Cyclopropyl;

(v) 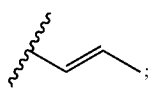;

(vi) 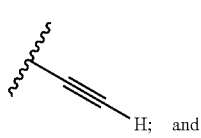H; and (vi) 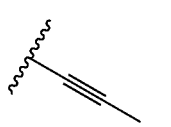

Thus in these embodiments where there is no double bond present between C2 and C3, $R^2$ may be selected from:

(i) H;

(ii) 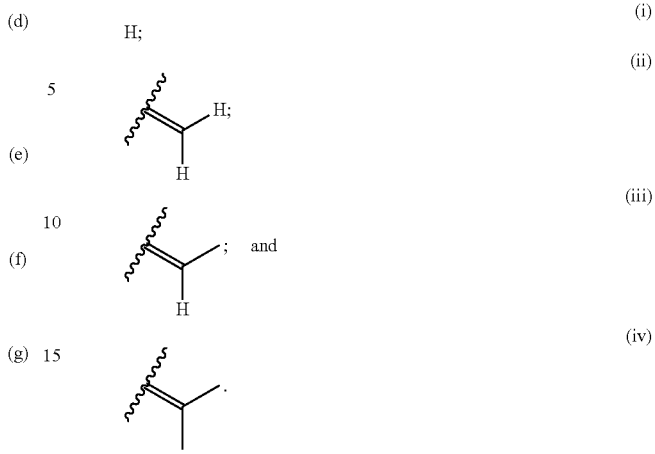H;

(iii) 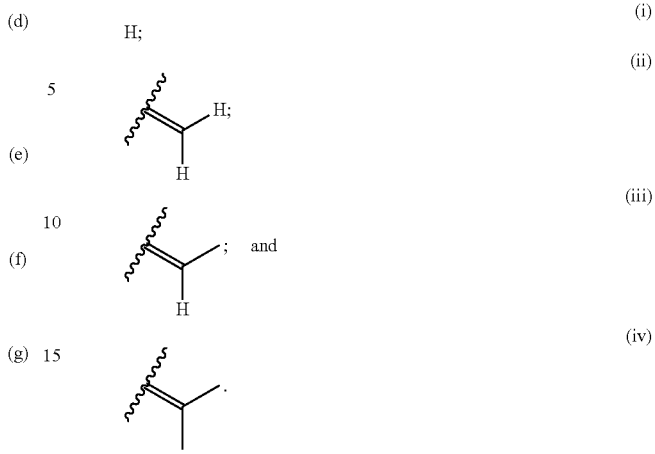; and (iv) 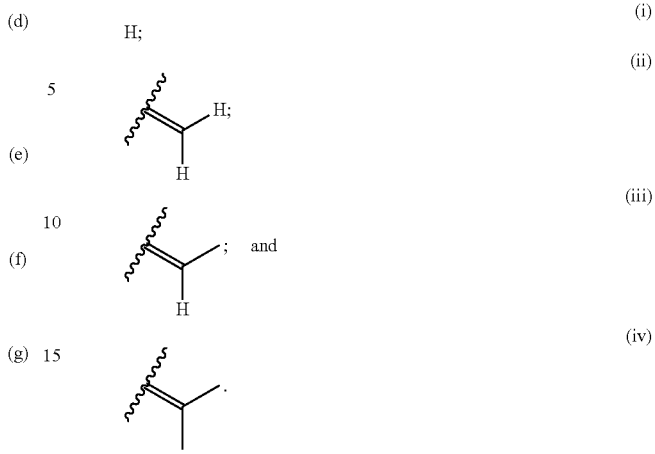.

Thus in these embodiments where there is a double bond present between C2' and C3', $R^{12}$ may be selected from:

(i) Methyl;

(ii) Ethyl;

(iii) Propyl;

(iv) Cyclopropyl;

(v) 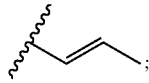;

(vi) 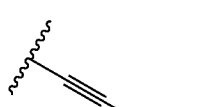H; and (vi) 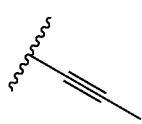

Thus in these embodiments where there is no double bond present between C2' and C3', $R^{12}$ may be selected from:

(i) H;

(ii) 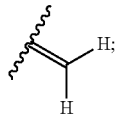H;

(iii) 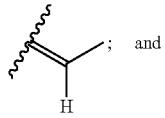; and

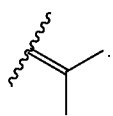

(iv)

In some of these embodiments both $R^2$ and $R^{12}$ comprise no more than 2 carbon atoms.

Thus in these embodiments where there is a double bond present between C2 and C3, $R^2$ may be selected from:

Methyl; (i)

Ethyl; and (ii)

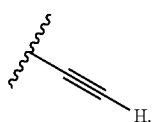

(vi)

Thus in these embodiments where there is no double bond present between C2 and C3, $R^2$ may be selected from:

H; (i)

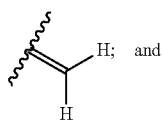

(ii)

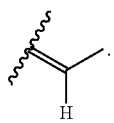

(iii)

Thus in these embodiments where there is a double bond present between C2' and C3', $R^{12}$ may be selected from:

Methyl; (i)

Ethyl; and (ii)

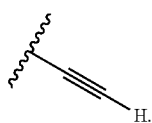

(vi)

Thus in these embodiments where there is no double bond present between C2' and C3', $R^{12}$ may be selected from:

H; (i)

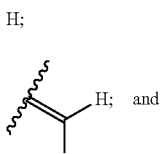

(ii)

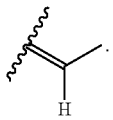

(iii)

In further of these embodiments both $R^2$ and $R^{12}$ comprise no more than 1 carbon atom.

Thus in these embodiments where there is a double bond present between C2 and C3, $R^2$ may be methyl. Thus in these embodiments where there is no double bond present between C2 and C3, $R^2$ may be selected from:

H; and (i)

(ii)

Thus in these embodiments where there is a double bond present between C2' and C3', $R^{12}$ may be methyl. Thus in these embodiments where there is no double bond present between C2' and C3', $R^{12}$ may be selected from:

H; and (i)

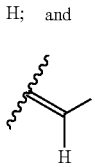

(ii)

Without wishing to be bound by theory, where the substituent at the $C_2$ position of the PBD dimers are small, the use of the glucuronide capping unit in these drug linkers is believed to be particularly advantageous, as it significantly increases the hydrophilicity of the drug linker, making the drug linkers easier to conjugate to a ligand unit.

These embodiments and preferences also apply to the second aspect of the invention.

Linker ($R^L$)

In some embodiments, $R^L$ is of formula IIIa.

In some embodiments, $R^{LL}$ is of formula IIIa'.

$G^L$

GL may be selected from

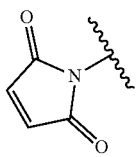

($G^{L1-1}$)

(G^{L1-2})
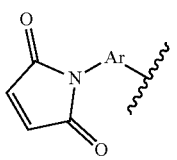
(G^{L2})
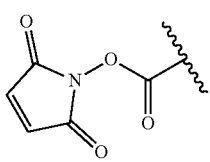
(G^{L3-1})
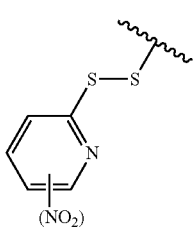
where the NO₂ group is optional
(G^{L3-2})
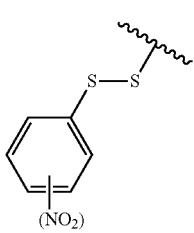
where the NO₂ group is optional
(G^{L3-3})
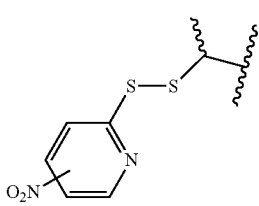
where the NO₂ group is optional
(G^{L3-4})
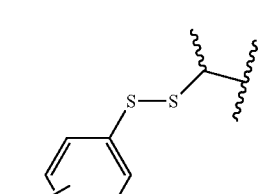
where the NO₂ group is optional
(G^{L4})
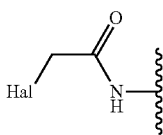
Where Hal = I, Br, Cl
(G^{L5})
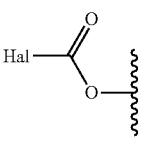
(G^{L6})
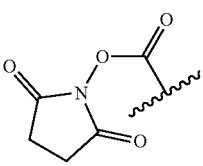
(G^{L7})
(G^{L8})
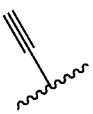
(G^{L9})
In some embodiments, $G^L$ is selected from $G^{L1-1}$ and $G^{L1-2}$. In some of these embodiments, $G^L$ is $G^{L1-1}$.
$G^{LL}$
$G^{LL}$ may be selected from:
(G^{LL1-1})
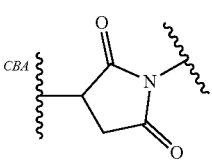
(G^{LL1-2})
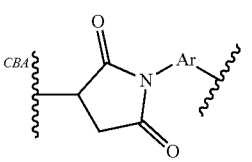
(G^{LL2})
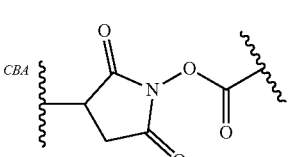

-continued (G^{LL3-1}) 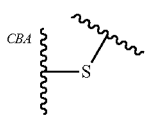

(G^{LL3-2}) 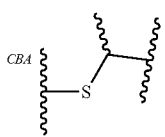

(G^{LL4}) 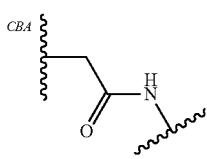

(G^{LL5}) 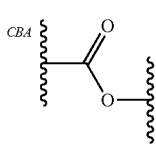

(G^{LL6}) 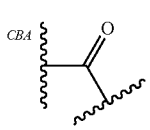

(G^{LL7}) 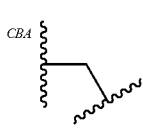

(G^{LL8-1}) 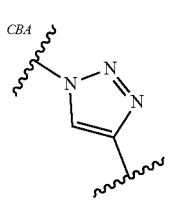

(G^{LL8-2}) 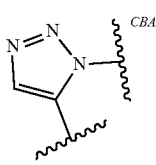

(G^{LL9-1}) 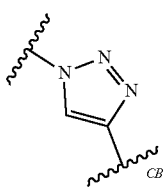

(G^{LL9-2}) 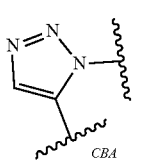

In some embodiments, $G^{LL}$ is selected from $G^{LL1-1}$ and $G^{LL1-2}$. In some of these embodiments, $G^{LL}$ is $G^{LL1-1}$.

X

X is:

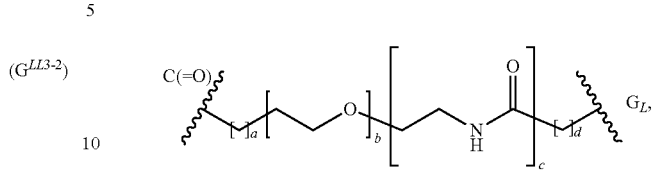

where a=0 to 5, b=0 to 16, c=0 or 1, d=0 to 5.

a may be 0, 1, 2, 3, 4 or 5. In some embodiments, a is 0 to 3. In some of these embodiments, a is 0 or 1. In further embodiments, a is 0.

b may be 0, 1, 2, 3, 4, 5, 6, 7, 8, 9, 10, 11, 12, 13, 14, 15 or 16. In some embodiments, b is 0 to 12. In some of these embodiments, b is 0 to 8, and may be 0, 2, 4 or 8.

c may be 0 or 1.

d may be 0, 1, 2, 3, 4 or 5. In some embodiments, d is 0 to 3. In some of these embodiments, d is 1 or 2. In further embodiments, d is 2.

In some embodiments of X, a is 0, c is 1 and d is 2, and b may be from 0 to 8. In some of these embodiments, b is 0, 4 or 8.

$Q^X$

In one embodiment, $Q^X$ is an amino acid residue. The amino acid may a natural amino acids or a non-natural amino acid.

In one embodiment, $Q^X$ is selected from: Phe, Lys, Val, Ala, Cit, Leu, Ile, Arg, and Trp, where Cit is citrulline.

In one embodiment, $Q^X$ comprises a dipeptide residue. The amino acids in the dipeptide may be any combination of natural amino acids and non-natural amino acids. In some embodiments, the dipeptide comprises natural amino acids. Where the linker is a cathepsin labile linker, the dipeptide is the site of action for cathepsin-mediated cleavage. The dipeptide then is a recognition site for cathepsin.

In one embodiment, $Q^X$ is selected from:
$^{CO}$-Phe-Lys-$^{NH}$,
$^{CO}$-Val-Ala-$^{NH}$,
$^{CO}$-Val-Lys-$^{NH}$,
$^{CO}$-Ala-Lys-$^{NH}$,
$^{CO}$-Val-Cit-$^{NH}$,
$^{CO}$-Phe-Cit-$^{NH}$,
$^{CO}$-Leu-Cit-$^{NH}$,
$^{CO}$-Ile-Cit-$^{NH}$,
$^{CO}$-Phe-Arg-$^{NH}$, and
$^{CO}$-Trp-Cit-$^{NH}$;
where Cit is citrulline.

Preferably, $Q^X$ is selected from:
$^{CO}$-Phe-Lys-$^{NH}$,
$^{CO}$-Val-Ala-$^{NH}$,
$^{CO}$-Val-Lys-$^{NH}$,
$^{CO}$-Ala-Lys-$^{NH}$,
$^{CO}$-Val-Cit-$^{NH}$.

Most preferably, $Q^X$ is selected from $^{CO}$-Phe-Lys-$^{NH}$, $^{CO}$-Val-Cit-$^{NH}$ and $^{CO}$-Val-Ala-$^{NH}$.

Other dipeptide combinations of interest include:
$^{CO}$-Gly-Gly-$^{NH}$,
$^{CO}$-Pro-Pro-$^{NH}$, and
$^{CO}$-Val-Glu-$^{NH}$.

Other dipeptide combinations may be used, including those described by Dubowchik et al., *Bioconjugate Chemistry*, 2002, 13, 855-869, which is incorporated herein by reference.

In some embodiments, $Q^X$ is a tripeptide residue. The amino acids in the tripeptide may be any combination of natural amino acids and non-natural amino acids. In some embodiments, the tripeptide comprises natural amino acids. Where the linker is a cathepsin labile linker, the tripeptide is the site of action for cathepsin-mediated cleavage. The tripeptide then is a recognition site for cathepsin.

In one embodiment, the amino acid side chain is chemically protected, where appropriate. The side chain protecting group may be a group as discussed below. Protected amino acid sequences are cleavable by enzymes. For example, a dipeptide sequence comprising a Boc side chain-protected Lys residue is cleavable by cathepsin.

Protecting groups for the side chains of amino acids are well known in the art and are described in the Novabiochem Catalog, and as described above.

In some embodiments, $R^L$ is of formula IIIb.
In some embodiments, $R^{LL}$ is formula IIIb'.

$R^{L1}$ and $R^{L2}$ are independently selected from H and methyl, or together with the carbon atom to which they are bound form a cyclopropylene or cyclobutylene group.

In some embodiments, both $R^{L1}$ and $R^{L2}$ are H.
In some embodiments, $R^{L1}$ is H and $R^{L2}$ is methyl.
In some embodiments, both $R^{L1}$ and $R^{L2}$ are methyl.
In some embodiments, $R^{L1}$ and $R^{L2}$ together with the carbon atom to which they are bound form a cyclopropylene group.
In some embodiments, $R^{L1}$ and $R^{L2}$ together with the carbon atom to which they are bound form a cyclobutylene group.

In the group IIIb, in some embodiments, e is 0. In other embodiments, e is 1 and the nitro group may be in any available position of the ring. In some of these embodiments, it is in the ortho position. In others of these embodiments, it is in the para position.

In one particular embodiment, the first aspect of the invention comprises a compound of formula Id:

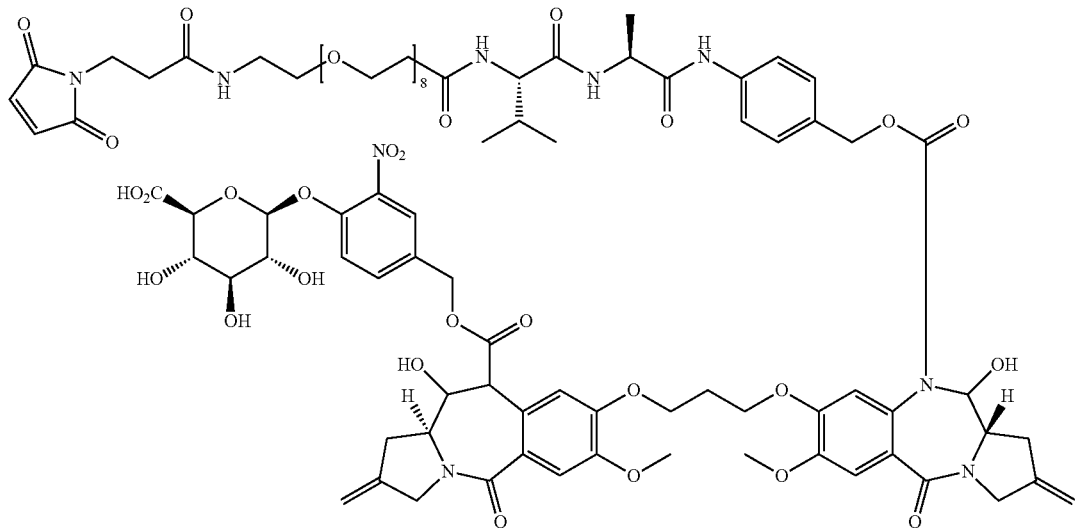

(Id)

In one particular embodiment, the second aspect of the invention, the Drug linker ($D^L$) is of formula (Id'):

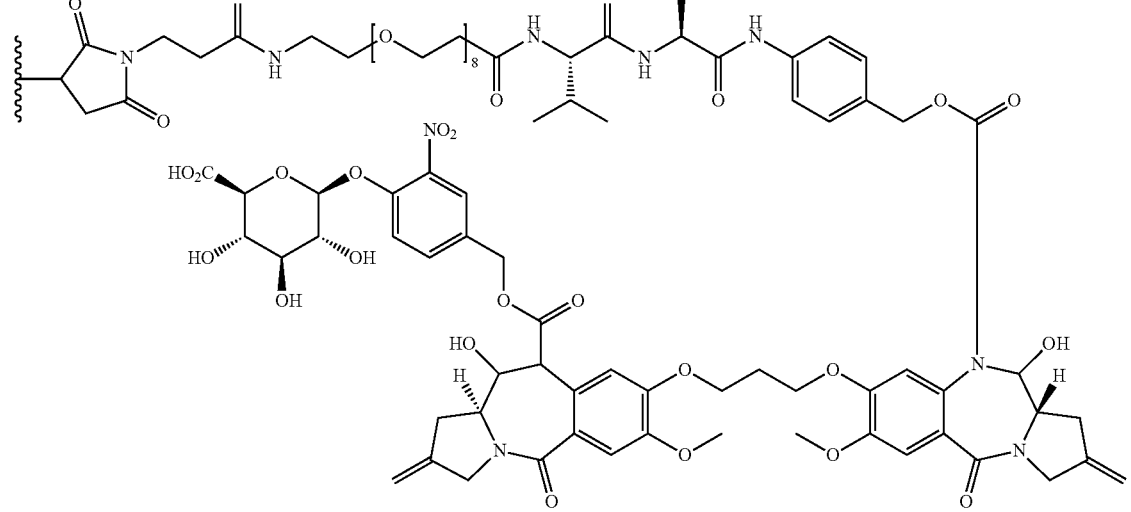

(Id')

Additional Background

In an impact study submitted to the 2014 Research Excellence Framework (REF) in the United Kingdom by University College London (available at http://impactref.ac.uk/casestudies2/refservice.svc/GetCaseStudyPDF/35393), it was commented that:

"The next generation of PBD dimers, which are more potent than SG2000, have been developed, including SG2057 and SG2202. They exhibit picomolar/sub-picomolar activity against a range of human tumour cell lines and demonstrate curative activity in human tumour xenograft models." making reference to:

Hartley J A, et al., *DNA interstrand cross-linking and in vivo antitumor activity of the extended pyrrolo[2,1-c][1,4] benzodiazepine dimer SG2057*. Invest New Drugs. 2012 June; 30(3):950-8. http://dx.doi.org/10.1007/s10637-011-9647-z (herein after "Hartley et al (2012)") and:

"The ability to generate such cytotoxic molecules that display exquisite potency suggested a potential role in strategies aimed at targeting and releasing highly cytotoxic agents directly at a tumour site. An example is as the 'warhead' component of an antibody drug conjugate (ADC). The fully synthetic PBD dimers are ideally suited for the role of warhead in an ADC approach."

The Hartley et al (2012) paper comments in its summary that "SG2057 is therefore a highly active antitumour agent, with more potent in vitro activity and superior in vivo activity to SG2000, warranting further development".

SG2057 has the structure:

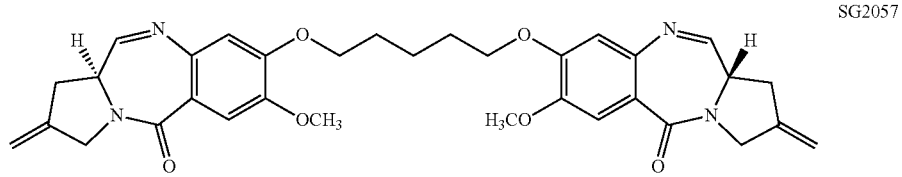

SG2057

Antibody drug conjugates using SG2057 as a warhead were first disclosed in WO 2011/130598. For example, claim 54 of this application includes the formula:

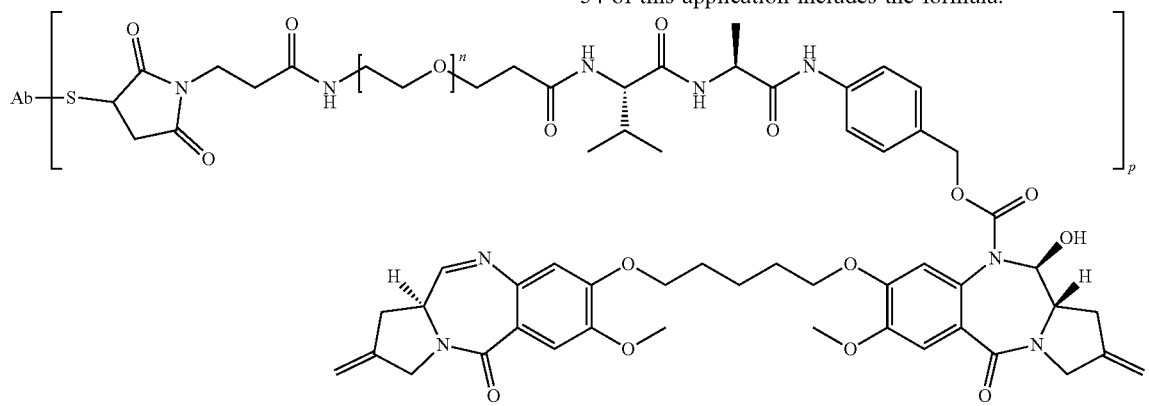

wherein n is from 1 to 24, more preferably 4 to 8. The following drug linkers were exemplified: n=4, 15c; n=8, 15d; n=24, 15e.

Claim 54 of this application also includes the formula:

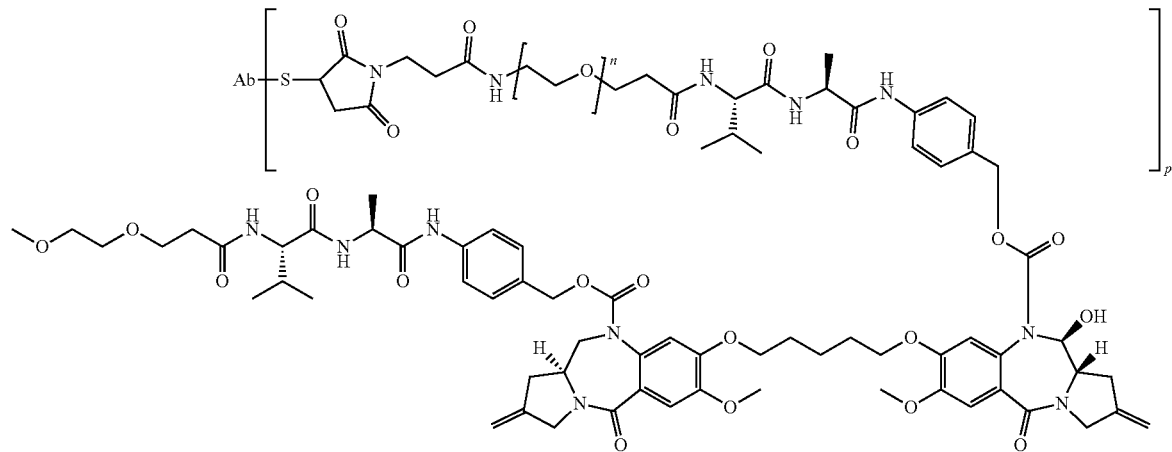

wherein n is from 1 to 24, more preferably 4 to 8. The following drug linkers were exemplified: n=8, 58; n=24, 61.

WO 2011/130598 also discloses antibody-drug conjugates including these drug linkers, for example 110 (anti-Steap1-15d), example 114 (tastuzumab-15d) and example 115 (tastuzumab-58).

WO 2013/055987 discloses the drug linkers 14 and 22:

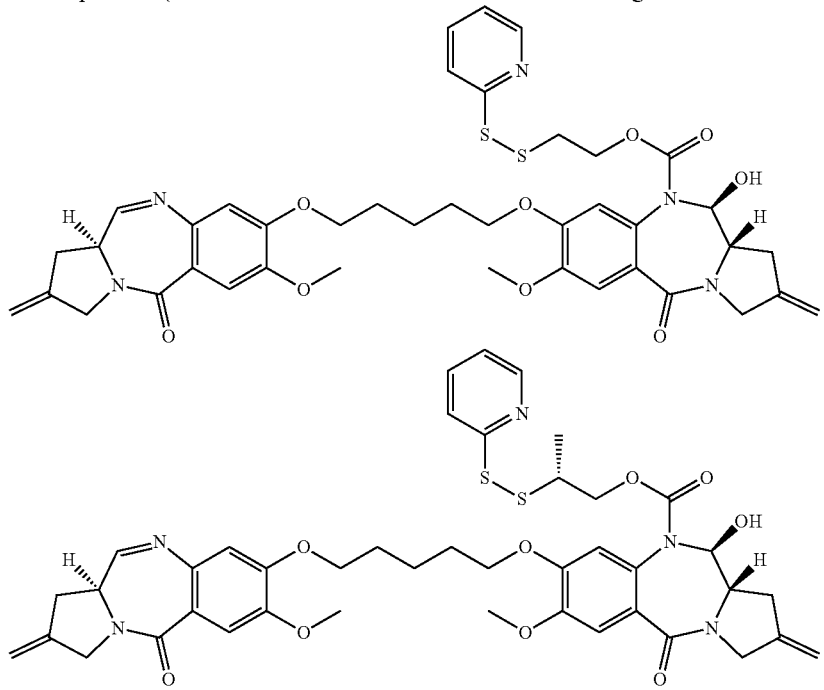

and their use in antibody-drug conjugates.

More recently, the warhead:

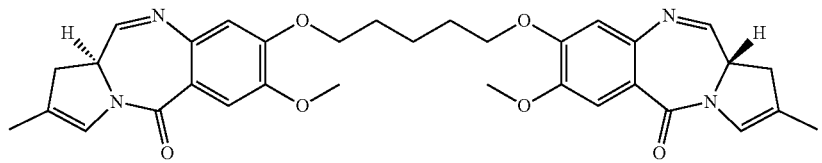

has been used in drug linkers and antibody-drug conjugates.

WO 2014/057074 discloses:

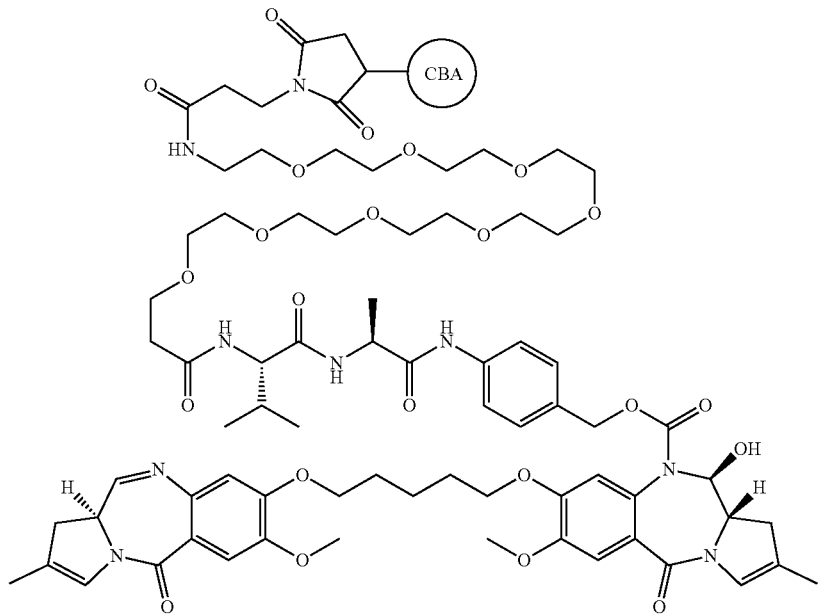

The present inventors have surprisingly found that although SG2000 is at least 10 times less cytotoxic than SG2057 (see Hartley et al 2012), particular antibody-drug conjugates, i.e. those of formula Id, appear to show at least comparable activity. These conjugates have been shown to have surprisingly well tolerated in toxicity studies in a variety of species. This leads to the conjugates exhibiting high therapeutic indices and thus are promising clinical candidates.

In some embodiments of the present invention, the C11 substituent may be in the following stereochemical arrangement relative to neighbouring groups:

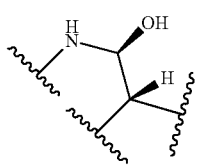

In other embodiments, the C11 substituent may be in the following stereochemical arrangement relative to neighbouring groups:

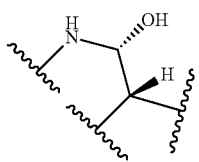

Compounds of particular interest include those of the examples

EXAMPLES

Flash chromatography was performed using a Biotage Isolera 1™ using gradient elution starting from either 88% hexane/EtOAc or 99.9% DCM/MeOH until all UV active components (detection at 214 and 254 nm) eluted from the column. The gradient was manually held whenever substantial elution of UV active material was observed. Fractions were checked for purity using thin-layer chromatography (TLC) using Merck Kieselgel 60 F254 silica gel, with fluorescent indicator on aluminium plates. Visualisation of TLC was achieved with UV light or iodine vapour unless otherwise stated. Extraction and chromatography solvents were bought and used without further purification from VWR U.K. All fine chemicals were purchased from Sigma-Aldrich or TCI Europe unless otherwise stated. Pegylated reagents were obtained from Quanta biodesign US via Stratech UK.

$^1$H and $^{13}$C NMR spectra were obtained on a Bruker Avance® 400 spectrometer. Coupling constants are quoted in hertz (Hz). Chemical shifts are recorded in parts per million (ppm) downfield from tetramethylsilane. Spin multiplicities are described as s (singlet), bs (broad singlet), d (doublet), t (triplet), and m (multiplet).

The analytical LC/MS conditions (for reaction monitoring and purity determination) were as follows: Positive mode electrospray mass spectrometry was performed using a Shimadzu Nexera®/Prominence® LCMS-2020. Mobile phases used were solvent A ($H_2O$ with 0.1% formic acid) and solvent B ($CH_3CN$ with 0.1% formic acid). Gradient for routine 3-minute run: Initial composition 5% B held over 25 seconds, then increased from 5% B to 100% B over a 1 minute 35 seconds' period. The composition was held for 50 seconds at 100% B, then returned to 5% B in 5 seconds and held there for 5 seconds. The total duration of the gradient run was 3.0 minutes. Gradient for 15-minute run: Initial composition 5% B held over 1 minute, then increased from 5% B to 100% B over a 9 minute period. The composition was held for 2 minutes at 100% B, then returned to 5% B in 10 seconds and held there for 2 minutes 50 seconds. The total duration of the gradient run was 15.0 minutes. Flow rate was 0.8 mL/minute (for 3-minute run) and 0.6 mL/minute (for 15-minute run). Detection was at 254 nm. Columns: Waters Acquity UPLC® BEH Shield RP18 1.7 μm 2.1×50 mm at 50° C. fitted with Waters Acquity UPLC® BEH Shield RP18 VanGuard Pre-column, 130A, 1.7 μm, 2.1 mm×5 mm (routine 3-minute run); and ACE Excel 2 C18-AR, 2μ, 3.0×100 mm fitted with Waters Acquity UPLC® BEH Shield RP18 VanGuard Pre-column, 130A, 1.7 μm, 2.1 mm×5 mm (15-minute run).

The preparative HPLC conditions were as follows: Reverse-phase ultra-fast high-performance liquid chromatography (UFLC) was carried out on a Shimazdzu Prominence® machine using a Phenomenex® Gemini NX 5μ C18 column (at 50° C.) dimensions: 150×21.2 mm. Eluents used were solvent A ($H_2O$ with 0.1% formic acid) and solvent B ($CH_3CN$ with 0.1% formic acid). All UFLC experiments were performed with gradient conditions: Initial composition 13% B increased to 60% B over a 15 minute period then increased to 100% B over 2 minutes. The composition was held for 1 minute at 100% B, then returned to 13% B in 0.1 minute and held there for 1.9 minutes. The total duration of the gradient run was 20.0 minutes. Flow rate was 20.0 mL/minute and detection was at 254 and 280 nm.

Synthesis of Key Intermediates
(a) Compound 5a
The following compound 5a:

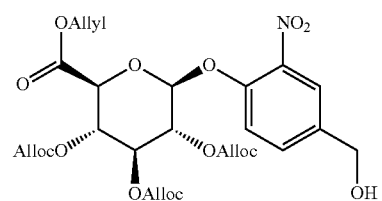

was synthesised as described (for compound 10) in Grinda, M., et al., *ChemMedChem* 2011 (5), 2137-2141 (DOI: 10.1002/cmdc.201100355).

(a) (S)-2-(methoxycarbonyl)-4-methylenepyrrolidinium chloride (I3)

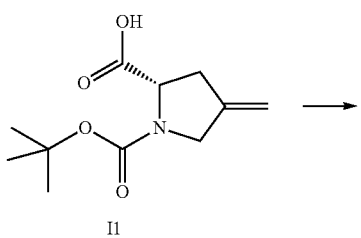

-continued

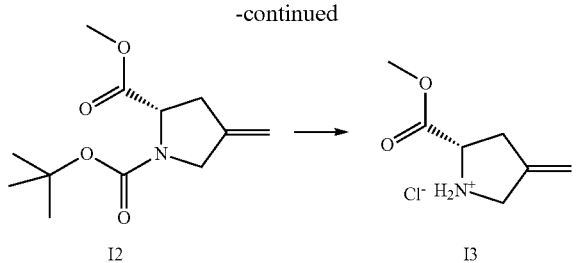

Commercially available proline derivative (I1) was obtained from Omegachem

(i) (S)-1-tert-butyl 2-methyl 4-methylenepyrrolidine-1,2-dicarboxylate (I2)

Potassium carbonate (19.92 g, 14 mmol, 3.0 eq.) was added to a stirred solution of the carboxylic acid 11 (10.92 g, 48 mmol, 1.0 eq.) in DMF (270 mL). The resulting white suspension was stirred at room temperature for 30 mins, at which point iodomethane (21.48 g, 9.5 mL, 151 mmol, 3.15 eq.) was added. The reaction mixture was allowed to stir at room temperature for 3 days. The DMF was removed by rotary evaporation under reduced pressure to afford a yellow residue which was partitioned between ethylacetate and water. The organic layer was separated and the aqueous phase was extracted with ethylacetate. The combined organic layers were washed with water brined and dried over magnesium sulphate. The ethylacetate was removed by rotary evaporation under reduced pressure to give the crude product as a yellow oil. The crude product was purified by flash chromatography [85% n-hexane/15% ethylacetate] to afford the product as a colourless oil (10.74 g, 93%).

(ii) (S)-2-(methoxycarbonyl)-4-methylenepyrrolidinium chloride (I3)

A solution of 4 M hydrochloric acid in dioxane (63 mL, 254.4 mmol, 4.5 eq.) was added to the Boc protected C-ring fragment I2 (13.67 g, 56.6 mmol, 1.0 eq.) at room temperature. Effervescence was observed indicating liberation of $CO_2$ and removal of the Boc group. The product precipitated as a white solid and additional dioxane was added to facilitate stirring the reaction mixture was allowed to stir for an hour and then diluted with diethyl ether. The precipitated product was collected by vacuum filtration and washed with additional diethyl ether. Air drying afforded the desired product as a white powder (9.42 g, 94%).

(b) ((Propane-1,3-diylbis(oxy))bis(2-amino-5-methoxy-4,1-phenylene))bis(((S)-2-(((tert-butyldimethylsilyl)oxy)methyl)-4-methylenepyrrolidin-1-yl)methanone) (I11)

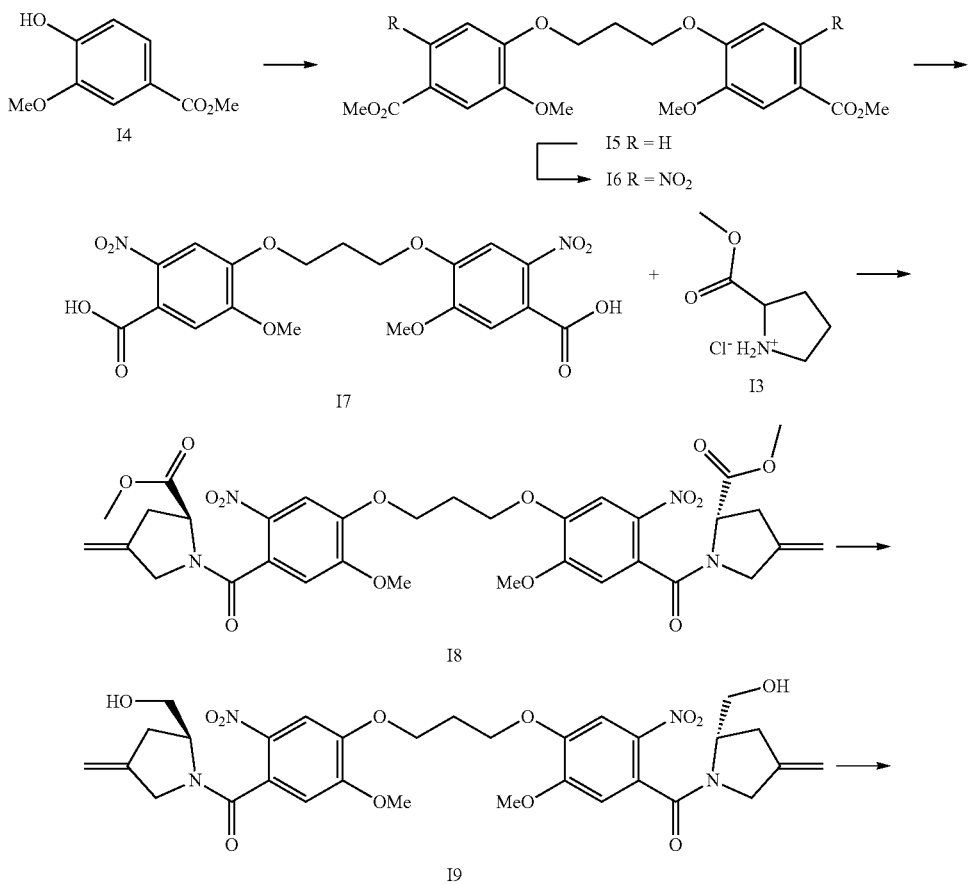

-continued

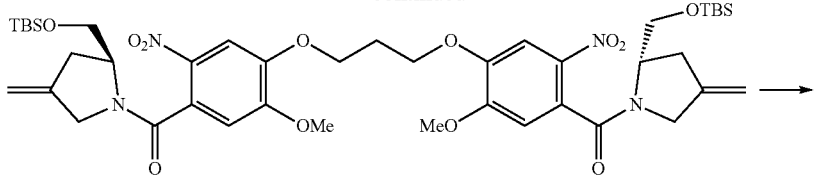

I10

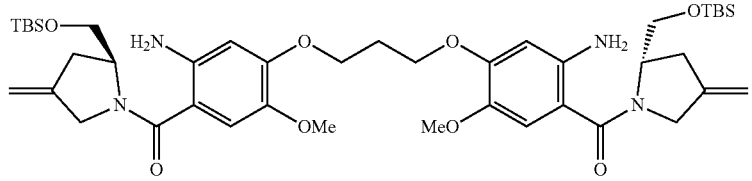

I11

(i) 1',3'-Bis[2-methoxy-4-(methoxycarbonyl)phenoxy]propane (I5)

Diisopropyl azodicarboxylate (71.3 mL, 73.2 g, 362 mmol) was added drop-wise over a period of 60 min to an overhead stirred solution of methyl vanillate I4 (60 g, 329 mmol) and $Ph_3P$ (129.4 g, 494 mmol) in anhydrous THF (800 mL) at 0-5° C. (ice/acetone) under a nitrogen atmosphere. The reaction mixture was allowed to stir at 0-5° C. for an additional 1 h after which time a solution of 1,3-propanediol (11.4 mL, 12.0 g, 158 mmol) in THF (12 mL) was added drop-wise over a period of 20 min. The reaction mixture was allowed to warm to room temperature and stirred for 5 days. The resulting white precipitate I3 was collected by vacuum filtration, washed with THF and dried in a vacuum desiccator to constant weight. Yield=54.68 g (84% based on 1,3-propanediol). Analytical Data: Purity satisfactory by LC/MS 3.20 min (ES+) m/z (relative intensity) 427 ([M+Na]$^+$·, 10); $^1$H NMR (400 MHz, CDCl$_3$) δ δ7.64 (dd, 2H, J=1.8, 8.3 Hz), 7.54 (d, 2H, J=1.8 Hz), 6.93 (d, 2H, J=8.5 Hz), 4.30 (t, 4H, J=6.1 Hz), 3.90 (s, 6H), 3.89 (s, 6H), 2.40 (p, 2H, J=6.0 Hz).

(ii) 1',3'-Bis[2-methoxy-4-(methoxycarbonyl)-5-nitrophenoxy]Propane (I6)

Solid $Cu(NO_3)_2 \cdot 3H_2O$ (81.54 g, 337.5 mmol) was added slowly to an overhead stirred slurry of the bis-ester I5 (54.68 g, 135 mmol) in acetic anhydride (650 mL) at 0-5° C. (ice/acetone). The reaction mixture was allowed to stir for 1 h at 0-5° C. and then allowed to warm to room temperature. A mild exotherm (c. 40-50° C.), accompanied by thickening of the mixture and evolution of $NO_2$ was observed at this stage. Additional acetic anhydride (300 mL) was added and the reaction mixture was allowed to stir for 16 h at room temperature. The reaction mixture was poured onto ice (~1.5 L), stirred and allowed to return to room temperature. The resulting yellow precipitate was collected by vacuum filtration and dried in a desiccator to afford the desired bis-nitro compound 16 as a yellow solid. Yield=66.7 g (100%). Analytical Data: Purity satisfactory by LC/MS 3.25 min (ES+) m/z (relative intensity) 517 ([M+Na]$^+$·, 40); $^1$H NMR (400 MHz, CDCl$_3$) δ 7.49 (s, 2H), 7.06 (s, 2H), 4.32 (t, 4H, J=6.0 Hz), 3.95 (s, 6H), 3.90 (s, 6H), 2.45-2.40 (m, 2H). See ref Thurston 1996.

(iii) 1',3'-Bis(4-carboxy-2-methoxy-5-nitrophenoxy)propane (I7)

A slurry of the methyl ester I6 (66.7 g, 135 mmol) in THF (700 mL) was treated with 1N NaOH (700 mL) and the reaction mixture was allowed to stir vigorously at room temperature. After 4 days stirring, the slurry became a dark coloured solution which was subjected to rotary evaporation under reduced pressure to remove THF. The resulting aqueous residue was acidified to pH 1 with concentrated HCl and the colourless precipitate I7 was collected and dried thoroughly in a vacuum oven (50° C.). Yield=54.5 g (87%). Analytical Data: Purity satisfactory by LC/MS 2.65 min (ES+) m/z (relative intensity) 489 ([M+Na]$^+$·, 30); $^1$H NMR (400 MHz, DMSO-d$_6$) δ 7.62 (s, 2H), 7.30 (s, 2H), 4.29 (t, 4H, J=6.0 Hz), 3.85 (s, 6H), 2.30-2.26 (m, 2H).

(iv) Dimethyl 1,1'-(4,4'-(propane-1,3-diylbis(oxy)) bis(5-methoxy-2-nitrobenzoyl))(2S,2's)-bis(4-methylenepyrrolidine-2-carboxylate) (I8)

A catalytic amount of anhydrous DMF (2.4 mL) was added to a stirred suspension of oxalyl chloride (14.7 g, 9.8 mL, 115.8 mmol, 3 eq.) and dimer core I7 (18 g, 38.6 mmol, 1 eq.) in anhydrous DCM (500 mL) at room temperature. Vigorous effervescence was observed after the addition of DMF and the reaction mixture was allowed to stir for 18 h in a round bottom flask fitted with a calcium chloride drying tube. The resulting clear solution was evaporated under reduced pressure and the solid triturated with ether. The solid product was collected by vacuum filtration, washed with additional ether and dried in vacuo at 40° C. for 1.5 h. This solid was then added portion wise to a suspension of the C-ring 3 (15.1 g, 84.9 mmol, 2.2 eq.) and TEA (19.5 g, 27 ml, 119.6 mmol, 5 eq.) in dry DCM (375 mL), maintaining the temperature between −40 and −50° C. with the aid of a dry ice/acetonitrile bath. The reaction mixture was allowed to stir at −40° C. for 1 h and then allowed to warm to room temperature at which point LCMS indicated the complete consumption of the starting material. The reaction mixture was diluted with additional DCM and washed sequentially with aqueous hydrochloric acid (1 M, 2×200 mL), saturated aqueous sodium bicarbonate (2×250 mL), water (250 mL), brine (250 mL), dried (MgSO$_4$). DCM was removed by rotary evaporation under reduced pressure to afford the product as a yellow foam (25.72 g, 94%). Analytical Data: RT 1.59 min; MS (ES$^+$) m/z (relative intensity) 713 ([M+H]$^+$·, 100)

(v) ((Propane-1,3-diylibis(oxy))bis(5-methoxy-2-nitro-4,1-phenylene))bis(((S)-2-(hydroxymethyl)-4-methylenepyrrolidin-1-yl)methanone) (I9)

Solid lithium borohydride (3.18 g, 146 mmol, 3 eq.) was added in one portion to a solution of the ester I8 (34.72 g, 48.7 mmol, 1 eq.) in dry THF (350 mL) under a nitrogen atmosphere at 0° C. (ice bath). The reaction mixture was allowed to stir at 0° C. for 30 mins and then allowed to warm to room temperature at which point precipitation of an orange gum was observed. The reaction mixture was allowed to stir at room temperature for a further 2 hours and then cooled in an ice bath and treated with water to give a yellow suspension. Hydrochloric acid (1 M) was carefully added until effervescence ceased. The reaction mixture was extracted with ethylacetate (×4) and the combined organic layers were washed with water (×1), brine (×1) and dried (MgSO$_4$). Ethylacetate was removed by rotary evaporation under reduced pressure to give a yellow foam. Purification by flash column chromatography [gradient elution DCM/MeOH 0% to 5% in 1% increments] gave the product as a pale yellow foam (23.1 g, 72%). Analytical Data: RT 1.23 min; MS (ES$^+$) m/z (relative intensity) 657 ([M+H]$^{+\cdot}$, 100)

(vi) ((Propane-1,3-diylibis(oxy))bis(5-methoxy-2-nitro-4,1-phenylene))bis(((S)-2-(((tert-butyldimethylsilyl)oxy)methyl)-4-methylenepyrrolidin-1-yl) methanone) (I10)

A solution of the bis-alcohol I9 (10 g, 15.2 mmol, 1 eq.), t-butyldimethylsilylchloride (5.97 g, 39.6 mmol, 2.6 eq.) and imidazole (5.38 g, 79 mmol, 5.2 eq.) in dry DMF (80 ml) was stirred at room temperature for 3 h. The reaction mixture was poured into water (500 mL) to give a yellow precipitate. The mixture was extracted with DCM (4×100 mL) and the combined extracts were washed with water and brine, dried (MgSO$_4$) and evaporated under reduced pressure to give a viscous yellow oil. Purification by column chromatography [biotage isolera, gradient elution hexane 60%/EtOAc 40% to EtOAc 100%, 8 column volumes 100 g snap Ultra® cartridge] gave the product as a yellow foam (11.8 g, 88%). Analytical Data: RT 2.20 min; MS (ES$^+$) m/z (relative intensity) 885 ([M+H]$^{+\cdot}$, 100), 907 ([M+Na]$^{+\cdot}$, 50)

(vii) ((Propane-1,3-diylbis(oxy))bis(2-amino-5-methoxy-4,1-phenylene))bis(((S)-2-(((tert-butyldimethylsilyl)oxy)methyl)-4-methylenepyrrolidin-1-yl) methanone) (I11)

Zinc powder (31.9 g, 488 mmol, 40 eq.) was activated by stirring/sonication with 1M HCl for 10 min. The Zinc was filtered washing with 1M HCl, water (×3) and MeOH (×2). The activated Zinc was added to a solution of the nitro-TBS compound I10 (10.8 g, 12.2 mmol, 1 eq.) in MeOH (88 mL) and 5% formic acid/MeOH solution (440 mL). The temperature rose to 37° C. and the reaction mixture changed from a yellow to a colourless solution. Once the exotherm had subsided (20 min.) the reaction was shown to be complete by LCMS. The reaction mixture was filtered through celite washing with EtOAc. The EtOAc portion was washed with saturated bicarbonate solution (×4) [caution effervescence!], water (×1), brine (×1), dried (MgSO$_4$) and evaporated under reduced pressure to give a yellow solid. Purification by flash column chromatography [n-hexane/EtOAc 50/50 v/v to EtOAc 100% in 10% increments] gave the product as a yellow foam (9.5 g, 86%). Analytical Data: RT 2.12 min; MS (ES$^+$) m/z (relative intensity) 825 ([M+H]$^+$, 60), 847 ([M+Na]$^+$, 30)

(c) Alloc-Val-Ala-PABOH (I16)

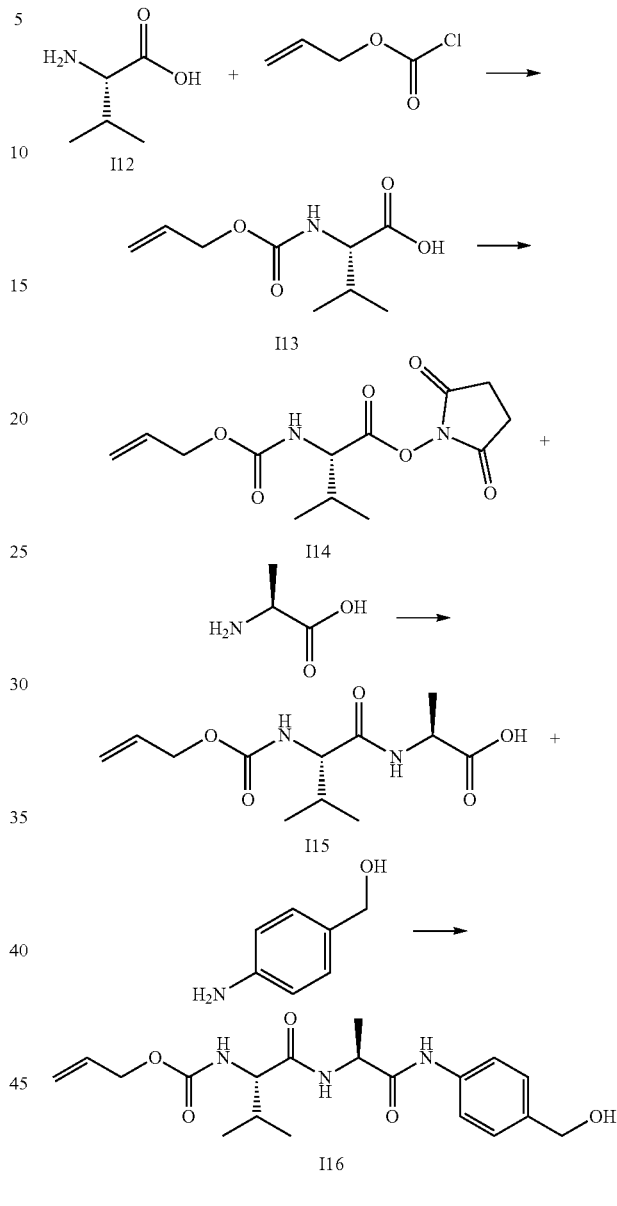

(i) Alloc-Val-OH (I13)

Allyl chloroformate (41 g, 36.2 mL, 0.34 mol, 1.2 eq.) was added dropwise to a stirred solution of L-valine I12 (33.25 g, 0.28 mol, 1 eq.) and potassium carbonate (58.9 g, 0.426 mol, 1.5 eq.) in water (650 mL) and THF (650 mL). The reaction mixture was stirred at room temperature for 18 h. The THF was evaporated under reduced pressure and the remaining solution was extracted with diethyl ether (or MTBE) (×2). The aqueous portion was acidified to pH 2 with conc. HCl and extracted with DCM (×3). The combined organic extracts were washed with brine (×1), dried (MgSO$_4$) and evaporated under reduced pressure to give a colourless oil (57.1 g). This was used in the next step without further purification.

Alloc-Val-OSu (I14)

To a stirred solution of compound I13 (57.1 g, 0.28 mol, 1 eq.) and N-hydroxysuccinimide (32.68 g, 0.28 mol, 1 eq.) in dry THF (800 mL) was added dicyclohexylcarbodiimide (58.6 g, 0.28 mol, 1 eq.). The reaction mixture was stirred at room temperature for 18 h. The reaction mixture was filtered. The solid was washed with THF and the combined filtrate was concentrated under reduced pressure. The oil/solid residue was re-dissolved in DCM and left to stand at 0° C. for 30 min. The suspension was filtered washing with cold DCM. Evaporation of the filtrate under reduced pressure gave the succinimide ester as a white solid which was used in the next step without further purification.

(iii) Alloc-Val-Ala-OH (I15)

A solution of Alloc-Val-OSu I14 (11.67 g, 39.0 mmol, 1 eq.) in THF (50 mL) was added to a solution of H-Ala-OH (3.66 g, 41.08 mmoL, 1.05 eq.) and NaHCO$_3$ (3.61 g, 43.03 mmol, 1.1 eq.) in THF (100 mL) and H$_2$O (100 mL). The mixture was stirred at room temperature for 72 h and the THF was evaporated under reduced pressure. The pH was adjusted to 3-4 with citric acid to precipitate a white gum. This was extracted with ethylacetate (6×150 mL) and the combined extracts were washed with H$_2$O (200 mL), brine (200 mL), dried (MgSO$_4$) and evaporated under reduced pressure to give a white solid. Trituration with diethyl ether (xs) afforded the pure product as a white powder (7.93 g, 74%). Analytical Data: RT 2.17 min; MS (ES$^+$) m/z (relative intensity) 295 ([M+Na]$^+$; 63), 273 ([M+1]$^+$; 60).

(iv) Alloc-Val-Ala-PABOH (I16)

EEDQ (4.79 g, 19.3 mmol, 1.05 eq.) was added to a solution of p-aminobenzyl alcohol (2.38 g, 19.3 mmol, 1.05 eq.) and Alloc-Val-Ala-OH I15 (5.02 g, 18.4 mmol, 1.0 eq) in dry THF (100 mL). The mixture was stirred at room temperature for 72 h. The solvent was evaporated under reduced pressure to give a pale brown solid. The solid was triturated with diethyl ether and filtered washing with an excess of diethyl ether. This afforded the product as a white solid (6.2 g, 89%). Analytical Data: RT 2.50 min; MS (ES$^+$) m/z (relative intensity) 400.6 ([M+Na]$^+$; 50), 378.6 ([M+1]$^+$; 60).

Example 1

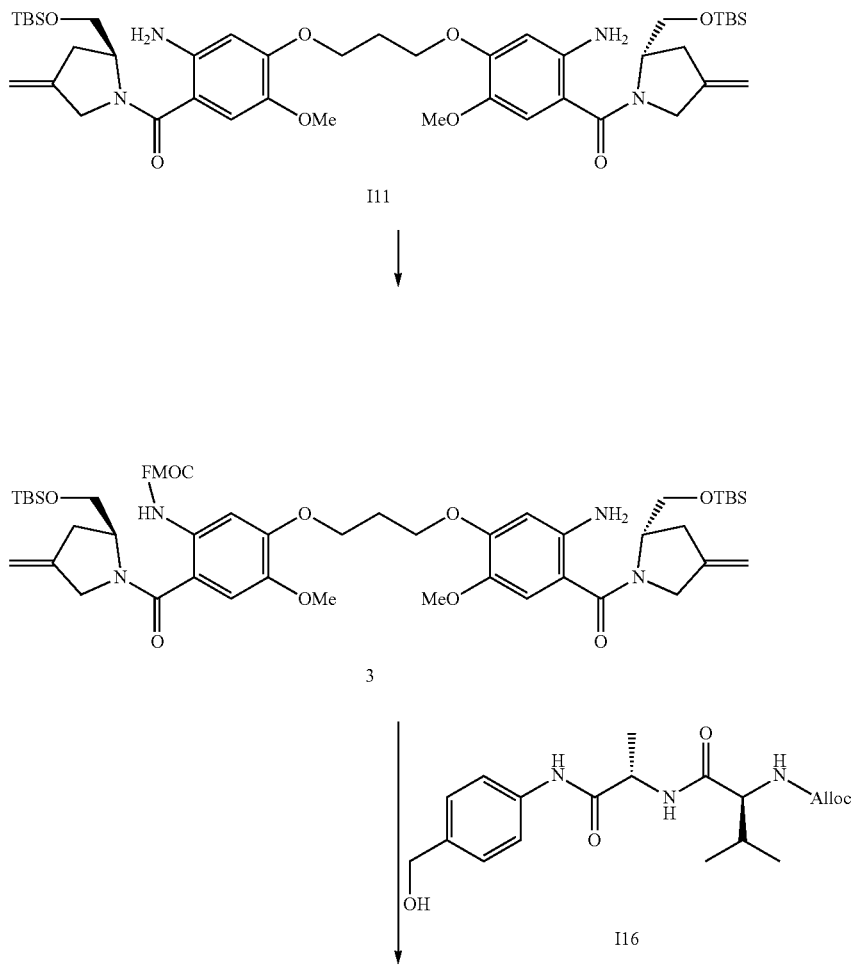

-continued
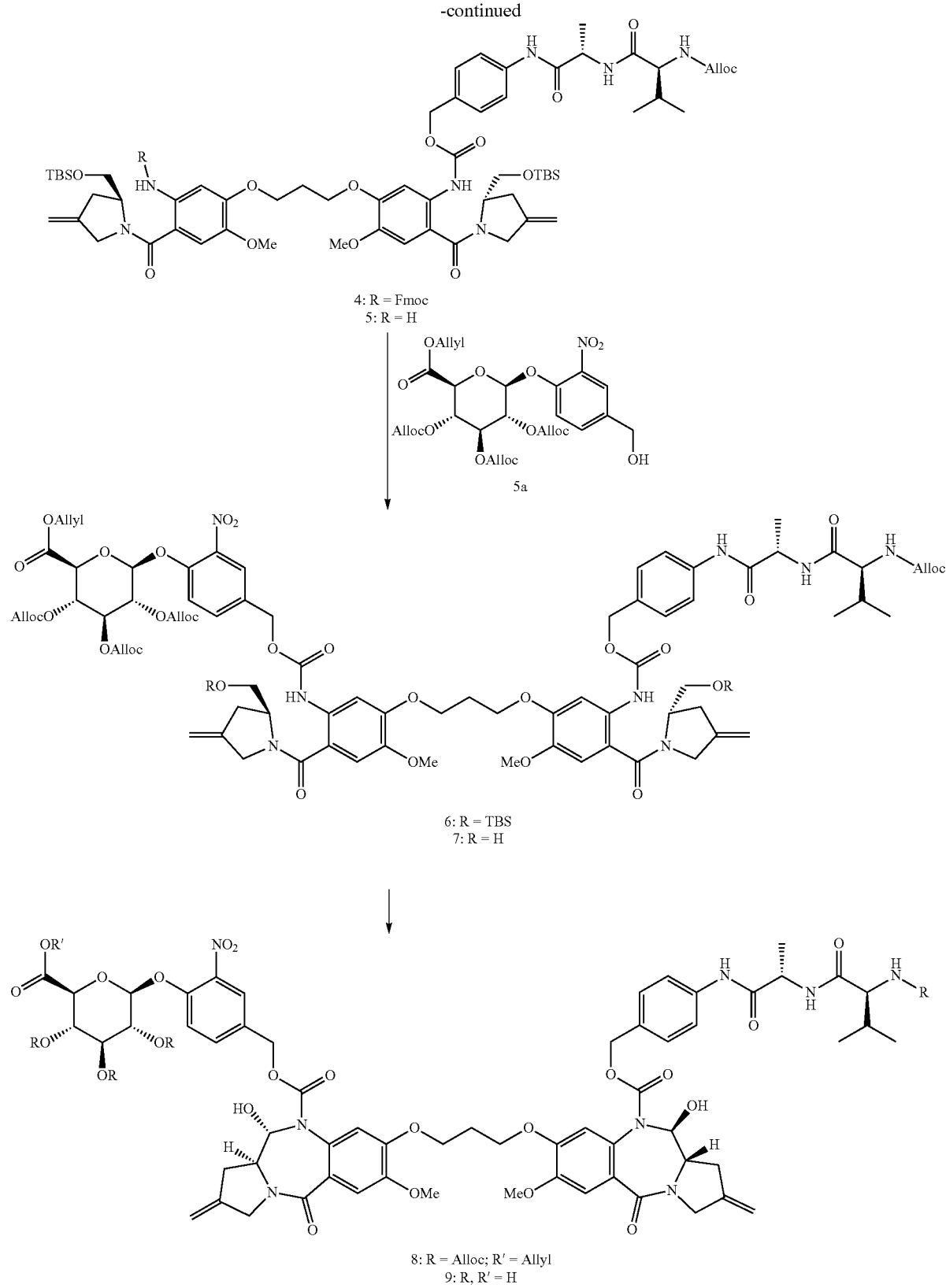

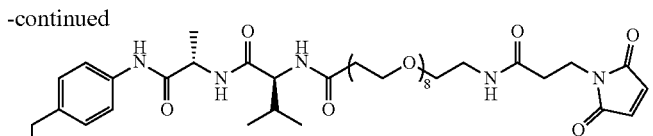
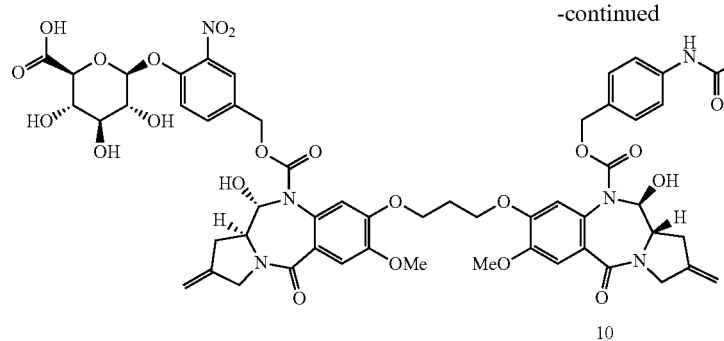

10

(a) (9H-Fluoren-9-yl)methyl (5-(3-(5-amino-4-((S)-2-(((tert-butyldimethylsilyl)oxy)methyl)-4-methyl-enepyrrolidine-1-carbonyl)-2-methoxyphenoxy)propoxy)-2-((S)-2-(((tert-butyldimethylsilyl)oxy)methyl)-4-methylenepyrrolidine-1-carbonyl)-4-methoxyphenyl)carbamate (3)

FmocCl (1.97 g, 7.63 mmol) was added to a stirred mixture of the bis-aniline I11 (6.99 g, 8.48 mmol) and Na₂CO₃ (2.25 g, 21.2 mmol) in THF (65 mL) and H₂O (65 mL). The mixture was allowed to stir room temperature for 16 hours where analysis by LC/MS revealed desired mono Fmoc product 3 at retention time 2.34 minutes, I %=40, ES+ m/z 1069 [M+Na]⁺·, 1047 [M+H]⁺· along with unreacted starting material at retention time 2.15 minutes, I %=12, and bis-Fmoc material at retention time 2.50 minutes, I %=45, ES+ m/z 1291 [M+Na]⁺·, 1269 [M+H]⁺·. The layers were separated and the aqueous phase extracted with DCM (2×20 mL) and the combined organic layers washed with H₂O (30 mL), brine (50 mL), dried (MgSO₄), filtered and evaporated in vacuo to give the crude product. Purification by Isolera™ (Hexane/EtOAc, SNAP Ultra 50 g, 100 mL per minute) provided the pure mono Fmoc product 3 as an orange foam (2.67 g, 39% yield based on FmocCl, eluting at 50% Hexane/EtOAc) unreacted bis-aniline 2 (1.78 g, eluting at 100% EtOAc) and bis-Fmoc (3.28 g, eluting at 70% Hexane/EtOAc).

(b) (9H-Fluoren-9-yl)methyl (5-(3-(5-(((((4-((S)-2-((S)-2-(((allyloxy)carbonyl)amino)-3-methylbutana-mido)propanamido)benzyl)oxy)carbonyl)amino)-4-((S)-2-(((tert-butyldimethylsilyl)oxy)methyl)-4-methylenepyrrolidine-1-carbonyl)-2-methoxyphenoxy)propoxy)-2-((S)-2-(((tert-butyldimethylsilyl)oxy)methyl)-4-methylenepyrrolidine-1-carbonyl)-4-methoxyphenyl)carbamate (4)

Triphosgene (26 mg, 86 μmol) was added to a stirred solution of the mono Fmoc product 3 (250 mg, 0.24 mmol) and TEA (73 μL, 53 mg, 0.53 mmol) in dry DCM (10 mL) at room temperature. After stirring for 10 minutes under argon, analysis by LC/MS revealed complete conversion to isocyanate (sampled in MeOH to give methyl carbamate, retention time 2.39 minutes, ES+ m/z 1127 [M+Na]⁺·, 1105 [M+H]⁺·). The mixture was treated with additional TEA (50 μL, 36 mg, 0.36 mmol) followed by the addition of linker I16 (90 mg, 0.24 mmol). After 4 hours stirring under argon, LC/MS revealed satisfactory conversion to carbamate 4 at retention time 2.34 minutes, ES+ m/z 1472 [M+Na]⁺·, 1451 [M+H]⁺·. The mixture was diluted with DCM (60 mL) and washed with saturated aqueous NH₄Cl (2×20 mL), H₂O (20 mL), brine (30 mL), dried (MgSO₄), filtered and evaporated in vacuo to give the crude product. Purification by Isolera™ (Hexane/EtOAc, SNAP Ultra 25 g, 75 mL per minute) provided the pure carbamate 4 (eluting at 28% Hexane/EtOAc) as a yellow foam (257 mg, 74% yield).

(c) 4-((S)-2-((S)-2-(((Allyloxy)carbonyl)amino)-3-methylbutanamido)propanamido)benzyl (5-(3-(5-amino-4-((S)-2-(((tert-butyldimethylsilyl)oxy)methyl)-4-methylenepyrrolidine-1-carbonyl)-2-methoxyphenoxy)propoxy)-2-((S)-2-(((tert-butyldimethylsilyl)oxy)methyl)-4-methylenepyrrolidine-1-carbonyl)-4-methoxyphenyl)carbamate (5)

Dimethylamine (16.5 mL of a 2.0M solution in THF, 33.0 mmol) was added to a stirred solution of the Fmoc protected compound 4 (2.39 g, 1.65 mmol) in THF (46 mL) at room temperature. After stirring for 1 hour at room temperature, analysis by LC/MS revealed reaction completion with desired product at retention time 2.17 minutes, ES+ m/z 1250 [M+Na]⁺·, 1228 [M+H]⁺·, along with Fmoc cleavage by-product at retention time 1.92 minutes and its DMA adduct at retention time 1.10 minutes. The mixture was evaporated in vacuo to give the crude product which was subsequently purified by Isolera™ (Hexane/EtOAc, SNAP Ultra 100 g, 100 mL per minute) to provide the pure aniline 5 (eluting at 100% EtOAc) as an orange foam (1.87 g, 92% yield).

(d) Allyl (2S,3S,4S,5R,6S)-6-(4-(((((5-(3-(5-(((((4-((S)-2-((S)-2-(((allyloxy)carbonyl)amino)-3-methylbutanamido)propanamido)benzyl)oxy)carbonyl)amino)-4-((S)-2-(((tert-butyldimethylsilyl)oxy)methyl)-4-methylenepyrrolidine-1-carbonyl)-2-methoxyphenoxy)propoxy)-2-((S)-2-(((tert-butyldimethylsilyl)oxy)methyl)-4-methylenepyrroldine-1-carbonyl)-4-methoxyphenyl)carbamoyl)oxy)methyl)-2-nitrophenoxy)3,4,5-tris(((allyoxy)carbonyl)oxy)tetrahydro-2H-pyran-2-carboxylate (6)

Triphosgene (161 mg, 0.54 mmol) was added to a stirred solution of the aniline 5 (1.85 g, 1.51 mmol) and pyridine (269 μL, 263 mg, 3.32 mmol) in dry DCM (20 mL) at room temperature. After stirring for 10 minutes under argon, analysis by LC/MS revealed complete conversion to isocyanate (sampled in MeOH to give methyl carbamate, retention time 2.21 minutes, ES+ m/z 1308 [M+Na]⁺·, 1286 [M+H]⁺·). The mixture was treated with additional pyridine (183 μL, 179 mg, 2.27 mmol) and dibutyltin dilaurate (179 μL, 191 mg, 0.30 mmol) followed by the addition of linker 5a (960 mg, 1.51 mmol). After 20 hours stirring under argon, LC/MS revealed satisfactory conversion to carbamate 6 (retention time 2.25 minutes, ES+ m/z 1915 [M+Na]$^{+\cdot}$, 1892 [M+H]$^{+\cdot}$). The mixture was diluted with DCM (60 mL) and washed with saturated NH$_4$Cl (2×20 mL), H$_2$O (20 mL), brine (30 mL), dried (MgSO$_4$), filtered and evaporated in vacuo to give the crude product. Purification by Isolera™ (Hexane/EtOAc, SNAP Ultra 100 g, 100 mL per minute) provided the pure carbamate 6 (eluting at 42% Hexane/EtOAc) as a yellow foam (2.01 g, 70% yield).

(e) Allyl (2S,3S,4S,5R,6S)-6-(4-(((((5-(3-(5-((((4-((S)-2-((S)-2-(((allyloxy)carbonyl)amino)-3-methylbutanamido)propanamido)benzyl)oxy)carbonyl)amino)-4-((S)-2-(hydroxymethyl)-4-methylenepyrrolidine-1-carbonyl)-2-methoxyphenoxy)propoxy)-2-((S)-2-(hydroxymethyl)-4-methylenepyrrolidine-1-carbonyl)-4-methoxyphenyl)carbamoyl)oxy)methyl)-2-nitrophenoxy)3,4,5-tris(((allyloxy)carbonyl)oxy)tetrahydro-2H-pyran-2-carboxylate (7)

Glacial acetic acid (18 mL) was added to a stirred solution of the TBS-protected compound 6 (2.12 g, 1.12 mmol) in THF (6 mL) and H$_2$O (6 mL). The reaction mixture was allowed to stir for 18 hours at room temperature after which time analysis by LC/MS revealed reaction completion with desired product observed at retention time 1.79 minutes, ES+ m/z 1663 [M+H]$^{+\cdot}$, 1686 [M+Na]$^{+\cdot}$. The reaction mixture was added drop-wise to a chilled (0-5° C.) saturated solution of NaHCO$_3$ (300 mL). The neutral solution was allowed to warm to room temperature and extracted with EtOAc (3×100 mL), the combined organic layers were washed with H$_2$O (50 mL), brine (50 mL), dried (MgSO$_4$), filtered and evaporated in vacuo to give the crude product. Purification by Isolera™ (DCM/MeOH, SNAP Ultra 100 g, 100 mL per minute) gave the bis-alcohol 7 (eluting at 93% DCM/MeOH) as a yellowish foam (1.43 g, 77% yield).

(f) 4-(((2S,3R,4S,5S,6S)-6-((allyloxy)carbonyl)-3,4,5-tris(((allyloxy)carbonyl)oxy)tetrahydro-2H-pyran-2-yl)oxy)-3-nitrobenzyl (11S,11aS)-8-(3-(((11S,11aS)-10-(((4-((S)-2-(((S)-2-(((allyloxy)carbonyl)amino)-3-methylbutanamido)propanamido)benzyl)oxy)carbonyl)-11-hydroxy-7-methoxy-2-methylene-5-oxo-2,3,5,10,11,11a-hexahydro-1H-pyrrolo[2,1-c][1,4]benzodiazepin-8-yl)oxy)propoxy)-11-hydroxy-7-methoxy-2-methylene-5-oxo-2,3,11,11a-tetrahydro-1H-pyrrolo[2,1-c][1,4]benzodiazepine 10(5H)-carboxylate (8)

45% IBX (264 mg, 0.43 mmol) was added to a stirred solution of the bis-OH 7 (300 mg, 0.18 mmol) in dry DMSO (5 mL). The mixture was heated to 30° C. under an argon atmosphere and reaction progress monitored by LC/MS. After 24 hours stirring, additional IBX (22 mg, 36 μmol) was added and the mixture stirred for another 24 hours. At this point analysis by LC/MS revealed predominantly a single peak corresponding to desired product at retention time 1.78 minutes, ES+ m/z 1682 [M+Na]$^{+\cdot}$. The reaction mixture was poured onto water (40 mL), filtered and the precipitate collected, washed with H$_2$O (50 mL) and the filtrate kept to one side. The residue (precipitate) was washed with DCM (120 mL) and the remaining undissolved precipitate washed with saturated aqueous NaHCO$_3$ (60 mL). The combined filtrates were transferred to a separating funnel and the layers separated. The aqueous phase was extracted with DCM (2×20 mL) and the combined organic layers washed with NaHCO$_3$ (2×50 mL), brine (60 mL), dried (MgSO$_4$), filtered and evaporated in vacuo to give the crude product. Purification by Isolera™ (DCM/MeOH, SNAP Ultra 25 g, 75 mL per minute) gave the cyclised product 8 (eluting at 94.5% DCM/MeOH) as a white foam (261 mg, 87% yield).

(g) (2S,3S,4S,5R,6S)-6-(4-((((11S,11aS)-8-(3-(((11S,11aS)-10-(((4-((S)-2-((S)-2-amino-3-methylbutanamido)propanamido)benzyl)oxy)carbonyl)-11-hydroxy-7-methoxy-2-methylene-5-oxo-2,3,5,10,11,11a-hexahydro-1H-pyrrolo[2,1-c][1,4]benzodiazepin-8-yl)oxy)propoxy)-11-hydroxy-7-methoxy-2-methylene-5-oxo-2,3,5,10,11,11a-hexahydro-1H-pyrrolo[2,1-c][1,4]benzodiazepine-10-carbonyl)oxy)methyl)-2-nitrophenoxy)-3,4,5-trihydroxytetrahydro-2H-pyran-2-carboxylic acid (9)

Pd(PPh$_3$)$_4$ (18.2 mg, 15.7 μmol) was added to a stirred solution of pyrrolidine (72 μL, 62 mg, 0.87 mmol) and the Alloc/allyl compound 8 (261 mg, 0.16 mmol) in dry DCM (3 mL). The reaction mixture was allowed to stir under an argon atmosphere where a precipitate began to form. After stirring for 30 minutes at room temperature analysis by LC/MS revealed reaction completion with desired product observed at retention time 1.13 minutes, ES+ m/z 1284 [M+H]$^{+\cdot}$. The solvent was removed by evaporation in vacuo and the resulting residue triturated with diethyl ether followed by additional evaporation in vacuo to provide the crude amine 9 as a solid which was carried through to the next step without further purification or analysis.

(h) (2S,3S,4S,5R,6S)-6-(4-((((11S,11aS)-8-(3-(((11S,11aS)-10-(((4-((2S,5S)-37-(2,5-dioxo-2,5-dihydro-1H-pyrrol-1-yl)-5-isopropyl-2-methyl-4,7,35-trioxo-10,13,16,19,22,25,28,31-octaoxa-3,6,34-triazaheptatriacontanamido)benzyl)oxy)carbonyl)-11-hydroxy-7-methoxy-2-methylene-5-oxo-2,3,5,10,11,11a-hexahydro-1H-pyrrolo[2,1-c][1,4]benzodiazepin-8-yl)oxy)propoxy)-11-hydroxy-7-methoxy-2-methylene-5-oxo-2,3,5,10,11,11a-hexahydro-1H-pyrrolo[2,1-c][1,4]benzodiazepine-10-carbonyl)oxy)methyl)-2-nitrophenoxy)-3,4,5-trihydroxytetrahydro-2H-pyran-2-carboxylic acid (10)

A solution of MAL-dPEG®8-TFP ester (132 mg, 0.18 mmol) in dry DCM (7 mL) was added to a stirred sample of the amine 9 (202 mg, 0.16 mmol), pyridine (24 μL, 23 mg, 0.3 mmol) and DMF (0.25 mL). The reaction mixture was allowed to stir under argon for 20 hours and began to darken in colour over time. Analysis by LC/MS revealed formation of desired product at retention time 1.38 minutes, ES+) m/z 1857 [M+H]$^{+\cdot}$, 1880 [M+Na]$^+$, along with unreacted amine at retention time 1.13 minutes. Additional MAL-dPEG®8-TFP ester (66 mg, 0.09 mmol), pyridine (12 μL, 11 mg, 0.15 mmol) and DCM (3 mL) were added and the mixture allowed to stir for a further three days. At this point a satisfactory amount of desired product had formed upon analysis by LC/MS and the solvent was removed by evaporation in vacuo. The crude product was purified by preparative HPLC to give the maleimide 10 as a white solid (55 mg, 19%): LC/MS (15-minute run), retention time 5.93 minutes, ES+ m/z 1857 [M+H]$^{+\cdot}$, 1880 [M+Na]$^{+\cdot}$; $^1$H NMR (400

MHz, d6-DMSO) δ 10.0 (br s, 2H), 8.25-8.12 (m, 1H), 7.99 (t, 1H, J=5.7 Hz), 7.87 (d, 1H, J=8.9 Hz), 7.73 (br s, 1H), 7.62-7.48 (m, 3H), 7.40 (d, 1H, J=8.7 Hz), 7.22-7.11 (m, 2H), 7.06 (s, 2H), 7.00 (s, 2H), 6.87 (s, 2H), 6.84-6.76 (m, 1H), 6.68-6.52 (m, 2H), 5.45-5.30 (m, 3H), 5.25-5.01 (m, 9H), 4.97-4.82 (m, 2H), 4.42-4.34 (m, 1H), 4.24-4.17 (m, 1H), 4.16-3.92 (m, 8H), 3.87-3.72 (m, 6H), 3.60 (t, 4H, J=7.2 Hz), 3.54-3.42 (m, 30H), 3.39-3.20 (m, 5H), 3.18-3.12 (m, 2H), 2.95-2.82 (m, 2H), 2.57-2.35 (m, 4H), 2.33 (t, 2H, J=7.4 Hz), 2.24-2.13 (m, 2H), 2.03-1.90 (m, 1H), 1.30 (d, 1H, J=7.0 Hz), 0.87 (d, 3H, J=6.7 Hz), 0.83 (d, 3H, J=6.7 Hz).
Example 2
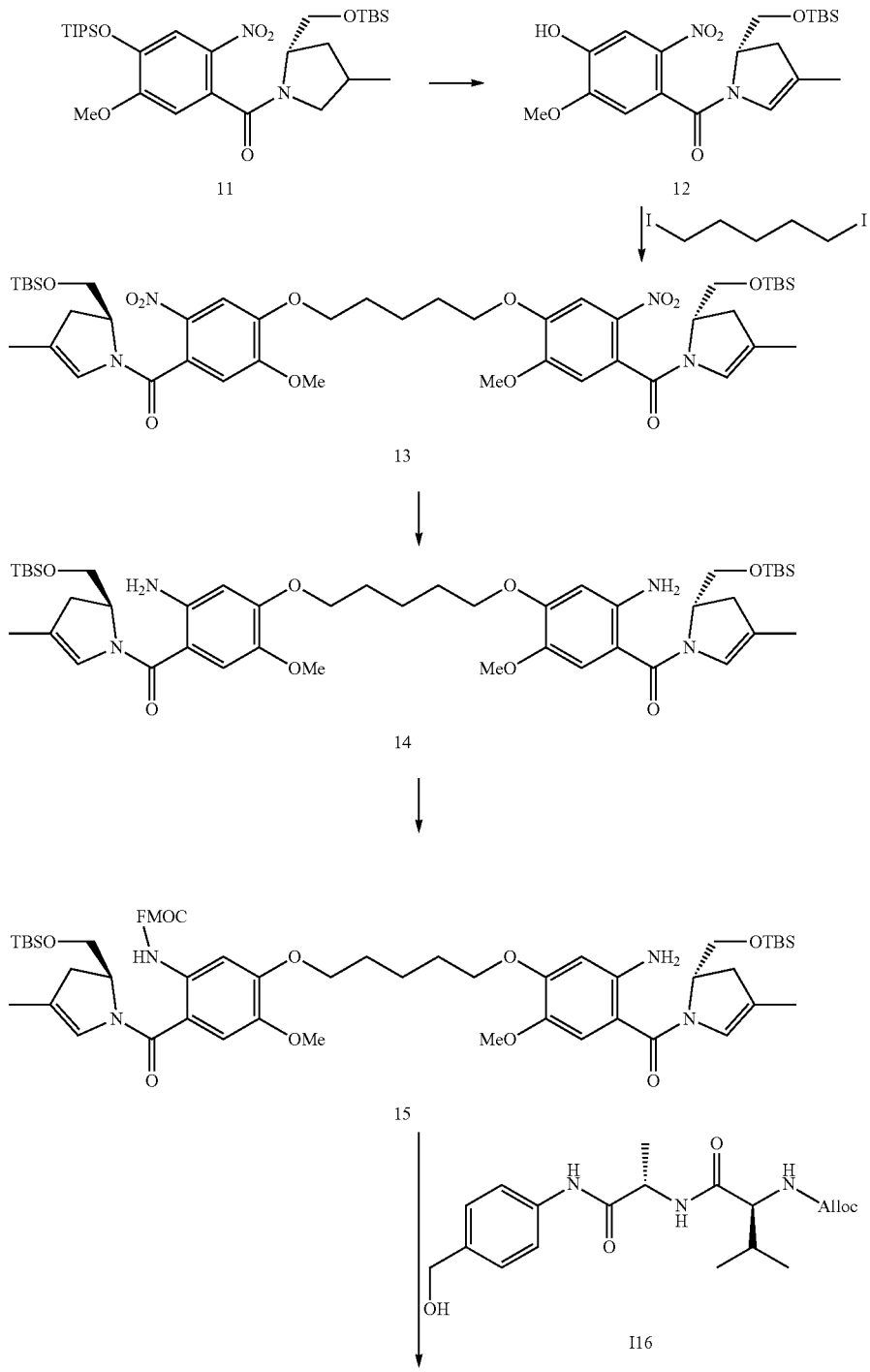

-continued
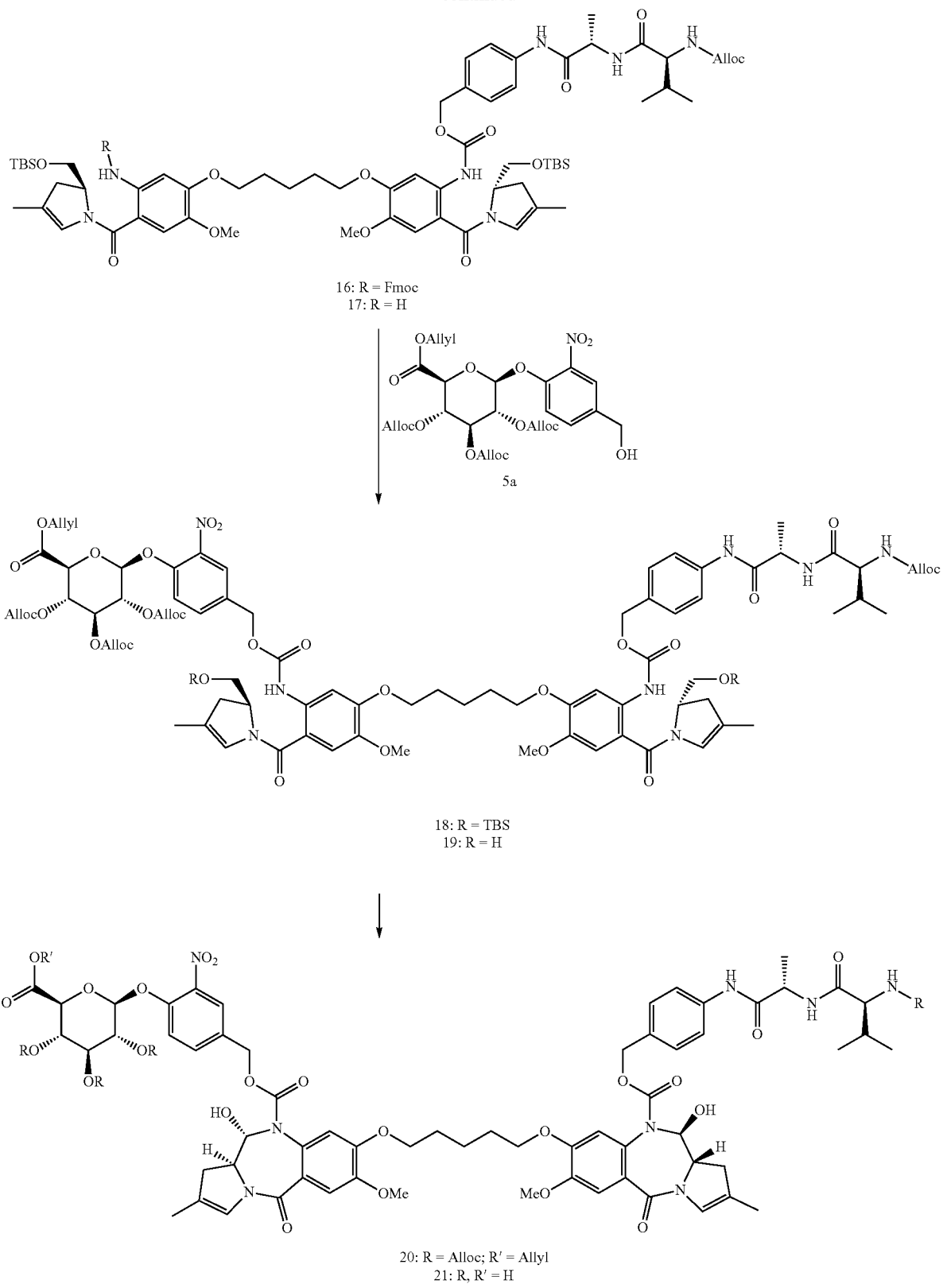

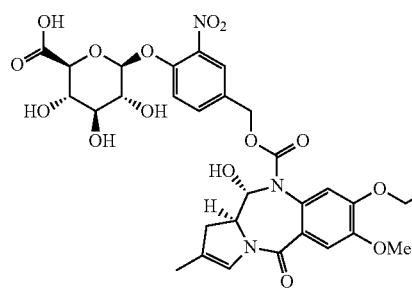
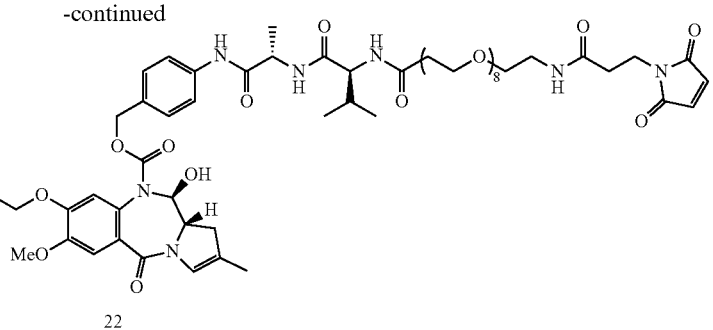

22

(a) (S)-(2-(((tert-butyldimethylsilyl)oxy)methyl)-4-Methyl-2,3-Dihydro-1H-Pyrrol-1-yl)(4-Hydroxy-5-Methoxy-2-Nitrophenyl)Methanone (12)

LiOAc (2.11 g, 20.7 mmol) was added to a stirred solution of the TIPS compound 11 (12 g, 20.7 mmol) in DMF (67 mL) and H$_2$O (3 mL) at room temperature. A colour change from yellow to red was observed. After 2 hours stirring at room temperature analysis by LC/MS revealed complete conversion to desired product at retention time 1.83 minutes, ES+ m/z 445 [M+Na]$^+$, 423 [M+H]$^+$. The mixture was diluted with H$_2$O (300 mL) and extracted with EtOAc (3×150 mL). The combined organic layers were washed 10% w/v citric acid (2×200 mL), H$_2$O (200 mL), brine (200 mL), dried (MgSO$_4$), filtered and evaporated in vacuo to give the crude product 12 as a yellow solid (8.74 g, 100% yield). Purity satisfactory, so material carried through to next step without further purification.

(b) ((Pentane-1,5-diylbis(oxy))bis(5-methoxy-2-nitro-4,1-phenylene))bis(((S)-2-(((tert-butyldimethylsilyl)oxy)methyl)-4-methyl-2,3-dihydro-1H-pyrrol-1-yl)methanone) (13)

1,5-diiodopentane (1.54 mL, 3.35 g, 10.4 mmol) was added to a stirred solution of the phenol 12 (8.74 g, 20.7 mmol), TBAI (750 mg, 2.05 mmol) and K$_2$CO$_3$ (3.15 g, 22.8 mmol) in dry DMF (60 mL). The reaction mixture was heated to 70° C. and stirred under an argon atmosphere for 16 hours at which point analysis by LC/MS revealed substantial product formation at retention time 2.21 minutes, ES+ m/z 935 [M+Na]$^+$, 913 [M+H]$^+$. The reaction mixture was allowed to cool to room temperature and the DMF was removed by evaporation in vacuo. The resulting residue was redissolved in EtOAc (200 mL) and the aqueous phase was washed with water (3×40 mL), brine (50 mL), dried (MgSO$_4$), filtered and evaporated in vacuo to provide the crude product. Purification by Isolera™ (Hexane/EtOAc, SNAP Ultra 100 g, 100 mL per minute) gave the bis-ether 13 (eluting at 60% Hexane/EtOAc) as a yellow foam (6.75 g, 71% yield).

(c) ((Pentane-1,5-diylbis(oxy))bis(2-amino-5-methoxy-4,1-phenylene))bis(((S)-2-(((tert-butyldimethylsilyl)oxy)methyl)-4-methyl-2,3-dihydro-1H-pyrrol-1-yl)methanone) (14)

Zinc dust (2.79 g, 42.8 mmol) was treated with 1N HCl (50 mL) and stirred for 10 minutes at room temperature. The mixture was then sonicated for 10 minutes and the activated Zinc collected by sinter vacuum filtration then washed with 1N HCl (25 mL), H$_2$O (20 mL), MeOH (20 mL) and dried in vacuo on the sinter filter pad. The activated zinc was added to a vigorously stirred solution of the bis-nitro compound 13 (974 mg, 1.07 mmol) in MeOH (15 mL) at room temperature. The reaction mixture was treated drop-wise with a solution of 5% v/v HCO$_2$H in MeOH (20 mL). A colour change from green to metallic grey and an exotherm to 37° C. were observed. The reaction mixture was allowed to cool to room temperature at which point analysis by LC/MS revealed complete conversion to desired product at retention time 2.19 minutes, ES+ m/z 875 [M+Na]$^+$, 853 [M+H]$^+$. The mixture was filtered through Celite® and the pad washed with EtOAc (75 mL). The filtrate was washed with saturated aqueous NaHCO$_3$ (3×20 mL), brine (50 mL), dried (MgSO$_4$), filtered and evaporated in vacuo to provide the crude bis-aniline 14 as a dark orange foam (840 mg, 92% yield). Purity satisfactory, so material carried through to next step without further purification.

(d) (9H-fluoren-9-yl)methyl(5-((5-(5-amino-4-((S)-2-(((tert-butyldimethylsilyl)oxy)methyl)-4-methyl-2,3-dihydro-1H-pyrrole-1-carbonyl)-2-methoxyphenoxy)pentyl)oxy)-2-((S)-2-(((tert-butyldimethylsilyl)oxy)methyl)-4-methyl-2,3-dihydro-1H-pyrrole-1-carbonyl)-4-methoxyphenyl)carbamate (15)

FmocCl (1.50 g, 5.93 mmol) was added to a stirred suspension of the bis-aniline 14 (6.74 g, 7.91 mmol) and Na$_2$CO$_3$ (2.10 g, 19.8 mmol) in THF (40 mL) and H$_2$O (40 mL). The mixture was allowed to stir at room temperature for 16 hours where analysis by LC/MS revealed desired mono Fmoc product 15 at retention time 2.41 minutes, I %=32, ES+ m/z 1098 [M+Na]$^+$, 1076 [M+H]$^+$ along with unreacted starting material at retention time 2.22 minutes, I %=30, and bis-Fmoc material at retention time 2.60 minutes, I %=36, ES+ m/z 1321 [M+Na]$^+$, 1298 [M+H]$^+$. The mixture was partitioned between H$_2$O (50 mL) and EtOAc (50 mL), the layers were separated and the organic layer washed with H$_2$O (30 mL), brine (40 mL), dried (MgSO$_4$), filtered and evaporated in vacuo to give the crude product. Purification by Isolera™ (Hexane/EtOAc, SNAP Ultra 100 g, 100 mL per minute) provided the pure mono Fmoc product 15 as an orange foam (2.43 g, 38% yield based on FmocCl, eluting at 58% Hexane/EtOAc) unreacted bis-aniline 14 (3.06 g, eluting at 40% Hexane/EtOAc) and bis-Fmoc (2.32 g, eluting at 74% Hexane/EtOAc).

(e) (9H-fluoren-9-yl)methyl(5-((5-(5-((((4-((S)-2-((S)-2-(((allyloxy)carbonyl)amino)-3-methylbutanamido)propanamido)benzyl)oxy)carbonyl)amino)-4-((S)-2-(((tert-butyldimethylsilyl)oxy)methyl)-4-methyl-2,3-dihydro-1H-pyrrole-1-carbonyl)-2-methoxyphenoxy)pentyl)oxy)-2-((S)-2-(((tert-butyldimethylsilyl)oxy)methyl)-4-methyl-2,3-dihydro-1H-pyrrole-1-carbonyl)-4-methoxyphenyl)carbamate (16)

Triphosgene (242 mg, 0.81 mmol) was added to a stirred solution of the mono Fmoc product 15 (2.43 g, 2.26 mmol) and TEA (692 µL, 502 mg, 4.97 mmol) in dry DCM (30 mL) at room temperature. After stirring for 10 minutes under argon, analysis by LC/MS revealed complete conversion to isocyanate (sampled in MeOH to give methyl carbamate, retention time 2.38 minutes, ES+ m/z 1156 [M+Na]$^{+\cdot}$, 1133 [M+H]$^{+\cdot}$). The mixture was treated with additional TEA (472 µL, 342 mg, 3.39 mmol) followed by the addition of linker I16 (852 mg, 2.26 mmol). After 3.5 hours stirring under argon, LC/MS revealed satisfactory conversion to carbamate 16 at retention time 2.33 minutes, ES+ m/z 1501 [M+Na]$^{+\cdot}$, 1479 [M+H]$^{+\cdot}$. The mixture was diluted with DCM (50 mL) and washed with saturated aqueous NH$_4$Cl (2×20 mL), brine (30 mL), dried (MgSO$_4$), filtered and evaporated in vacuo to give the crude product. Purification by Isolera™ (Hexane/EtOAc, SNAP Ultra 100 g, 100 mL per minute) provided the pure carbamate 16 (eluting at 46% Hexane/EtOAc) as a yellow foam (2.26 g, 68% yield).

(f) 4-((S)-2-((S)-2-(((allyloxy)carbonyl)amino)-3-methylbutanamido)propanamido)benzyl (5-((5-(5-amino-4-((S)-2-(((tert-butyldimethylsilyl)oxy)methyl)-4-methyl-2, 3-dihydro-1H-pyrrole-1-carbonyl)-2-methoxyphenoxy)pentyl)oxy)-2-((S)-2-(((tert-butyldimethylsilyl)oxy)methyl)-4-methyl-2,3-dihydro-1H-pyrrole-1-carbonyl)-4-methoxyphenyl)carbamate (17)

Dimethylamine (15.0 mL of a 2.0M solution in THF, 30.6 mmol) was added to a stirred solution of the Fmoc protected compound 16 (2.26 g, 1.65 mmol) in THF (20 mL) at room temperature. After stirring for 1 hour at room temperature, analysis by LC/MS revealed reaction completion with desired product at retention time 2.17 minutes, ES+ m/z 1279 [M+Na]$^{+\cdot}$, 1257 [M+H]$^{+\cdot}$, along with Fmoc cleavage by-product at retention time 1.79 minutes and its DMA adduct at retention time 0.97 minutes. The mixture was evaporated in vacuo to give the crude product which was subsequently purified by Isolera™ (Hexane/EtOAc, SNAP Ultra 100 g, 100 mL per minute) to provide the pure aniline 17 (eluting at 18% Hexane/EtOAc) as an orange foam (1.94 g, 100% yield).

(g) Allyl(2S,3S,4S,5R,6S)-6-(4-((((5-((5-(5-((((4-((S)-2-((S)-2-(((allyloxy)carbonyl)amino)-3-methylbutanamido)propanamido)benzyl)oxy)carbonyl)amino)-4-((S)-2-(((tert-butyldimethylsilyl)oxy)methyl)-4-methyl-2,3-dihydro-1H-pyrrole-1-carbonyl)-2-methoxyphenoxy)pentyl)oxy)-2-((S)-2-(((tert-butyldimethylsilyl)oxy)methyl)-4-methyl-2,3-dihydro-1H-pyrrole-1-carbonyl)-4-methoxyphenyl)carbamoyl)oxy)methyl)-2-nitrophenoxy)-3,4,5-tris(((allyloxy)carbonyl)oxy)tetrahydro-2H-pyran-2-carboxylate (18)

Triphosgene (165 mg, 0.55 mmol) was added to a stirred solution of the aniline 17 (1.94 g, 1.54 mmol) and pyridine (274 µL, 268 mg, 3.39 mmol) in dry DCM (20 mL) at room temperature. After stirring for 10 minutes under argon, analysis by LC/MS revealed complete conversion to isocyanate (sampled in MeOH to give methyl carbamate, retention time 2.21 minutes, ES+ m/z 1337 [M+Na]$^{+\cdot}$, 1315 [M+H]$^{+\cdot}$). The mixture was treated with additional pyridine (187 µL, 183 mg, 2.31 mmol) and dibutyltin dilaurate (179 µL, 191 mg, 0.30 mmol) followed by the addition of linker 5a (984 mg, 1.54 mmol). After 18 hours stirring under argon, LC/MS revealed satisfactory conversion to carbamate 18 at retention time 2.23 minutes, ES+ m/z 1942 [M+Na]$^{+\cdot}$, 1920 [M+H]$^{+\cdot}$. The mixture was diluted with DCM (30 mL) and washed with saturated NH$_4$Cl (2×20 mL), H$_2$O (20 mL), brine (40 mL), dried (MgSO$_4$), filtered and evaporated in vacuo to give the crude product. Purification by Isolera™ (Hexane/EtOAc, SNAP Ultra 100 g, 100 mL per minute) provided the pure carbamate 18 (eluting at 43% Hexane/EtOAc) as a yellow foam (2.17 g, 74% yield).

(h) Allyl(2S,3S,4S,5R,6S)-6-(4-((((5-((5-(5-((((4-((S)-2-((S)-2-(((allyloxy)carbonyl)amino)-3-methylbutanamido)propanamido)benzyl)oxy)carbonyl)amino)-4-((S)-2-(hydroxymethyl)-4-methyl-2,3-dihydro-1H-pyrrole-1-carbonyl)-2-methoxyphenoxy)pentyl)oxy)-2-((S)-2-(hydroxymethyl)-4-methyl-2,3-dihydro-1H-pyrrole-1-carbonyl)-4-methoxyphenyl)carbamoyl)oxy)methyl)-2-nitrophenoxy)-3,4,5-tris((allyloxy)carbonyl)oxy)tetrahydro-2H-pyran-2-carboxylate (19)

Glacial acetic acid (18 mL) was added to a stirred solution of the TBS-protected compound 18 (2.17 g, 1.13 mmol) in THF (6 mL) and H$_2$O (6 mL). The reaction mixture was allowed to stir for 18 hours at room temperature after which time analysis by LC/MS revealed reaction completion with desired product observed at retention time 1.82 minutes, ES+ m/z 1691 [M+H]$^{+\cdot}$, 1714 [M+Na]$^{+\cdot}$. The reaction mixture was added drop-wise to a chilled (0-5° C.) saturated solution of NaHCO$_3$ (300 mL). The neutral solution was allowed to warm to room temperature and extracted with EtOAc (3×100 mL), the combined organic layers were washed with brine (50 mL), dried (MgSO$_4$), filtered and evaporated in vacuo to give the crude product. Purification by Isolera™ (DCM/MeOH, SNAP Ultra 100 g, 100 mL per minute) gave the bis-alcohol 19 (eluting at 96.5% DCM/MeOH) as a white foam (1.31 g, 69% yield).

(i) 4-(((2S,3R,4S,5S,6S)-6-((allyloxy)carbonyl)-3,4,5-tris(((allyloxy)carbonyl)oxy)tetrahydro-2H-pyran-2-yl)oxy)-3-nitrobenzyl(11S,11aS)-8-((5-(((11S,11aS)-10-(((4-((S)-2-((S)-2-(((allyloxy)carbonyl)amino)-3-methylbutanamido)propanamido)benzyl)oxy)carbonyl)-11-hydroxy-7-methoxy-2-methyl-5-oxo-5,10,11,11a-tetrahydro-1H-pyrrolo[2,1-c][1,4]benzodiazepin-8-yl)oxy)pentyl)oxy)-11-hydroxy-7-methoxy-2-methyl-5-oxo-11,11a-dihydro-1H-pyrrolo[2,1-c][1,4]benzodiazepine-10(5H)-carboxylate (20)

45% IBX (269 mg, 0.43 mmol) was added to a stirred solution of the bis-OH 19 (300 mg, 0.18 mmol) in dry DMSO (5 mL). The mixture was heated to 30° C. under an argon atmosphere and reaction progress monitored by LC/MS. After 24 hours stirring, additional IBX (22 mg, 36 µmol) was added and the mixture stirred for another 24 hours. At this point analysis by LC/MS revealed formation of product at retention time 1.79 minutes, ES+ m/z 1710 [M+Na]$^{+\cdot}$. The reaction mixture was added drop-wise to a saturated aqueous NaHCO$_3$ solution (100 mL) and extracted with DCM (2×75 mL). The combined organic layers were washed with saturated aqueous NaHCO$_3$ (2×20 mL), H$_2$O (30 mL), brine (40 mL), dried (MgSO$_4$), filtered and evaporated in vacuo to give the crude product. Purification by Isolera™ (DCM/MeOH, SNAP Ultra 25 g, 75 mL per minute) gave the cyclised product 11 (eluting at 97.4% DCM/MeOH) as a white foam (136 mg, 46% yield).

(j) Alternate Synthesis of 4-(((2S,3R,4S,5S,6S)-6-((allyloxy)carbonyl)-3,4,5-tris(((allyloxy)carbonyl)oxy)tetrahydro-2H-pyran-2-yl)oxy)-3-nitrobenzyl (11S,11aS)-8-((5-(((11S,11aS)-10-(((4-((S)-2-((S)-2-(((allyloxy)carbonyl)amino)-3-methylbutanamido)propanamido)benzyl)oxy)carbonyl)-11-hydroxy-7-methoxy-2-methyl-5-oxo-5,10,11,11a-tetrahydro-1H-pyrrolo[2,1-c][1,4]benzodiazepin-8-yl)oxy)pentyl)oxy)-11-hydroxy-7-methoxy-2-methyl-5-oxo-11,11a-dihydro-1H-pyrrolo[2,1-c][1,4]benzodiazepine-10(5H)-carboxylate (20)

TEMPO (6.6 mg, 42 µmol) and DAIB (125 mg, 0.39 mmol) were added to a stirred solution of the bis-OH 19 (300 mg, 0.18 mmol) in dry DCM (15 mL) at room temperature. The mixture was stirred under an argon atmosphere and reaction progress monitored by LC/MS. After 24 hours stirring, additional TEMPO (6.6 mg, 42 µmol) and DAIB (25 mg, 78 µmol) were added and the mixture stirred for another 24 hours. At this point analysis by LC/MS revealed formation of product at retention time 1.79 minutes, ES+ m/z 1710 [M+Na]$^+$. The mixture was diluted with DCM (50 mL) and washed with saturated aqueous sodium thiosulfate (40 mL), saturated aqueous NaHCO$_3$ (30 mL), brine (40 mL), dried (MgSO$_4$), filtered and evaporated in vacuo to give the crude product. Purification by Isolera™ (DCM/MeOH, SNAP Ultra 25 g, 75 mL per minute) gave the cyclised product 21 (eluting at 96.5% DCM/MeOH) as a white foam (231 mg, 78% yield).

(k) (2S,3S,4S,5R,6S)-6-(4-((((11S,11aS)-8-((5-(((11S,11aS)-10-(((4-((S)-2-(((S)-2-amino-3-methylbutanamido)propanamido)benzyl)oxy)carbonyl)-11-hydroxy-7-methoxy-2-methyl-5-oxo-5,10,11,11a-tetrahydro-1H-pyrrolo[2,1-c][1,4]benzodiazepin-8-yl)oxy)pentyl)oxy)-11-hydroxy-7-methoxy-2-methyl-5-oxo-5,10,11,11a-tetrahydro-1H-pyrrolo[2,1-c][1,4]benzodiazepine-10-carbonyl)oxy)methyl)-2-nitrophenoxy)-3,4,5-trihydroxytetrahydro-2H-pyran-2-carboxylic acid (21)

Pd(PPh$_3$)$_4$ (15.8 mg, 13.7 µmol) was added to a stirred solution of pyrrolidine (63 µL, 54 mg, 0.75 mmol) and the Alloc/allyl compound 20 (231 mg, 0.14 mmol) in dry DCM (4 mL). The reaction mixture was allowed to stir under an argon atmosphere where a precipitate began to form. After stirring for 30 minutes at room temperature analysis by LC/MS revealed reaction completion with desired product observed at retention time 1.18 minutes, ES+ m/z 1312 [M+H]$^+$. The solvent was removed by evaporation in vacuo and the resulting residue triturated with diethyl ether followed by additional evaporation in vacuo to provide the crude amine 12 as a solid which was carried through to the next step without further purification or analysis.

(l) (2S,3S,4S,5R,6S)-6-(4-((((11S,11aS)-8-((5-(((11S,11aS)-10-(((4-((2S,5S)-37-(2,5-dioxo-2,5-dihydro-1H-pyrrol-1-yl)-5-isopropyl-2-methyl-4,7,35-trioxo-10,13,16,19,22,25,28,31-octaoxa-3,6,34-triazaheptatriacontanamido)benzyl)oxy)carbonyl)-11-hydroxy-7-methoxy-2-methyl-5-oxo-5,10,11,11a-tetrahydro-1H-pyrrolo[2,1-c][1,4]benzodiazepin-8-yl)oxy)pentyl)oxy)-11-hydroxy-7-methoxy-2-methyl-5-oxo-5,10,11,11a-tetrahydro-1H-pyrrolo[2,1-c][1,4]benzodiazepine-10-carbonyl)oxy)methyl)-2-nitrophenoxy)-3,4,5-trihydroxytetrahydro-2H-pyran-2-carboxylic acid (22)

A solution of MAL-dPEG®8-TFP ester (122 mg, 0.16 mmol) in dry DCM (5 mL) was added to a stirred sample of the amine 21 (180 mg, 0.16 mmol), pyridine (28 µL, 27 mg, 0.34 mmol) and DMF (0.25 mL). The reaction mixture was allowed to stir under argon for 20 hours and began to darken in colour over time. Analysis by LC/MS revealed formation of desired product at retention time 1.43 minutes, ES– m/z 1884 [M–H]$^+$, along with unreacted amine at retention time 1.18 minutes. Additional MAL-dPEG®8-TFP ester (66 mg, 0.09 mmol), pyridine (12 µL, 11 mg, 0.15 mmol) and DCM (3 mL) were added and the mixture allowed to stir for a further three days. At this point a satisfactory amount of desired product had formed upon analysis by LC/MS and the solvent was removed by evaporation in vacuo. The crude product was purified by preparative HPLC to give the maleimide 22 as a white solid (55 mg, 19%): LC/MS (15-minute run), retention time 5.82 minutes, ES+ m/z 1886 [M+H]$^+$, 1908 [M+Na]$^+$; $^1$H NMR (400 MHz, d6-DMSO) δ 9.98 (br s, 2H), 8.25-8.15 (m, 1H), 7.99 (t, 1H, J=5.7 Hz), 7.87 (d, 1H, J=8.7 Hz), 7.69 (br s, 1H), 7.62-7.48 (m, 3H), 7.37 (d, 1H, J=8.9 Hz), 7.21-7.09 (m, 2H), 7.04 (s, 1H), 7.03 (s, 1H), 6.98 (s, 2H), 6.79 (s, 1H), 6.74 (s, 1H), 6.72-6.65 (m, 2H), 6.62-6.58 (m, 2H), 5.63-5.50 (m, 2H), 5.41-5.32 (m, 2H), 5.25-5.05 (m, 4H), 4.93-4.80 (m, 2H), 4.41-4.32 (m, 1H), 4.23-4.16 (m, 1H), 4.00-3.90 (m, 4H), 3.87-3.72 (m, 6H), 3.70-3.60 (m, 2H), 3.58 (t, 4H, J=7.2 Hz), 3.52-3.43 (m, 28H), 3.39-3.20 (m, 5H), 3.18-3.10 (m, 2H), 2.95-2.82 (m, 2H), 2.53-2.34 (m, 4H), 2.31 (t, 2H, J=7.3 Hz), 1.99-1.90 (m, 1H), 1.82-1.68 (m, 4H), 1.73 (s, 6H), 1.60-1.47 (m, 2H), 1.28 (d, 1H, J=7.0 Hz), 0.85 (d, 3H, J=6.8 Hz), 0.81 (d, 3H, J=6.8 Hz).

Example 3

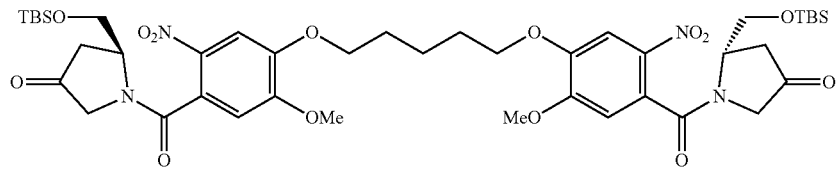

23

↓

-continued
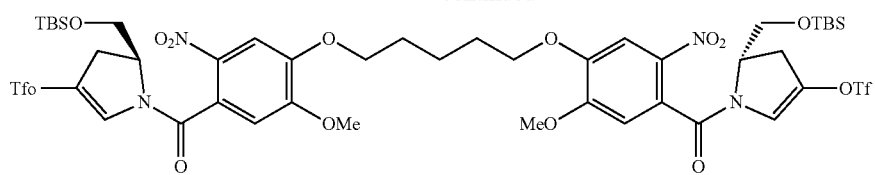
24
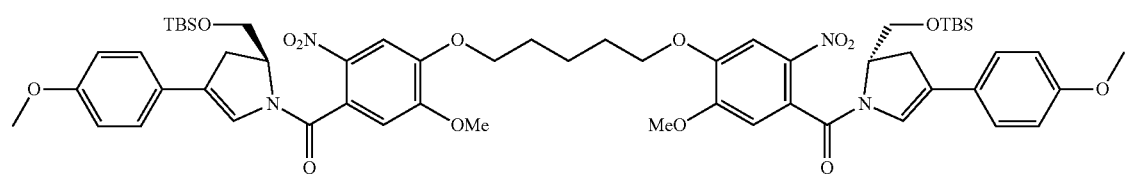
25
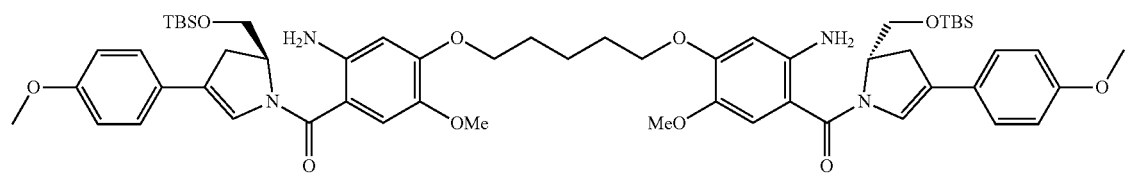
26
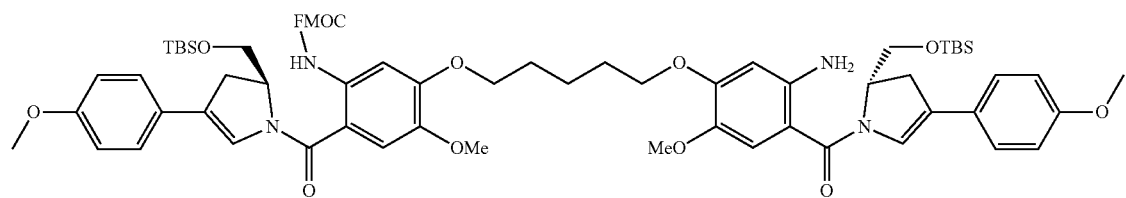
27
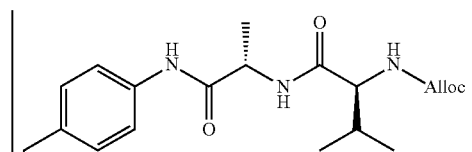
I16

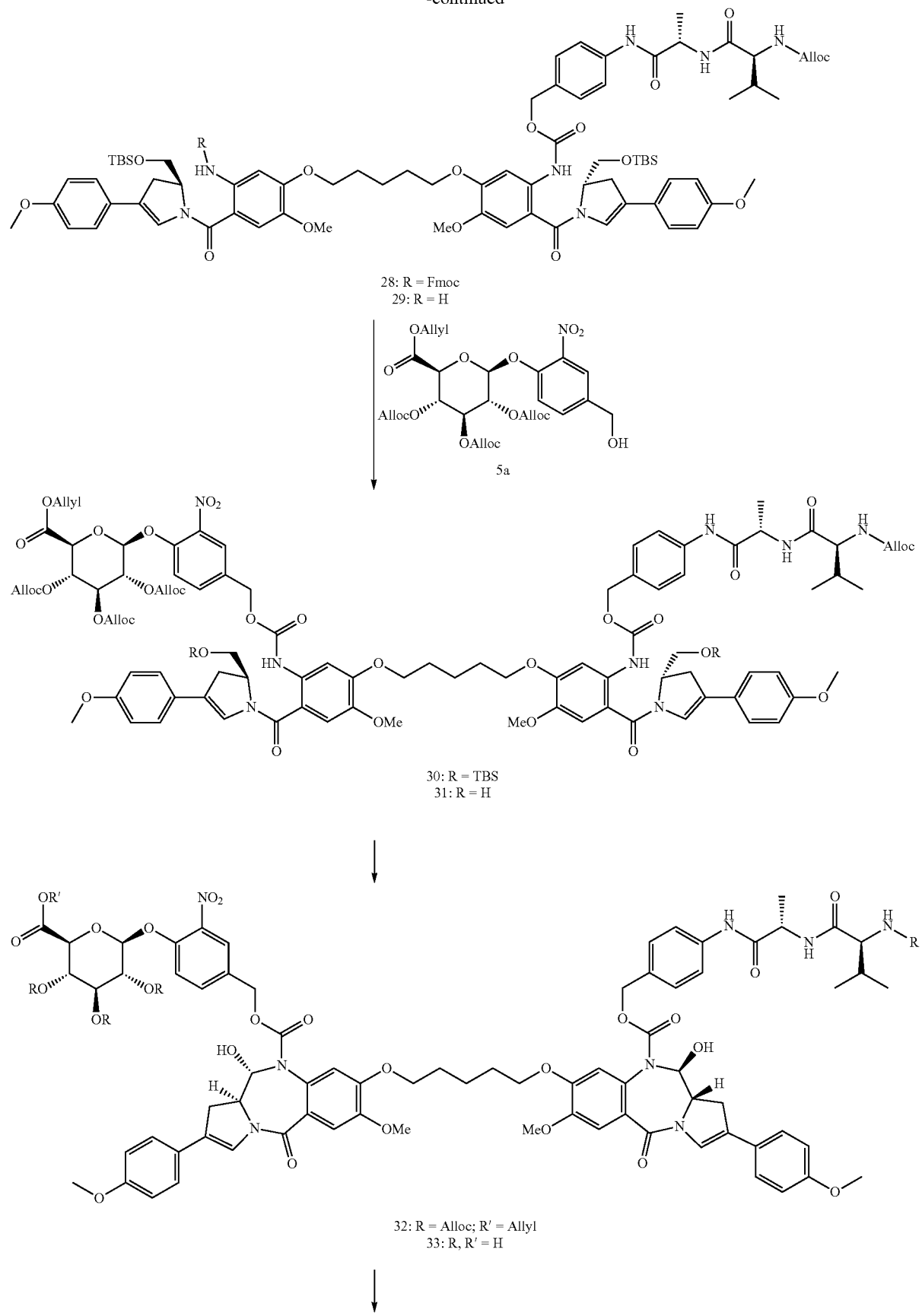

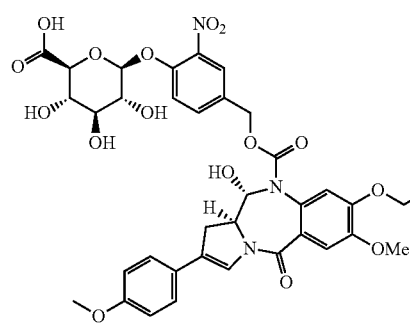
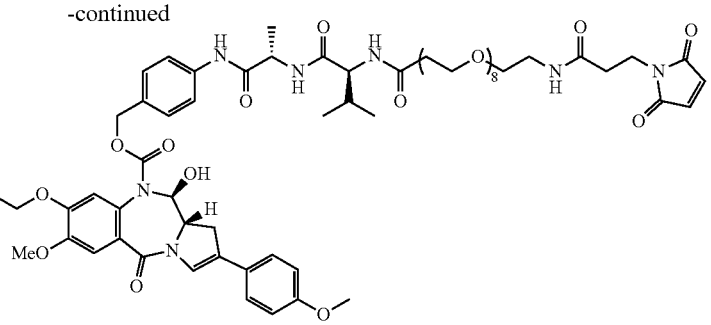

34

Compound 23 is compound 46 in WO2014/057074.

(a) (5S,5'S)-(4,4'-(Pentane-1,5-diylbis(oxy))bis(5-methoxy-2-nitrobenzoyl))bis(5-(((tert-butyldimethylsilyl)oxy)methyl)-4,5-dihydro-1H-pyrrole-1,3-diyl) bis(trifluoromethanesulfonate) (24)

Anhydrous 2,6-lutidine (8.90 mL, 8.22 g, 76.7 mmol) was added via syringe to a stirred solution of bis-ketone 23 (5.41 g, 5.90 mmol) in dry DCM (200 mL) at −45° C. (dry ice/acetonitrile) under an argon atmosphere. Anhydrous trifluoromethanesulfonic anhydride (5.96 mL, 10.0 g, 35.5 mmol), taken from a freshly opened ampoule, was then added via syringe, while maintaining the temperature at −40° C. or below. The reaction mixture was allowed to stir at −45° C. for 1 hour at which point analysis by LC/MS revealed conversion to product at retention time retention time 2.23 minutes, ES+ m/z 1203 [M+Na]$^{+\cdot}$, 1181 [M+H]$^{+\cdot}$. The cold reaction mixture was immediately diluted with DCM (200 mL) and washed with water (1×200 mL), 5% citric acid solution (2×200 mL), saturated aqueous NaHCO$_3$ (200 mL), brine (300 mL), dried (MgSO$_4$), filtered and evaporated in vacuo to provide the crude product. Purification by Isolera™ (Hexane/EtOAc, SNAP Ultra 100 g, 100 mL per minute) afforded the bis-enol triflate 3 (eluting at 78% Hexane/EtOAc) as a yellow foam (5.02 g, 72% yield).

(b) ((Pentane-1,5-diylbis(oxy))bis(5-methoxy-2-nitro-4,1-phenylene))bis(((S)-2-(((tert-butyldimethylsilyl)oxy)methyl)-4-(4-methoxyphenyl)-2,3-dihydro-1H-pyrrol-1-yl)methanone) (25)

Pd(PPh$_3$)$_4$ (196 mg, 0.17 mmol) was added to a stirred mixture of the bis-enol triflate 24 (5.02 g, 4.25 mmol), 4-methoxyphenylboronic acid (1.68 g, 11.1 mmol), Na$_2$CO$_3$ (1.44 g, 13.6 mmol), EtOH (20 mL), toluene (40 mL) and water (20 mL). The reaction mixture was heated at 30° C. and stirred under an argon atmosphere for 3 hours after which time complete conversion to desired product was observed by LC/MS, retention time 2.23 minutes, ES+ m/z 1120 [M+Na]$^{+\cdot}$, 1098 [M+H]$^{+\cdot}$. The reaction mixture was partitioned between EtOAc (200 mL) and H$_2$O (100 mL) and the aqueous layer extracted with EtOAc (3×30 mL). The combined organic layers were washed with H$_2$O (2×50 mL), brine (50 mL), dried (MgSO$_4$), filtered and evaporated in vacuo to provide the crude product. Purification by Isolera™ (Hexane/EtOAc, SNAP Ultra 100 g, 100 mL per minute) afforded bis-C2-aryl compound 25 (eluting at 63% Hexane/EtOAc) as a yellowish foam (3.11 g, 67% yield).

(c) ((Pentane-1,5-diylbis(oxy))bis(2-amino-5-methoxy-4,1-phenylene))bis(((S)-2-(((tert-butyldimethylsilyl)oxy)methyl)-4-(4-methoxyphenyl)-2,3-dihydro-1H-pyrrol-1-yl)methanone) (26)

Non-activated zinc (4.13 g, 63.1 mmol) was added to a vigorously stirred solution of the bis-nitro compound 25 (1.73 g, 1.58 mmol) in EtOH (15 mL) and EtOAc (15 mL) at room temperature. The reaction mixture was treated with water (1 mL) then drop-wise with a solution of 5% v/v HCO$_2$H in MeOH (19 mL). A colour change from green to metallic grey and an exotherm to 40° C. were observed. The reaction mixture was allowed to cool to room temperature at which point analysis by LC/MS revealed complete conversion to desired product at retention time 2.19 minutes, ES+ m/z 1060 [M+Na]$^{+\cdot}$, 1038 [M+H]$^{+\cdot}$. The mixture was filtered through Celite® and the pad washed with EtOAc (100 mL). The filtrate was washed with saturated aqueous NaHCO$_3$ (3×50 mL) [care: effervescence!], brine (50 mL), dried (MgSO$_4$), filtered and evaporated in vacuo to provide the crude bis-aniline 26 as a dark orange foam (1.56 g, 95% yield). Purity satisfactory, so material carried through to next step without further purification.

(d) (9H-Fluoren-9-yl)methyl(5-((5-(5-amino-4-((S)-2-(((tert-butyldimethylsilyl)oxy)methyl)-4-(4-methoxyphenyl)-2,3-dihydro-1H-pyrrole-1-carbonyl)-2-methoxyphenoxy)pentyl)oxy)-2-((S)-2-(((tert-butyldimethylsilyl)oxy)methyl)-4-(4-methoxyphenyl)-2,3-dihydro-1H-pyrrole-1-carbonyl)-4-methoxyphenyl)carbamate (27)

FmocCl (1.22 g, 4.70 mmol) was added to a stirred suspension of the bis-aniline 26 (6.50 g, 6.27 mmol) and Na$_2$CO$_3$ (1.66 g, 15.7 mmol) in THF (32 mL) and H$_2$O (32 mL). The mixture was allowed to stir at room temperature for 3 hours where analysis by LC/MS revealed desired mono Fmoc product 27 at retention time 2.33 minutes, I %=51, ES+ m/z 1282 [M+Na]$^{+\cdot}$, 1260 [M+H]$^{+\cdot}$ along with unreacted starting material at retention time 2.19 minutes, I %=24, and bis-Fmoc material at retention time 2.47 minutes, I %=24, ES+ m/z 1504 [M+Na]$^+$, 1482 [M+H]$^{+\cdot}$. The mixture was partitioned between H$_2$O (50 mL) and EtOAc (75 mL), the layers were separated and the aqueous phase extracted with EtOAc (2×25 mL). The combined organic layers were washed with H$_2$O (30 mL), brine (40 mL), dried (MgSO$_4$), filtered and evaporated in vacuo to give the crude product. Purification by Isolera™ (Hexane/EtOAc, SNAP Ultra 100 g, 100 mL per minute) provided the pure mono Fmoc product 27 as an orange foam (3.31 g, 56% yield based on FmocCl, eluting at 53% Hexane/EtOAc) unreacted bis-aniline 26 (2.09 g, eluting at 40% Hexane/EtOAc) and bis-Fmoc (1.39 g, eluting at 68% Hexane/EtOAc).

(e) (9H-Fluoren-9-yl)methyl(5-((5-(5-((((4-((S)-2-((S)-2-(((allyloxy)carbonyl)amino)-3-methylbutanamido)propanamido)benzyl)oxy)carbonyl)amino)-4-((S)-2-(((tert-butyldimethylsilyl)oxy)methyl)-4-(4-methoxyphenyl)-2,3-dihydro-1H-pyrrole-1-carbonyl)-2-methoxyphenoxy)pentyl)oxy)-2-((S)-2-(((tert-butyldimethylsilyl)oxy)methyl)-4-(4-methoxyphenyl)-2,3-dihydro-1H-pyrrole-1-carbonyl)-4-methoxyphenyl)carbamate (28)

Triphosgene (281 mg, 0.81 mmol) was added to a stirred solution of the mono Fmoc product 27 (3.31 g, 2.63 mmol) and TEA (805 μL, 584 mg, 5.79 mmol) in dry DCM (35 mL) at room temperature. After stirring for 10 minutes under argon, analysis by LC/MS revealed complete conversion to isocyanate (sampled in MeOH to give methyl carbamate, retention time 2.35 minutes, ES+ m/z 1340 [M+Na]+·, 1318 [M+H]+·). The mixture was treated with additional TEA (549 μL, 398 mg, 3.95 mmol) followed by the addition of linker I16 (992 mg, 2.63 mmol). After 20 hours stirring under argon, LC/MS revealed conversion to desired carbamate 28 at retention time 2.33 minutes, I %=40, ES+ m/z 1685 [M+Na]+·, along with Fmoc cleaved material 29 at retention time 2.19 minutes, I %=28, ES+ m/z 1463 [M+Na]+·, 1441 [M+H]+·. The mixture was diluted with DCM (40 mL) and washed with saturated aqueous NH4Cl (2×30 mL), brine (50 mL), dried (MgSO4), filtered and evaporated in vacuo to give the crude product. Purification by Isolera™ (Hexane/EtOAc, SNAP Ultra 100 g, 100 mL per minute) provided the pure carbamate 28 as a yellow foam (1.64 g, 38% yield, eluting at 40% Hexane/EtOAc) along with Fmoc cleaved product 29 (1.31 g, eluting at 20% Hexane/EtOAc).

(f) 4-((S)-2-((S)-2-(((allyloxy)carbonyl)amino)-3-methylbutanamido)propanamido)benzyl (5-((5-(5-amino-4-((S)-2-(((tert-butyldimethylsilyl)oxy)methyl)-4-(4-methoxyphenyl)-2,3-dihydro-1H-pyrrole-1-carbonyl)-2-methoxyphenoxy)pentyl)oxy)-2-((S)-2-(((tert-butyldimethylsilyl)oxy)methyl)-4-(4-methoxyphenyl)-2,3-dihydro-1H-pyrrole-1-carbonyl)-4-methoxyphenyl)carbamate (29)

Dimethylamine (9.9 mL of a 2.0M solution in THF, 19.7 mmol) was added to a stirred solution of the Fmoc protected compound 28 (1.64 g, 0.99 mmol) in THF (15 mL) at room temperature. After stirring for 1.5 hours at room temperature, analysis by LC/MS revealed reaction completion with desired product at retention time 2.19 minutes, ES+ m/z 1463 [M+Na]+·, 1441 [M+H]+·, along with Fmoc cleavage by product DMA adduct at retention time 0.97 minutes. The mixture was evaporated in vacuo to give the crude product which was subsequently purified by Isolera™ (Hexane/EtOAc, SNAP Ultra 100 g, 100 mL per minute) to provide the pure aniline 29 (eluting at 20% Hexane/EtOAc) as an orange foam (1.36 g, 96% yield).

(g) Allyl(2S,3S,4S,5R,6S)-6-(4-(((((5-((5-(5-((((4-((S)-2-((S)-2-(((allyloxy)carbonyl)amino)-3-methylbutanamido)propanamido)benzyl)oxy)carbonyl)amino)-4-((S)-2-(((tert-butyldimethylsilyl)oxy)methyl)-4-(4-methoxyphenyl)-2,3-dihydro-1H-pyrrole-1-carbonyl)-2-methoxyphenoxy)pentyl)oxy)-2-((S)-2-(((tert-butyldimethylsilyl)oxy)methyl)-4-(4-methoxyphenyl)-2,3-dihydro-1H-pyrrole-1-carbonyl)-4-methoxyphenyl)carbamoyl)oxy)methyl)-2-nitrophenoxy)-3,4,5-tris((allyloxy)carbonyl)oxy)tetrahydro-2H-pyran-2-carboxylate (30)

Triphosgene (198 mg, 0.67 mmol) was added to a stirred solution of the aniline 29 (2.67 g, 1.85 mmol) and pyridine (329 μL, 322 mg, 4.07 mmol) in dry DCM (25 mL) at room temperature. After stirring for 10 minutes under argon, analysis by LC/MS revealed complete conversion to isocyanate (sampled in MeOH to give methyl carbamate, retention time 2.22 minutes, ES+ m/z 1521 [M+Na]+·, 1499 [M+H]+·). The mixture was treated with additional pyridine (224 μL, 220 mg, 2.78 mmol) and dibutyltin dilaurate (219 μL, 234 mg, 0.37 mmol) followed by the addition of linker 5a (1.18 g, 1.85 mmol). After 16 hours stirring under argon, LC/MS revealed consumption of isocyanate and decrease in signal intensity for linker 5a but no M$^{2+}$ for desired product at retention time 2.23 minutes. The mixture was diluted with DCM (30 mL) and washed with saturated NH4Cl (2×30 mL), brine (40 mL), dried (MgSO4), filtered and evaporated in vacuo to give the crude product. Purification by Isolera™ (Hexane/EtOAc, SNAP Ultra 100 g, 100 mL per minute) provided the pure carbamate 30 (eluting at 39% Hexane/EtOAc) as a yellow foam (2.40 g, 62% yield).

(h) Allyl(2S,3S,4S,5R,6S)-6-(4-(((((5-((5-(5-((((4-((S)-2-((S)-2-(((allyloxy)carbonyl)amino)-3-methylbutanamido)propanamido)benzyl)oxy)carbonyl)amino)-4-((S)-2-(hydroxymethyl)-4-(4-methoxyphenyl)-2,3-dihydro-1H-pyrrole-1-carbonyl)-2-methoxyphenoxy)pentyl)oxy)-2-((S)-2-(hydroxymethyl)-4-(4-methoxyphenyl)-2,3-dihydro-1H-pyrrole-1-carbonyl)-4-methoxyphenyl)carbamoyl)oxy)methyl)-2-nitrophenoxy)-3,4,5-tris((allyloxy)carbonyl)oxy)tetrahydro-2H-pyran-2-carboxylate (31)

Glacial acetic acid (21 mL) was added to a stirred solution of the TBS-protected compound 30 (2.40 g, 1.14 mmol) in THF (7 mL) and H2O (7 mL). The reaction mixture was allowed to stir for 16 hours at room temperature after which time analysis by LC/MS revealed reaction completion with desired product observed at retention time 1.88 minutes, ES+ m/z 1876 [M+H]+·, 1898 [M+Na]+·. The reaction mixture was added drop-wise to a chilled (0-5° C.) saturated solution of NaHCO3 (350 mL). The neutral solution was allowed to warm to room temperature and partitioned with EtOAc (200 mL). The aqueous phase was extracted with EtOAc (2×50 mL), the combined organic layers were washed with NaHCO3 (2×60 mL), brine (70 mL), dried (MgSO4), filtered and evaporated in vacuo to give the crude product. Purification by Isolera™ (DCM/MeOH, SNAP Ultra 100 g, 100 mL per minute) gave the bis-alcohol 31 (eluting at 95.6% DCM/MeOH) as a yellowish foam (2.07 g, 97% yield).

(i) 4-(((2S,3R,4S,5S,6S)-6-((allyloxy)carbonyl)-3,4,
5-tris((allyloxy)carbonyl)oxy)tetrahydro-2H-pyran-
2-yl)oxy)-3-nitrobenzyl(11S,11aS)-8-((5-(((11S,
11aS)-10-(((4-((S)-2-((S)-2-(((allyloxy)carbonyl)
amino)-3-methylbutanamido)propanamido)benzyl)
oxy)carbonyl)-11-hydroxy-7-methoxy-2-(4-
methoxyphenyl)-5-oxo-5,10,11,11a-tetrahydro-1H-
pyrrolo[2,1-c][1,4]benzodiazepin-8-yl)oxy)pentyl)
oxy)-11-hydroxy-7-methoxy-2-(4-methoxyphenyl)-
5-oxo-11,11a-dihydro-1H-pyrrolo[2,1-c][1,4]
benzodiazepine-10(5H)-carboxylate (32)

Cu(NCCH$_3$)$_4$·CF$_3$SO$_3$ (2 mg, 5.3 µmmol) was added to a stirred solution of the bis-OH 31 (100 mg, 53 µmmol) and the Stahl aerobic oxidation TEMPO solution (27 µL of a 0.2M solution in CH$_3$CN, 5.3 µmmol) in CH$_3$CN (1 mL). The reaction mixture was allowed to stir under an air atmosphere (balloon) for 3 hours at which point analysis by LC/MS revealed no apparent change in retention time or ES+. Additional Cu(NCCH$_3$)$_4$·CF$_3$SO$_3$ (2 mg, 5.3 µmmol) and Stahl aerobic oxidation TEMPO solution (27 µL of a 0.2M solution in CH$_3$CN, 5.3 µmmol) were added and the reaction mixture allowed to stir for a further 16 hours. Analysis by LC/MS again revealed no change in retention time, however, ES+ showed absence of starting material m/z and strong presence of desired product m/z 1894 [M+Na]+·. The solvent was removed by evaporation in vacuo and the resulting residue purified by Isolera™ (DCM/MeOH, SNAP Ultra 10 g, 36 mL per minute) to give the cyclised product 32 (eluting at 96.2% DCM/MeOH) as a white foam (91 mg, 92% yield).

(j) (2S,3S,4S,5R,6S)-6-(4-((((11S,11aS)-8-((5-
(((11S,11aS)-10-(((4-((S)-2-((S)-2-amino-3-meth-
ylbutanamido)propanamido)benzyl)oxy)carbonyl)-
11-hydroxy-7-methoxy-2-(4-methoxyphenyl)-5-oxo-
5,10,11,11a-tetrahydro-1H-pyrrolo[2,1-c][1,4]
benzodiazepin-8-yl)oxy)pentyl)oxy)-11-hydroxy-7-
methoxy-2-(4-methoxyphenyl)-5-oxo-5,10,11,11a-
tetrahydro-1H-pyrrolo[2,1-c][1,4]benzodiazepine-
10-carbonyl)oxy)methyl)-2-nitrophenoxy)-3,4,5-
trihydroxytetrahydro-2H-pyran-2-carboxylic acid
(33)

Pd(PPh$_3$)$_4$ (15.0 mg, 12.8 µmol) was added to a stirred solution of pyrrolidine (59 µL, 50 mg, 0.70 mmol) and the Alloc/allyl compound 32 (240 mg, 0.13 mmol) in dry DCM (5 mL). The reaction mixture was allowed to stir under an argon atmosphere, after stirring for 30 minutes at room temperature analysis by LC/MS revealed reaction completion with desired product observed at retention time 1.31 minutes, ES+ m/z 1496 [M+H]+·. The solvent was removed by evaporation in vacuo and the resulting residue triturated with diethyl ether, sonicated, followed by additional evaporation in vacuo to provide the crude amine 33 as a yellow solid which was carried through to the next step without further purification or analysis.

(k) (2S,3S,4S,5R,6S)-6-(4-((((11S,11aS)-8-((5-
(((11S,11aS)-10-(((4-((2S,5S)-37-(2,5-dioxo-2,5-
dihydro-1H-pyrrol-1-yl)-5-isopropyl-2-methyl-4,7,
35-trioxo-10,13,16,19,22,25,28,31-octaoxa-3,6,34-
triazaheptatriacontanamido)benzyl)oxy)carbonyl)-
11-hydroxy-7-methoxy-2-(4-methoxyphenyl)-5-oxo-
5,10,11,11a-tetrahydro-1H-pyrrolo[2,1-c][1,4]
benzodiazepin-8-yl)oxy)pentyl)oxy)-11-hydroxy-7-
methoxy-2-(4-methoxyphenyl)-5-oxo-5,10,11,11a-
tetrahydro-1H-pyrrolo[2,1-c][1,4]benzodiazepine-
10-carbonyl)oxy)methyl)-2-nitrophenoxy)-3,4,5-
trihydroxytetrahydro-2H-pyran-2-carboxylic acid
(34)

A solution of MAL-dPEG®8-TFP ester (114 mg, 0.15 mmol) in dry DCM (5 mL) was added to a stirred sample of the amine 33 (191 mg, 0.13 mmol) and pyridine (26 µL, 25 mg, 0.32 mmol). The reaction mixture was allowed to stir under argon for 20 hours and began to darken in colour over time. Analysis by LC/MS revealed formation of desired product at retention time 1.59 minutes (desired m/z for M$^{2+}$ not detected during reaction monitoring) along with unreacted amine at retention time 1.31 minutes. Additional MAL-dPEG®8-TFP ester (114 mg, 0.15 mmol), pyridine (26 µL, 25 mg, 0.32 mmol) and DCM (3 mL) were added and the mixture allowed to stir for a further six days. At this point a satisfactory amount of desired product had formed upon analysis by LC/MS and the solvent was removed by evaporation in vacuo. The crude product was purified by Isolera™ (DCM/MeOH, SNAP Ultra 10 g, 36 mL per minute, eluting at 82% DCM/MeOH) followed by preparative HPLC to give the maleimide 34 as a slightly yellow solid (46 mg, 13%): LC/MS (15-minute run), retention time 6.71 minutes, ES+ m/z 1036 [M$^{2+}$.+H], 1058 [M$^{2+}$+Na], 1046 [M+Na]$^{2+}$; $^1$H NMR (400 MHz, d6-DMSO) δ 10.02 (br s, 2H), 8.27-8.16 (m, 1H), 8.01 (t, 1H, J=5.6 Hz), 7.90 (d, 1H, J=8.6 Hz), 7.72 (br s, 1H), 7.60-7.51 (m, 3H), 7.46-7.38 (m, 5H), 7.23-7.15 (m, 2H), 7.11 (s, 1H), 7.09 (s, 1H), 6.99 (s, 2H), 6.92 (d, 2H, J=8.9 Hz), 6.91 (d, 2H, J=8.9 Hz), 6.88-6.77 (m, 6H), 5.70-5.60 (m, 2H), 5.39-5.33 (m, 2H), 5.24-5.09 (m, 4H), 4.96-4.81 (m, 2H), 4.42-4.34 (m, 1H), 4.24-4.17 (m, 1H), 4.04-3.93 (m, 4H), 3.87-3.79 (m, 8H), 3.77 (s, 6H), 3.59 (t, 4H, J=7.3 Hz), 3.52-3.46 (m, 28H), 3.40-3.26 (m, 7H, obscured by H$_2$O), 3.19-3.11 (m, 2H), 2.95-2.82 (m, 2H), 2.53-2.31 (m, 4H), 2.02-1.92 (m, 1H), 1.86-1.73 (m, 4H), 1.62-1.52 (m, 2H), 1.30 (d, 1H, J=7.0 Hz), 0.87 (d, 3H, J=6.7 Hz), 0.83 (d, 3H, J=6.8 Hz).

Example 4

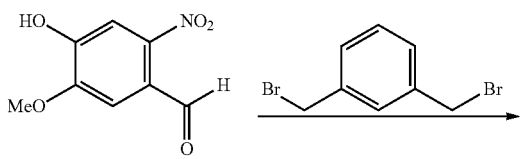

35

-continued
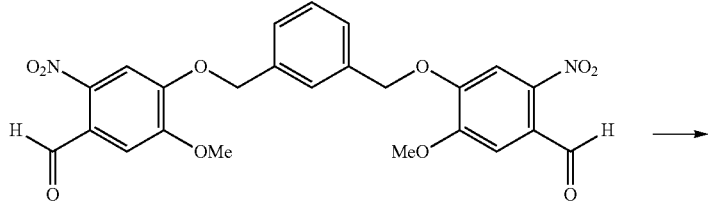
36
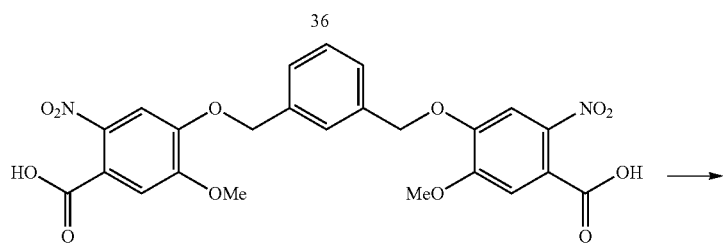
37
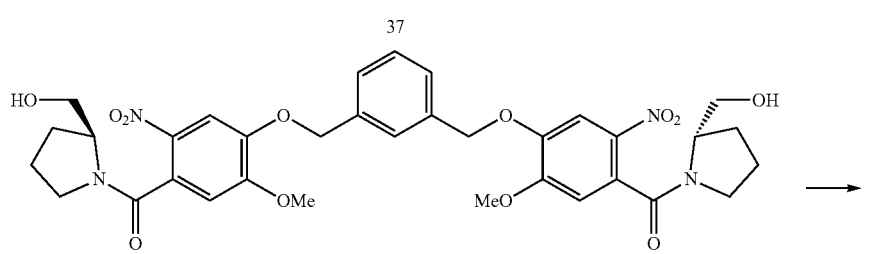
38
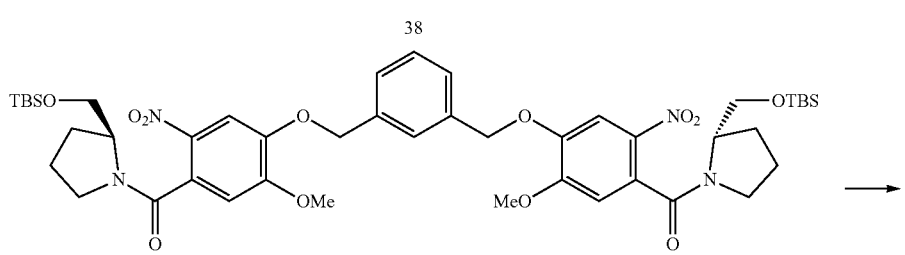
39
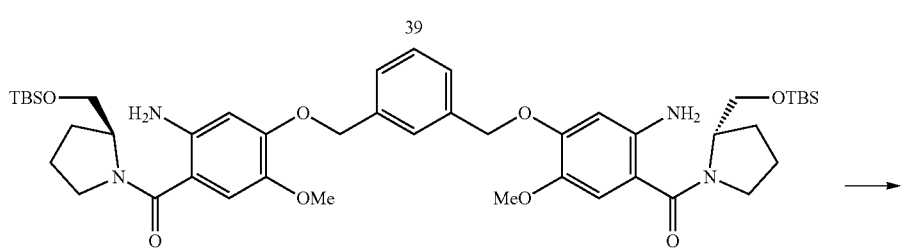
40
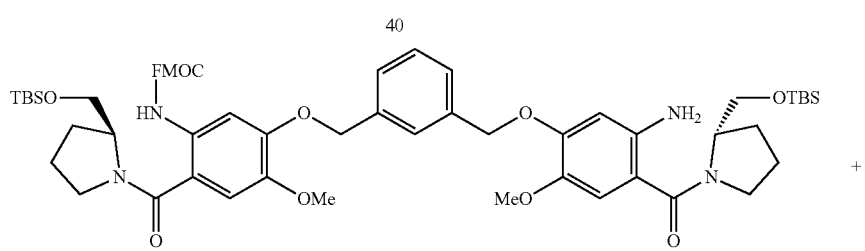
+
41
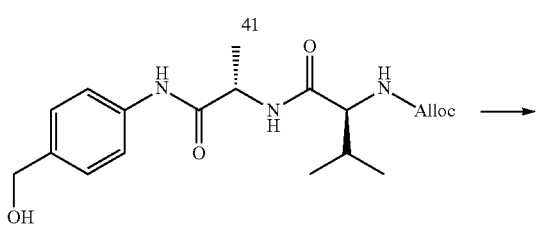
I16

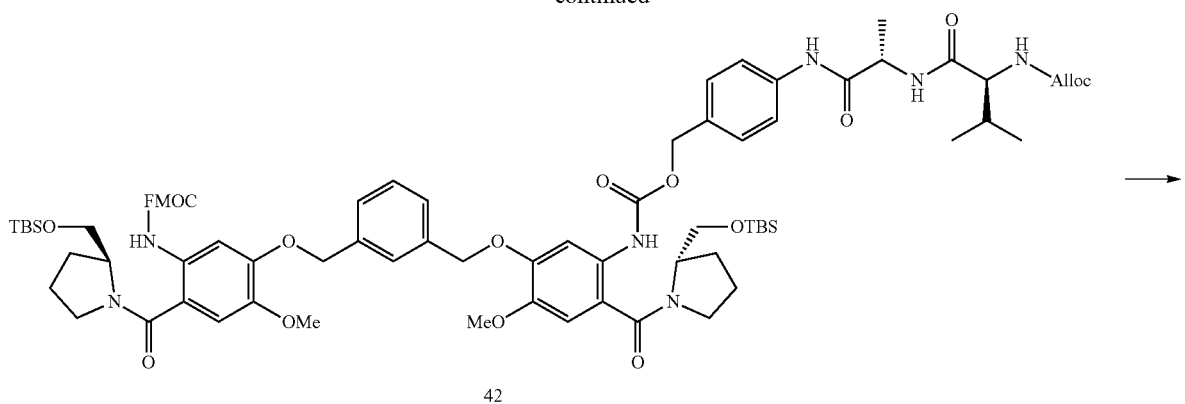
42
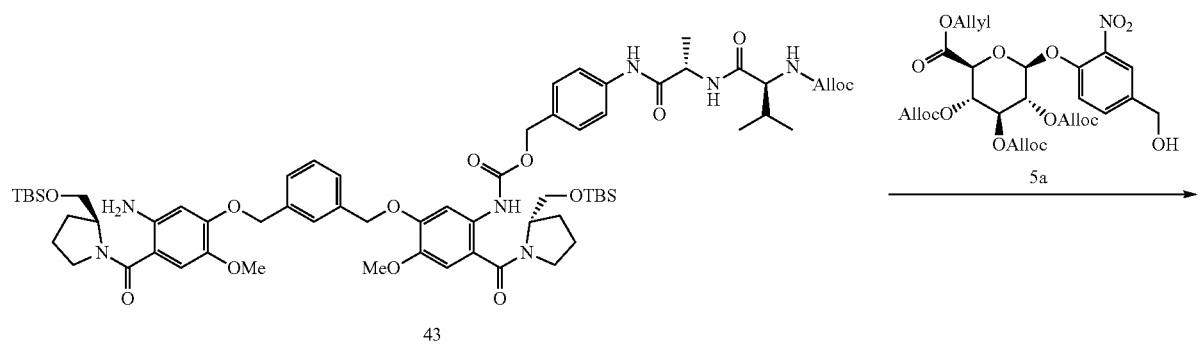
43
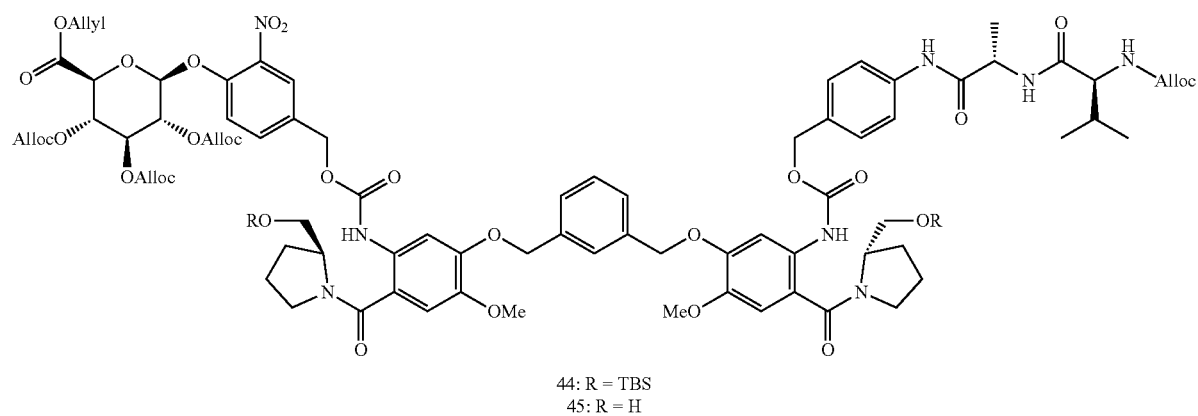
44: R = TBS
45: R = H

-continued

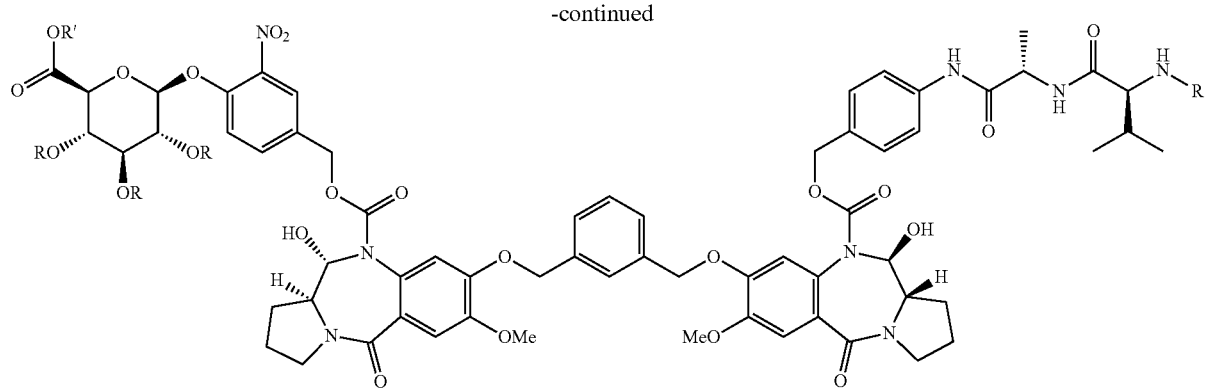

46: R = Alloc; R' = Allyl
47: R, R' = H

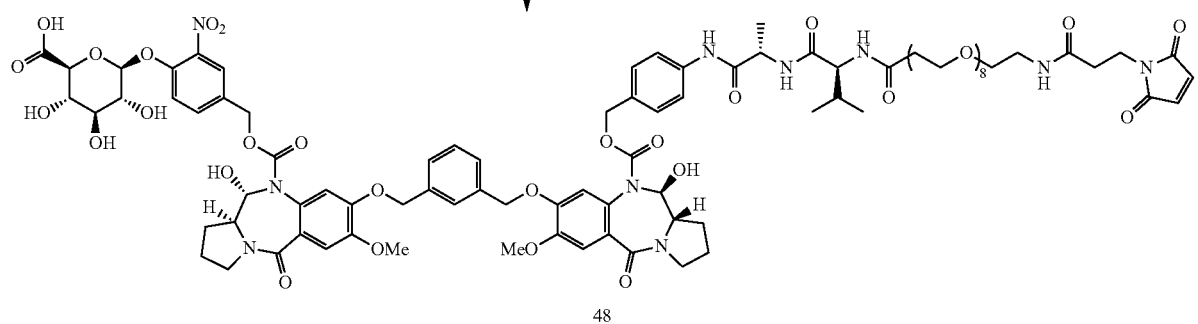

48

(a) 4,4'-((1,3-phenylenebis(methylene))bis(oxy))bis(5-methoxy-2-nitrobenzaldehyde) (36)

1,3-bis(bromomethyl)benzene (5.0 g, 19.1 mmol) was added to a stirred solution of the phenol 35 (7.5 g, 38.2 mmol), TBAI (705 mg, 1.91 mmol) and $K_2CO_3$ (5.81 g, 42.0 mmol) in dry DMF (60 mL). The reaction mixture was heated to 70° C. and stirred under an argon atmosphere for 2 hours at which point analysis by LC/MS revealed substantial product formation at retention time 1.67 minutes, ES+ m/z 519 [M+Na]$^+$, 497 [M+H]$^+$. The reaction mixture was allowed to cool to room temperature and the DMF was removed by evaporation in vacuo. The resulting residue was diluted with water (300 mL) and the orange precipitate 36 collected by vacuum filtration then washed with $H_2O$, diethyl ether and dried in a vacuum oven to constant weight (9.18 g, 97% yield).

(b) 4,4'-((1,3-phenylenebis(methylene))bis(oxy))bis(5-methoxy-2-nitrobenzoic acid) (37)

A solution of sodium chlorite (8.44 g, 92.7 mmol, 80% technical grade) and sodium dihydrogenphosphate monobasic (6.2 g, 51.8 mmol) in water (140 mL) was added to a solution of the aldehyde 36 (9.18 g, 18.5 mmol) in tetrahydrofuran (100 mL) at room temperature. Hydrogen peroxide (30% w/w, 53 mL, 518 mmol) was immediately added drop-wise to the vigorously stirred biphasic mixture. Effervescence and an exotherm to 30° C. were observed along with a colour change from orange to pale yellow and dissolution of the suspension. The reaction mixture was cooled in an ice bath and acidified to pH2 with concentrated hydrochloric acid. The reaction mixture was then extracted with EtOAc (4×150 mL) and the combined organic phase washed with brine (2×100 mL), dried (MgSO$_4$), filtered and evaporated in vacuo to provide the crude acid 37. The solid was triturated with diethyl ether and dried in a vacuum oven to constant weight (9.90 g, >100% yield). Purity satisfactory by LC/MS (retention time 1.56 minutes, ES− m/z 527 [M+H]$^+$).

(c) (((1,3-phenylenebis(methylene))bis(oxy))bis(5-methoxy-2-nitro-4,1-phenylene))bis(((S)-2-(hydroxymethyl)pyrrolidin-1-yl)methanone) (38)

DMF (12 drops) was added to a stirred suspension of the bis-nitrobenzoic acid 37 (9.90 g, 18.7 mmol) and oxalyl chloride (4.9 mL, 7.1 g, 56.3 mmol) in anhydrous DCM (130 mL). Following initial effervescence the reaction suspension became a solution and the mixture was allowed to stir at room temperature for 16 hours. The majority of solvent was removed by evaporation in vacuo and the concentrated solution was triturated with diethyl ether. The resulting yellow precipitate (LC/MS sampled in MeOH gave methyl ester at retention time 1.69 minutes, ES+ m/z 579 [M+Na]$^+$) was collected by vacuum filtration, washed with cold diethyl ether and dried for 1 hour in a vacuum oven at 40° C. The solid acid chloride was added portion-wise to a stirred suspension of (S)-(+)-2-pyrrolidinemethanol (4.35 g, 4.25 mL, 43.0 mmol) and TEA (13.0 mL, 9.46 g, 93.5 mmol) in DCM (100 mL) at −40° C. (dry ice/CH$_3$CN). After 1 hour stirring, the reaction was complete as judged by LC/MS with exclusively desired product at retention time 1.44 minutes, ES+ m/z 717 [M+Na]$^+$, 695 [M+H]$^+$. The mixture was diluted with DCM (100 mL) and washed with 1N HCl (3×50 mL), saturated NaHCO$_3$ (3×40 mL), brine (70 mL), dried (MgSO$_4$), filtered and the solvent evaporated in vacuo to give the pure product 38 as a yellow solid (12.7 g, 100% yield).

(d) ((((1,3-phenylenebis(methylene))bis(oxy))bis(5-methoxy-2-nitro-4,1-phenylene))bis(((S)-2-(((tert-butyldimethylsilyl)oxy)methyl)pyrrolidin-1-yl)methanone) (39)

TBSCl (8.27 g, 54.9 mmol) was added to a stirred solution of the bis-alcohol 38 (12.7 g, 18.3 mmol) and imidazole (7.47 g, 110 mmol) in dry DCM (100 mL). After stirring at room temperature for 1.5 hours analysis by LC/MS revealed complete conversion to desired product at retention time 2.11 minutes, ES+ m/z 946 [M+Na]$^+$, 924 [M+H]$^+$. The mixture was diluted with DCM (100 mL) and washed with water (2×75 mL), brine (80 mL), dried (MgSO$_4$), filtered and the solvent evaporated in vacuo to give the crude product 39 as a yellow foam (16.7 g, 99% yield). Material sufficiently pure to carry through to next step without further purification (e) (((1,3-phenylenebis(methylene))bis(oxy))bis(2-amino-5-methoxy-4,1-phenylene))bis(((S)-2-(((tert-butyldimethylsilyl)oxy)methyl)pyrrolidin-1-yl)methanone) (40)

Non-activated zinc (18.5 g, 282 mmol) was added to a vigorously stirred solution of the bis-nitro compound 39 (6.50 g, 7.10 mmol) in EtOH (65 mL) and EtOAc (65 mL) at room temperature. The reaction mixture was treated with water (6.5 mL) then drop-wise with a solution of 5% v/v HCO$_2$H in EtOH (130 mL). A colour change from green to metallic grey and an exotherm to 37° C. were observed. The reaction mixture was allowed to cool to room temperature at which point analysis by LC/MS revealed complete conversion to desired product at retention time 2.04 minutes, ES+ m/z 885 [M+Na]$^+$, 863 [M+H]$^+$. The mixture was filtered through Celite® and the pad washed with EtOAc (200 mL). The filtrate was washed with saturated aqueous NaHCO$_3$ (3×100 mL) [care: effervescence!], brine (150 mL), dried (MgSO$_4$), filtered and evaporated in vacuo to provide the crude bis-aniline 40 as a dark orange foam (5.41 g, 89% yield). Purity satisfactory, so material carried through to next step without further purification.

(f) (9H-fluoren-9-yl)methyl (5-((3-((5-amino-4-((S)-2-(((tert-butyldimethylsilyl)oxy)methyl)pyrrolidine-1-carbonyl)-2-methoxyphenoxy)methyl)benzyl)oxy)-2-((S)-2-(((tert-butyldimethylsilyl)oxy)methyl)pyrrolidine-1-carbonyl)-4-methoxyphenyl)carbamate (41)

FmocCl (1.43 g, 5.50 mmol) was added to a stirred suspension of the bis-aniline 40 (6.34 g, 7.35 mmol) and Na$_2$CO$_3$ (1.95 g, 18.4 mmol) in THF (32 mL) and H$_2$O (32 mL). The mixture was allowed to stir at room temperature for 2 hours where analysis by LC/MS revealed desired mono Fmoc product 41 at retention time 2.24 minutes, I %=41, ES+ m/z 1108 [M+Na]$^+$, 1086 [M+H]$^+$ along with unreacted starting material at retention time 2.03 minutes, I %=19, and bis-Fmoc material at retention time 2.39 minutes, I %=40, ES+ m/z 1330 [M+Na]$^+$, 1308 [M+H]$^+$. The mixture was partitioned between H$_2$O (50 mL) and EtOAc (50 mL), the layers were separated and the organic layer washed with H$_2$O (30 mL), brine (50 mL), dried (MgSO$_4$), filtered and evaporated in vacuo to give the crude product. Purification by Isolera™ (heptane/EtOAc, SNAP Ultra 100 g, 100 mL per minute) provided the pure mono Fmoc product 41 as an orange foam (2.40 g, 40% yield based on FmocCl, eluting at 30% heptane/EtOAc) unreacted bis-aniline 40 (1.72 g, eluting at 100% EtOAc) and bis-Fmoc (1.95 g, eluting at 69% heptane/EtOAc).

(g) (9H-fluoren-9-yl)methyl(5-((3-((5-((((4-((S)-2-((S)-2-(((allyloxy)carbonyl)amino)-3-methylbutanamido)propanamido)benzyl)oxy)carbonyl)amino)-4-((S)-2-(((tert-butyldimethylsilyl)oxy)methyl)pyrrolidine-1-carbonyl)-2-methoxyphenoxy)methyl)benzyl)oxy)-2-((S)-2-(((tert-butyldimethylsilyl)oxy)methyl)pyrrolidine-1-carbonyl)-4-methoxyphenyl)carbamate (42)

Triphosgene (236 mg, 0.80 mmol) was added to a stirred solution of the mono Fmoc product 41 (2.40 g, 2.21 mmol) and TEA (676 µL, 491 mg, 4.86 mmol) in dry DCM (30 mL) at room temperature. After stirring for 10 minutes under argon, analysis by LC/MS revealed complete conversion to isocyanate (sampled in MeOH to give methyl carbamate, retention time 2.27 minutes, ES+ m/z 1166 [M+Na]$^+$, 1144 [M+H]$^+$). The mixture was treated with additional TEA (461 µL, 335 mg, 3.32 mmol) followed by the addition of linker 116 (835 mg, 2.21 mmol). After 2.5 hours stirring under argon, LC/MS revealed satisfactory conversion to carbamate 9 at retention time 2.24 minutes, ES+ m/z 1511 [M+Na]$^+$, 1489 [M+H]$^+$. The mixture was diluted with DCM (50 mL) and washed with saturated aqueous NH$_4$Cl (2×40 mL), brine (50 mL), dried (MgSO$_4$), filtered and evaporated in vacuo to give the crude product. Purification by Isolera™ (heptane/EtOAc, SNAP Ultra 100 g, 100 mL per minute) provided the pure carbamate 42 (eluting at 38% heptane/EtOAc) as a yellow foam (2.40 g, 73% yield).

(h) 4-((S)-2-((S)-2-(((allyloxy)carbonyl)amino)-3-methylbutanamido)propanamido)benzyl (5-((3-((5-amino-4-((S)-2-(((tert-butyldimethylsilyl)oxy)methyl)pyrrolidine-1-carbonyl)-2-methoxyphenoxy)methyl)benzyl)oxy)-2-((S)-2-(((tert-butyldimethylsilyl)oxy)methyl)pyrrolidine-1-carbonyl)-4-methoxyphenyl)carbamate (43)

Dimethylamine (16.1 mL of a 2.0M solution in THF, 32.2 mmol) was added to a stirred solution of the Fmoc protected compound 42 (2.40 g, 1.61 mmol) in THF (20 mL) at room temperature. After stirring for 1 hour at room temperature, analysis by LC/MS revealed reaction completion with desired product at retention time 2.07 minutes, ES+ m/z 1289 [M+Na]$^+$, 1267 [M+H]$^+$, along with Fmoc cleavage by-product at retention time 1.74 minutes and its DMA adduct at retention time 0.95 minutes. The mixture was evaporated in vacuo to give the crude product which was subsequently purified by Isolera™ (heptane/EtOAc, SNAP Ultra 100 g, 100 mL per minute) to provide the pure aniline 43 (eluting at 100% EtOAc) as a white foam (1.77 g, 87% yield).

(i) Allyl(2S,3S,4S,5R,6S)-6-(4-(((((5-((3-((5-((((4-((S)-2-((S)-2-(((allyloxy)carbonyl)amino)-3-methylbutanamido)propanamido)benzyl)oxy)carbonyl)amino)-4-((S)-2-(((tert-butyldimethylsilyl)oxy)methyl)pyrrolidine-1-carbonyl)-2-methoxyphenoxy)methyl)benzyl)oxy)-2-((S)-2-(((tert-butyldimethylsilyl)oxy)methyl)pyrrolidine-1-carbonyl)-4-methoxyphenyl)carbamoyl)oxy)methyl)-2-nitrophenoxy)-3,4,5-tris((allyloxy)carbonyl)oxy)tetrahydro-2H-pyran-2-carboxylate (44)

Triphosgene (150 mg, 0.50 mmol) was added to a stirred solution of the aniline 43 (1.77 g, 1.40 mmol) and pyridine (249 µL, 243 mg, 3.08 mmol) in dry DCM (20 mL) at room temperature. After stirring for 10 minutes under argon, analysis by LC/MS revealed complete conversion to isocyanate (sampled in MeOH to give methyl carbamate, retention time 2.11 minutes, ES+ m/z 1347 [M+Na]+·, 1325 [M+H]+·). The mixture was treated with additional pyridine (170 µL, 166 mg, 2.10 mmol) and dibutyltin dilaurate (165 µL, 177 mg, 0.28 mmol) followed by the addition of linker 5a (891 mg, 1.40 mmol). After 24 hours stirring under argon, LC/MS revealed satisfactory conversion to carbamate 44 at retention time 2.16 minutes, ES+ m/z 1952 [M+Na]+·, 1930 [M+H]+·. The mixture was diluted with DCM (40 mL) and washed with saturated NH₄Cl (2×35 mL), brine (30 mL), dried (MgSO₄), filtered and evaporated in vacuo to give the crude product. Purification by Isolera™ (heptane/EtOAc, SNAP Ultra 100 g, 100 mL per minute) provided the pure carbamate 44 (eluting at 32% heptane/EtOAc) as a white solid (2.16 g, 80% yield).

(j) Allyl(2S,3S,4S,5R,6S)-6-(4-(((((5-((3-((5-((((4-((S)-2-((S)-2-(((allyloxy)carbonyl)amino)-3-methylbutanamido)propanamido)benzyl)oxy)carbonyl)amino)-4-((S)-2-(hydroxymethyl)pyrrolidine-1-carbonyl)-2-methoxyphenoxy)methyl)benzyl)oxy)-2-((S)-2-(hydroxymethyl)pyrrolidine-1-carbonyl)-4-methoxyphenyl)carbamoyl)oxy)methyl)-2-nitrophenoxy)-3,4,5-tris(((allyloxy)carbonyl)oxy)tetrahydro-2H-pyran-2-carboxylate (45)

Glacial acetic acid (18 mL) was added to a stirred solution of the TBS-protected compound 44 (2.16 g, 1.12 mmol) in THF (6 mL) and H₂O (6 mL). The reaction mixture was allowed to stir for 5 hours at room temperature after which time analysis by LC/MS revealed reaction completion with desired product observed at retention time 1.77 minutes, ES+ m/z 1702 [M+H]+·, 1724 [M+Na]+·. The reaction mixture was added drop-wise to a chilled (0-5° C.) saturated solution of NaHCO₃ (300 mL). The neutral solution was allowed to warm to room temperature and extracted with EtOAc (3×50 mL), the combined organic layers were washed with brine (60 mL), dried (MgSO₄), filtered and evaporated in vacuo to give the crude product. Purification by Isolera™ (DCM/MeOH, SNAP Ultra 100 g, 100 mL per minute) gave the bis-alcohol 45 (eluting at 94.8% DCM/MeOH) as a white foam (1.86 g, 98% yield).

(k) 4-(((2S,3R,4S,5S,6S)-6-((allyloxy)carbonyl)-3,4,5-tris(((allyloxy)carbonyl)oxy)tetrahydro-2H-pyran-2-yl)oxy)-3-nitrobenzyl(11S,11aS)-8-((3-((((11S,11aS)-10-(((4-((S)-2-((S)-2-(((allyloxy)carbonyl)amino)-3-methylbutanamido)propanamido)benzyl)oxy)carbonyl)-11-hydroxy-7-methoxy-5-oxo-2,3,5,10,11,11a-hexahydro-1H-pyrrolo[2,1-c][1,4]benzodiazepin-8-yl)oxy)methyl)benzyl)oxy)-11-hydroxy-7-methoxy-5-oxo-2,3,11,11a-tetrahydro-1H-pyrrolo[2,1-c][1,4]benzodiazepine-10(5H)-carboxylate (46)

45% IBX (263 mg, 0.42 mmol) was added to a stirred solution of the bis-OH 45 (300 mg, 0.18 mmol) in dry DMSO (4 mL). The mixture was heated to 30° C. under an argon atmosphere and reaction progress monitored by LC/MS. After 24 hours stirring, additional IBX (2×22 mg, 2×36 µmol) was added and the mixture stirred for another 28 hours. At this point analysis by LC/MS revealed formation of resolved product at retention time 1.72 minutes, ES+ m/z 1698 [M+H]+·, 1720 [M+Na]+·. The reaction mixture was added drop-wise to a saturated aqueous NaHCO₃ solution (100 mL) and extracted with DCM (2×40 mL). The combined organic layers were washed with brine (40 mL), dried (MgSO₄), filtered and evaporated in vacuo to give the crude product. Purification by Isolera™ (DCM/MeOH, SNAP Ultra 25 g, 75 mL per minute) gave the cyclised product 46 (eluting at 96.5% DCM/MeOH) as a white foam (219 mg, 73% yield).

(l) (2S,3S,4S,5R,6S)-6-(4-(((((11S,11aS)-8-((3-(((((11S,11aS)-10-(((4-((S)-2-((S)-2-amino-3-methylbutanamido)propanamido)benzyl)oxy)carbonyl)-11-hydroxy-7-methoxy-5-oxo-2,3,5,10,11,11a-hexahydro-1H-pyrrolo[2,1-c][1,4]benzodiazepin-8-yl)oxy)methyl)benzyl)oxy)-11-hydroxy-7-methoxy-5-oxo-2,3,5,10,11,11a-hexahydro-1H-pyrrolo[2,1-c][1,4]benzodiazepine-10-carbonyl)oxy)methyl)-2-nitrophenoxy)-3,4,5-trihydroxytetrahydro-2H-pyran-2-carboxylic acid (47)

Pd(PPh₃)₄ (13.0 mg, 11.1 µmol) was added to a stirred solution of pyrrolidine (51 µL, 43 mg, 0.61 mmol) and the Alloc/allyl compound 46 (189 mg, 0.11 mmol) in dry DCM (2 mL). The reaction mixture was allowed to stir under an argon atmosphere for 30 minutes at room temperature where analysis by LC/MS revealed reaction completion with desired product observed at retention time 1.13 minutes, ES+ m/z 1322 [M+H]+·. The solvent was removed by evaporation in vacuo and the resulting residue triturated with diethyl ether followed by additional evaporation in vacuo to provide the crude amine 47 as a solid which was carried through to the next step without further purification or analysis.

(m) (2S,3S,4S,5R,6S)-6-(4-(((((11S,11aS)-8-((3-(((((11S,11aS)-10-(((4-((2S,5S)-37-(2,5-dioxo-2,5-dihydro-1H-pyrrol-1-yl)-5-isopropyl-2-methyl-4,7,35-trioxo-10,13,16,19,22,25,28,31-octaoxa-3,6,34-triazaheptatriacontanamido)benzyl)oxy)carbonyl)-11-hydroxy-7-methoxy-5-oxo-2,3,5,10,11,11a-hexahydro-1H-pyrrolo[2,1-c][1,4]benzodiazepin-8-yl)oxy)methyl)benzyl)oxy)-11-hydroxy-7-methoxy-5-oxo-2,3,5,10,11,11a-hexahydro-1H-pyrrolo[2,1-c][1,4]benzodiazepine-10-carbonyl)oxy)methyl)-2-nitrophenoxy)-3,4,5-trihydroxytetrahydro-2H-pyran-2-carboxylic acid (48)

A solution of MAL-dPEG®8-TFP ester (123 mg, 0.16 mmol) in dry DCM (2 mL) was added to a stirred sample of the amine 47 (147 mg, 0.11 mmol) and pyridine (22 μL, 22 mg, 0.28 mmol). The reaction mixture was allowed to stir under argon for 20 hours and began to darken in colour over time. Analysis by LC/MS revealed formation of desired product at retention time 1.37 minutes, ES+ m/z 1896 [M+H]+·, 1918 [M+Na]. along with trace unreacted amine at retention time 1.13 minutes. Substantial decomposition of product and the solvent was removed by evaporation in vacuo. The crude product was purified by preparative HPLC to give the maleimide 48 as a white solid (75 mg, 36%): LC/MS (15-minute run), retention time 5.48 minutes, ES+ m/z 1896 [M+H]+·, 1918 [M+Na]+·; $^1$H NMR (400 MHz, d6-DMSO) δ 9.92 (br s, 2H), 8.20-8.14 (m, 1H), 8.01 (t, 1H, J=5.6 Hz), 7.87 (d, 1H, J=8.7 Hz), 7.73 (br s, 1H), 7.62-7.36 (m, 8H), 7.23-7.15 (m, 2H), 7.11 (s, 1H), 7.09 (s, 1H), 7.00 (s, 2H), 6.99 (s, 1H), 6.94 (s, 1H), 6.62-6.51 (m, 2H), 5.53-5.41 (m, 3H), 5.35-5.85 (m, 9H), 4.41-4.32 (m, 1H), 4.23-4.16 (m, 1H), 4.00-3.90 (m, 2H), 3.81 (s, 3H), 3.80 (s, 3H), 3.61-3.58 (m, 4H), 3.52-3.45 (m, 28H), 3.42-3.23 (m, 9H), 3.18-3.12 (m, 2H), 2.50-2.35 (m, 2H), 2.34-2.31 (m, 2H), 2.10-1.8 (m, 9H), 1.28 (d, 1H, J=7.1 Hz), 0.87 (d, 3H, J=6.7 Hz), 0.83 (d, 3H, J=6.8 Hz).

Example 5

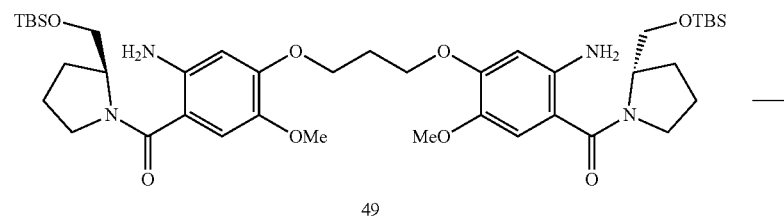

49

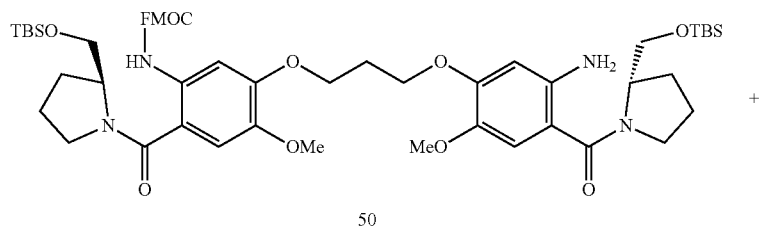

50

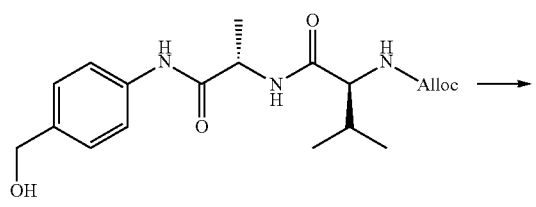

I16

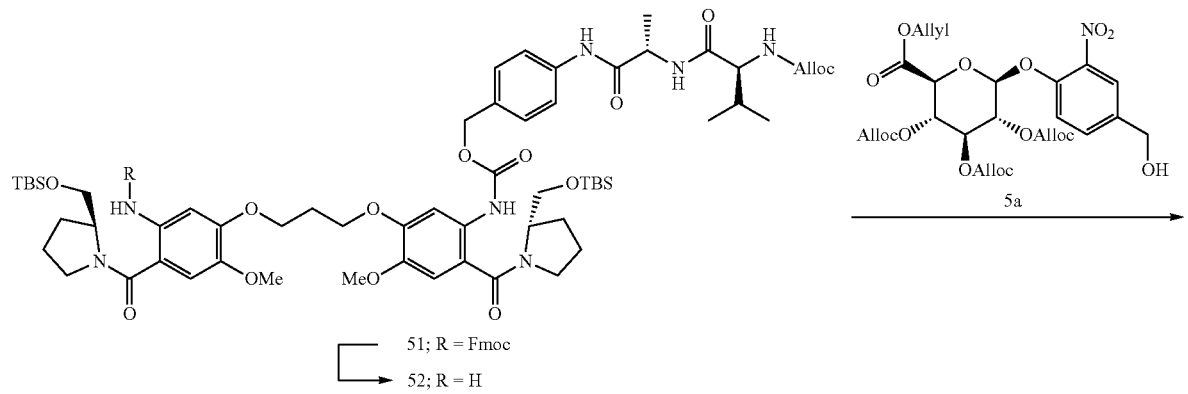

51; R = Fmoc
52; R = H

-continued

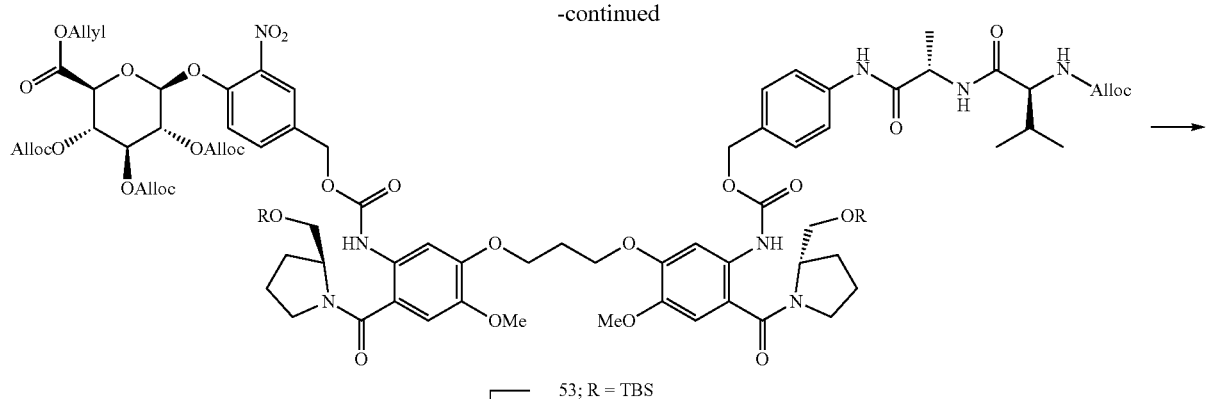

53; R = TBS
54; R = H

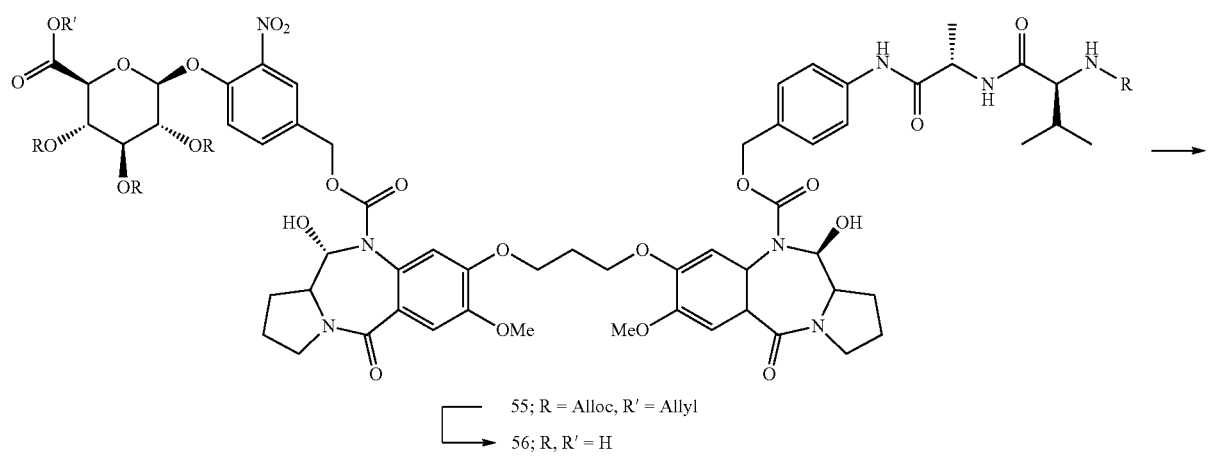

55; R = Alloc, R' = Allyl
56; R, R' = H

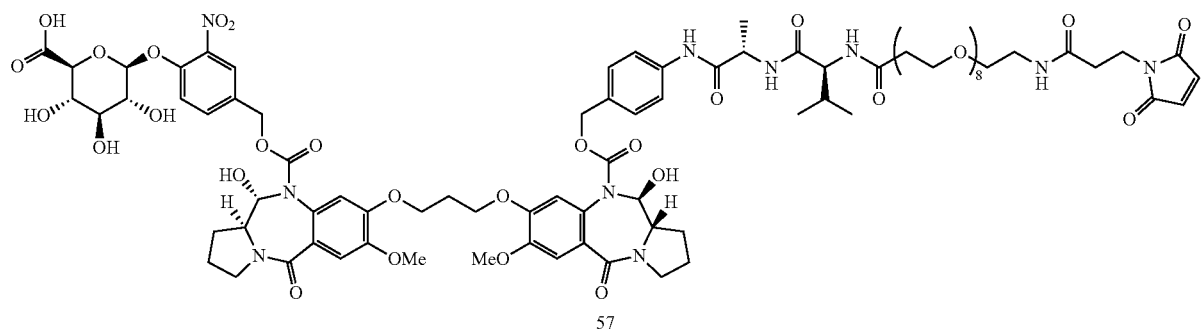

57

(a) (9H-fluoren-9-yl)methyl(5-(3-(5-amino-4-((S)-2-(((tert-butyldimethylsilyl)oxy)methyl)pyrrolidine-1-carbonyl)-2-methoxyphenoxy)propoxy)-2-((S)-2-(((tert-butyldimethylsilyl)oxy)methyl)pyrrolidine-1-carbonyl)-4-methoxyphenyl)carbamate (50)

FmocCl (1.58 g, 6.09 mmol) was added to a stirred mixture of the bis-aniline 49 (6.50 g, 8.12 mmol) and Na$_2$CO$_3$ (2.15 g, 20.3 mmol) in THF (35 mL) and H$_2$O (35 mL). The mixture was allowed to stir room temperature for 2.5 hours where analysis by LC/MS revealed desired mono Fmoc product 50 at retention time 2.19 minutes, I %=49, ES+ m/z 1046 [M+Na]$^+$, 1024 [M+H]$^+$ along with unreacted starting material at retention time 1.96 minutes, I %=19, and bis-Fmoc material at retention time 2.34 minutes, I %=32, ES+ m/z 1270 [M+Na]$^+$, 1246 [M+H]$^+$. The mixture was partitioned between H$_2$O (50 mL) and EtOAc (50 mL), the layers were separated and the aqueous phase was extracted with EtOAc (2×25 mL). The combined organic layers were washed with H$_2$O (30 mL), brine (50 mL), dried (MgSO$_4$), filtered and evaporated in vacuo to give the crude product. Purification by Isolera™ (heptane/EtOAc, SNAP Ultra 100 g, 100 mL per minute) provided the pure mono Fmoc product 50 as an orange foam (3.61 g, 58% yield based on FmocCl, eluting at 61% heptane/EtOAc) unreacted bis-aniline 2 (2.04 g, eluting at 100% EtOAc) and bis-Fmoc (1.71 g, eluting at 30% heptane/EtOAc).

(b) 4-((S)-2-((S)-2-(((allyloxy)carbonyl)amino)-3-methylbutanamido)propanamido)benzyl (5-(3-(5-((((9H-fluoren-9-yl)methoxy)carbonyl)amino)-4-((S)-2-(((tert-butyldimethylsilyl)oxy)methyl)pyrrolidine-1-carbonyl)-2-methoxyphenoxy)propoxy)-2-((S)-2-(((tert-butyldimethylsilyl)oxy)methyl)pyrrolidine-1-carbonyl)-4-methoxyphenyl) carbamate (51)

Triphosgene (377 mg, 1.27 mmol) was added to a stirred solution of the mono Fmoc product 50 (3.61 g, 3.53 mmol) and TEA (1.08 mL, 784 mg, 7.70 mmol) in dry DCM (40 mL) at room temperature. After stirring for 10 minutes under argon, analysis by LC/MS revealed complete conversion to isocyanate (sampled in MeOH to give methyl carbamate, retention time 2.23 minutes, ES+ m/z 1104 [M+Na]$^{+\cdot}$, 1082 [M+H]$^{+\cdot}$). The mixture was treated with additional TEA (737 µL, 535 mg, 5.30 mmol) followed by the addition of linker 116 (1.33 g, 3.53 mmol). After 2.5 hours stirring under argon, LC/MS revealed satisfactory conversion to carbamate 51 at retention time 2.21 minutes, ES+ m/z 1449 [M+Na]$^{+\cdot}$, 1427 [M+H]$^{+\cdot}$. The mixture was diluted with DCM (50 mL) and washed with saturated aqueous NH$_4$Cl (2×30 mL), H$_2$O (30 mL), brine (50 mL), dried (MgSO$_4$), filtered and evaporated in vacuo to give the crude product. Purification by Isolera™ (heptane/EtOAc, SNAP Ultra '100 g, 100 mL per minute) provided the pure carbamate 51 (eluting at 40% Hexane/EtOAc) as a yellow foam (3.34 g, 66% yield).

(c) 4-((S)-2-((S)-2-(((allyloxy)carbonyl)amino)-3-methylbutanamido)propanamido)benzyl (5-(3-(5-amino-4-((S)-2-(((tert-butyldimethylsilyl)oxy)methyl)pyrrolidine-1-carbonyl)-2-methoxyphenoxy)propoxy)-2-((S)-2-(((tert-butyldimethylsilyl)oxy)methyl)pyrrolidine-1-carbonyl)-4-methoxyphenyl) carbamate (52)

Dimethylamine (23.4 mL of a 2.0M solution in THF, 46.8 mmol) was added to a stirred solution of the Fmoc protected compound 51 (3.34 g, 2.34 mmol) in THF (15 mL) at room temperature. After stirring under argon for 1 hour at room temperature, analysis by LC/MS revealed reaction completion with desired product at retention time 2.02 minutes, ES+ m/z 1227 [M+Na]$^{+\cdot}$, 1205 [M+H]$^{+\cdot}$, along with Fmoc cleavage by-product at retention time 1.72 minutes and its DMA adduct at retention time 0.93 minutes. The mixture was evaporated in vacuo to give the crude product which was subsequently purified by Isolera™ (heptane/EtOAc, SNAP Ultra 100 g, 100 mL per minute) to provide the pure aniline 52 (eluting at 100% EtOAc) as an orange foam (2.51 g, 89% yield).

(d) Allyl(2S,3S,4S,5R,6S)-6-(4-(((((5-(3-(5-((((4-((S)-2-((S)-2-(((allyloxy)carbonyl)amino)-3-methylbutanamido)propanamido)benzyl)oxy)carbonyl)amino)-4-((S)-2-(((tert-butyldimethylsilyl)oxy)methyl)pyrrolidine-1-carbonyl)-2-methoxyphenoxy)propoxy)-2-((S)-2-(((tert-butyldimethylsilyl)oxy)methyl)pyrrolidine-1-carbonyl)-4-methoxyphenyl)carbamoyl)oxy)methyl)-2-nitrophenoxy)-3,4,5-tris((allyloxy)carbonyl)oxy)tetrahydro-2H-pyran-2-carboxylate (53)

Triphosgene (222 mg, 0.75 mmol) was added to a stirred solution of the aniline 52 (2.51 g, 2.08 mmol) and pyridine (370 µL, 362 mg, 4.58 mmol) in dry DCM (30 mL) at room temperature. After stirring for 10 minutes under argon, analysis by LC/MS revealed complete conversion to isocyanate (sampled in MeOH to give methyl carbamate, retention time 2.06 minutes, ES+ m/z 1285 [M+Na]$^{+\cdot}$, 1263 [M+H]$^{+\cdot}$). The mixture was treated with additional pyridine (252 µL, 247 mg, 3.12 mmol) and dibutyltin dilaurate (247 µL, 263 mg, 0.42 mmol) followed by the addition of linker 5a (1.33 g, 2.08 mmol). After 28 hours stirring under argon, LC/MS revealed satisfactory conversion to carbamate 53 (retention time 2.12 minutes, ES+ m/z 1890 [M+Na]$^{+\cdot}$, 1868 [M+H]$^{+\cdot}$). The mixture was diluted with DCM (40 mL) and washed with saturated NH$_4$Cl (3×30 mL), brine (50 mL), dried (MgSO$_4$), filtered and evaporated in vacuo to give the crude product. Purification by Isolera™ (heptane/EtOAc, SNAP Ultra 100 g, 100 mL per minute) provided the pure carbamate 53 (eluting at 37% heptane/EtOAc) as a yellow foam (3.12 g, 80% yield).

(e) Allyl(2S,3S,4S,5R,6S)-6-(4-(((((5-(3-(5-((((4-((S)-2-((S)-2-(((allyloxy)carbonyl)amino)-3-methylbutanamido)propanamido)benzyl)oxy)carbonyl)amino)-4-((S)-2-(hydroxymethyl)pyrrolidine-1-carbonyl)-2-methoxyphenoxy)propoxy)-2-((S)-2-(hydroxymethyl)pyrrolidine-1-carbonyl)-4-methoxyphenyl)carbamoyl)oxy)methyl)-2-nitrophenoxy)-3,4,5-tris(((allyloxy)carbonyl)oxy)tetrahydro-2H-pyran-2-carboxylate (54)

Glacial acetic acid (24 mL) was added to a stirred solution of the TBS-protected compound 53 (3.12 g, 1.67 mmol) in THF (8 mL) and H$_2$O (8 mL). The reaction mixture was allowed to stir for 18 hours at room temperature after which time analysis by LC/MS revealed reaction completion with desired product observed at retention time 1.72 minutes, ES+ m/z 1640 [M+H]$^{+\cdot}$, 1662 [M+Na]$^{+\cdot}$. The reaction mixture was added drop-wise to a chilled (0-5° C.) saturated solution of NaHCO$_3$ (450 mL). The neutral solution was allowed to warm to room temperature and extracted with EtOAc (3×80 mL), the combined organic layers were washed with brine (80 mL), dried (MgSO$_4$), filtered and evaporated in vacuo to give the crude product. Purification by Isolera™ (DCM/MeOH, SNAP Ultra 100 g, 100 mL per minute) gave the bis-alcohol 54 (eluting at 96.6% DCM/MeOH) as a white foam (2.05 g, 75% yield).

(f) 4-(((2S,3R,4S,5S,6S)-6-((allyloxy)carbonyl)-3,4,5-tris(((allyloxy)carbonyl)oxy)tetrahydro-2H-pyran-2-yl)oxy)-3-nitrobenzyl(11S,11aS)-8-(3-(((11S,11aS)-10-(((4-((S)-2-((S)-2-(((allyloxy)carbonyl)amino)-3-methylbutanamido)propanamido)benzyl)oxy)carbonyl)-11-hydroxy-7-methoxy-5-oxo-2,3,5,10,11,11a-hexahydro-1H-pyrrolo[2,1-c][1,4]benzodiazepin-8-yl)oxy)propoxy)-11-hydroxy-7-methoxy-5-oxo-2,3,11,11a-tetrahydro-1H-pyrrolo[2,1-c][1,4]benzodiazepine-10(5H)-carboxylate (55)

45% IBX (273 mg, 0.44 mmol) was added to a stirred solution of the bis-OH 54 (300 mg, 0.18 mmol) in dry DMSO (4 mL). The mixture was heated to 30° C. under an argon atmosphere and reaction progress monitored by LC/MS. After 24 hours stirring, additional IBX (26 mg, 42 µmol) was added and the mixture stirred for another 24 hours. At this point analysis by LC/MS revealed predominantly a single peak corresponding to desired product at retention time 1.68 minutes, ES+ m/z 1658 [M+Na]$^{+\cdot}$. The reaction mixture was added drop-wise to a chilled saturated aqueous NaHCO$_3$ solution (100 mL) and extracted with DCM (2×40 mL). The combined organic layers were washed with brine (40 mL), dried (MgSO$_4$), filtered and evaporated in vacuo to give the crude product. Purification by Isolera™ (DCM/MeOH, SNAP Ultra 25 g, 75 mL per minute) gave the cyclised product 55 (eluting at 97% DCM/MeOH) as a white foam (256 mg, 87% yield).

(g) (2S,3S,4S,5R,6S)-6-(4-((((11S,11aS)-8-(3-(((11S,11aS)-10-(((4-((S)-2-((S)-2-amino-3-methylbutanamido)propanamido)benzyl)oxy)carbonyl)-11-hydroxy-7-methoxy-5-oxo-2,3,5,10,11,11a-hexahydro-1H-pyrrolo[2,1-c][1,4]benzodiazepin-8-yl)oxy)propoxy)-11-hydroxy-7-methoxy-5-oxo-2,3,5,10,11,11a-hexahydro-1H-pyrrolo[2,1-c][1,4]benzodiazepine-10-carbonyl)oxy)methyl)-2-nitrophenoxy)-3,4,5-trihydroxytetrahydro-2H-pyran-2-carboxylic acid (56)

Pd(PPh$_3$)$_4$ (18.1 mg, 15.7 μmol) was added to a stirred solution of pyrrolidine (72 μL, 62 mg, 0.86 mmol) and the Alloc/allyl compound 55 (256 mg, 0.16 mmol) in dry DCM (2 mL). The reaction mixture was allowed to stir under an argon atmosphere where a precipitate began to form. After stirring for 30 minutes at room temperature analysis by LC/MS revealed reaction completion with desired product observed at retention time 1.07 minutes, ES+ m/z 1260 [M+H]$^+$. The solvent was removed by evaporation in vacuo and the resulting residue triturated with diethyl ether followed by additional evaporation in vacuo to provide the crude amine 56 as a solid which was carried through to the next step without further purification or analysis.

(h) (2S,3S,4S,5R,6S)-6-(4-((((11S,11aS)-8-(3-(((11S,11aS)-10-(((4-((2S,5S)-37-(2,5-dioxo-2,5-dihydro-1H-pyrrol-1-yl)-5-isopropyl-2-methyl-4,7,35-trioxo-10,13,16,19,22,25,28,31-octaoxa-3,6,34-triazaheptatriacontanamido)benzyl)oxy)carbonyl)-11-hydroxy-7-methoxy-5-oxo-2,3,5,10,11,11a-hexahydro-1H-pyrrolo[2,1-c][1,4]benzodiazepin-8-yl)oxy)propoxy)-11-hydroxy-7-methoxy-5-oxo-2,3,5,10,11,11a-hexahydro-1H-pyrrolo[2,1-c][1,4]benzodiazepine-10-carbonyl)oxy)methyl)-2-nitrophenoxy)-3,4,5-trihydroxytetrahydro-2H-pyran-2-carboxylic acid (57)

A solution of MAL-dPEG®8-TFP ester (140 mg, 0.19 mmol) in dry DCM (2 mL) was added to a stirred sample of the amine 56 (198 mg, 0.16 mmol), pyridine (32 μL, 31 mg, 0.39 mmol) and DMF (0.25 mL). The reaction mixture was allowed to stir under argon for 20 hours and began to darken in colour over time. Analysis by LC/MS revealed formation of desired product at retention time 1.31 minutes, ES+ m/z 1834 [M+H]$^+$, 1857 [M+Na]$^+$, along with unreacted amine at retention time 1.07 minutes. Additional MAL-dPEG®8-TFP ester (70 mg, 0.09 mmol), pyridine (16 μL, 16 mg, 0.2 mmol) and DCM (2 mL) were added and the mixture allowed to stir for a further 24 hours. The solvent volume was then reduced by 50% by evaporation in vacuo, at this point a satisfactory amount of desired product had formed upon analysis by LC/MS and the solvent was completely removed by evaporation in vacuo. The crude product was purified by preparative HPLC to give the maleimide 56 as a white solid (48 mg, 17%): LC/MS (15-minute run), retention time 5.22 minutes, ES+ m/z 1834 [M+H]$^+$, 1856 [M+Na]$^+$; $^1$H NMR (400 MHz, d6-DMSO) δ 9.99 (br s, 2H), 8.24-8.17 (m, 1H), 8.01 (t, 1H, J=5.6 Hz), 7.88 (d, 1H, J=8.7 Hz), 7.74 (br s, 1H), 7.64-7.50 (m, 3H), 7.44-7.34 (m, 1H), 7.23-7.13 (m, 2H), 7.06 (s, 2H), 7.00 (s, 2H), 6.86 (s, 1H), 6.79 (s, 1H), 6.59-6.47 (m, 2H), 5.52-5.37 (m, 3H), 5.32-5.02 (m, 4H), 4.98-4.84 (m, 2H), 4.44-4.34 (m, 1H), 4.24-4.19 (m, 1H), 4.17-3.96 (m, 5H), 3.92-3.84 (m, 1H), 3.77 (s, 6H), 3.60 (t, 4H, J=7.3 Hz), 3.54-3.45 (m, 29H), 3.40-3.24 (m, 8H), 3.19-3.12 (m, 2H), 2.57-2.35 (m, 2H), 2.34-2.30 (m, 2H), 2.25-2.12 (m, 2H), 2.10-1.78 (m, 9H), 1.30 (d, 1H, J=6.9 Hz), 0.87 (d, 3H, J=6.7 Hz), 0.83 (d, 3H, J=6.7 Hz).

Example 6

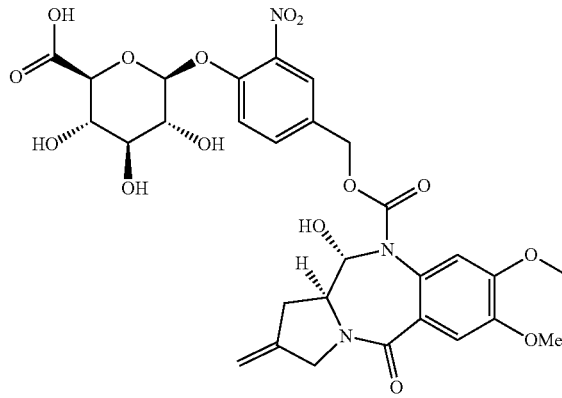
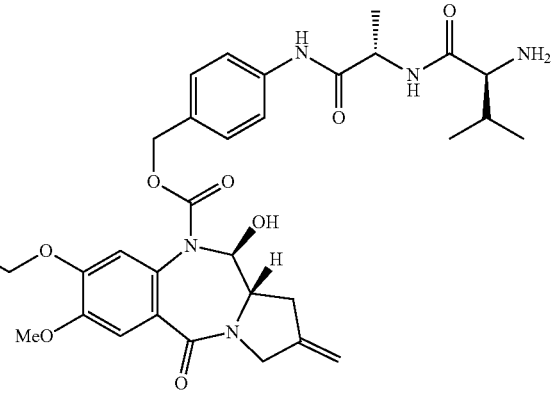

9
↓

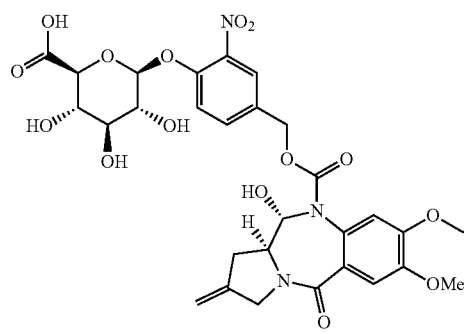
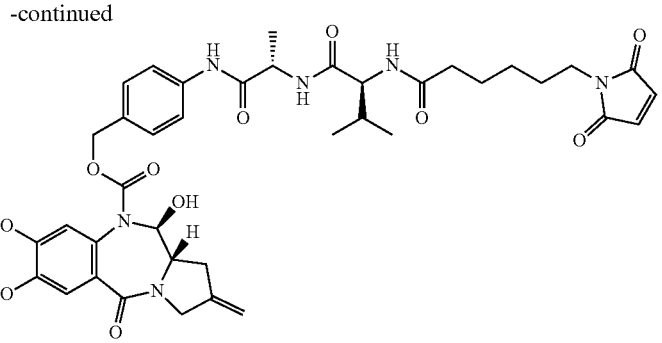

58

(2S,3S,4S,5R,6S)-6-(4-(((((11S,11aS)-8-(3-(((11S,11aS)-10-(((4-((S)-2-((S)-2-(6-(2,5-dioxo-2,5-dihydro-1H-pyrrol-1-yl)hexanamido)-3-methylbutanamido)propanamido)benzyl)oxy)carbonyl)-11-hydroxy-7-methoxy-2-methylene-5-oxo-2,3,5,10,11,11a-hexahydro-1H-pyrrolo[2,1-c][1,4]benzodiazepin-8-yl)oxy)propoxy)-11-hydroxy-7-methoxy-2-methylene-5-oxo-2,3,5,10,11,11a-hexahydro-1H-pyrrolo[2,1-c][1,4]benzodiazepine-10-carbonyl)oxy)methyl)-2-nitrophenoxy)-3,4,5-trihydroxytetrahydro-2H-pyran-2-carboxylic acid (58)

A solution of 6-maleimidohexanoic acid N-hydroxysuccinimide ester (51 mg, 0.17 mmol) in dry DCM (2 mL) was added to a stirred sample of the amine 9 (141 mg, 0.11 mmol), pyridine (22 μL, 21 mg, 0.33 mmol) and DMF (0.25 mL). The reaction mixture was allowed to stir under argon for 20 hours and began to darken in colour over time. Analysis by LC-MS revealed formation of desired product at retention time 1.42 minutes, ES-m/z 1474 [M−H]⁻, along with trace unreacted amine at retention time 1.12 minutes. The solvent was removed by evaporation in vacuo and the resulting residue purified by Isolera™ (DCM/MeOH, SNAP Ultra 10 g, 36 mL per minute, eluting at 80% DCM/MeOH) to give 90 mg of enriched 58. Further purification by preparative HPLC gave the maleimide 58, as a white solid (26 mg, 16%): LC-MS (15-minute run), retention time 5.85 minutes, ES+ m/z 1477 [M+H]⁺·, 1499 [M+Na]⁺·; ¹H NMR (400 MHz, d6-DMSO) δ 10.0 (br s, 2H), 8.16 (d, 1H, J=7.0 Hz), 7.80 (d, 1H, J=8.6 Hz), 7.74 (br s, 1H), 7.62-7.50 (m, 3H), 7.39 (d, 1H, J=8.7 Hz), 7.22-7.11 (m, 2H), 7.06 (s, 2H), 7.00 (s, 2H), 6.89 (s, 2H), 6.84-6.78 (m, 1H), 6.68-6.56 (m, 2H), 5.45-5.30 (m, 3H), 5.29-5.01 (m, 9H), 4.98-4.85 (m, 2H), 4.42-4.33 (m, 1H), 4.24-3.92 (m, 9H), 3.77 (s, 6H), 3.44 (t, 2H, J=9.5 Hz), 3.39-3.30 (m, 2H), 2.93-2.80 (m, 2H), 2.57-2.35 (m, 2H), 2.23-2.06 (m, 4H) 2.03-1.90 (m, 1H), 1.48 (p, 4H, J=7.3 Hz), 1.30 (d, 3H, J=7.0 Hz), 1.18 (p, 2H, J=7.6 Hz), 0.86 (d, 3H, J=6.7 Hz), 0.83 (d, 3H, J=6.7 Hz).

Example 7

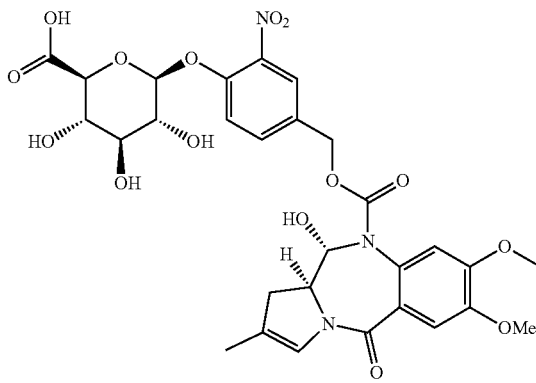
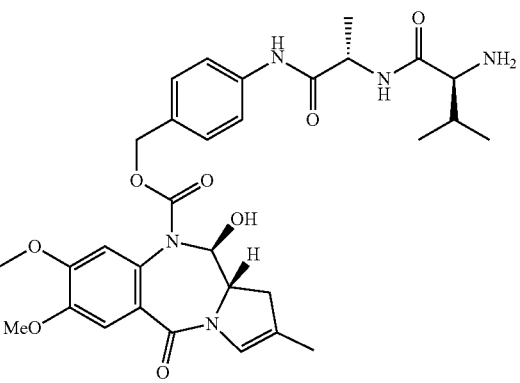

21

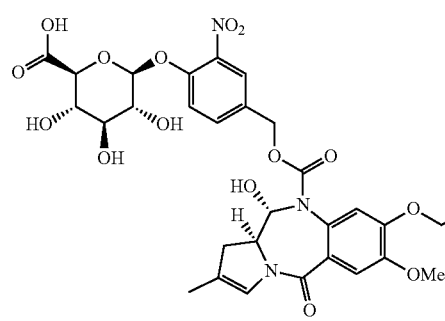
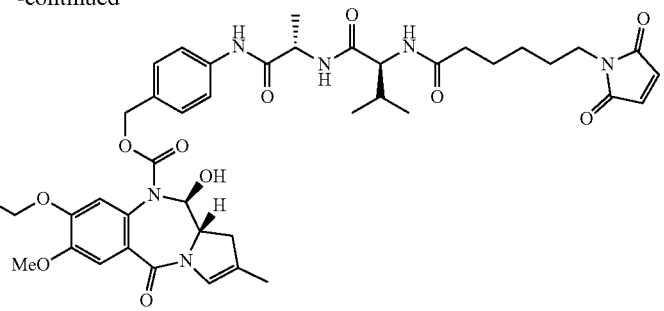

59

(2S,3S,4S,5R,6S)-6-(4-((((11S,11aS)-8-((5-(((11S,
11aS)-10-(((4-((S)-2-((S)-2-(6-(2,5-dioxo-2,5-di-
hydro-1H-pyrrol-1-yl)hexanamido)-3-methylbutana-
mido)propanamido)benzyl)oxy)carbonyl)-11-
hydroxy-7-methoxy-2-methyl-5-oxo-5,10,11,11a-
tetrahydro-1H-pyrrolo[2,1-c][1,4]benzodiazepin-8-
yl)oxy)pentyl)oxy)-11-hydroxy-7-methoxy-2-
methyl-5-oxo-5,10,11,11a-tetrahydro-1H-pyrrolo[2,
1-c][1,4]benzodiazepine-10-carbonyl)oxy)methyl)-
2-nitrophenoxy)-3,4,5-trihydroxytetrahydro-2H-
pyran-2-carboxylic acid (59)

A solution of 6-maleimidohexanoic acid N-hydroxysuc-
cinimide ester (42 mg, 0.14 mmol) in dry DCM (2 mL) was
added to a stirred sample of the amine 21 (118 mg, 0.09
mmol) and pyridine (18 μL, 18 mg, 0.23 mmol). The
reaction mixture was allowed to stir under argon for 24
hours and began to darken in colour over time. Analysis by
LC-MS revealed formation of desired product at retention
time 1.45 minutes, ES– m/z 1502 [M–H]⁻, along with trace
unreacted amine at retention time 1.15 minutes. The solvent
was removed by evaporation in vacuo and the resulting
residue purified by Isolera™ (DCM/MeOH, SNAP Ultra 10
g, 36 mL per minute, eluting at 66% DCM/MeOH) to give
76 mg of enriched 59. Further purification by preparative
HPLC gave the maleimide 59 as a white solid (27 mg, 20%):
LC-MS (15-minute run), retention time 6.13 minutes, ES+
m/z 1505 [M+H]⁺, 1527 [M+Na]⁺; ¹H NMR (400 MHz,
d6-DMSO) δ 9.95 (br s, 2H), 8.15 (d, 1H, J=6.9 Hz), 7.80
(d, 1H, J=8.7 Hz), 7.87 (d, 1H, J=8.7 Hz), 7.71 (br s, 1H),
7.62-7.48 (m, 3H), 7.39 (d, 1H, J=8.6 Hz), 7.21-7.12 (m,
2H), 7.06 (s, 1H), 7.05 (s, 1H), 6.99 (s, 2H), 6.82 (s, 1H),
6.76 (s, 1H), 6.72-6.65 (m, 2H), 6.62 (s, 2H), 5.63-5.50 (m,
2H), 5.48-5.40 (m, 2H), 5.31-5.08 (m, 6H), 4.98-4.82 (m,
3H), 4.43-4.34 (m, 1H), 4.21-4.14 (m, 1H), 4.03-3.86 (m,
4H), 3.79 (s×2, 6H), 3.72-3.61 (m, 2H), 3.38-3.35 (m, 2H),
2.98-2.85 (m, 2H), 2.59-2.42 (m, 2H), 2.23-2.06 (m, 2H),
2.00-1.88 (m, 1H), 1.82-1.68 (m, 4H), 1.74 (s, 6H), 1.61-
1.41 (m, 8H), 1.22-1.14 (m, 2H), 1.28 (d, 1H, J=7.0 Hz),
0.86 (d, 3H, J=6.7 Hz), 0.82 (d, 3H, J=6.8 Hz).

Example 8—Conjugation

Conjugate Tratuzumab-10 (ConjA)

A 50 mM solution of DL-dithiothreitol (DTT) in phos-
phate-buffered saline pH 7.4 (PBS) was added (80 molar
equivalent/antibody, 16 micromoles, 320 μL) to a 12.0 mL
solution of antibody, Trastuzumab (30 mg, 200 nanomoles)
in reduction buffer containing PBS and 1 mM ethylenedi-
aminetetraacetic acid (EDTA) and a final antibody concen-
tration of 2.5 mg/mL. The reduction mixture was allowed to
react at room temperature for 4-5 hours (or until full
reduction is observed by UHPLC) in an orbital shaker with
gentle (50 rpm) shaking. The reduced antibody was buffer
exchanged, via spin filter centrifugation, into a reoxidation
buffer containing PBS and 1 mM EDTA to remove all the
excess reducing agent. A 50 mM solution of dehydroascor-
bic acid (DHAA, 20 molar equivalent/antibody, 4 micro-
moles, 80 μL) in DMSO was added and the reoxidation
mixture was allowed to react for 16 hours at room tempera-
ture with gentle (50 rpm) shaking at an antibody concen-
tration of 1.5 mg/mL (or more DHAA added and reaction
left for longer until full reoxidation of the cysteine thiols to
reform the inter-chain cysteine disulfides is observed by
UHPLC). The reoxidation mixture was then sterile-filtered
and diluted in a conjugation buffer containing PBS and 1
mM EDTA for a final antibody concentration of 1.0 mg/mL.
Compound 10 was added as a DMSO solution (10 molar
equivalent/antibody, 1 micromole, in 1.5 mL DMSO) to 13.5
mL of this reoxidised antibody solution (15 mg, 100 nano-
moles) for a 10% (v/v) final DMSO concentration. The
solution was mixed for 1.5 hours at room temperature, then
the conjugation was quenched by addition of N-acetyl
cysteine (15 micromoles, 150 μL at 100 mM), then purified
by spin filtration using a 15 mL Amicon Ultracell 50 kDa
MWCO spin filter, sterile-filtered and analysed.

UHPLC analysis on a Shimadzu Prominence system
using a Phenomenex Aeris 3.6u XB-C18 150 mm×2.1 mm
column eluting with a gradient of water and acetonitrile on
a reduced sample of ConjA at 280 nm and 330 nm (Com-
pound 10 specific) shows unconjugated light chains and a
mixture of unconjugated heavy chains and heavy chains
attached to a single molecule of compound 10, consistent
with a drug-per-antibody ratio (DAR) of 1.89 molecules of
compound 10 per antibody.

UHPLC analysis on a Shimadzu Prominence system
using a Tosoh Bioscience TSKgel SuperSW mAb HTP 4 μm
4.6×150 mm column (with a 4 μm 3.0×20 mm guard
column) eluting with 0.3 mL/minute sterile-filtered SEC
buffer containing 200 mM potassium phosphate pH 6.95,
250 mM potassium chloride and 10% isopropanol (v/v) on
a sample of ConjA at 280 nm shows a monomer purity of
99%. UHPLC SEC analysis gives a concentration of final
ConjA at 1.45 mg/mL in 8.5 mL, obtained mass of ConjA is
12.3 mg (82% yield).

Conjugate Tratuzumab-22 (ConjB)

A 50 mM solution of DL-dithiothreitol (DTT) in phos-
phate-buffered saline pH 7.4 (PBS) was added (80 molar
equivalent/antibody, 42.7 micromoles, 853 μL) to a 20.0 mL
solution of antibody, Trastuzumab (80 mg, 533 nanomoles)
in reduction buffer containing PBS and 1 mM ethylenediaminetetraacetic acid (EDTA) and a final antibody concentration of 4.0 mg/mL. The reduction mixture was allowed to react at room temperature for 4-5 hours (or until full reduction is observed by UHPLC) in an orbital shaker with gentle (60 rpm) shaking. The reduced antibody was buffer exchanged, via spin filter centrifugation, into a reoxidation buffer containing PBS and 1 mM EDTA to remove all the excess reducing agent. A 50 mM solution of dehydroascorbic acid (DHAA, 20 molar equivalent/antibody, 10.7 micromoles, 213 µL) in DMSO was added and the reoxidation mixture was allowed to react for 16 hours at room temperature with gentle (50 rpm) shaking at an antibody concentration of 1.5 mg/mL (or more DHAA added and reaction left for longer until full reoxidation of the cysteine thiols to reform the inter-chain cysteine disulfides is observed by UHPLC). The reoxidation mixture was then sterile-filtered and diluted in a conjugation buffer containing PBS and 1 mM EDTA for a final antibody concentration of 1.0 mg/mL. Compound 22 was added as a DMSO solution (10 molar equivalent/antibody, 1.33 micromoles, in 2.0 mL DMSO) to 18.0 mL of this reoxidised antibody solution (20 mg, 133 nanomoles) for a 10% (v/v) final DMSO concentration. The solution was mixed for 1.5 hours at room temperature, then the conjugation was quenched by addition of N-acetyl cysteine (20 micromoles, 200 µL at 100 mM), then purified by spin filtration using a 15 mL Amicon Ultracell 50 kDa MWCO spin filter, sterile-filtered and analysed.

UHPLC analysis on a Shimadzu Prominence system using a Phenomenex Aeris 3.6u XB-C18 150 mm×2.1 mm column eluting with a gradient of water and acetonitrile on a reduced sample of ConjB at 280 nm and 330 nm (Compound 22 specific) shows unconjugated light chains and a mixture of unconjugated heavy chains and heavy chains attached to a single molecule of Compound 22, consistent with a drug-per-antibody ratio (DAR) of 1.71 molecules of Compound 22 per antibody.

UHPLC analysis on a Shimadzu Prominence system using a Tosoh Bioscience TSKgel SuperSW mAb HTP 4 µm 4.6×150 mm column (with a 4 µm 3.0×20 mm guard column) eluting with 0.3 mL/minute sterile-filtered SEC buffer containing 200 mM potassium phosphate pH 6.95, 250 mM potassium chloride and 10% isopropanol (v/v) on a sample of ConjB at 280 nm shows a monomer purity of 99%. UHPLC SEC analysis gives a concentration of final ConjB at 1.39 mg/mL in 10.3 mL, obtained mass of ConjB is 14.3 mg (72% yield).

Conjugate Tratuzumab-34 (ConjC)

A 50 mM solution of DL-dithiothreitol (DTT) in phosphate-buffered saline pH 7.4 (PBS) was added (80 molar equivalent/antibody, 42.7 micromoles, 853 µL) to a 20.0 mL solution of antibody, Trastuzumab (80 mg, 533 nanomoles) in reduction buffer containing PBS and 1 mM ethylenediaminetetraacetic acid (EDTA) and a final antibody concentration of 4.0 mg/mL. The reduction mixture was allowed to react at room temperature for 4-5 hours (or until full reduction is observed by UHPLC) in an orbital shaker with gentle (60 rpm) shaking. The reduced antibody was buffer exchanged, via spin filter centrifugation, into a reoxidation buffer containing PBS and 1 mM EDTA to remove all the excess reducing agent. A 50 mM solution of dehydroascorbic acid (DHAA, 20 molar equivalent/antibody, 10.7 micromoles, 213 µL) in DMSO was added and the reoxidation mixture was allowed to react for 16 hours at room temperature with gentle (50 rpm) shaking at an antibody concentration of 1.5 mg/mL (or more DHAA added and reaction left for longer until full reoxidation of the cysteine thiols to reform the inter-chain cysteine disulfides is observed by UHPLC). The reoxidation mixture was then sterile-filtered and diluted in a conjugation buffer containing PBS and 1 mM EDTA for a final antibody concentration of 1.0 mg/mL. Compound 34 was added as a DMSO solution (10 molar equivalent/antibody, 1.33 micromoles, in 2.0 mL DMSO) to 18.0 mL of this reoxidised antibody solution (20 mg, 133 nanomoles) for a 10% (v/v) final DMSO concentration. The solution was mixed for 1.5 hours at room temperature, then the conjugation was quenched by addition of N-acetyl cysteine (20 micromoles, 200 µL at 100 mM), then purified by spin filtration using a 15 mL Amicon Ultracell 50 kDa MWCO spin filter, and further purified on an AKTA™ Start FPLC using a GE Healthcare HiLoad™ 26/600 column packed with Superdex 200 PG, eluting with 2.5 mL/min PBS. Fractions corresponding to ConjC monomer peak were pooled, concentrated using a 15 mL Amicon Ultracell 50 KDa MWCO spin filter, sterile-filtered and analysed.

UHPLC analysis on a Shimadzu Prominence system using a Phenomenex Aeris 3.6u XB-C18 150 mm×2.1 mm column eluting with a gradient of water and acetonitrile on a reduced sample of ConjC at 280 nm and 330 nm (Compound 34 specific) shows unconjugated light chains and a mixture of unconjugated heavy chains and heavy chains attached to a single molecule of Compound 34, consistent with a drug-per-antibody ratio (DAR) of 1.66 molecules of Compound 34 per antibody.

UHPLC analysis on a Shimadzu Prominence system using a Tosoh Bioscience TSKgel SuperSW mAb HTP 4 µm 4.6×150 mm column (with a 4 µm 3.0×20 mm guard column) eluting with 0.3 mL/minute sterile-filtered SEC buffer containing 200 mM potassium phosphate pH 6.95, 250 mM potassium chloride and 10% isopropanol (v/v) on a sample of ConjC at 280 nm shows a monomer purity of 99%. UHPLC SEC analysis gives a concentration of final ConjC at 1.36 mg/mL in 10.4 mL, obtained mass of ConjC is 14.1 mg (71% yield).

Conjugate Tratuzumab-10 (ConjD)

A 50 mM solution of DL-dithiothreitol (DTT) in phosphate-buffered saline pH 7.4 (PBS) was added (150 molar equivalent/antibody, 40 micromoles, 800 µL) to a 16.0 mL solution of antibody, Tratuzumab (40 mg, 267 nanomoles) in reduction buffer containing PBS and 1 mM ethylenediaminetetraacetic acid (EDTA) and a final antibody concentration of 2.5 mg/mL. The reduction mixture was allowed to react at room temperature for 4 hours (or until full reduction is observed by UHPLC) in an orbital shaker with gentle (50 rpm) shaking. The reduced antibody solution was buffer exchanged (to remove all the excess reducing agent), via spin filter centrifugation, into a conjugation buffer containing PBS and 1 mM EDTA for a final antibody concentration of 2.5 mg/mL. Compound 10 was added as a DMSO solution (25 molar equivalent/antibody, 1.67 micromoles, in 0.4 mL DMSO) to 3.6 mL of this reduced antibody solution (10 mg, 67 nanomoles) for a 10% (v/v) final DMSO concentration. The solution was mixed for 1.5 hours at room temperature, then the conjugation was quenched by addition of N-acetyl cysteine (8.33 micromoles, 83.3 µL at 100 mM), then purified on an AKTA™ Start FPLC using a GE Healthcare HiLoad™ 26/600 column packed with Superdex 200 PG, eluting with 2.5 mL/min PBS. Fractions corresponding to ConjD monomer peak were pooled, concentrated using a 15 mL Amicon Ultracell 50 KDa MWCO spin filter, sterile-filtered and analysed.

UHPLC analysis on a Shimadzu Prominence system using a Phenomenex Aeris 3.6u XB-C18 150 mm×2.1 mm column eluting with a gradient of water and acetonitrile on a reduced sample of ConjD at 280 nm and 330 nm (Compound 10 specific) shows a mixture of unconjugated light chains, light chains attached to a single molecule of Compound 10, unconjugated heavy chains and heavy chains attached to up to three molecules of Compound 10, consistent with a drug-per-antibody ratio (DAR) of 7.47 molecules of Compound 10 per antibody.

UHPLC analysis on a Shimadzu Prominence system using a Tosoh Bioscience TSKgel SuperSW mAb HTP 4 µm 4.6×150 mm column (with a 4 µm 3.0×20 mm guard column) eluting with 0.3 mL/minute sterile-filtered SEC buffer containing 200 mM potassium phosphate pH 6.95, 250 mM potassium chloride and 10% isopropanol (v/v) on a sample of ConjD at 280 nm shows a monomer purity of 99%. UHPLC SEC analysis gives a concentration of final ConjD at 1.90 mg/mL in 4.4 mL, obtained mass of ConjA is 8.4 mg (84% yield).

Conjugate Tratuzumab-22 (ConjE)

A 50 mM solution of DL-dithiothreitol (DTT) in phosphate-buffered saline pH 7.4 (PBS) was added (150 molar equivalent/antibody, 40 micromoles, 800 mL) to a 16.0 mL solution of antibody, Tratuzumab (40 mg, 267 nanomoles) in reduction buffer containing PBS and 1 mM ethylenediaminetetraacetic acid (EDTA) and a final antibody concentration of 2.5 mg/mL. The reduction mixture was allowed to react at room temperature for 4 hours (or until full reduction is observed by UHPLC) in an orbital shaker with gentle (50 rpm) shaking.

The reduced antibody solution was buffer exchanged (to remove all the excess reducing agent), via spin filter centrifugation, into a conjugation buffer containing PBS and 1 mM EDTA for a final antibody concentration of 2.5 mg/mL. Compound 22 was added as a DMSO solution (25 molar equivalent/antibody, 1.67 micromoles, in 0.4 mL DMSO) to 3.6 mL of this reduced antibody solution (10 mg, 67 nanomoles) for a 10% (v/v) final DMSO concentration. The solution was mixed for 1.5 hours at room temperature, then the conjugation was quenched by addition of N-acetyl cysteine (8.33 micromoles, 83.3 mL at 100 mM), then purified on an AKTA™ Start FPLC using a GE Healthcare HiLoad™ 26/600 column packed with Superdex 200 PG, eluting with 2.5 mL/min PBS. Fractions corresponding to ConjE monomer peak were pooled, concentrated using a 15 mL Amicon Ultracell 50 KDa MWCO spin filter, sterile-filtered and analysed.

UHPLC analysis on a Shimadzu Prominence system using a Phenomenex Aeris 3.6u XB-C18 150 mm×2.1 mm column eluting with a gradient of water and acetonitrile on a reduced sample of ConjE at 280 nm and 330 nm (Compound 22 specific) shows a mixture of unconjugated light chains, light chains attached to a single molecule of Compound 22, unconjugated heavy chains and heavy chains attached to up to three molecules of Compound 22, consistent with a drug-per-antibody ratio (DAR) of 7.39 molecules of Compound 22 per antibody.

UHPLC analysis on a Shimadzu Prominence system using a Tosoh Bioscience TSKgel SuperSW mAb HTP 4 µm 4.6×150 mm column (with a 4 µm 3.0×20 mm guard column) eluting with 0.3 mL/minute sterile-filtered SEC buffer containing 200 mM potassium phosphate pH 6.95, 250 mM potassium chloride and 10% isopropanol (v/v) on a sample of ConjE at 280 nm shows a monomer purity of 96%. UHPLC SEC analysis gives a concentration of final ConjE at 1.93 mg/mL in 4.6 mL, obtained mass of ConjE is 8.9 mg (89% yield).

Conjugate Tratuzumab-34 (ConjF)

A 50 mM solution of DL-dithiothreitol (DTT) in phosphate-buffered saline pH 7.4 (PBS) was added (150 molar equivalent/antibody, 10 micromoles, 200 µL) to a 4.0 mL solution of antibody (10 mg, 66.7 nanomoles) in reduction buffer containing PBS and 1 mM ethylenediaminetetraacetic acid (EDTA) and a final antibody concentration of 2.5 mg/mL. The reduction mixture was allowed to react at room temperature for 4 hours (or until full reduction is observed by UHPLC) in an orbital shaker with gentle (50 rpm) shaking. The reduced antibody solution was buffer exchanged (to remove all the excess reducing agent), via spin filter centrifugation, into a conjugation buffer containing PBS and 1 mM EDTA for a final antibody concentration of 2.5 mg/mL. Compound 34 was added as a DMSO solution (25 molar equivalent/antibody, 1.67 micromoles, in 0.4 mL DMSO) to 3.6 mL of this reduced antibody solution (10 mg, 67 nanomoles) for a 10% (v/v) final DMSO concentration. The solution was mixed for 0.75 hours at room temperature, then the conjugation was quenched by addition of N-acetyl cysteine (8.33 micromoles, 83.3 µL at 100 mM), then purified on an AKTA™ Start FPLC using a GE Healthcare HiLoad™ 26/600 column packed with Superdex 200 PG, eluting with 2.5 mL/min PBS. Fractions corresponding to ConjF peak were pooled, concentrated using a 15 mL Amicon Ultracell 50 KDa MWCO spin filter, re-purified on an AKTA™ Start FPLC using a GE Healthcare HiLoad™ 26/600 column packed with Superdex 200 PG, eluting with 2.5 mL/min PBS. Fractions corresponding to ConjF peak were pooled, concentrated using a 15 mL Amicon Ultracell 50 KDa MWCO spin filter, sterile-filtered and analysed.

UHPLC analysis on a Shimadzu Prominence system using a Phenomenex Aeris 3.6u XB-C18 150 mm×2.1 mm column eluting with a gradient of water and acetonitrile on a reduced sample of ConjF at 280 nm and 330 nm (Compound 34 specific) shows a mixture of unconjugated light chains, light chains attached to a single molecule of Compound 34, unconjugated heavy chains and heavy chains attached to up to three molecules of Compound 34, consistent with a drug-per-antibody ratio (DAR) of 7.41 molecules of Compound 34 Per Antibody.

UHPLC analysis on a Shimadzu Prominence system using a Tosoh Bioscience TSKgel SuperSW mAb HTP 4 µm 4.6×150 mm column (with a 4 µm 3.0×20 mm guard column) eluting with 0.3 mL/minute sterile-filtered SEC buffer containing 200 mM potassium phosphate pH 6.95, 250 mM potassium chloride and 10% isopropanol (v/v) on a sample of ConjF at 280 nm shows a monomer purity of 0% (100% dimer-trimer). UHPLC SEC analysis gives a concentration of final ConjF at 1.09 mg/mL in 4.4 mL, obtained mass of ConjF is 4.8 mg (48% yield).

Conjugate Tratuzumab-58 (ConjG)

A 50 mM solution of Dithiothreitol (DTT) in phosphate-buffered saline pH 7.4 (PBS) was added (120 molar equivalent/antibody, 32 micromoles, 0.64 mL at 50 mM) to a 3.7 mL solution of antibody (40 mg, 0.267 micromoles) in reduction buffer containing PBS and 1 mM ethylenediaminetetraacetic acid (EDTA) and a final antibody concentration of 2.0 mg/mL. The reduction mixture was heated at +25° C. for 4 hours (or until full reduction observed by UHPLC) in an orbital shaker with gentle (60 rpm) shaking. After cooling down to room temperature, the reduced antibody was buffer exchanged, via spin filter using 50 KDa MWCO vivaspin, into a reoxidation buffer containing PBS pH 7.4 and 1 mM EDTA to remove all the excess reducing agent. A 50 mM solution of dehydroascorbic acid (DHAA, 20 molar equivalent/antibody, 5.3 micromoles, 0.1 mL at 50 mM) in DMSO was added and the reoxidation mixture was allowed to react for 16 hours at room temperature with gentle (60 rpm) shaking at an antibody concentration of ~2.0 mg/mL (or until full reoxidation of the cysteine thiols to reform the inter-chain cysteine disulfides is observed by UHPLC). The reoxidation mixture was centrifuged for 3 min at 4000 rpm and then sterile-filtered using 0.22 μm membrane filter. Compound 58 was added as a DMSO solution (11 molar equivalent/antibody, 1.46 micromoles, in 0.9 mL DMSO) to 9.1 mL of this reoxidised antibody solution (20 mg, 0.13 micromoles) for a 10% (v/v) final DMSO concentration. The solution was shaken for 3 hours at +25° C. and then the conjugation was quenched with N-acetyl cysteine (7.3 micromoles, 0.07 mL at 100 mM).

Excess free drug was removed via spin filter using 50 kDa MWCO vivaspin into buffer containing PBS pH 7.4. Extent of free drug removal was monitored by UHPLC-RP using neat conjugate. After complete removal of free drug, ConjG was filtered using 0.22 μm, Mustang filter under sterile atmosphere and then stored at +4° C.

UHPLC analysis on a Shimadzu Prominence system using a Phenomenex Aeris 3.6u XB-C18 150×2.1 mm column eluting with a gradient of water and acetonitrile on a reduced sample of Conjugate at 214 nm and 330 nm (Compound 58 specific) shows unconjugated light chains and a mixture of unconjugated heavy chains and heavy chains attached to a single molecule of Compound 58, consistent with a drug-per-antibody ratio (DAR) of 1.83 molecules of Compound 58 per antibody.

UHPLC analysis on a Shimadzu Prominence system using a Tosoh Bioscience TSKgel SuperSW mAb HTP 4 μm 4.6×150 mm column (with a 4 μm 3.0×20 mm guard column) eluting with 0.3 mL/minute sterile-filtered SEC buffer containing 200 mM potassium phosphate pH 6.95, 250 mM potassium chloride and 10% isopropanol (v/v) on a sample of ConjG at 280 nm shows a monomer purity of greater than 99%. UHPLC SEC analysis gives a concentration of final ConjG at 1.34 mg/mL in 8.9 mL, obtained mass of ConjG is 11.9 mg (60% yield).

Conjugate Tratuzumab-59 (ConjH)

Antibody (30 mg) was loaded onto solid support and reduced, reoxidised, conjugated to Compound 59, purified, released from the resin and formulated onto 25 mM Histidine, 200 mM Sucrose, Tween-20 0.02%, pH 6.0 according to the method described in US2014-0037961A1, which is incorporated herein by reference.

UHPLC analysis on a Shimadzu Prominence system using a Phenomenex Aeris 3.6u XB-C18 150×2.1 mm column eluting with a gradient of water and acetonitrile on a reduced sample of Conjugate at 214 nm and 330 nm (Compound 59 specific) shows unconjugated light chains and a mixture of unconjugated heavy chains and heavy chains attached to a single molecule of Compound 59, consistent with a drug-per-antibody ratio (DAR) of 1.9 molecules of Compound 59 per antibody.

UHPLC analysis on a Shimadzu Prominence system using a Tosoh Bioscience TSKgel SuperSW mAb HTP 4 μm 4.6×150 mm column (with a 4 μm 3.0×20 mm guard column) eluting with 0.3 mL/minute sterile-filtered SEC buffer containing 200 mM potassium phosphate pH 6.95, 250 mM potassium chloride and 10% isopropanol (v/v) on a sample of ConjH at 280 nm shows a monomer purity of greater than 97%. UHPLC SEC analysis gives a concentration of final ConjH at 1.49 mg/mL in 7.5 mL, obtained mass of ConjH is 11.2 mg (37% yield).

Conjugate Tratuzumab-48 (CoqI)

A 50 mM solution of Dithiothreitol (DTT) in phosphate-buffered saline pH 7.4 (PBS) was added (80 molar equivalent/antibody, 21.4 micromoles, 0.43 mL at 50 mM) to a 3.7 mL solution of antibody (40 mg, 0.267 micromoles) in reduction buffer containing PBS and 1 mM ethylenediaminetetraacetic acid (EDTA) and a final antibody concentration of 2.0 mg/mL. The reduction mixture was heated at +25° C. for 4 hours (or until full reduction observed by UHPLC) in an orbital shaker with gentle (60 rpm) shaking. After cooling down to room temperature, the reduced antibody was buffer exchanged, via spin filter using 50 KDa MWCO vivaspin, into a reoxidation buffer containing PBS pH 7.4 and 1 mM EDTA to remove all the excess reducing agent. A 50 mM solution of dehydroascorbic acid (DHAA, 20 molar equivalent/antibody, 5.3 micromoles, 0.1 mL at 50 mM) in DMSO was added and the reoxidation mixture was allowed to react for 16 hours at room temperature with gentle (60 rpm) shaking at an antibody concentration of ~2.0 mg/mL (or until full reoxidation of the cysteine thiols to reform the inter-chain cysteine disulfides is observed by UHPLC). The reoxidation mixture was centrifuged for 3 min at 4000 rpm and then sterile-filtered using 0.22 μm membrane filter. Compound 48 was added as a DMSO solution (11 molar equivalent/antibody, 1.46 micromoles, in 1.7 mL DMSO) to 16.8 mL of this reoxidised antibody solution (20 mg, 0.13 micromoles) for a 10% (v/v) final DMSO concentration. The solution was shaken for 3 hours at +25° C. and then the conjugation was quenched with N-acetyl cysteine (7.3 micromoles, 0.07 mL at 100 mM).

Excess free drug was removed via spin filter using 50 kDa MWCO vivaspin into buffer containing PBS pH 7.4. Extent of free drug removal was monitored by UHPLC-RP using neat conjugate. After complete removal of free drug, ADC was filtered using 0.22 μm, Mustang filter under sterile atmosphere and then stored at +4° C.

UHPLC analysis on a Shimadzu Prominence system using a Phenomenex Aeris 3.6u XB-C18 150×2.1 mm column eluting with a gradient of water and acetonitrile on a reduced sample of Conjugate at 214 nm and 330 nm (Compound 48 specific) shows unconjugated light chains and a mixture of unconjugated heavy chains and heavy chains attached to a single molecule of Compound 48, consistent with a drug-per-antibody ratio (DAR) of 1.86 molecules of Compound 48 per antibody.

UHPLC analysis on a Shimadzu Prominence system using a Tosoh Bioscience TSKgel SuperSW mAb HTP 4 μm 4.6×150 mm column (with a 4 μm 3.0×20 mm guard column) eluting with 0.3 mL/minute sterile-filtered SEC buffer containing 200 mM potassium phosphate pH 6.95, 250 mM potassium chloride and 10% isopropanol (v/v) on a sample of ConjI at 280 nm shows a monomer purity of greater than 99%. UHPLC SEC analysis gives a concentration of final ConjI at 1.7 mg/mL in 7.3 mL, obtained mass of ConjI is 12.4 mg (62% yield).

Conjugate Tratuzumab-57 (ConjJ)

A 50 mM solution of Dithiothreitol (DTT) in phosphate-buffered saline pH 7.4 (PBS) was added (80 molar equivalent/antibody, 21.4 micromoles, 0.43 mL at 50 mM) to a 3.7 mL solution of antibody (40 mg, 0.267 micromoles) in reduction buffer containing PBS and 1 mM ethylenediaminetetraacetic acid (EDTA) and a final antibody concentration of 2.0 mg/mL. The reduction mixture was heated at +25° C. for 4 hours (or until full reduction observed by UHPLC) in an orbital shaker with gentle (60 rpm) shaking. After cooling down to room temperature, the reduced antibody was buffer exchanged, via spin filter using 50 KDa MWCO vivaspin, into a reoxidation buffer containing PBS pH 7.4 and 1 mM EDTA to remove all the excess reducing agent. A 50 mM solution of dehydroascorbic acid (DHAA, 20 molar equivalent/antibody, 5.3 micromoles, 0.1 mL at 50 mM) in DMSO was added and the reoxidation mixture was allowed to react for 16 hours at room temperature with gentle (60 rpm) shaking at an antibody concentration of ~2.0 mg/mL (or until full reoxidation of the cysteine thiols to reform the inter-chain cysteine disulfides is observed by UHPLC). The reoxidation mixture was centrifuged for 3 min at 4000 rpm and then sterile-filtered using 0.22 μm membrane filter. Compound 57 was added as a DMSO solution (11 molar equivalent/antibody, 1.46 micromoles, in 1.7 mL DMSO) to 16.8 mL of this reoxidised antibody solution (20 mg, 0.13 micromoles) for a 10% (v/v) final DMSO concentration. The solution was shaken for 3 hours at +25° C. and then the conjugation was quenched with N-acetyl cysteine (7.3 micromoles, 0.07 mL at 100 mM).

Excess free drug was removed via spin filter using 50 kDa MWCO vivaspin into buffer containing PBS pH 7.4. Extent of free drug removal was monitored by UHPLC-RP using neat conjugate. After complete removal of free drug, ADC was filtered using 0.22 μm, Mustang filter under sterile atmosphere and then stored at +4° C.

UHPLC analysis on a Shimadzu Prominence system using a Phenomenex Aeris 3.6u XB-C18 150×2.1 mm column eluting with a gradient of water and acetonitrile on a reduced sample of Conjugate at 214 nm and 330 nm (Compound 57 specific) shows unconjugated light chains and a mixture of unconjugated heavy chains and heavy chains attached to a single molecule of Compound 57, consistent with a drug-per-antibody ratio (DAR) of 1.87 molecules of Compound 57 per antibody.

UHPLC analysis on a Shimadzu Prominence system using a Tosoh Bioscience TSKgel SuperSW mAb HTP 4 μm 4.6×150 mm column (with a 4 μm 3.0×20 mm guard column) eluting with 0.3 mL/minute sterile-filtered SEC buffer containing 200 mM potassium phosphate pH 6.95, 250 mM potassium chloride and 10% isopropanol (v/v) on a sample of ConjJ at 280 nm shows a monomer purity of greater than 100%. UHPLC SEC analysis gives a concentration of final ConjJ at 0.86 mg/mL in 10.3 mL, obtained mass of ConjJ is 8.9 mg (45% yield).

Example 9

In Vitro Testing of Compound 10

DU145 (2000/well, 72 hour assay) and MDA-MB-361 (5000/well, 144 hour assay) cells were plated in culture medium to tissue culture-treated 96-well plates at a volume of 80 μL per well and allowed to adhere overnight. For warhead dilutions, first a 60× concentration of each dose to be tested was prepared by diluting the test articles in DMSO. The 60× dilutions of warhead were then further diluted to a 5× concentration in either cell culture medium alone or cell culture medium containing 5× β-glucuronidase enzyme (Sigma Cat # G0799-25KU). 20 μL of cell culture medium containing test article+/−enzyme was added to cells in triplicate wells, and the final dose curve ranged from 6.4 nM to 61 pM in a stepwise 1:4 serial dilution series. DMSO alone diluted to the culture medium was used as the controls. The treated cells were cultured at 37° C./5% $CO_2$ for 72 to 144 hours (depending on established growth kinetics of each particular cell line). At the end of the assay, CellTiter-Glo® (CTG) Luminescent Viability Assay (Promega) was used to determine relative cytotoxicity. 100 μL of CTG reagent was added to each well, and plates were incubated for 10 minutes at room temperature with gentle shaking, absorbance of each sample was read at 560 nM using an EnVision luminometer (Perkin Elmer). The percent cell viability was calculated by the following formula:

(average luminescence of treated samples/average luminescence of control samples)×100.

$IC_{50}$ values were determined using logistic non-linear regression analysis with GraphPad Prism software.

| Compound 10 | No glucuronidase | With glucuronidase |
|---|---|---|
| DU145 - $IC_{50}$ | 6.84 μM | 201 nM |
| MDA-MB-361 - $IC_{50}$ | 778 nM | 32 nM |

In Vitro Testing of ConjA

A similar method was used as described above with MDA-MB-361 (HER2 high, 5000 cells/well, 144 hr assay) and MCF-7 cells (HER2 low, 1500 cells/well, 144 hr assay). Cell plating density and duration of the assay were determined based on established growth kinetics of each particular cell line. A 5× concentration of each dose of ADC to be tested was prepared by diluting the test articles in culture medium. Twenty μL of ADC was added to the cells in triplicate wells with a final dose curve ranging from 3 μg/mL to 11 pg/mL in a 1:4 serial dilution series. The treated cells were cultured at 37° C./5% $CO_2$ for 144 hours and the CellTiter-Glo® (CTG) Luminescent Viability Assay (Promega) was used to determine relative cytotoxicity as described above.

| $IC_{50}$ | MDA-MB-361 | MCF-7 |
|---|---|---|
| ConjA | 14.5 ng/mL | ~3 μg/mL |

Testing of ConjB and ConjC in Cells with siRNA Knock Down of β-Glucuronidase

HER2-overexpressing SKOV3 cells were subjected to reverse transfection to knock down GUSB expression levels. First, a 4× stock of RNAiMAX (final concentration of 0.125 ul/well, Life Technologies) and a 4× stock of siRNA oligos (Non-targeting/Negative siRNA, GAPDH siRNA and GUSB siRNA final concentration of 100 nM/well, Life Technologies) were prepared in OptiMEM medium. An RNAiMAX/OptiMEM only mixture was included as the lipid control. The 4× RNAiMAX solution and 4× siRNA solutions were brought to 2× by mixing in a one to one ratio, and the RNAiMAX/siRNA mixture was left to incubate at room temperature for 20 minutes. After incubation, 40 μl of the RNAiMAX/siRNA mixtures and lipid control were added per well to tissue culture-treated 96-well plates and 40 μl of cell solution was added onto the lipid/siRNA mixture, with a final plating density of 2000 cells/well. Plates were cultured at 37° C./5% $CO_2$ for 72 hours at which point 20 μl of a 5× concentration of each dose of ConjB/ConjC was added to the cells in duplicate wells with a final dose curve ranging from 10 μg/mL to 0.15 ng/mL in a 1:4 serial dilution series. The ADC treated cells were cultured at 37° C./5% $CO_2$ for an additional 72 hours and the CellTiter-Glo® (CTG) Luminescent Viability Assay (Promega) was used to determine relative cytotoxicity as described above. Efficiency of the siRNA knock down was determined by RNA expression levels and measurement of β-glucuronidase enzyme activity.

The results are shown in FIG. 1 (ConjB) and FIG. 2 (ConjC), wherein the followed symbols are used:

| | |
|---|---|
| ▼ | Untrasfected |
| ● | Lipid Only |
| ◆ | Ne siRNA oligo2 |
| ▲ | GUSB oligo3 |
| ▼ | GAPDH oligo2 |
| ✕ | Neg2 siRNA tox |
| ✱ | GUSB siRNA tox |
| ★ | GAPDH siRNA tox |

| $IC_{50}$ (ng/mL) | Untrans-fected | Neg siRNA oligo2 | Lipid only | GUSB oligo3 | GAPDH oligo2 |
|---|---|---|---|---|---|
| ConjB | 12.66 | 18.19 | 13.1 | 26.05 | 27.84 |
| ConjC | 4.871 | 13.07 | 5.818 | 31.59 | 23.00 |

Also noticeable is the much higher maximum kill for ConjC.

Example 10—In Vitro Testing

Medium from sub-confluent (80-90% confluency) cell culture in a T75 flask was aspirated and the flask rinsed with PBS (about 20 ml) and emptied. Trypsin-EDTA (5 ml) was added, the flask returned to the 37° C. gassed incubator for up to about 5 minutes, then rapped sharply to dislodge and dissociate cells from the plastic. The cell suspension was transferred to a sterile 50 ml screw-top centrifuge tube, diluted with growth medium to a final volume of 15 ml, then centrifuged (400 g for 5 min). The supernatant was aspirated and the pellet re-suspended in 10 ml culture medium. Repeated pipetting may be necessary to produce monodisperse cell suspensions. The cell concentration and viability are measured of trypan blue cell stained cells, and counted using the LUNA-11™ Automated Cell Counter. Cells were diluted to $2 \times 10^5$/ml, dispensed (50 µl/well) into 96 well flat bottom plates and incubated overnight before use.

A stock solution (1 ml) of antibody drug conjugate (ADC) (20 µg/ml) was made by dilution of filter-sterilised ADC into cell culture medium. A set of 8×10-fold dilutions of stock ADC were made in a 24 well plate by serial transfer of 100 µl onto 900 µl of cell culture medium.

ADC dilution was dispensed (50 µl/well) into 4 replicate wells of the 96-well plate, containing 50 µl cell suspension seeded the previous day. Control wells received 50 µl cell culture medium. The 96-well plate containing cells and ADCs was incubated at 37° C. in a $CO_2$-gassed incubator for the exposure time.

At the end of the incubation period, cell viability was measured by MTS assay. MTS (Promega) was dispensed (20 µl per well) into each well and incubated for 4 hours at 37° C. in the $CO_2$-gassed incubator. Well absorbance was measured at 490 nm. Percentage cell survival was calculated from the mean absorbance in the 4 ADC-treated wells compared to the mean absorbance in the 4 control untreated wells (100%). $IC_{50}$ was determined from the doses-response data using Graph Pad Prism using the non-linear curve fit algorithm: sigmoidal, 4PL X is log(concentration).

| Cell Line | Description | ADC Exposure | Cell growth medium |
|---|---|---|---|
| MDA MB 468 | HER2 negative, Breast carcinoma | 4 days | RPMI 1640 with glutamax, 10% (v/v) HyClone ™ Fetal Bovine Serum |
| NCIN87 | Gastric carcinoma | 7 days | RPMI 1640 with glutamax, 10% (v/v) HyClone ™ Fetal Bovine Serum |

| | $IC_{50}$ (nM) in: | |
|---|---|---|
| ADC | MDMA MB 468 | NCI-N87 |
| ConjA | >100 | 0.263 |
| ConjB | >100 | 0.0222 |
| ConjC | 68 | 0.0013 |
| ConjD | >100 | 0.185 |
| ConjE | >100 | 0.0023 |
| ConjF | 81 | 0.0003 |

| ADC | $EC_{50}$ (µg/ml) |
|---|---|
| ConjA | 0.0133 |
| ConjB | 0.00141 |
| ConjC | 0.00000187 |
| ConjD | 0.00271 |
| ConjE | 0.00000203 |
| ConjF | $3 \times 10^{-16}$ |
| ConjG | 0.00369 |
| ConjH | 0.000496 |
| ConjI | 0.00844 |
| ConjJ | 0.0829 |

Example 11—Xenograft Testing

NCI-N87 Xenografted Mice

Female severe combined immune-deficient mice (Fox Chase SCID®, C.B-17/Icr-Prkdcscid, Charles River) were ten weeks old with a body weight (BW) range of 16.5 to 21.1 grams on Day 1 of the study. The animals were fed ad libitum water (reverse osmosis, 1 ppm Cl), and NIH 31 Modified and Irradiated Lab Diet® consisting of 18.0% crude protein, 5.0% crude fat, and 5.0% crude fibre. The mice were housed on irradiated Enricho'cobs™ Laboratory Animal Bedding in static micro-isolators on a 12-hour light cycle at 20-22° C. (68-72° F.) and 40-60% humidity. CR Discovery Services specifically complies with the recommendations of the *Guide for Care and Use of Laboratory Animals* with respect to restraint, husbandry, surgical procedures, feed and fluid regulation, and veterinary care. The animal care and use program at CR Discovery Services is accredited by the Association for Assessment and Accreditation of Laboratory Animal Care International (AAALAC), which assures compliance with accepted standards for the care and use of laboratory animals.

Tumour Cell Culture

Human NCI-N87 gastric carcinoma lymphoma cells were cultured in RPMI-1640 medium supplemented with 10% fetal bovine serum, 2 mM glutamine, 100 units/mL penicillin, 100 µg/mL streptomycin sulfate and 25 µg/mL gentamicin. The cells were grown in tissue culture flasks in a humidified incubator at 37° C., in an atmosphere of 5% $CO_2$ and 95% air.

In Vivo Implantation and Tumour Growth

The NCI-N87 cells used for implantation were harvested during log phase growth and Re-suspended in phosphate buffered saline (PBS) containing 50% Matrigel™ (BD Biosciences). On the day of tumour implant, each test mouse was injected subcutaneously in the right flank with $1\times10^7$ cells (0.1 mL cell suspension), and tumour growth was monitored as the average size approached the target range of 100 to 150 mm$^3$. Fourteen days later, designated as Day 1 of the study, mice were sorted according to calculated tumour size into groups each consisting of ten animals with individual tumour volumes ranging from 108 to 144 mm$^3$ and group mean tumour volumes of 115 mm$^3$.

Tumours were measured in two dimensions using calipers, and volume was calculated using the formula:

$$\text{Tumour Volume (mm}^3) = \frac{w^2 x l}{2}$$

where w=width and l=length, in mm, of the tumour. Tumour weight may be estimated with the assumption that 1 mg is equivalent to 1 mm$^3$ of tumour volume.

Treatment

Treatment began on Day 1 in groups of 10 mice (n=10) with established subcutaneous NCI-N87 tumours (108-144 mm$^3$). Trastuzumab-10 (ConjA) was administered intravenously once on Day 1 (qd×1). A vehicle-treated group served as the control group for efficacy analysis. Tumours were measured twice per week until the study was ended on Day 79. Each mouse was euthanized when its tumour reached the endpoint volume of 800 mm$^3$ or on the final day, whichever came first. The time to endpoint (TTE) was calculated for each mouse.

Treatment outcome was determined from percent tumour growth delay (% TGD), defined as the percent increase in median TTE for treated versus control mice, with differences between groups deemed statistically significant at P≤0.05 using logrank survival analysis. Mice were monitored for complete regression (CR) and partial regression (PR) responses.

Treatment tolerability was assessed by body weight measurements and frequent observation for signs of treatment-related side effects. Treatment tolerability was assessed by body weight measurements and frequent observation for signs of treatment-related side effects. All regimens were well tolerated. The median TTE for vehicle-treated controls was 50.7 days, establishing a maximum possible TGD of 28.3 days (56%) for the 79-day study.

The minimum effective dose was defined as the minimum dosage required to produce tumour stasis for twenty-eight days after test article administration. Based on visual inspection of the mean and median tumour volume plots and percent change of tumour volume from Day 1, trastuzumab-10 (ConjA) at 1.0 mg/kg, appeared to be the dosage that achieved a response consistent with the minimum effective dose Two of the 0.3 mg/kg group animals were end of study survivors with an MTV of 708 mm$^3$. Eight of the 1.0 mg/kg group animals were end of study survivors with an MTV of 650 mm$^3$. The results are illustrated in FIG. 3.

JIMT-1 Xenografted Mice

Mice

Female severe combined immunodeficient mice (Fox Chase SCID®, CB17/Icr-Prkdcscid/IcrIcoCrl, Charles River) were ten weeks old with a body weight (BW) range of 15.1 to 22.2 g on Day 1 of the study.

Tumour Cell Culture

JIMT-1 human breast carcinoma cells were grown in DMEM containing 10% fetal bovine serum, 100 units/mL penicillin G sodium, 100 µg/mL streptomycin sulphate, 25 µg/mL gentamicin, and 2 mM glutamine. Cell cultures were maintained in tissue culture flasks in a humidified incubator at 37° C., in an atmosphere of 5% $CO_2$ and 95% air.

In Vivo Implantation and Tumour Growth

The JIMT-1 cells used for implantation were harvested during exponential growth and re-suspended in 50% Matrigel (BD Biosciences): 50% phosphate buffered saline at a concentration of $5\times10^7$ cells/mL. On the day of tumour implant, each test mouse was injected subcutaneously in the right flank with $1\times10^7$ cells (0.2 mL cell suspension), and tumour growth was monitored as the average size approached the target range of 100 to 150 mm$^3$. Tumours were measured in two dimensions using calipers, and volume was calculated using the formula:

$$\text{Tumour Volume (mm}^3) = \frac{w^2 x l}{2}$$

where w=width and l=length, in mm, of the tumour. Tumour weight may be estimated with the assumption that 1 mg is equivalent to 1 mm$^3$ of tumour volume.

Treatment

Treatment began on Day 1 in groups of 10 mice (n=10) with established subcutaneous JIMT-1 tumours with volume range (88-196 mm$^3$) and group mean timour volume of 120 to 122 mm$^3$. Trastuzumab-10 (ConjA) was administered intravenously once on Day 1 (qd×1). A vehicle-treated group served as the control group for efficacy analysis. Tumours were measured twice per week until the study was ended on Day 59. Each mouse was euthanized when its tumour reached the endpoint volume of 1000 mm$^3$ or on the final day, whichever came first. The time to endpoint (TTE) was calculated for each mouse.

Treatment outcome was determined from percent tumour growth delay (% TGD), defined as the percent increase in median TTE for treated versus control mice, with differences between groups deemed statistically significant at P≤0.05 using logrank survival analysis. Mice were monitored for complete regression (CR) and partial regression (PR) responses. Treatment tolerability was assessed by body weight measurements and frequent observation for signs of treatment-related side effects. All regimens were well tolerated. The median TTE for vehicle-treated controls was 48.4 days, establishing a maximum possible TGD of 10.6 days (22%) for the 59-day study. All ADC regimens tested produced significant survival benefit compared to vehicle-treated controls (P<0.01).

The minimum effective dose was defined as the minimum dosage required to produce tumour stasis for twenty-eight days after test article administration. Based on visual inspection of the mean and median tumour volume plots and percent change of tumour volume from Day 1, trastuzumab-10 (ConjA) at 1.0 mg/kg, appeared to be the dosage that achieved a response consistent with the minimum effective dose.

A dose-dependent effect was observed where the 0.3 mg/kg group median tumour volume slowly increased through Day 34 then progressed thereafter, while the 1.0 mg/kg group showed static median tumour volume through Day 38 which progressed thereafter. The median TTE for the 0.3 mg/kg group was 56.9 days corresponding to a significant TGD of 8.5 days (18%) versus the control (P<0.05). The 0.3 mg/kg group had no objective regression responses. Five of the 0.3 mg/kg group animals were end of study survivors with an MTV of 486 mm³.

The median TTE for the 1.0 mg/kg group was a maximal 59.0 days corresponding to a significant TGD of 10.6 days (22%) versus the control (P<0.001). The 1.0 mg/kg group had no objective regression responses. Nine of the 1.0 mg/kg group animals were 'end of study' survivors with an MTV of 446 mm3. The 0.3 and 1.0 mg/kg groups were significantly different from one another (P<0.05).

The results are illustrated in FIG. 4.

Example 12—Toxicity Studies/Therapeutic Index

Rat Study:

A single dose toxicity study was used to determine the maximum tolerated dose (MTD) and safety profile of Trastuzumab-10 (ConjA). Male Sprague Dawley rats (ENVIGO) were dosed once by slow bolus intravenous injection via the tail vein with vehicle control (25 mM Histidine, 200 mM Sucrose, pH 6.0) or test material (ConjA). Parameters evaluated during the study included mortality, physical examinations, cageside observations, body weights, body weight changes, clinical pathology (clinical chemistry, hematology, and coagulation), and gross pathology findings. All animals in groups 1-6 were terminated on Study Day (SD) 29, except one animal in Group 6 who was terminated on Study Day (SD) 25.

| Group | Treatment | Dose Route | Dose (mg/kg) | Frequency | Male Rats Main Study N |
|---|---|---|---|---|---|
| 1 | Control | IV | 0 | Single | 5 |
| 2 | ConjA | IV | 4 | Single | 5 |
| 3 | ConjA | IV | 6 | Single | 5 |
| 4 | ConjA | IV | 8 | Single | 5 |
| 5 | ConjA | IV | 12 | Single | 5 |
| 6 | ConjA | IV | 14 | Single | 5 |

Control = 25 mM Histidine-HCl, 200 mM sucrose, pH 6.0

Tolerability was determined based on toxicity end points, including decreased absolute reticulocytes, white blood cells and cellular components, as well as macroscopic and microscopic lesions in the lungs. The major finding at dose levels of ≥4 mg/kg were histopathological observations of lung lesions. At the 4 mg/kg dose, findings were mild and considered reversible. As the dose increased, the lung lesions were of increasing severity and were not considered reversible. Based on this finding, the maximum tolerated dose (MTD) in the rat after a single dose of ConjA was determined to be 6 mg/kg.

Therapeutic Index

The Therapeutic Index can be calculated by dividing the maximum tolerated single dose (MTD) of non-targeted ADC in rat, by the minimal effective single dose (MED) of the a targeted ADC. The MED is the single dose necessary to achieve tumour stasis in an in vivo model at 28 days (for NCI-N87 xenograft).

Thus for conjugates of compound 10, the therapeutic index is the MTD of 6 mg/kg divided by the MED which is 1.0 mg/kg (see above), giving a Therapeutic Index of 6.

All documents and other references mentioned above are herein incorporated by reference.

The invention claimed is:

1. A compound of formula I:

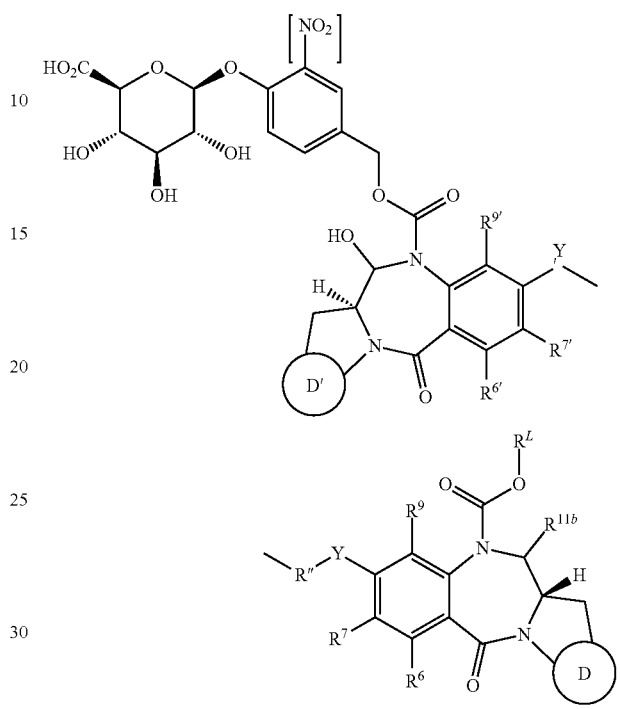

I or a pharmaceutically acceptable salt thereof, wherein:

the square brackets indicate the $NO_2$ group is optional;

D represents either group D1 or D2:

D1

D2 the dotted line indicates the optional presence of a double bond between C2 and C3;

when there is a double bond present between C2 and C3, $R^2$ is selected from the group consisting of:

(ia) phenyl, naphthyl, azulenyl or $C_{5-10}$ heteroaryl, optionally substituted by one or more substituents selected from the group consisting of: halo, nitro, cyano, —$OR^B$, carboxy, $C(=O)OR^B$, $C_{1-7}$ alkyl, $C_{3-7}$ heterocyclyl and bis-oxy-$C_{1-3}$ alkylene, wherein $R^B$ is selected from a $C_{1-7}$ alkyl group, a $C_{3-20}$ heterocyclyl group or a phenyl, naphthyl, azulenyl, anthracenyl, phenanthrenyl, napthacenyl, pyrenyl, or $C_{5-20}$ heteroaryl;

(ib) $C_{1-5}$ saturated aliphatic alkyl;

(ic) $C_{3-6}$ saturated cycloalkyl;

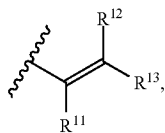
(id)

wherein each of $R^{11}$, $R^{12}$ and $R^{13}$ are independently selected from H, $C_{1-3}$ saturated alkyl, $C_{2-3}$ alkenyl, $C_{2-3}$ alkynyl and cyclopropyl, where the total number of carbon atoms in the $R^2$ group is no more than 5;

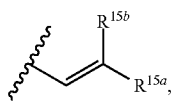
(ie)

wherein one of $R^{15a}$ and $R^{15b}$ is H and the other is selected from: phenyl, which phenyl is optionally substituted by a group selected from halo, methyl, methoxy; pyridyl; and thiophenyl; and

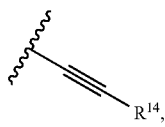
(if)

where $R^{14}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;

when there is a single bond present between C2 and C3, $R^2$ is selected from H, OH, F, diF and

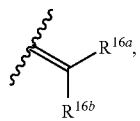

where $R^{16a}$ and $R^{16b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{16a}$ and $R^{16b}$ is H, the other is selected from nitrile and a $C_{1-4}$ alkyl ester;

D' represents either group D'1 or D'2:

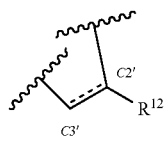
D'1

-continued

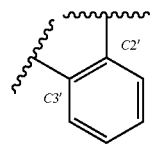
D'2 wherein the dotted line indicates the optional presence of a double bond between C2' and C3';

when there is a double bond present between C2' and C3', $R^{12}$ is selected from the group consisting of:

(iia) phenyl, naphthyl, azulenyl or $C_{5-10}$ heteroaryl, optionally substituted by one or more substituents selected from the group comprising: halo, nitro, cyano, —$OR^B$, carboxy, —C(=O)$OR^B$, $C_{1-7}$ alkyl, $C_{3-7}$ heterocyclyl and bis-oxy-$C_{1-3}$ alkylene, wherein $R^B$ is selected from a $C_{1-7}$ alkyl group, a $C_{3-20}$ heterocyclyl group or a phenyl, naphthyl, azulenyl, anthracenyl, phenanthrenyl, napthacenyl, pyrenyl or $C_{5-20}$ heteroaryl;

(iib) $C_{1-5}$ saturated aliphatic alkyl;

(iic) $C_{3-6}$ saturated cycloalkyl;

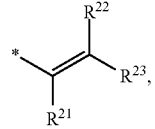
(iid)

wherein each of $R^{21}$, $R^{22}$ and $R^{23}$ are independently selected from H, $C_{1-3}$ saturated alkyl, $C_{2-3}$ alkenyl, $C_{2-3}$ alkynyl and cyclopropyl, where the total number of carbon atoms in the $R^{12}$ group is no more than 5;

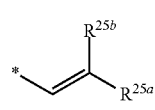
(iie)

wherein one of $R^{25a}$ and $R^{25b}$ is H and the other is selected from: phenyl, which phenyl is optionally substituted by a group selected from halo, methyl, methoxy; pyridyl; and thiophenyl; and

(iif)

where $R^{24}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;

when there is a single bond present between C2' and C3', $R^{12}$ is selected from H, OH, F, diF and

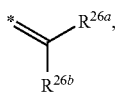

where $R^{26a}$ and $R^{26b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{26a}$ and $R^{26b}$ is H, the other is selected from nitrile and a $C_{1-4}$ alkyl ester;

$R^6$ and $R^9$ are independently selected from H, R, OH, OR, SH, SR, $NH_2$, NHR, NRR', nitro, $Me_3Sn$ and halo;

where R and R' are independently selected from $C_{1-12}$ alkyl, $C_{3-20}$ heterocyclyl and phenyl, naphthyl, azulenyl, anthracenyl, phenanthrenyl, napthacenyl, pyrenyl or $C_{5-20}$ heteroaryl;

$R^7$ is selected from H, R, OH, OR, SH, SR, $NH_2$, NHR, NRR', nitro, $Me_3Sn$ and halo;

R" is a $C_{3-12}$ alkylene group, which chain may be interrupted by one or more heteroatoms selected from O, S, $NR^{N2}$ (where $R^{N2}$ is H or $C_{1-4}$ alkyl), and/or aromatic rings selected from benzene or pyridine;

Y and Y' are selected from O, S, or NH;

$R^{6'}$, $R^{7'}$, $R^{9'}$ are selected from the same groups as $R^6$, $R^7$ and $R^9$ respectively;

$R^{11b}$ is selected from OH, $OR^A$, where $R^A$ is $C_{1-4}$ alkyl; and $R^L$ is a linker for connection to a cell binding agent, which is:

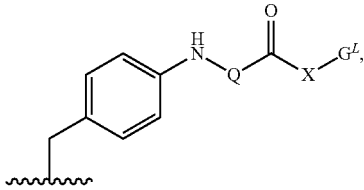

IIIa wherein
Q is:

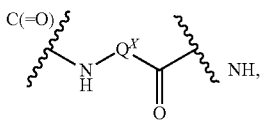

where $Q^X$ is such that Q is an amino-acid residue, a dipeptide residue or a tripeptide residue;

X is:

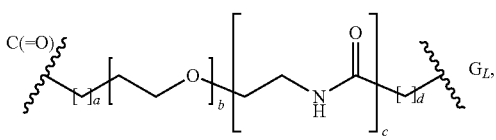

where a=0 to 5, b=0 to 16, c=0 or 1, =0 to 5;

$G^L$ is selected from:

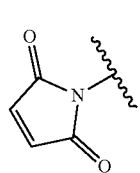
($G^{L1-1}$)

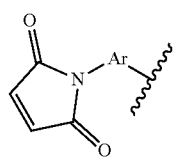
($G^{L1-2}$)

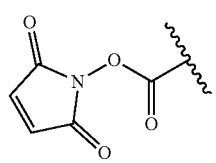
($G^{L2}$)

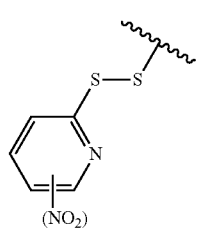
($G^{L3-1}$)

where the $NO_2$ group is optional

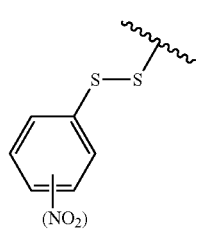
($G^{L3-2}$)

where the $NO_2$ group is optional

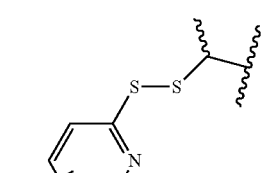
($G^{L3-3}$)

where the $NO_2$ group is optional

-continued (G$^{L3\text{-}1}$)
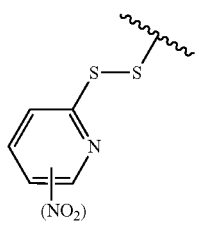
where the NO$_2$ group is optional (G$^{L3\text{-}4}$)
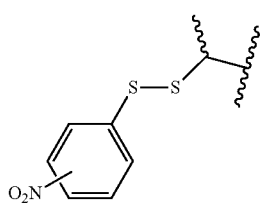
where the NO$_2$ group is optional (G$^{L4}$)
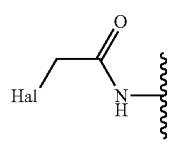
Where Hal = I, Br, Cl (G$^{L5}$)
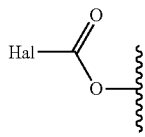

(G$^{L6}$)
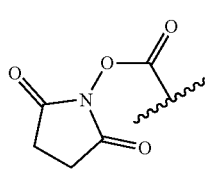

(G$^{L7}$)

(G$^{L8}$)

(G$^{L9}$)

where Ar is phenylene;
wherein the heterocyclyl group in C$_{3\text{-}7}$ heterocyclyl contains 1 to 4 ring heteroatoms selected from N, O and S;
wherein the heterocyclyl group in C$_{3\text{-}20}$ heterocyclyl contains 1 to 10 ring heteroatoms selected from N, O and S; and
wherein the heteroaryl group in C$_{5\text{-}10}$ heteroaryl contains 1 to 4 ring heteroatoms selected from N, O and S wherein the heteroaryl group in C$_{5\text{-}20}$ heteroaryl contains 1 to 10 ring heteroatoms selected from N, O and S.

2. A compound according to claim 1, wherein:
a) both Y and Y' are O; and/or
b) R" is C$_{3\text{-}7}$ alkylene or a group of formula:

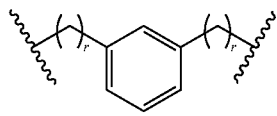

where r is 1 or 2; and/or
c) R$^9$ is H; and/or
d) R$^6$ is H; and/or
e) R$^7$ is selected from H, OH and OR or a C$_{1\text{-}4}$ alkyloxy group.

3. A compound according to claim 1, wherein:
a) D is D1, there is a double bond between C2 and C3, and R$^2$ is a C$_{5\text{-}7}$ aryl group, wherein R$^2$ optionally bears one to three substituent groups selected from methoxy, ethoxy, fluoro, chloro, cyano, bis-oxy-methylene, methyl-piperazinyl, morpholino and methyl-thiophenyl; or
b) D is D1, there is a double bond between C2 and C3, and R$^2$ is a C$_{8\text{-}10}$ aryl group, wherein R$^2$ optionally bears one to three substituent groups selected from methoxy, ethoxy, fluoro, chloro, cyano, bis-oxy-methylene, methyl-piperazinyl, morpholino and methyl-thiophenyl; or
c) D is D1, there is a double bond between C2 and C3, and R$^2$ is methyl, ethyl or propyl; or
d) there is a double bond between C2 and C3, and R$^2$ is cyclopropyl; or
e) wherein D is D1, there is a double bond between C2 and C3, and R$^2$ is a group of formula:

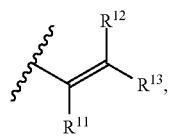

wherein:
i) the total number of carbon atoms in the R$^2$ group is no more than 4; and/or
ii) one of R$^{11}$, R$^{12}$ and R$^{13}$ is H, with the other two groups being selected from H, C$_{1\text{-}3}$ saturated alkyl, C$_{2\text{-}3}$ alkenyl, C$_{2\text{-}3}$ alkynyl and cyclopropyl; or
iii) two of R$^{11}$, R$^{12}$ and R$^{13}$ are H, with the other group being selected from H, C$_{1\text{-}3}$ saturated alkyl, C$_{2\text{-}3}$ alkenyl, C$_{2\text{-}3}$ alkynyl and cyclopropyl; or
f) D is D1, there is a double bond between C2 and C3, and R$^2$ is the group:

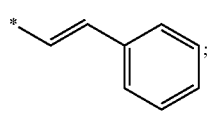

or
g) D is D1, there is a double bond between C2 and C3, and R$^2$ is a group of formula:

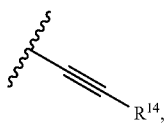

wherein $R^{14}$ is selected from H, methyl, ethyl, ethenyl and ethynyl.

4. A compound according to claim 1, wherein
a) D is D1, there is a single bond between C2 and C3, and $R^2$ is H; or
b) D is D1, there is a single bond between C2 and C3, $R^2$ is

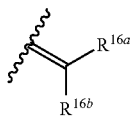

and $R^{16a}$ and $R^{16b}$ are both H; or
c) D is D1, there is a single bond between C2 and C3, $R^2$ is

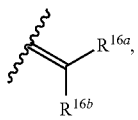

and $R^{16a}$ and $D^{16b}$ are both methyl; or
d) D is D1, there is a single bond between C2 and C3, $R^2$ is

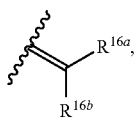

one of $R^{16a}$ and $R^{16b}$ is H, and the other is selected from $C_{1-4}$ saturated alkyl.

5. A compound according to claim 1, wherein:
a) D' is D'1, there is a double bond between C2' and C3', and $R^{12}$ is a $C_{5-7}$ aryl group, wherein $R^{12}$ optionally bears one to three substituent groups selected from methoxy, ethoxy, fluoro, chloro, cyano, bis-oxy-methylene, methyl-piperazinyl, morpholino and methyl-thiophenyl; or
b) D' is D'1, there is a double bond between C2' and C3', and $R^{12}$ is a $C_{8-10}$ aryl group, wherein $R^{12}$ optionally bears one to three substituent groups selected from methoxy, ethoxy, fluoro, chloro, cyano, bis-oxy-methylene, methyl-piperazinyl, morpholino and methyl-thiophenyl; or
c) D' is D'1, there is a double bond between C2' and C3', and $R^{12}$ is methyl, ethyl or propyl; or
d) D' is D'1, there is a double bond between C2' and C3', and $R^{12}$ is cyclopropyl; or
e) D' is D'1, there is a double bond between C2' and C3', and $R^{12}$ is a group of formula:

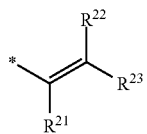

wherein:
  i) the total number of carbon atoms in the $R^{12}$ group is no more than 3;
  ii) one of $R^{21}$, $R^{22}$ and $R^{23}$ is H, with the other two groups being selected from H, $C_{1-3}$ saturated alkyl, $C_{2-3}$ alkenyl, $C_{2-3}$ alkynyl and cyclopropyl; or
  iii) two of $R^{21}$, $R^{22}$ and $R^{23}$ are H, with the other group being selected from H, $C_{1-3}$ saturated alkyl, $C_{2-3}$ alkenyl, $C_{2-3}$ alkynyl and cyclopropyl; or
f) D' is D'1, there is a double bond between C2' and C3', and $R^{12}$ is the group:

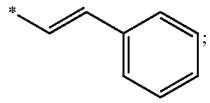 [SMILES: */C=C/c1ccccc1]

or
g) D' is D'1, there is a double bond between C2' and C3', and $R^{12}$ is a group of formula:

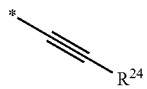

wherein $R^{24}$ is selected from H, methyl, ethyl, ethenyl and ethynyl.

6. A compound according to claim 1, wherein
a) D' is D'1, there is a single bond between C2' and C3', and $R^{12}$ is H; or
b) D' is D'1, there is a single bond between C2' and C3', $R^{12}$ is

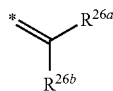

and $R^{26a}$ and $R^{26b}$ are both H; or
c) D' is D'1, there is a single bond between C2' and C3', $R^{12}$ is

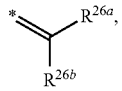

and $R^{26a}$ and $R^{26b}$ are both methyl; or
d) D' is D'1, there is a single bond between C2' and C3', $R^{12}$ is

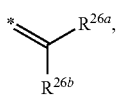

one of $R^{26a}$ and $R^{26b}$ is H, and the other is selected from $C_{1-4}$ saturated alkyl, $C_{2-3}$ alkenyl.

7. A compound according to claim 1, wherein:
a) $R^{6'}$ is selected from the same groups as $R^6$, $R^{7'}$ is selected from the same groups as $R^7$, $R^{9'}$ is selected from the same groups as $R^9$ and Y' is selected from the same groups as Y; and/or
b) $R^{6'}$ is the same groups as $R^6$, $R^{7'}$ is the same groups as $R^7$, $R^{9'}$ is the same groups as $R^9$ and Y' is the same groups as Y; and/or
c) $R^{12}$ is the same group as $R^2$.

8. A compound according to claim 1, which is of formula Ia-1, Ia-2 or Ia-3:

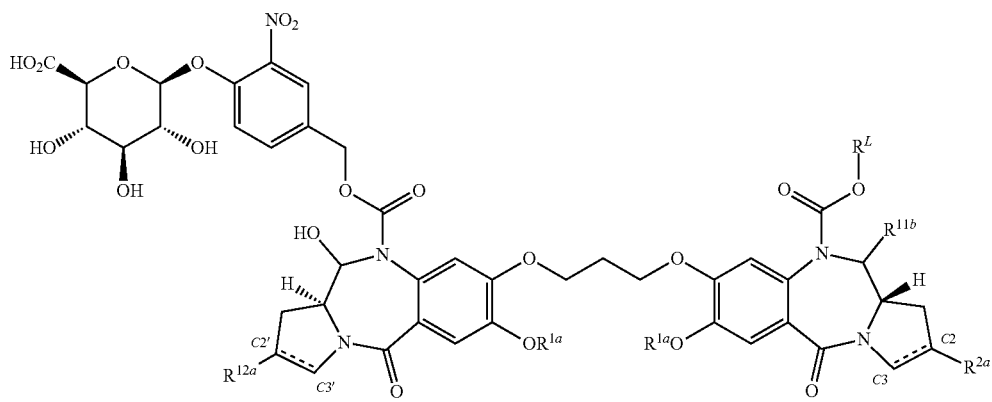

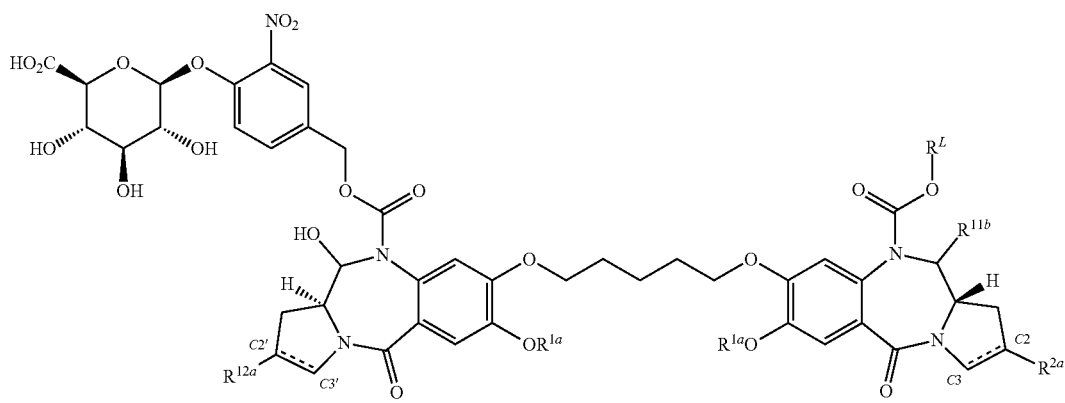

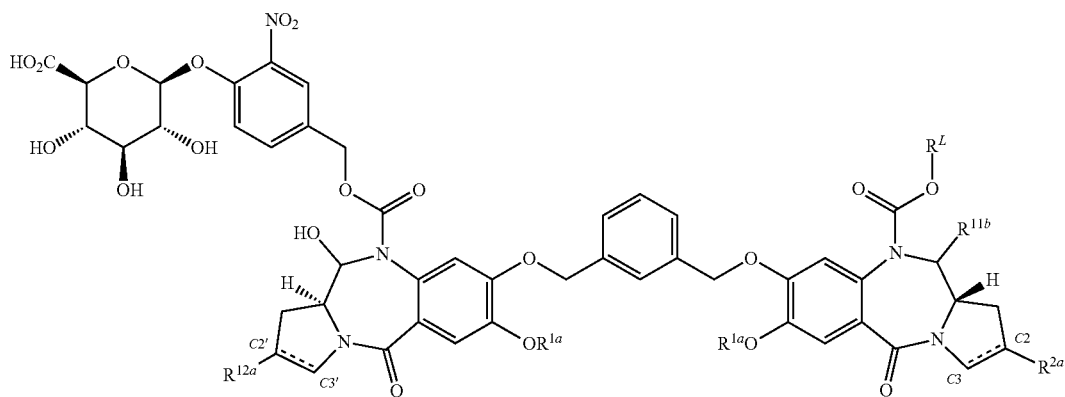

where $R^{2a}$ and $R^{12a}$ are the same and are selected from:

(a)
(b)
(c)
(d)
(e)
(f)
(g) and
(h)

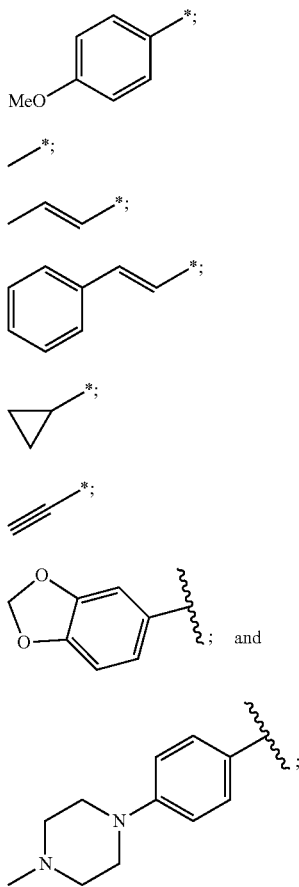

$R^{1a}$ is selected from methyl and benzyl;

$R^L$ and $R^{11b}$ are as defined in claim 1.

9. A compound according to claim 1, wherein both $R^2$ and $R^{12}$ comprise no more than 3 carbon atoms.

10. A compound according to claim 1, wherein $R^{IIb}$ is OH or $OR^A$, where $R^A$ is $C_{1-4}$ alkyl, optionally wherein $R^A$ is methyl.

11. A compound according to claim 1, wherein $Q^X$ is:
  a) an amino acid residue selected from Phe, Lys, Val, Ala, Cit, Leu, Ile, Arg, and Trp; or
  b) a dipeptide residue selected from:
    $^{CO}$-Phe-Lys-$^{NH}$,
    $^{CO}$-Val-Ala-$^{NH}$,
    $^{CO}$-Val-Lys-$^{NH}$,
    $^{CO}$-Ala-Lys-$^{NH}$,
    $^{CO}$_Val-Cit-$^{NH}$,
    $^{CO}$-Phe-Cit-$^{NH}$,
    $^{CO}$-Leu-Cit-$^{NH}$,
    $^{CO}$-Ile-Cit-$^{NH}$,
    $^{CO}$-Phe-Arg-$^{NH}$, and
    $^{CO}$-Trp-Cit-$^{NH}$; or
  c) a tripeptide residue.

12. A compound according to claim 1, wherein
  a) a is 0 to 3; and/or
  b) b is 0 to 12; and/or
  c) d is 0 to 3.

13. A compound according to claim 1, wherein a is 0, c is 1 and d is 2, and b is from 0 to 8.

14. A compound according to claim 1, wherein the compound is of formula
Id:

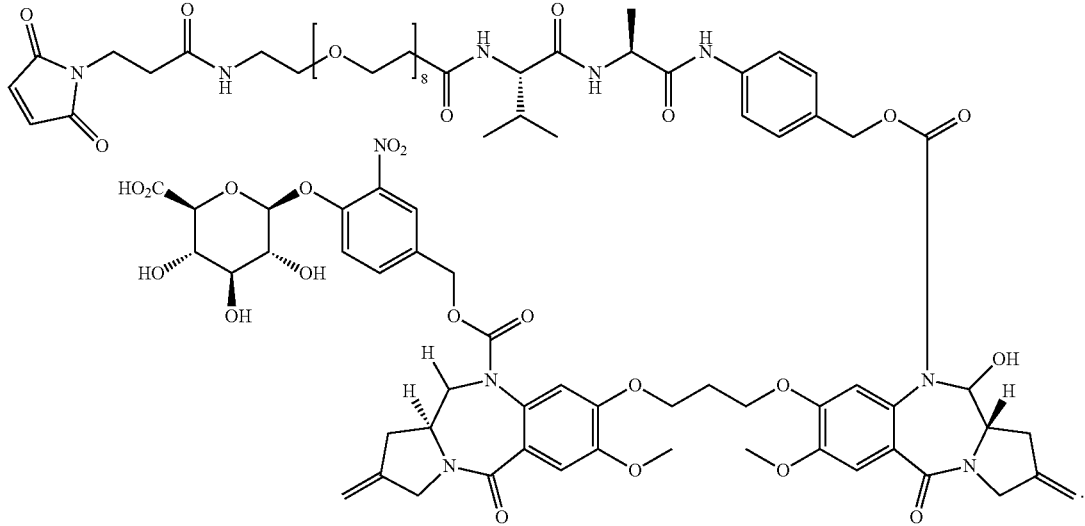

(Id)

15. A conjugate of formula I:

$$L\text{-}(D^L)_p \qquad (I)$$

wherein L is a Ligand unit, $D^L$ is a Drug Linker unit of formula I':

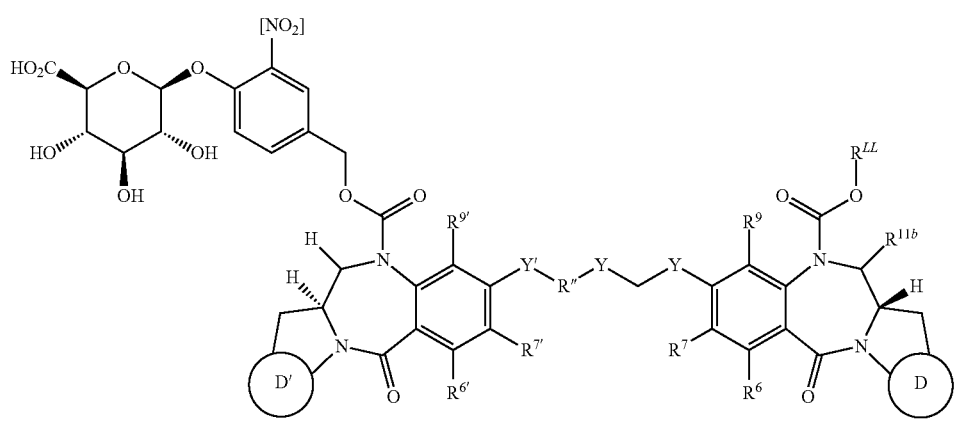

wherein D, $R^2$, $R^6$, $R^7$, $R^9$, $R^{11b}$, Y, R", Y', D', $R^{6'}$, $R^{7'}$, $R^{9'}$, and $R^{12}$, including the presence or absence of double bonds between C2 and C3 and C2' and C3' respectively, are as defined in claim 1;

wherein p is an integer from 1 to 20;

$R^{LL}$ is a linker for connection to a cell binding agent, which is:

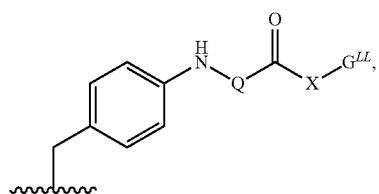
IIIa' where Q and X are as defined in claim 1 and $G^{LL}$ is selected from:

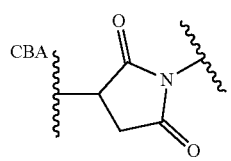
($G^{LL1-1}$)

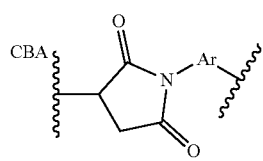
($G^{LL1-2}$)

-continued

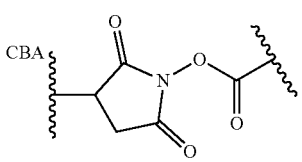
($G^{LL2}$)

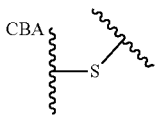
($G^{LL3-1}$)

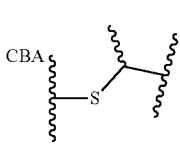
($G^{LL3-2}$)

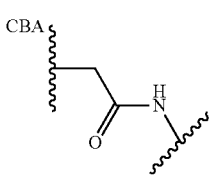
($G^{LL4}$)

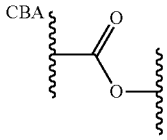
($G^{LL5}$)

-continued

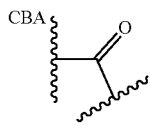
(G^{LL6})

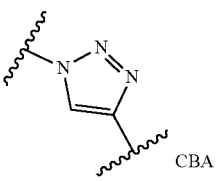
(G^{LL9-1})

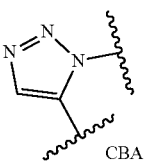
(G^{LL9-2})

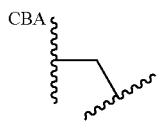
(G^{LL7})

where Ar is phenylene.

16. A conjugate according to claim 15, wherein $G^{LL}$ is selected from $G^{LL1\text{-}1}$ and $G^{LL1\text{-}2}$.

17. A conjugate according to claim 15, wherein $D^L$ is of formula (Id'):

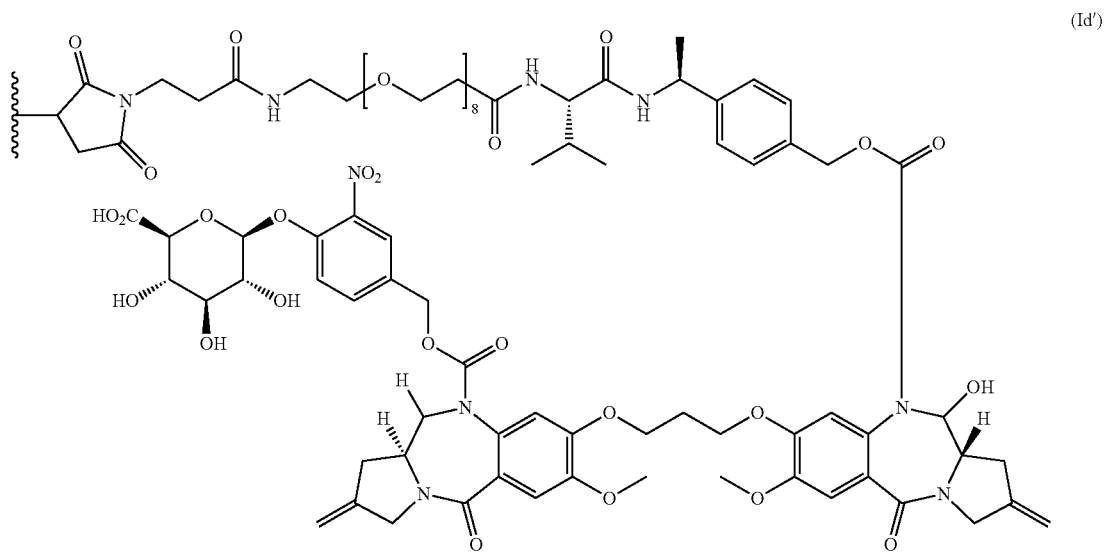
(Id')

-continued

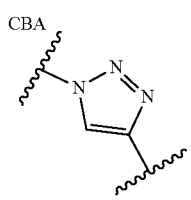
(G^{LL8-1})

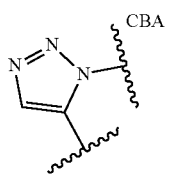
(G^{LL8-2})

18. A conjugate according to claim 15, wherein the Ligand Unit is an antibody or an active fragment thereof.

19. The conjugate according to claim 18, wherein the antibody or antibody fragment is an antibody or antibody fragment for a tumour-associated antigen, optionally wherein the antibody or antibody fragment is an antibody which binds to one or more tumor-associated antigens or cell-surface receptors selected from (1)-(88):

(1) BMPR1B;
(2) E16;
(3) STEAP1;
(4) 0772P;
(5) MPF;
(6) Napi3b;
(7) Sema 5b;
(8) PSCA hlg;
(9) ETBR;
(10) MSG783;
(11) STEAP2;
(12) TrpM4;
(13) CRIPTO;

(14) CD21;
(15) CD79b;
(16) FcRH2;
(17) HER2;
(18) NCA;
(19) MDP;
(20) IL20R-alpha;
(21) Brevican;
(22) EphB2R;
(23) ASLG659;
(24) PSCA;
(25) GEDA;
(26) BAFF-R;
(27) CD22;
(28) CD79a;
(29) CXCR5;
(30) HLA-DOB;
(31) P2X5;
(32) CD72;
(33) LY64;
(34) FcRH1;
(35) IRTA2;
(36) TENB2;
(37) PSMA—FOLH1;
(38) SST;
(38.1) SSTR2;
(38.2) SSTR5;
(38.3) SSTR1;
(38.4) SSTR3;
(38.5) SSTR4;
(39) ITGAV;
(40) ITGB6;
(41) CEACAM5;
(42) MET;
(43) MUC1;
(44) CA9;
(45) EGFRvIII;
(46) CD33;
(47) CD19;
(48) IL2RA;
(49) AXL;
(50) CD30—TNFRSF8;
(51) BCMA-TNFRSF17;
(52) CT Ags—CTA;
(53) CD174 (Lewis Y)—FUT3;
(54) CLEC14A;
(55) GRP78—HSPA5;
(56) CD70;
(57) Stem Cell specific antigens;
(58) ASG-5;
(59) ENPP3;
(60) PRR4;
(61) GCC-GUCY2C;
(62) Liv-1—SLC39A6;
(63) 5T4;
(64) CD56—NCMA1;
(65) CanAg;
(66) FOLR1;
(67) GPNMB;
(68) TIM-1—HAVCR1;
(69) RG-1/Prostate tumor target Mindin—Mindin/RG-1;
(70) B7-H4—VTCN1;
(71) PTK7;
(72) CD37;
(73) CD138—SDC1;
(74) CD74;
(75) Claudins—CLs;
(76) EGFR;
(77) Her3;
(78) RON—MST1R;
(79) EPHA2;
(80) CD20—MS4A1;
(81) Tenascin C—TNC;
(82) FAP;
(83) DKK-1;
(84) CD52;
(85) CS1—SLAMF7;
(86) Endoglin—ENG;
(87) Annexin Al—ANXA1;
(88) V-CAM (CD106)—VCAM1.

20. The conjugate of claim 18 wherein the antibody or antibody fragment is a cysteine-engineered antibody.

21. The conjugate according to claim 15 wherein p is an integer from 1 to 8.

22. A composition comprising a mixture of conjugates according to claim 15, wherein the average p in the mixture of conjugate compounds is about 1 to about 8.

23. A pharmaceutical composition comprising the conjugate of claim 15 a pharmaceutically acceptable diluent, carrier or excipient.

24. A method of inhibiting growth of carcinoma cells which comprises contacting cancer cells with the pharmaceutical composition of claim 23, wherein the carcinoma cells are gastric carcinoma cells or breast carcinoma cells, and whereby growth of the cancer cells is inhibited.

25. The method of claim 24, wherein the carcinoma cells are in a human.

26. The method of claim 24, which further comprises contacting the carcinoma cells with a chemotherapeutic agent.

* * * * *

UNITED STATES PATENT AND TRADEMARK OFFICE
CERTIFICATE OF CORRECTION

PATENT NO. : 10,799,595 B2  
APPLICATION NO. : 16/340973  
DATED : October 13, 2020  
INVENTOR(S) : Philip Wilson Howard and Stephen John Gregson Page 1 of 3

It is certified that error appears in the above-identified patent and that said Letters Patent is hereby corrected as shown below:

In the Claims

In Claim 1, Column 170, beginning at Line 17, in formula I, "Y" should read --Y'--.
Formula I should read:

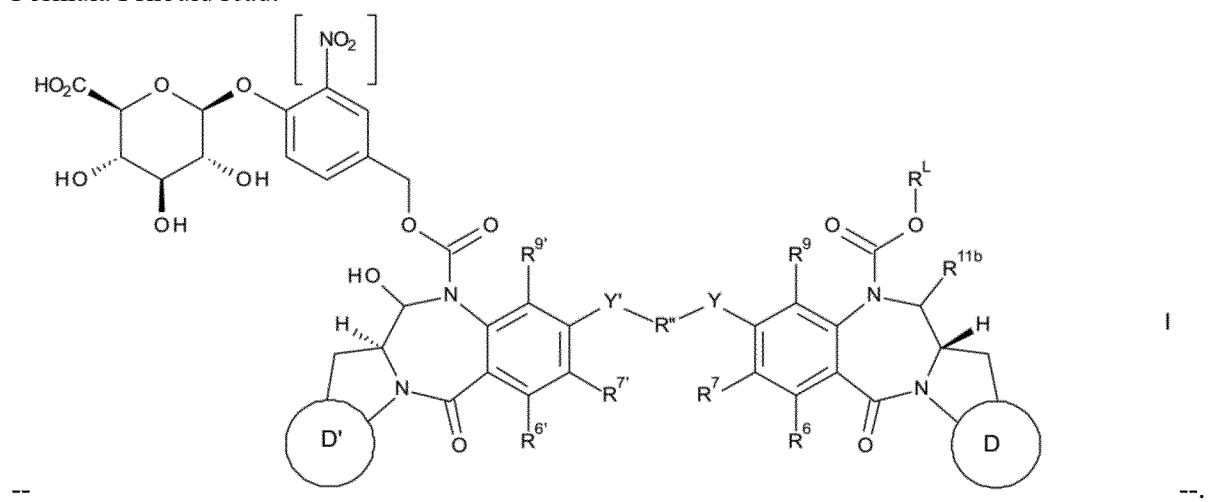

--                                                                           --.

In Claim 1, Column 173, at Line 68, "= 0 to 5" should read --d = 0 to 5--.

Signed and Sealed this  
Ninth Day of November, 2021

Drew Hirshfeld  
*Performing the Functions and Duties of the*  
*Under Secretary of Commerce for Intellectual Property and*  
*Director of the United States Patent and Trademark Office*

CERTIFICATE OF CORRECTION (continued)

U.S. Pat. No. 10,799,595 B2

Page 2 of 3

In Claim 14, Columns 181 to 182, at Line 56, in Formula Id, "H" should read --HO--.
Formula Id should read:

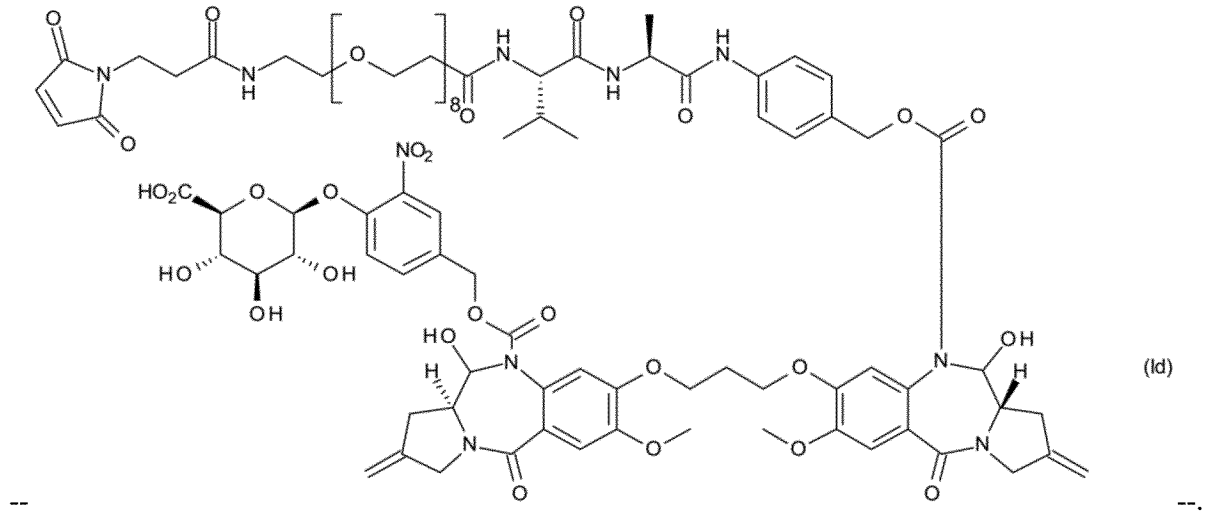

In Claim 15, Columns 183 to 184, at Line 17, in Formula I', "H" should read --HO--. At Line 17, in Formula I', the second instance of "—Y—" should be deleted.
Formula I' should read:

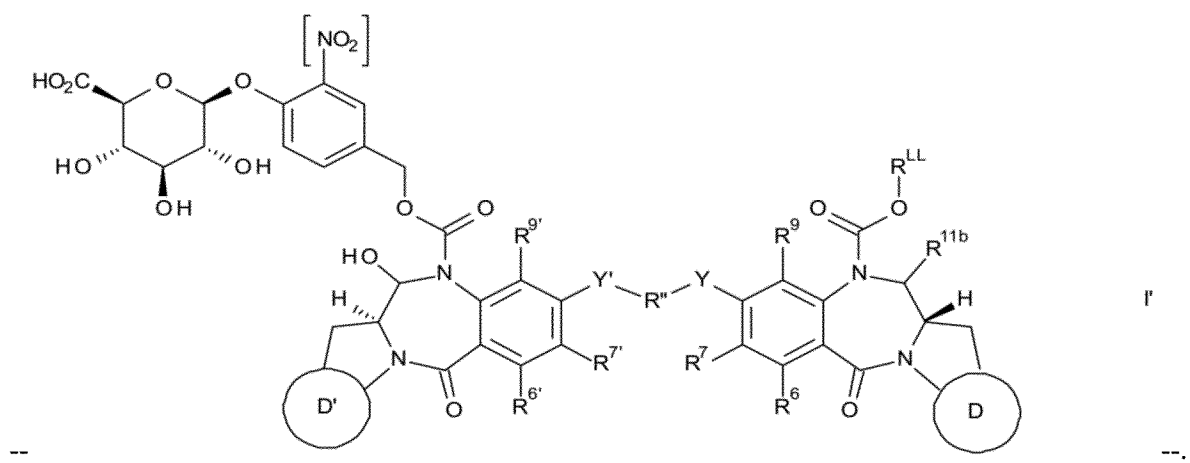

CERTIFICATE OF CORRECTION (continued)
U.S. Pat. No. 10,799,595 B2

In Claim 17, Column 185 to 186, at Line 37, Formula Id', "H" should read --HO--. At Line 17, in Formula Id', at Line 25,  is missing.

Formula Id' should read as follows:

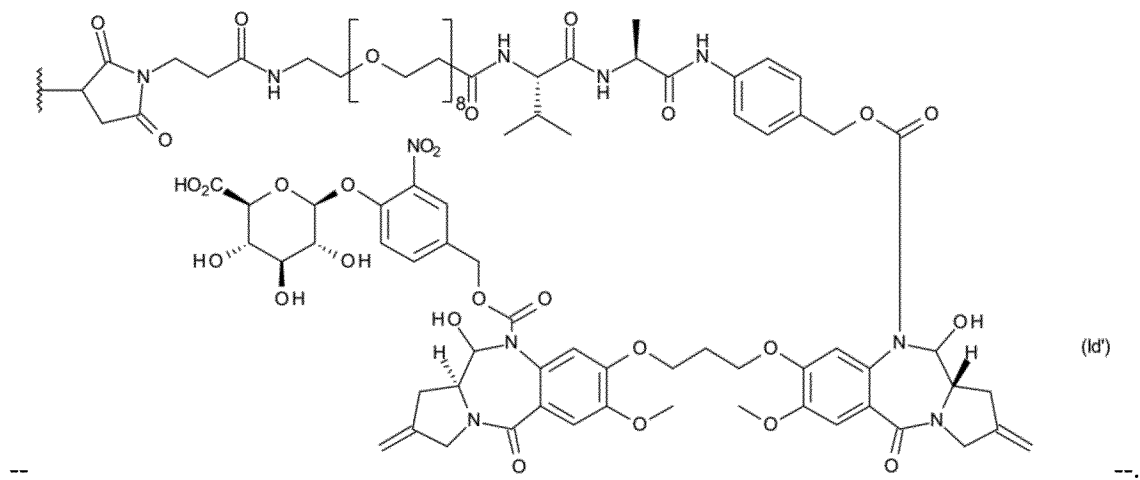

-- --.